US009844590B2

(12) United States Patent
Korber et al.

(10) Patent No.: US 9,844,590 B2
(45) Date of Patent: Dec. 19, 2017

(54) MOSAIC CLADE M HUMAN IMMUNODEFICIENCY VIRUS TYPE 1 (HIV-1) GAG IMMUNOGENS

(71) Applicants: LOS ALAMOS NATIONAL SECURITY, LLC, Los Alamos, NM (US); BETH ISRAEL DEACONESS MEDICAL CENTER, Boston, MA (US); DUKE UNIVERSITY, Durham, NC (US); THE UAB RESEARCH FOUNDATION, Birmingham, AL (US)

(72) Inventors: Bette T. Korber, Los Alamos, NM (US); William Fischer, Los Alamos, NM (US); Norman Letvin, Boston, MA (US); Hua-Xin Liao, Durham, NC (US); Barton F. Haynes, Durham, NC (US); Beatrice H. Hahn, Birmingham, AL (US)

(73) Assignees: Duke University, Durham, NC (US); Los Alamos National Security, LLC, Los Alamos, NM (US); Beth Israel Deconess Medical Center, Boston, MA (US); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 14/726,373

(22) Filed: May 29, 2015

(65) Prior Publication Data

US 2015/0265700 A1 Sep. 24, 2015

Related U.S. Application Data

(60) Division of application No. 12/737,761, filed as application No. PCT/US2009/004664 on Aug. 14, 2009, now Pat. No. 9,044,445, which is a continuation of application No. 12/192,015, filed on Aug. 14, 2008, now Pat. No. 7,951,377, and a continuation-in-part of application No. 11/990,222, filed as application No. PCT/US2006/032907 on Aug. 23, 2006, now Pat. No. 8,119,140.

(60) Provisional application No. 60/739,413, filed on Nov. 25, 2005, provisional application No. 60/710,154, filed on Aug. 23, 2005.

(51) Int. Cl.
*A61K 39/21* (2006.01)
*C07K 14/005* (2006.01)
*A61K 39/12* (2006.01)
*C12N 7/00* (2006.01)
*A61K 39/00* (2006.01)

(52) U.S. Cl.
CPC .............. *A61K 39/21* (2013.01); *A61K 39/12* (2013.01); *C07K 14/005* (2013.01); *C12N 7/00* (2013.01); *A61K 2039/53* (2013.01); *A61K 2039/70* (2013.01); *C12N 2710/24143* (2013.01); *C12N 2740/16022* (2013.01); *C12N 2740/16034* (2013.01); *C12N 2740/16122* (2013.01); *C12N 2740/16134* (2013.01); *C12N 2740/16234* (2013.01); *C12N 2740/16334* (2013.01)

(58) Field of Classification Search
CPC .......... A61K 39/21; C12N 2740/16122; C12N 2740/16134
See application file for complete search history.

(56) References Cited

U.S. PATENT DOCUMENTS

| | | |
|---|---|---|
| 5,580,859 A | 12/1996 | Felgner et al. |
| 5,589,466 A | 12/1996 | Felgner et al. |
| 5,703,055 A | 12/1997 | Felgner et al. |
| 6,710,173 B1 | 3/2004 | Binley et al. |
| 7,655,774 B2 | 2/2010 | Mullins et al. |
| 7,951,377 B2 | 5/2011 | Korber et al. |
| 8,119,140 B2 | 2/2012 | Korber et al. |
| 9,011,873 B2 | 4/2015 | Korber et al. |
| 9,011,875 B2 | 4/2015 | Korber et al. |
| 9,044,445 B2 | 6/2015 | Korber et al. |
| 2002/0198162 A1 | 12/2002 | Punnonen et al. |
| 2003/0044421 A1 | 3/2003 | Emini et al. |
| 2003/0104011 A1 | 6/2003 | Rios |
| 2003/0147888 A1 | 8/2003 | Haynes et al. |
| 2003/0180314 A1 | 9/2003 | DeGroot |
| 2003/0194411 A1 | 10/2003 | Rubinstein et al. |
| 2004/0001851 A1 | 1/2004 | Haynes et al. |
| 2005/0137387 A1 | 6/2005 | Mullins et al. |
| 2006/0216305 A1 | 9/2006 | Lal et al. |
| 2006/0275897 A1 | 12/2006 | Nabel et al. |
| 2007/0178562 A1 | 8/2007 | Haynes et al. |
| 2009/0324631 A1 | 12/2009 | Korber et al. |
| 2011/0150915 A1 | 6/2011 | Korber et al. |

(Continued)

FOREIGN PATENT DOCUMENTS

| | | |
|---|---|---|
| WO | 2002/004493 | 1/2002 |
| WO | 2005/001029 A2 | 1/2005 |
| WO | 2005/012502 | 2/2005 |

(Continued)

OTHER PUBLICATIONS

Gag GenBank accession No. U52953.

(Continued)

*Primary Examiner* — Jeffrey Parkin
(74) *Attorney, Agent, or Firm* — Baker Donelson

(57) ABSTRACT

The present invention relates, in general, to an immunogenic composition (e.g., a vaccine) and, in particular, to a polyvalent immunogenic composition, such as a polyvalent HIV vaccine, and to methods of using same. The invention further relates to methods that use a genetic algorithm to create sets of polyvalent antigens suitable for use, for example, in vaccination strategies.

9 Claims, 109 Drawing Sheets

(56) References Cited

U.S. PATENT DOCUMENTS

| | | | |
|---|---|---|---|
| 2011/0301328 | A1 | 12/2011 | Korber et al. |
| 2012/0121631 | A1 | 5/2012 | Korber et al. |

FOREIGN PATENT DOCUMENTS

| | | |
|---|---|---|
| WO | 2005/028625 | 3/2005 |
| WO | 2005/035555 | 4/2005 |
| WO | 2007/024941 | 3/2007 |
| WO | 2007/047916 | 4/2007 |
| WO | 2010/019262 | 2/2010 |
| WO | 2012/047267 | 4/2012 |

OTHER PUBLICATIONS

Nef core GenBank accession No. AF069670.

Nef core GenBank accession No. K02083.

Nef core GenBank accession No. U52953.

Barugahare et al., "Human Immunodeficiency Virus-Specific Responses in Adult Ugandans: Patterns of Cross-Clade Recognition," J. Virol. Apr. 2005; 79:7 4132-4139.

Oxenius, et al., "HIV-Specific Cellular Immune Response is Inversely Correlated with Disease Progression as Defined by Decline of CD4+ T Cells in Relation to HIV RNA Load," J Infect Dis. (2004) 189 (7): 1199-1208.

Barouch et al., "Control of Viremia and Prevention of Clinical AIDS in Rhesus Monkeys by Cytokine-Augmented DNA Vaccination", Science Oct. 20, 2000: vol. 290, Issue 5491, pp. 486-492.

Schmitz et al., "Control of Viremia in Simian Immunodeficiency Virus Infection by CD8+ Lymphocytes," Science Feb. 5, 1999: vol. 283, Issue 5403, pp. 857-860.

Barouch et al., "Viral Escape from Dominant Simian Immunodeficiency Virus Epitope-Specific Cytotoxic T Lymphocytes in DNA-Vaccinated Rhesus Monkeys," J. Virol. Jul. 2003; 77:13 7367-7375.

Moore and Burton, "Urgently needed: a filter for the HIV-1 vaccine pipeline," Nat Med. Aug. 2004;10(8):769-71.

Altfeld et al., "Enhanced detection of human immunodeficiency virus type 1-specific T-cell responses to highly variable regions by using peptides based on autologous virus sequences," J Virol. Jul. 2003;77(13):7330-40.

Norris et al., "Fine specificity and cross-clade reactivity of HIV type 1 Gag-specific CD4+ T cells," AIDS Res Hum Retroviruses. Mar. 2004;20(3):315-25.

Jones et al. "Determinants of Human Immunodeficiency Virus Type 1 Escape from the Primary CD8+ Cytotoxic T Lymphocyte Response," J Exp Med. Nov. 15, 2004;200(10):1243-56.

Allen et al. "De Novo Generation of Escape Variant-Specific CD8+ T-Cell Responses following Cytotoxic T-Lymphocyte Escape in Chronic Human Immunodeficiency Virus Type 1 Infection" J. Virol. Oct. 15, 2005; 79:20 12952-12960.

Feeney et al., "HIV-1 viral escape in infancy followed by emergence of a variant-specific CTL response," J Immunol. Jun. 15, 2005;174(12):7524-30.

Killian et al., "Clonal breadth of the HIV-1-specific T-cell receptor repertoire in vivo as determined by subtractive analysis," AIDS. Jun. 10, 2005;19(9):887-96.

Milicic et al., "CD8+ T Cell Epitope-Flanking Mutations Disrupt Proteasomal Processing of HIV-1 Nef," J Immunol 2005 175:4618-4626.

Kong et al., "Immunogenicity of Multiple Gene and Clade Human Immunodeficiency Virus Type 1 DNA Vaccines," J. Virol. Dec. 2003; 77:23 12764-12772.

Yusmin et al., "Clustering Patterns of Cytotoxic T-Lymphocyte Epitopes in Human Immunodeficiency Virus Type 1 (HIV-1) Proteins Reveal Imprints of Immune Evasion on HIV-1 Global Variation," J. Virol. Sep. 2002; 76:17 8757-8768.

Lee et al., "T Cell Cross-Reactivity and Conformational Changes during TCR Engagement," J Exp Med 2004 200:1455-1466.

Williamson et al., "Characterization and selection of HIV-1 subtype C isolates for use in vaccine development," AIDS Res Hum Retroviruses. Feb. 2003;19(2):133-44.

Frahm et al., "Consistent Cytotoxic-T-Lymphocyte Targeting of Immunodominant Regions in Human Immunodeficiency Virus across Multiple Ethnicities" J. Virol. Mar. 2004; 78:5 2187-2200.

Lichterfeld et al., "HIV-1 Nef is preferentially recognized by CD8 T cells in primary HIV-1 infection despite a relatively high degree of genetic diversity," AIDS. Jul. 2, 2004;18(10):1383-92.

Hel et al., "Improved Vaccine Protection from Simian AIDS by the Addition of Nonstructural Simian Immunodeficiency Virus Genes," J Immunol 2006 176:85-96.

Blagoveshchenskaya et al., "HIV-1 Nef downregulates MHC-I by a PACS-1- and PI3K-regulated ARF6 endocytic pathway," Cell. Dec. 13, 2002;111(6):853-66.

Masemola et al., "Hierarchical Targeting of Subtype C Human Immunodeficiency Virus Type 1 Proteins by CD8+ T Cells: Correlation with Viral Load," J. Virol. Apr. 2004; 78:7 3233-3243.

Bansal et al., "CD8 T-cell responses in early HIV-1 infection are skewed towards high entropy peptides," AIDS. Feb. 18, 2005;19(3):241-50.

Seaman et al., "Multiclade Human Immunodeficiency Virus Type 1 Envelope Immunogens Elicit Broad Cellular and Humoral Immunity in Rhesus Monkeys," J. Virol. Mar. 2005; 79:5 2956-2963.

Singh et al., "The Role of T Cell Antagonism and Original Antigenic Sin in Genetic Immunization," J Immunol 2002 169:6779-6786.

André et al., "Increased Immune Response Elicited by DNA Vaccination with a Synthetic gp120 Sequence with Optimized Codon Usage," J. Virol. Feb. 1998 ; 72:2 1497-1503.

Haas et al., "Codon usage limitation in the expression of HIV-1 envelope glycoprotein," Curr Biol. Mar. 1, 1996;6(3):315-24.

Ammaranond et al., "A new variant cytotoxic T lymphocyte escape mutation in HLA-B27-positive individuals infected with HIV type 1," AIDS Res Hum Retroviruses. May 2005;21(5):395-7.

Kiepiela et al., "Dominant influence of HLA-B in mediating the potential co-evolution of HIV and HLA," Nature. Dec. 9, 2004;432(7018):769-75.

Altfeld et al, "HIV-1 superinfection despite broad CDS+ T-cell responses containing replication of the primary virus", Nature, 420(6914):434-439 (2002).

Barouch et al., "Mosaic HIV-1 Vaccines Expand the Breadth and Depth of Cellular Immune Responses in Rhesus Monkeys", Nat Med., 16(3):319-323 (2010).

Desrosiers, "Prospects for an AIDS Vaccine", Nature Medicine, 10(3):221-223 (2004).

Doria-Rose et al, "Human Immunodeficiency Virus Type 1 Subtype B Ancestral Envelope Protein is Functional and Elicits Neutralizing Antibodies in Rabbits Similar to Those Elicited by a Circulating Subtype B Envelope", Journal of ViroloRJI, 79(17): 11214-11224 (2005).

Fischer et al, "Polyvalent vaccines for optimal coverage of potential T-cell epitopes in global HIV-1 variants", Nature Medicine, 13(1): 100-106 (2007).

Gallo, "The end or the beginning of the drive to an HIV-preventive vaccine: a view from over 20 years," The Lancet, 366:1894-1898. (2005).

Gao et al, "Antigenicity and Immunogenicity of a Synthetic Human Immunodeficiency Virus Type 1 Group M Consensus Envelope Glycoprotein", Journal o{ViroloKJI, 79(2): 1154-1163 (2005).

Gaschen et al, "Diversity Considerations in HIV-1 Vaccine Selection", Science, 296(5577):2354-2360 (2002).

Go et al., "Giycosylation Site-Specific Analysis of Clade C HIV-1 Envelope Proteins", Journal ofProteome Research, 8(9):4231-4242 (Author Manuscript). (2009).

Hanke et al, "DNA multi-CTL epitope vaccines for HIV and Plasmodium falciparum: immunogenicity in mice", Vaccine, 16(4):426-435 (1998).

Haynes et al, "Aiming to induce broadly reactive neutralizing antibody responses with HIV-1 vaccine candidates," Expert Rev. Vaccines, 5(3)347-363 (2006).

International Search Report dated Apr. 6, 2010 issued in International Appln. No. PCTIUS2009/004664.

(56) References Cited

OTHER PUBLICATIONS

International Search Authority Written Opinion dated Apr. 6, 2010 issued in International Appln. No. PCTIUS09/004664.
International Search Report dated Jul. 3, 2008 issued in International Appln. No. PCTIUS06/32907.
International Search Report dated Aug. 27, 2008 issued in International Appln. No. PCTIUS06/32907.
International Search Report dated Apr. 18, 2012 issued in International Appln. No. PCTIUS2011/001664.
International Search Authority Written Opinion dated Apr. 18, 2012 issued in International Appln. No. PCTIUS2011100166.
International Search Report dated Aug. 27, 2008 issued in WO 2007/024941.
International Search Report dated Aug. 27, 2008 in WO 2007/024941 (Korber).
Kong et al., "Expanded Breadth of the T-Cell Response to Mosaic Human Immunodeficiency Virus Type 1 Envelope DNA Vaccination", Journal ofViroloKJI, 83(5):2201-2215 (2009).
Korber et al., "T-Cell Vaccine Strategies for Human Immunodeficiency Virus, the Virus with a Thousand Faces", Journal ofViroloKJI, 83(17).8300-8314 (2009).
Korber et al, "Evolutionary and immunological implications of contemporary HIV-1 variation", British Medical Bulletin, 58:19-42 (2001).
Letvin, N., "Progress and obstacles in the development of an AIDS vaccine" (2006).
Liao et al., "A Group M Consensus Envelope Glycoprotein Induces Antibodies that Neutralize Subsets of Subtype Band C HIV-1 Primary Viruses", Virology, 353:268-282 (Author Manuscript). (2006).
McMichael, A. J., "HIV vaccines", Ann. Rev. Immunol., 24:227-255 (2006).
Nabel et al, "HIV vaccine strategies", Vaccine, 20(15):1945-1947 (2002).
Santra et al., "Mosaic Vaccines Elicit CD8+ T lymphocyte Responses in Monkeys that Confer Enhanced Immune Coverage of Diverse HIV Strains", Nat Med., 16(3):324-328 (2010).
Santra et al., "A centralized gene-based HIV-1 vaccine elicits broad cross-clade cellular immune responses in rhesus monkeys", PNAS, 105(30):10489-10494 (2008).
Shinoda et al, "Polygene DNA vaccine induces a high level of protective effect against HIV-vaccinia virus challenge in mice", Vaccine, 22:3676-3690 (2004).
Supplementary European Search Report dated Jul. 11, 2012 issued in EP 09 80 698.
Supplementary European Search Report dated Oct. 25, 2012 issued in EP 06802155.
Supplementary European Search Report dated Nov. 9, 2012 issued in EP 06802155.
Tomaras et al., "Initial B-Cell Responses to Transmitted Human Immunodeficiency Virus Type 1: Virion-Binding Immunoglobulin M (IgM) and IgG Antibodies Followed by Plasma Anti-GP41 Antibodies with Ineffective Control of Initial Viremia", Journal of ViroloRJI, 82(24): 14229-14263. (2008).
Walker et al., "Toward an AIDS vaccine", Science, 320:760-765 (2008).
Weaver et al., "Cross-Subtype T-Cell Immune Responses Induced by a Human Immunodeficiency Virus Type 1 Group M Consensus Env. Immunogen", Journal o/Virology, 80(14):6745-6756. (2006).
Ferrari, G, et al; Identification of highly conserved and broadly cross-reactive HIV type 1 cytotoxic T lymphocyte epitopes as candidate immunogens for inclusion in *Mycobacterium bovis* BCG-vectored HIV vaccines; AIDS Res Hum Retroviruses; Sep. 20, 2000; 16(14); 1433-43.
Robertson, DL, et al; Recombination in HIV-1; Nature; Mar. 9, 1995; 374(6518); 124-6.
Sbai, H, et al; Use of T cell epitopes for vaccine development; Curr Drug Targets Infect Disord.; Nov. 2001; 1(3); 303-13.
European search report and opinion dated May 11, 2017.
Gag GenBank accession No. AF004885.
Gag GenBank accession No. K03455.
Gag GenBank Accession Nos. U52953, p. 1 of 4.
GenBank accession No. AF530576.
GenBank accession No. AF533131.
GenBank accession No. AY173953.
GenBank accession No. AY856956.
GenBank accession No. AY857186.
Net core GenBank accession No. AF069670.
Net core GenBank accession No. K02083.
NEF core GenBank Accession Nos. U52953, p. 2 of 4.
Peng et al., "Replicating Ad-recombinants encoding non-myristoylated rather than wild-type HIV Nef elicit enhanced cellular immunity", AIDS, 20:2149-2157 (2006).

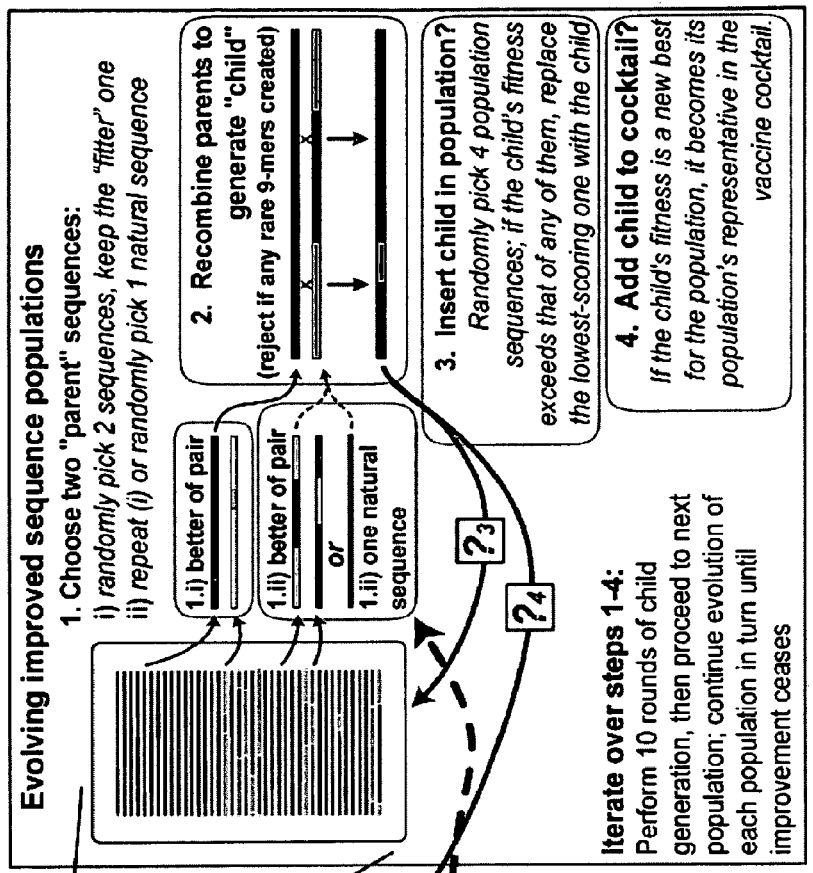
Fig. 2C
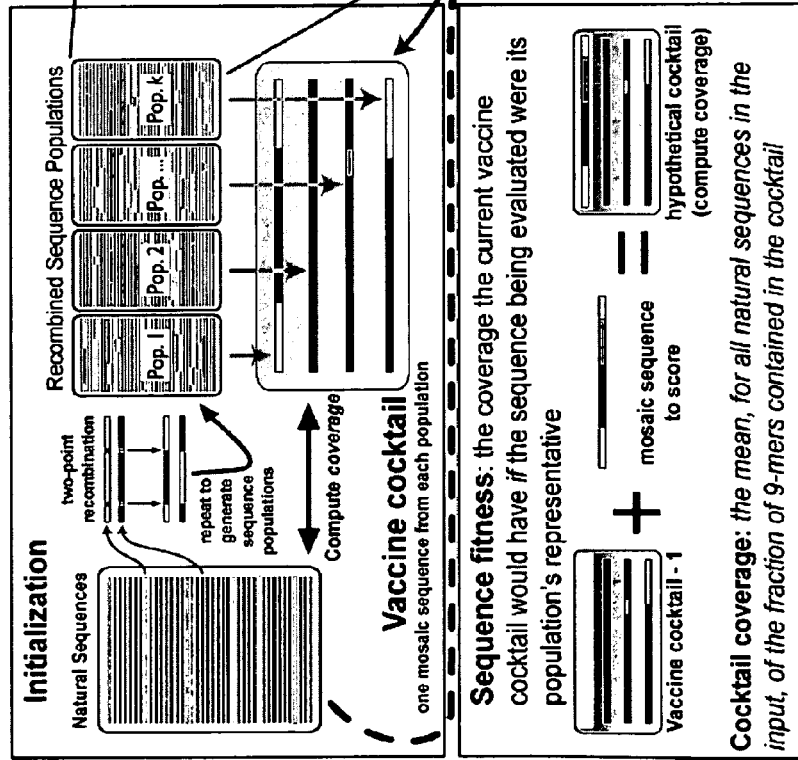
Fig. 2A
Fig. 2B

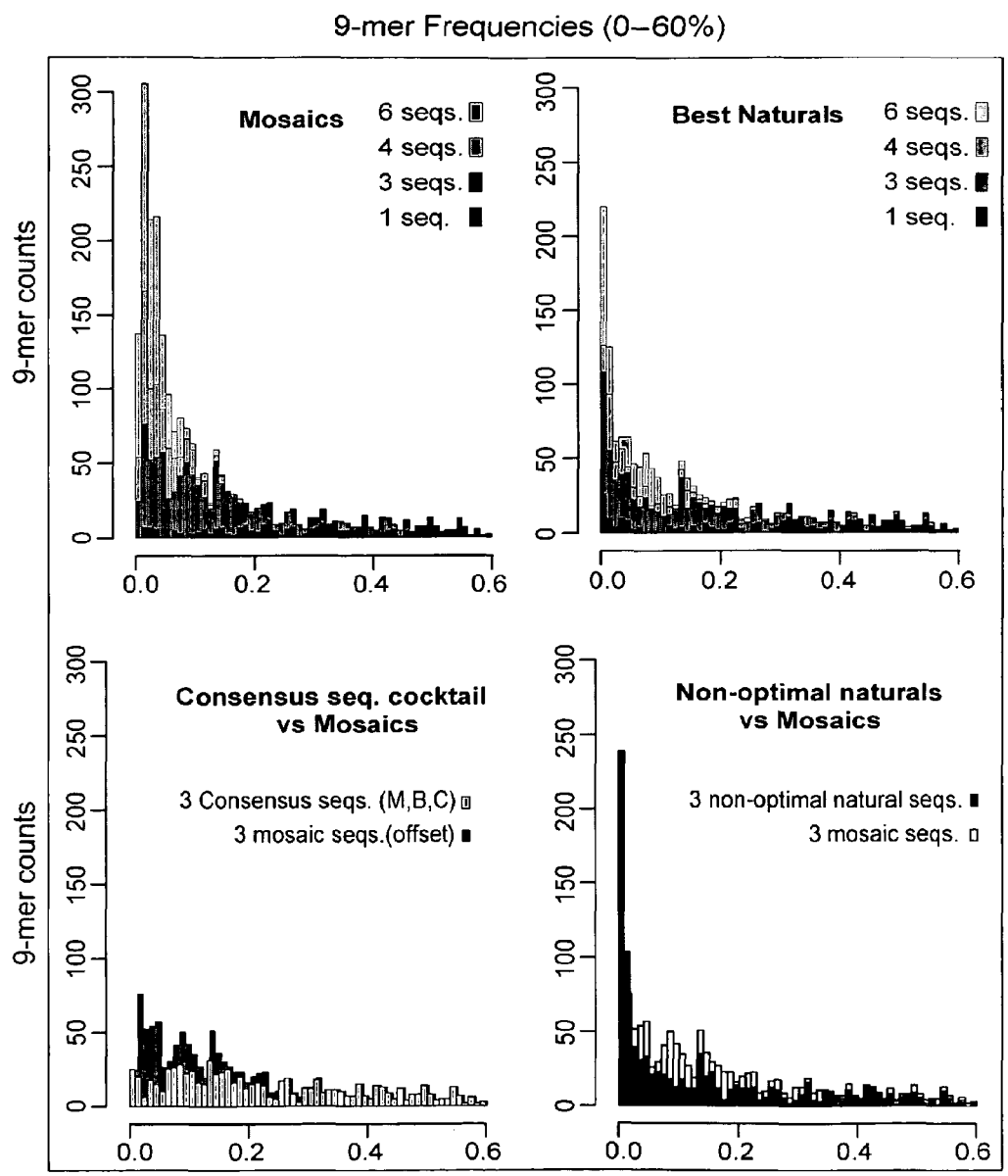

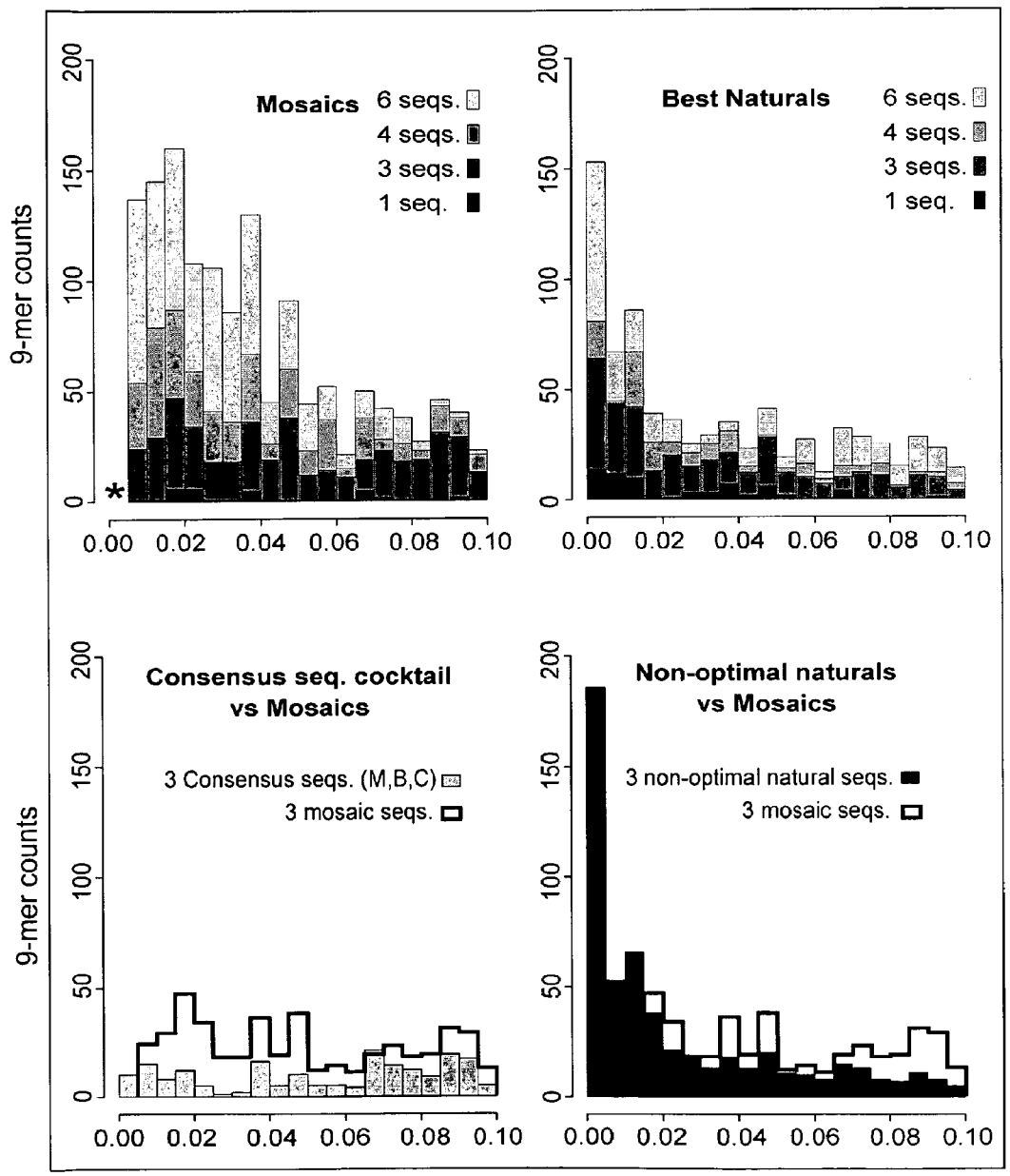

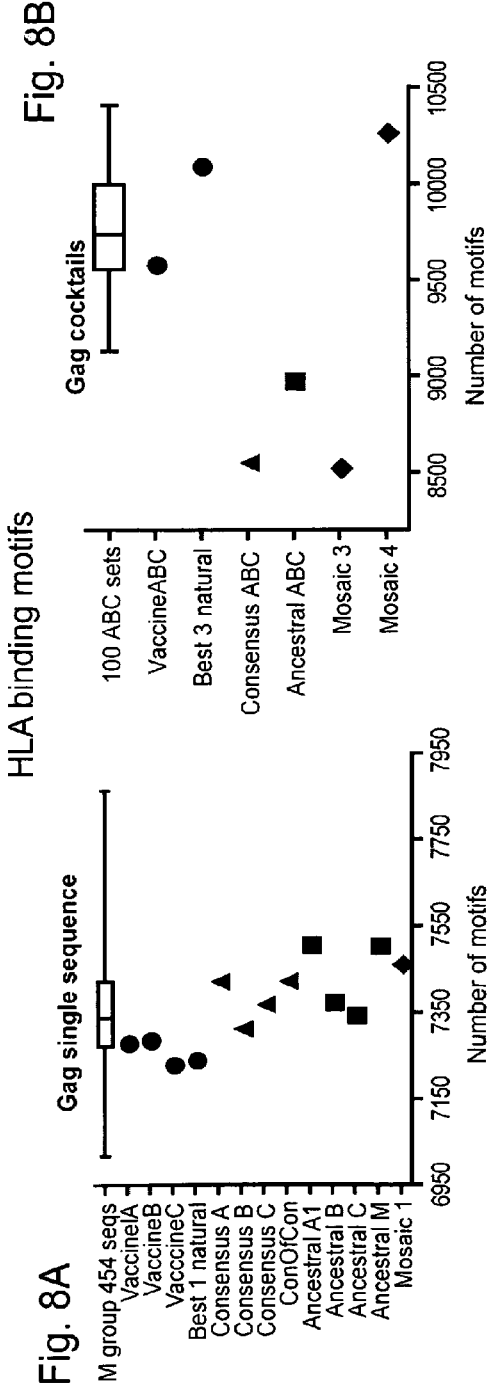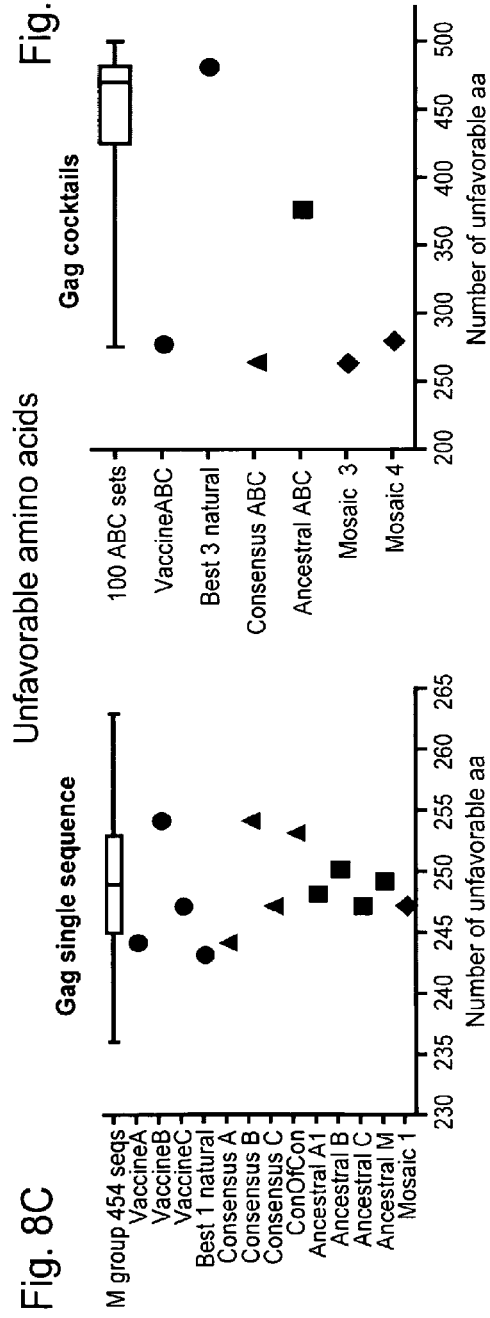

Fig. 9

>nef_coreB.syn1.1
EVGFPVRPQVPLRPMTYKGALDLSHFLKEKGGLEGLIYSQKRQDILDLWVYHTQGYFPDW
QNYTPGPGIRYPLTFGWCFKLVPVE >nef_coreB.syn3.1
EVGFPVKPQVPLRPMTYKAAVDLSHFLKEKGGLEGLVYSQKRQDILDLWIYHTQGYFPDW
QNYTPGPGTRFPLTFGWCFKLVPVD
>nef_coreB.syn3.2
EVGFPVTPQVPLRPMTYKGALDLSHFLREKGGLEGLIYSQKRQEILDLWVYHTQGYFPDW
HNYTPGPGVRYPLTFGWCFKLVPVE
>nef_coreB.syn3.3
EVGFPVRPQVPLRPMTYKAALDLSHFLKEKGGLEGLIHSQRRQDILDLWVYHTQGFFPDW
QNYTPGPGIRYPLTFGWCYKLVPVE >nef_coreB.syn4.1
EVGFPVTPQVPLRPMTYKAAVDLSHFLREKGGLEGLIHSQKRQDILDLWIYHTQGYFPDW
QNYTPGPGIRYPLTFGWCYKLVPVE
>nef_coreB.syn4.2
DVGFPVRPQIPLRPMTYKAALDLSHFLREKGGLEGLVYSQKRQDILDLWVYHTQGFFPDW
QNYTPGPGTRFPLTFGWCFKLVPVD
>nef_coreB.syn4.3
EVGFPVRPQVPLRPMTYKGAVDLSHFLKEKGGLEGLIYSQKRQEILDLWVYHTQGYFPDW
GNYTPGPGTRYPLTFGWCLKLVPVE
>nef_coreB.syn4.4
EVGFPVKPQVPLRPMTYKGALDLSHFLKEKGGLDGLIYSQRRQDILDLWVYNTQGYFPDW
HNYTPGPGVRYPLTFGWCFKLVPVE >nef_coreB.syn6.1
EVGFPIRPQVPLRPMTFKGALDLSHFLKEKGGLDGLIYSQKRQEILDLWVYHTQGYFPDW
HNYTPGPGIRYPLCFGWCFKLVPVE
>nef_coreB.syn6.2
EVGFPVTPQVPLRPMTYKGAVDLSHFLKEQGGLEGLIYSQRRQDILDLWIYNTQGYFPDW
QCYTPGPGVRFPLTFGWCFKLEPVD
>nef_coreB.syn6.3
EVGFPVKPQVPLRPMTYKAAVDLSHFLKEKGGLEGLIYSQKRQDILDLWIYHTQGYFPDW
QNYTPGPGIRYPLTFGWCLKLVPVE
>nef_coreB.syn6.4
DVGFPVRPQVPLRPMTYKAALDLSHFLKEEGGLEGLIYSQQRQDILDLWVYHTQGFFPDW
QNYTPGPGTRYPLTFGWCYKLVPVE
>nef_coreB.syn6.5
EVGFPVRPQIPLRPMTYKGALDLSHFLREKGGLEGLVYSQKRQDILDLWVHHTQGYFPDW
GNYTPGPGTRFPLTFGWCFKLVPVD
>nef_coreB.syn6.6
EVGFPVRPQVPLRPMTYKGAFDLSHFLKDKGGLEGLIHSQKRQDILDLWVYNTQGYFPDW
QNYTPGPGVRYPLTFGWCFKLVPLE >nef_coreC.syn1.1
EVGFPVRPQVPLRPMTYKAAFDLSFFLKEKGGLEGLIYSKKRQEILDLWVYHTQGFFPDW
QNYTPGPGVRYPLTFGWCFKLVPVD

Fig. 9 cont'd-1

```
>nef_coreC.syn3.1
EVGFPVTPQVPLRPMTFKGAFDLGFFLKEKGGLDGLIYSKKRQDILDLWVYHTQGYFPDW
QNYTPGPGVRYPLTFGWCYKLVPVD
>nef_coreC.syn3.2
EVGFPVKPQVPLRPMTYKAAFDLSFFLKDKGGLEGLIWSKKRQEILDLWVYHTQGFFPDW
QNYTPGPGIRYPLTFGWPFKLVPVD
>nef_coreC.syn3.3
EVGFPVRPQVPLRPMTYKGAFDLSFFLKEKGGLEGLIYSKKRQEILDLWVYNTQGFFPDW
HNYTPGPGVRFPLTFGWCFKLVPVD >nef_coreC.syn4.1
EVGFPVRPQVPLRPMTYKGAFDLSFFLKEKGGLEGLIWSKKRQEILDLWVYNTQGYFPDW
QCYTPGPGVRFPLTFGWCFKLVPVD
>nef_coreC.syn4.2
DVGFPVRPQVPVRPMTYKAAFDLSFFLKDKGGLEGLIHSKRRQDILDLWVYNTQGFFPDW
HNYTPGPGIRYPLTFGWCFKLVPVD
>nef_coreC.syn4.3
EVGFPVKPQVPLRPMTYKAAVDLSFFLKEKGGLEGLIYSKKRQEILDLWVYHTQGFFPDW
QNYTPGPGTRYPLTFGWPFKLVPVD
>nef_coreC.syn4.4
EVGFPVTPQVPLRPMTFKGAFDLGFFLKEKGGLDGLIYSKKRQDILDLWVYHTQGYFPDW
QNYTPGPGVRYPLTFGWCYKLVPVD >nef_coreC.syn6.1
DVGFPVRPQVPLRPMTYKGAFDLSFFLKEKGGLDGLIYSKKRQEILDLWVYNTQGYFPDW
QCYTPGPGVRYPLTFGWCYKLVPVD
>nef_coreC.syn6.2
EVGFPVKPQVPVRPMTYKAAFDLSFFLKDKGGLEGLIWSKKRQEILDLWVYHTQGFFPDW
QNYTPGPGIRYPLTFGWCFKLVPVD
>nef_coreC.syn6.3
EVGFPVKPQVPLRPMTFKGAFDLGFFLKEKGGLEGLIYSKQRQDILDLWVYHTQGFFPDW
HNYTPGPGVRLPLTFGWCFKLVPVD
>nef_coreC.syn6.4
GVGFPVRPQVPVRPMTYKAAFDLGFFLKDKGGLEGLIYSKKRQDILDLWVYNTQGFFPDW
QNYTPGPGVRFPLTFGWCFKLVPVD
>nef_coreC.syn6.5
EVGFPVTPQVPLRPMTYKAAVDLSWFLKEKGGLDGLIYSRKRQEILDLWVHHTQGFFPDW
QNYTPGPGTRFPLTFGWCFKLVPVD
>nef_coreC.syn6.6
EVGFPVRPQVPVRPMTYKGAVDLSFFLKEKGGLEGLIHSKRRQDILDLWVYHTQGYFPDW
QNYTPGPGTRYPLTFGWPFKLVPVD >nef_coreM.syn1.1
EVGFPVRPQVPLRPMTYKGALDLSHFLKEKGGLEGLIYSKKRQEILDLWVYHTQGYFPDW
QNYTPGPGVRYPLTFGWCFKLVPVD
```

Fig. 9 cont'd-2

```
>nef_coreM.syn3.1
DVGFPVRPQVPLRPMTYKAAVDLSHFLKEKGGLEGLVYSQKRQDILDLWVYHTQGFFPDW
QNYTPGPGVRYPLTFGWCYKLVPVD
>nef_coreM.syn3.2
EVGFPVRPQVPVRPMTYKGAFDLSFFLKEKGGLEGLIYSKKRQEILDLWVYHTQGYFPDW
HNYTPGPGTRFPLTFGWCFKLVPVD
>nef_coreM.syn3.3
EVGFPVKPQVPLRPMTYKGALDLSHFLKEKGGLDGLIYSKKRQDILDLWVYNTQGYFPDW
QNYTPGPGIRYPLTFGWCFKLVPVE >nef_coreM.syn4.1
EVGFPVTPQVPLRPMTFKGAFDLGFFLKEKGGLEGLIYSKKRQEILDLWVYHTQGFFPDW
QNYTPGPGTRYPLCFGWCFKLVPVE
>nef_coreM.syn4.2
EVGFPVKPQVPLRPMTYKAAVDLSHFLKEKGGLEGLVYSQKRQDILDLWVYHTQGYFPDW
QNYTPGPGIRYPLTFGWCYKLVPVD
>nef_coreM.syn4.3

DVGFPVRPQVPLRPMTYKGALDLSHFLKEEGGLEGLIYSQKRQEILDLWVYNTQGYFPDW
QNYTPGPGVRYPLTFGWCFKLVPVD
>nef_coreM.syn4.4
EVGFPVRPQVPVRPMTYKGAFDLSFFLKEKGGLDGLIYSKKRQDILDLWVYNTQGFFPDW
HNYTPGPGTRFPLTFGWCFELVPVD >nef_coreM.syn6.1
EVGFPVRPQVPTRPMTYKGAVDLSHFLKEKGGLEGLVYSQKRQDILDLWVHHTQGFFPDW
QNYTPGPGTRYPLTFGWPFKLVPVD
>nef_coreM.syn6.2
DVGFPVRPQVPVRPMTYKAAFDLSFFLREKGGLDGLIYSKKRQDILDLWVYNTQGYFPDW
QNYTPGPGVRFPLTFGWCFELVPVD
>nef_coreM.syn6.3
NVGFPVRPQVPLRPMTFKGAFDLGFFLKEKGGLEGLIYSKKRQEILDLWVYHTQGYFPDW
HNYTPGPGTRFPLTFGWCFKLVPVE
>nef_coreM.syn6.4
EVGFPVTPQVPLRPMTYKGAFDLSFFLKEKGGLDGLIYSRKRQEILDLWVYNTQGFFPDW
QNYTPGPGIRYPLTFGWCFKLVPMD
>nef_coreM.syn6.5
EVGFPVKPQVPLRPMTYKAAVDLSHFLREKGGLEGLIHSQRRQDILDLWIYHTQGYFPDW
QCYTPGPGVRYPLTFGWCYKLVPVD
>nef_coreM.syn6.6
GVGFPVRPQIPLRPMTYKGALDLSHFLKEEGGLEGLIYSQKRQDILDLWVYHTQGFFPDW
HNYTPGPGIRYPLCFGWCFKLVPVD
```

Fig. 9 cont'd-3

>gagB.syn1.1
MGARASVLSGGELDRWEKIRLRPGGKKKYKLKHIVWASRELERFAVNPGLLETSEGCRQI
LGQLQPSLQTGSEELRSLYNTVATLYCVHQRIEVKDTKEALDKIEEEQNKSKKKAQQAAA
DTGNSSQVSQNYPIVQNLQGQMVHQAISPRTLNAWVKVVEEKAFSPEVIPMFSALSEGAT
PQDLNTMLNTVGGHQAAMQMLKETINEEAAEWDRLHPVHAGPIAPGQMREPRGSDIAGTT
STLQEQIGWMTNNPPIPVGEIYKRWIILGLNKIVRMYSPTSILDIRQGPKEPFRDYVDRF
YKTLRAEQASQEVKNWMTETLLVQNANPDCKTILKALGPAATLEEMMTACQGVGGPGHKA
RVLAEAMSQVTNSATIMMQRGNFRNQRKTVKCFNCGKEGHIAKNCRAPRKKGCWKCGKEG
HQMKDC-TERQANFLGKIWPSHKG-RPGNFLQSRP------------------EPTAP
PEESFRFGEETTTPSQKQEPIDKELYPLASLRSLFGNDPSSQ >gagB.syn3.1
MGARASILSGGELDRWEKIRLRPGGKKQYRLKHIVWASRELERFAINPGLLETSDGCRQI
LGQLQPALQTGSEELKSLFNTVATLYCVHQRIDVKDTKEALDKIEEEQNKSKKKAQQAAA
DTGNSSQVSQNYPIVQNIQGQMVHQAISPRTLNAWVKVIEEKAFSPEVIPMFSALSEGAT
PQDLNTMLNTVGGHQAAMQMLKETINEEAADWDRLHPVHAGPIAPGQMREPRGSDIAGTT
STLQEQIGWMTNNPPIPVGEIYKRWIIMGLNKIVRMYSPSSILDIKQGPKEPFRDYVDRF
YKVLRAEQASQEVKNWMTETLLVQNSNPDCKTILKALGPGATLEEMMTACQGVGGPGHKA
RVLAEAMSQMTNSATIMMQKGNFRNQRKPVKCFNCGKEGHIAKNCRAPRKKGCWKCGREG
HQMKDC-TERQANFLGKIWPSYKG-RPGNFLQNRP------------------EPTAP
PAESFRFGEETTTPSQKQETIDKELYPLASLRSLFGSDPSSQ >gagB.syn3.2
MGARASVLSGGQLDRWEKIRLRPGGKKKYRLKHLVWASRELERFAVNPGLLETAEGCRQI
LEQLQPSLQTGSEELRSLFNTVAVLYCVHQRIEVKDTKEALDKVEEEQNKSKKKAQQTAA
DTGNNSQVSQNYPIVQNMQGQMVHQALSPRTLNAWVKVIEEKAFSPEVIPMFTALSEGAT
PQDLNTMLNTVGGHQAAMQMLKDTINEEAAEWDRLHPVQAGPVAPGQIREPRGSDIAGST
STLQEQIGWMTSNPPIPVGEIYKRWIILGLNKIVRMYSPVSILDIRQGPKEPFRDYVDRF
YKTLRAEQATQEVKNWMTETLLVQNANPDCKTILKALGPGATLEEMMTACQGVGGPSHKA
RVLAEAMSQVTNSATIMMQRGNFRNQRKIVKCFNCGKEGHIARNCRAPRKRGCWKCGKEG
HQMKDC-NERQANFLGKIWPSHKG-RPGNFLQSRP------------------EPSAP
PEESFRFGEEKTTPSQKQEPIDKDLYPLASLKSLFGNDPSLQ >gagB.syn3.3
MGARASVLSGGELDKWEKIRLRPGGKKKYKLKHIVWASRELERFAVNPGLLETSEGCRQI
LGQLQPSLQTGSEELRSLYNTVATLYCVHQKIEVKDTKEALEKIEEEQNKCKKKAQQAAA
GTGNSSQVSQNYPIVQNLQGQMVHQPISPRTLNAWVKVVEEKAFSPEVIPMFSALAEGAT
PQDLNTMLNTVGGHQAAMQMLKETINEEAAEWDRLHPVHAGPVAPGQMRDPRGSDIAGTT
SNLQEQIGWMTHNPPIPVGDIYKRWIILGLNKIVRMYSPTSILDIRQGPKESFRDYVDRF
YKTLRAEQASQDVKNWMTETLLVQNANPDCRTILKALGPAATLEEMMTACQGVGGPSHKA
RILAEAMSQVTNPATIMMQRGNFRNQRKTVKCFNCGKEGHLARNCRAPRKKGCWKCGKEG
HQMKEC-TERQANFLGKIWPSHKG-RPGNFLQSRP------------------EPTAP
PEESFRFGEETATPPQKQEPIDKELYPLTSLRSLFGNDPSSQ >gagB.syn4.1
MGARASVLSGGQLDRWEKIRLRPGGKKKYRLKHLVWASRELERFAVNPGLLETAEGCRQI
LEQLQPSLQTGSEELRSLFNTVATLYCVHQRIDVKDTKEALDKIEEEQNKCKKKAQQAAA
DTGNSSQVSQNYPIVQNIQGQMVHQALSPRTLNAWVKVVEEKAFSPEVIPMFTALSEGAT
PQDLNTMLNTVGGHQAAMQMLKETINEEAAEWDRLHPVQAGPVAPGQMREPRGSDIAGST
STLQEQIGWMTNNPPIPVGDIYKRWIILGLNKIVRMYSPVSILDIRQGPKESFRDYVDRF
YKVLRAEQASQEVKNWMTETLLVQNANPDCRTILKALGPAATLEEMMTACQGVGGPGHKA

Fig. 9 cont'd-4

```
RVLAEAMSQMTNSATIMMQRGNFRNQRKTVKCFNCGKEGHIAKNCRAPRKKGCWKCGKEG
HQMKEC-TERQANFLGKIWPSYKG-RPGNFLQSRP-------------------EPSAP
PAESFRFGEETTTPSQKQETIDKELYPLTSLRSLFGNDPSLQ
>gagB.syn4.2
MGARASVLSGGELDKWEKIRLRPGGKKKYKLKHIVWASRELERFAINPGLLETSEGCRQI
LGQLQPALQTGSEELRSLYNTVATLYCVHQKIEVKDTKEALEKVEEEQNKSKQKAQQAAA
DTGNNSQVSQNYPIVQNLQGQMVHQAISPRTLNAWVKVIEEKAFSPEVIPMFAALSEGAT
PQDLNTMLNTVGGHQAAMQMLKETINEEAADWDRLHPVHAGPIAPGQIREPRGSDIAGTT
SNLQEQIAWMTNNPPIPVGEIYKRWIIMGLNKIVRMYSPTSILDIKQGPKEPFRDYVDRF
YRTLRAEQASQDVKNWMTETLLVQNANPDCRTILKALGPGATLEEMMTACQGVGGPSHKA
RVLAEAMSQVTNPATIMMQRGNFRNQRKPVKCFNCGKEGHLAKNCRAPRKRGCWKCGKEG
HQMKDC-NERQANFLGKIWPSHKG-RPGNFLQNRP-------------------EPSAP
PEESFRFGEETATPSQKQEPIDKELYPLASLRSLFGSDPSSQ
>gagB.syn4.3
MGARASILSGGELDRWEKIRLRPGGKKQYRLKHIVWASRELERFAVNPGLLETSEGCKQI
LEQLQPALQTGSEELKSLYNTVAVLYCVHQRIEIKDTKEALEKIEEEQNKSKKKAQQTAA
DTGNNSQVSQNYPIVQNLQGQMVHQPISPRTLNAWVKVIEEKAFSPEVIPMFSALAEGAT
PQDLNTMLNTVGGHQAAMQMLKETINEEAAEWDRLHPVHAGPVAPGQMRDPRGSDIAGTT
SNLQEQIGWMTSNPPIPVGEIYKRWIILGLNKIVRMYSPTSILDIRQGPKEPFRDYVDRF
YKTLRAEQATQEVKNWMTETLLVQNANPDCKTILKALGPGATLEEMMTACQGVGGPSHKA
RILAEAMSQVTNSATVMMQRGNFRNQRKTIKCFNCGKEGHLARNCRAPRKKGCWKCGREG
HQMKDC-TERQANFLGKIWPSYKG-RPGNFLQNRP-------------------EPTAP
PAESFRFGEETTTPPQKQEPIDKELYPLASLKSLFGNDPSSQ
>gagB.syn4.4
MGARASVLSGGKLDKWEKIRLRPGGKKKYQLKHIVWASRELERFALNPGLLETSDGCRQI
LGQLQPSLQTGSEELKSLFNTVAVLYCVHQRIEVKDTKEALDKVEEEQNKSKKKAQQAAA
GTGNSSQVSQNYPIVQNMQGQMVHQALSPRTLNAWVKVIEEKAFSPEVIPMFSALSEGAT
PQDLNTMLNTVGGHQAAMQMLKDTINEEAAEWDRVHPVHAGPIAPGQMREPRGSDIAGTT
STLQEQIGWMTHNPPIPVGEIYKRWIILGLNKIVRMYSPSSILDIRQGPKEPFRDYVDRF
YKTLRAEQASQEVKNWMTETLLVQNSNPDCKTILKALGPAATLEEMMTACQGVGGPSHKA
RVLAEAMSQVTNSATIMMQKGNFRNQRKIVKCFNCGKEGHIARNCRAPRKKGCWRCGKEG
HQMKDC-TERQVNFLGKIWPSYKG-RPGNFLQSRP-------------------EPTAP
PEESFRFGEEKTTPSQKQEPIDKDLYPLASLKSLFGNDPLSQ >gagB.syn6.1
MGARASILSGGELDRWEKIRLRPGGSKKYRLKHIVWASRELERFAVNPGLLETAEGCRQI
LGQLQPSLQTGSEELRSLYNTIATLYCVHQRIEIKDTKEALEKIEEEQNKSKKKAQQTAA
DTGNNSQVSQNYPIVQNLQGQMVHQPISPRTLNAWVKVVEEKAFSPEVIPMFSALAEGAT
PQDLNTMLNTVGGHQAAMQMLKETINEEAAEWDRLHPVHAGPVAPGQIREPRGSDIAGTT
SNLQEQIGWMTSNPPIPVGEIYKRWIILGLNKIVRMYSPISILDIRQGPKEPFRDYVDRF
YRTLRAEQASQDVKNWMTETLLVQNANPDCKTILKALGPGATLEEMMTACQGVGGPGHKA
RVLAEAMSQVTNSATVMMQRGNFRNQRRTVKCFNCGKEGHIARNCRAPRKKGCWKCGQEG
HQMKDC-TERQANFLGKIWPSYKG-RPGNFLQSRP-------------------EPTAP
PAESFRFGEETTTPPQKQEPIDKELYPLTSLKSLFGNDPSSQ
>gagB.syn6.2
MGARASVLSGGKLDRWEKIRLRPGGKKKYRLKHVVWASRELERFAVNPGLLESSEGCRQI
LEQLQPSLQTGSEELRSLFNTVATLYCVHQRIDVKDTKEALDKIEEEQNKCKKKAQQAAA
DTGNNSQVSQNYPIVQNLQGQMVHQPISPRTLNAWVKVVEEKAFSPEVIPMFAALSEGAT
PQDLNTMLNTVGGHQAAMQMLKETINEEAAEWDRVHPVHAGPIAPGQMREPRGSDIAGST
STLQEQIGWMTNNPPIPVGDIYKRWIILGLNKIVRMYSPASILDIRQGPKEPFRDYVDRF
YKTLRAEQATQEVKNWMTETLLVQNANPDCRTILKALGPGATLEEMMTACQGVGGPGHKA
RVLAEAMSQMTNSATIMMQKGNFRNQRKTIKCFNCGKEGHIARNCKAPRKKGCWKCGREG
HQMKDC-IERQANFLGKIWPSHKG-RPGNFLQNRP-------------------EPTAP
PEESFRFGEETATPPQKQEPIDKELYPLASLKSLFGSDPSSQ
```

Fig. 9 cont'd-5

>gagB.syn6.3
MGARASVLSGGELDRWEKIRLRPGGKKKYRLKHLVWASRELERFAVNPGLLETSDGCRQI
LGQLQPALQTGSEELKSLYNTVATLYCVHQKIDVRDTKEALDKIEEEQNKSKQKAQQAAA
DTGNSSQVSQNYPIVQNIQGQMVHQAISPRTLNAWVKVVEEKAFSPEVIPMFTALSEGAT
PQDLNTMLNTVGGHQAAMQMLKETINEEAAEWDRLHPVQAGPVAPGQMREPRGSDIAGTT
STLQEQIGWMTHNPPIPVGEIYKRWIIMGLNKIVRMYSPSSILDIRQGPKESFRDYVDRF
YKVLRAEQASQEVKNWMTETLLVQNANPDCKTILKALGPGATLEEMMTACQGVGGPSHKA
RVLAEAMSQVTNSATIMMQRGNFRNQRKTVKCFNCGKEGHIAKNCRAPRKRGCWKCGKEG
HQMKEC-TERQANFLGKIWPSHKG-RPGNFLQSRP-------------------EPTAP
PEESFRFGEEKTTPSQKQETIDKELYPLASLRSLFGNDPSSQ
>gagB.syn6.4
MGARASVLSGGELDKWEKIRLRPGGKKKYQLKHIVWASRELERFAVNPGLLETSEGCKQI
LEQLQPALQTGSEELRSLYNTIAVLYCVHQKIEIKDTKEALDKVEEEQNKSKKKAQQAAA
GTGNSSQVSQNYPIVQNLQGQMVHQPLSPRTLNAWVKVVEEKAFSPEVIPMFTALSEGAT
PQDLNTMLNTVGGHQAAMQMLKETINEEAADWDRLHPVHAGPIAPGQMREPRGSDIAGST
STLQEQIGWMTHNPPIPVGDIYKRWIILGLNKIVRMYSPTSILDIKQGPKEPFRDYVDRF
YKTLRAEQATQEVKNWMTETLLVQNANPDCRTILKALGPAATLEEMMTACQGVGGPSHKA
RILAEAMSQVTNPATIMMQRGNFRNQRKPVKCFNCGKEGHIARNCRAPRKRGCWKCGKEG
HQMKDC-TERQVNFLGKIWPSHKG-RPGNFLQNRP-------------------EPSAP
PAESFRFGEETTTPSQKQEPIDKEMYPLASLRSLFGSDPSSQ
>gagB.syn6.5
MGARASVLSGGQLDRWEKIRLRPGGKKQYRLKHIVWASRELERFAINPGLLETSEGCRQI
LGQLQPSLQTGSEELKSLFNTVAVLYCVHQRIEVKDTKEALEKVEEEQNKSKKKAQQAAA
DTGNSSQVSQNYPIVQNLQGQMVHQALSPRTLNAWVKVIEEKAFSPEVIPMFSALSEGAT
PQDLNTMLNTVGGHQAAMQMLKDTINEEAAEWDRLHPVHAGPVAPGQMRDPRGSDIAGTT
STLQEQIAWMTNNPPIPVGEIYKRWIILGLNKIVRMYSPTSILDIRQGPKEPFRDYVDRF
YKVLRAEQASQDVKNWMTETLLVQNANPDCKTILKALGPAATLEEMMTACQGVGGPGHKA
RVLAEAMSQVTNSTTIMMQRGNFRNQRKIVKCFNCGKEGHLAKNCRAPRKKGCWKCGKEG
HQMKEC-TERQANFLGKIWPSHKG-RPGNFLQSRP-------------------EPSAP
PEESFRFGEETATPSQKQEPIDKDLYPLASLKSLFGNDPLSQ
>gagB.syn6.6
MGARASVLSGGKLDKWEKIRLRPGGKKKYKLKHIVWASRELERFALNPGLLETSEGCRQI
LRQLQPSLQTGSEELRSLYNTVATLYCVHQKIEVKDTKEALEKIEEEQNKSKKKAQQTAA
DTGNNSQVSQNYPIVQNMQGQMVHQALSPRTLNAWVKVVEEKAFSPEVIPMFSALSEGAT
PQDLNTMLNTVGGHQAAMQMLKDTINEEAAEWDRLHPAQAGPIAPGQIREPRGSDIAGTT
SNLQEQIAWMTHNPPIPVGDIYKRWIILGLNKIVRMYSPVSILDIRQGPKEPFRDYVDRF
YKTLRAEQASQEVKNWMTETLLVQNSNPDCKTILKALGPGATLEEMMTACQGVGGPGHKA
RVLAEAMSQVTNPATIMMQKGNFKNQRKTVKCFNCGKEGHLARNCRAPRKKGCWRCGKEG
HQMKDC-NERQANFLGKIWPSHKG-RPGNFLQSRP-------------------EPTAP
PEESFRFGEETTTPAQKQEPIDKELYPLTSLRSLFGNDPSLQ
>gagC.syn1.1
MGARASILRGGKLDKWEKIRLRPGGKKHYMLKHLVWASRELERFALNPGLLETSEGCKQI
IKQLQPALQTGTEELRSLYNTVATLYCVHEKIEVRDTKEALDKIEEEQNKSQQKTQQAKA
ADG---KVSQNYPIVQNLQGQMVHQAISPRTLNAWVKVIEEKAFSPEVIPMFTALSEGAT
PQDLNTMLNTVGGHQAAMQMLKDTINEEAAEWDRLHPVHAGPIAPGQMREPRGSDIAGTT
STLQEQIAWMTSNPPIPVGDIYKRWIILGLNKIVRMYSPVSILDKGPKEPFRDYVDRF
FKTLRAEQATQDVKNWMTDTLLVQNANPDCKTILRALGPGATLEEMMTACQGVGGPSHKA
RVLAEAMSQ-ANNTNIMMQRSNFKGSKRIVKCFNCGKEGHIARNCRAPRKKGCWKCGKEG
HQMKDC-TERQANFLGKIWPSHKG-RPGNFLQSRPE------PTAPPA-------EPTAP
PAESFRFEE--TTPAPKQEPKDRE--PLTSLKSLFGSDPLSQ
>gagC.syn3.1
MGARASVLRGEKLDKWERIRLRPGGKKHYMLKHLVWASRELERFALNPSLLETSEGCKQI
IQQLQPALKTGTEELRSLFNTVATLYCVHAGIEVRDTKEALDKIEEEQNCQQKTQQAKE
ADG---KVSQNYPIVQNLQGQMVHQALSPRTLNAWVKVIEEKAFSPEVIPMFTALSEGAT

Fig. 9 cont'd-6

```
PSDLNTMLNTVGGHQAAMQMLKDTINEEAAEWDRLHPVQAGPVAPGQMREPRGSDIAGTT
SNLQEQIAWMTGNPPVPVGDIYKRWIILGLNKIVRMYSPVSILDIRQGPKEPFRDYVDRF
FKTLRAEQSTQEVKNWMTETLLVQNANPDCKTILRALGPAASLEEMMTACQGVGGPSHKA
RVLAEAMSQ-ANSTNIMMQRGNFKGPKRIIKCFNCGKEGHLARNCRAPRKKGCWKCGKEG
HQMKDC-IERQANFLGKIWPSNKG-RPGNFLQNRPE-----PTAPPVEPTAPPAEPTAP
PAESFKFEE--TTPAPKQEPKDRE--PLTSLRSLFGSDPLSQ
>gagC.syn3.2
MGARASILRGEKLDTWEKIRLRPGGRKHYMLKHIVWASRELEKFALNPGLLETSEGCKQI
MKQLQPALQTGTEELKSLYNTVATLYCVHEKIEVRDTKEAVDKIEEEQNKSQQKTQQAKA
ADE---KVSQNYPIVQNIQGQMVHQPISPRTLNAWVKVIEEKGFNPEVIPMFTALSEGAT
PQDLNTMLNTVGGHQAAMQMLKDTINDEAAEWDRLHPVHAGPIAPGQMREPRGSDIAGST
STLQEQITWMTSNPPVPVGEIYKRWIILGLNKIVRMYSPVSILDIKQGPKEPFRDYVDRF
FKVLRAEQATQDVKNWMTDTLLIQNANPDCKTILKALGPGASLEEMMTACQGVGGPGHKA
RVLAEAMSQ-ANNTNIMMQRSNFKGPKRIVKCFNCGKEGHIAKNCRAPRKKGCWKCGQEG
HQMKDC-TERQANFLGKIWPSQKG-RPGNFLQNRP------------------EPSAP
PAESFRFGE--TTPAPKQELKDRE--PLTSLKSLFGSDPLSQ
>gagC.syn3.3
MGARASILRGGKLDKWEKIRLRPGGKKRYMLKHLIWASRELERFALNPGLLETAEGCKQI
IKQLQPALQTGTEELRSLYNTVATLYCVHKRIDVRDTKEALDKIEEEQNKIQQKTQQAKA
ADG---KVSQNYPIVQNAQGQMVHQAISPRTLNAWVKVVEEKAFSPEIIPMFTALSEGAT
PQDLNSMLNAVGGHQAAMQMLKDTINEEAAEWDRVHPVHAGPVAPGQIREPRGSDIAGTT
STLQEQIAWMTSNPPIPVGDIYKRWIIMGLNKIVRMYSPVSILDIKQGPKESFRDYVDRF
FKTLRAEQATQEVKNWMTDTLLVQNANPDCKTILRALGPATLEEMMTACQGVGGPSHKA
RVLAEAMSQ-TNSA-ILMQRSNFKGSKRIVKCFNCGKEGHIARNCRAPRKRGCWKCGKEG
HQMKEC-TERQANFLGKIWPSHKG-RPGNFLQSRP------------------EPTAP
PAESFRFEE--TTPAPKQESKDRE--PLISLKSLFGNDPLSQ >gagC.syn4.1
MGARASVLRGEKLDTWERIKLRPGGKKHYMIKHLVWASRELEKFALNPGLLETSEGCKQI
IQQLQPALKTGTEEELKSLYNTVATLYCVHERIDVRDTKEALDKIEEEQNKIQQKTQQAKE
ADG---KVSQNYPIVQNAQGQMVHQALSPRTLNAWVKVVEEKAFSPEIIPMFTALSEGAT
PSDLNTMLNTIGGHQAAMQMLKDTINDEAAEWDRLHPVHAGPIAPGQIREPRGSDIAGTT
STLQEQITWMTSNPPVPVGEIYKRWIILGLNKIVRMYSPVSILDIKQGPKESFRDYVDRF
FKTLRAEQSTQEVKNWMTETLLVQNANPDCKTILKALGPGATLEEMMTACQGVGGPGHKA
RVLAEAMSQ-TNSA-ILMQRSNFKGSKRIVKCFNCGREGHIARNCKAPRKKGCWKCGKEG
HQMKDC-IERQANFLGKIWPSHKG-RPGNFLQNRPE------PTAPP--------EPTAP
PAESFRFGE--TTPAPKQEQKDRE--PLISLKSLFGSDPLLQ
>gagC.syn4.2
MGARASILRGEKLDKWERIRLRPGGKKHYMLKHLVWASRELDRFALNPGLLETSDGCKQI
IKQLHPALQTGTEELRSLFNTVATLYCVHAGIEVRDTKEAVDKIEEEQNKSQQKTQQAKA
ADE---KVSQNYPIVQNIQGQMVHQPISPRTLNAWVKVIEEKAFSPEVIPMFTALSDGAT
PQDLNTMLNTVGGHQAAMQMLKDTINEEAAEWDRIHPVHAGPVAPGQMRDPRGSDIAGST
STLQEQIAWMTNNPPVPVGDIYKRWIIMGLNKIVRMYSPVSILDIRQGPKEPFRDYVDRF
FRTLRAEQATQDVKNWMTDTLLIQNANPDCKTILRALGPGASLEEMMTACQGVGGPGHKA
RVLAEAMSQ-ANNTNIMMQKSNFKGPKRTVKCFNCGKEGHIARNCRAPRKRGCWKCGKEG
HQMKEC-TERQANFLGKIWPSQKG-RPGNFLQSRP------------------EPSAP
PAESFRFEE--TTPAPKQESKDRE--PLTSLKSLFGSDPSSQ
>gagC.syn4.3
MGARASILRGGKLDTWEKIRLRPGGKKRYMLKHLIWASRELERFALNPSLLETSEGCKQI
MKQLQPALQTGTEELRSLYNTVATLYCVHKGIKVQDTKEALDKIEEEQKKSQQKTQQAEA
ADK--GKVSQNYPIVQNLQGQMVHQPLSPRTLNAWVKVIERKAFSPEVIPMFSALSEGAT
PQDLNSMLNAVGGHQAAMQMLKDTINEEAAEWDRVHPVHAGPIAPGQMREPRGSDIAGTT
SNLQEQIAWMTSNPPIPVGDIYKRWIVLGLNKIVRMYSPVSILDIKQGPKEPFRDYVDRF
FKTLRAEQATQEVKNWMTDTLLVQNANPDCKTILRALGPAASLEEMMTACQGVGGPGHKA
```

Fig. 9 cont'd-7

```
RVLAEAMSQ-ANS-NIMMQRGNFKGPKRIIKCFNCGKEGHLARNCRAPRKKGCWKCGREG
HQMKDC-TERQANFLGKIWPSNKG-RPGNFLQSRP------------------EPTAP
PAESFGFGE--TTPAPKQELKDRE--PLTSLKSLFGNDPLSQ
>gagC.syn4.4
MGARASILRGGKLDKWEKIRLRPGGRKHYMLKHIVWASRELERFALNPGLLETAEGCKQI
IKQLQPALQTGTEELKSLFNTVATLYCVHEKIEVRDTKEALDKIEEEQNKCQQKTQQAKA
ADG---KVSQNYPIVQNLQGQMVHQAISPRTLNAWVKVIEEKGFNPEVIPMFTALSEGAA
PQDLNTMLNTIGGHQAAMQMLKDTINEEAAEWDRLHPVQAGPVAPGQMREPRGSDIAGTT
SSLQEQIAWMTGNPPVPVGDIYKRWIILGLNKIVRMYSPVSILDIRQGPKEPFRDYVDRF
FKVLRAEQATQDVKNWMTETLLVQNANPDCKTILRALGPGATLEEMMTACQGVGGPSHKA
RVLAEAMSQ-ANNANIMMQRSNFKGPKRIVKCFNCGKEGHIAKNCRAPRKKGCWKCGQEG
HQMKDC-NERQANFLGRIWPSHKG-RPGNFIQSRPEPTAPLEPTAPPA-------EPTAP
PAESFKFEE--TTPAPKQEPKDRE--PLTSLRSLFGSDPLSQ >gagC.syn6.1
MGARASVLRGEKLDTWERIKLRPGGKKHYMIKHLVWASRELEKFALNPGLLETAEGCKQI
IRQLQPALQTGTEELRSLYNTVATLYCVHKRIDVRDTKEALDKIEEEQNSQQKAQQAKA
ADG---KVSQNYPIVQNLQGQMVHQSLSPRTLNAWVKVIERKAFSPEVIPMFSALSEGAT
PQDLNTMLNTVGGHQAAMQMLKDTINEEAAEWDRIHPVHAGPIAPGQMREPRGSDIAGTT
STLQEQITWMTSNPPVPVGEIYKRWIILGLNKIVRMYSPVSILDIRQGPKEPFRDYVDRF
FKTLRAEQSTQEVKNWMTDTLLAQNANPDCKIILRGLGPGATLEEMMTACQGVGGPGHKA
RVLAEAMSQ-ANS-NILMQRSNFKGPRRTIKCFNCGKEGHLAKNCRAPRKKGCWKCGKEG
HQMKEC-TERQANFLGKIWPSQKG-RPGNFLQSRP------------------EPSAP
PAESFRFEE--TTPALKQEPKDRE--PLTSLRSLFGSDPLSQ
>gagC.syn6.2
MGASASILRGEKLDRWEKIRLRPGGKKCYMLKHIIWASKELERFALNPGLLETSEGCKQI
MKQLQPALQTGTEELKSLYNTVATLYCVHEKIEVRDTKEALDKIEEEQKKSQQKTQQAEA
ADK--GKVSQNYPIVQNAQGQMVHQALSPRTLNAWVKVVEEKAFSPEIIPMFTALSEGAA
PQDLNTMLNTVGGHQAAMQMLKDTINEEAAEWDRVHPVHAGPIAPGQIREPRGSDIAGTT
STLQEQVAWMTSNPPVPVGDIYKRWIVLGLNKIVRMYSPVSILDIKQGPKEPFRDYVDRF
FKTLRAEQSSQEVKNWMTDTLLVQNANPDCKTILRALGPAASLEEMMTACQGVGGPSHKA
RVLAEAMSQ-ANSTNIMMQRGNFKGPKRIVKCFNCGREGHIARNCRAPRKKGCWKCGQEG
HQMKDC-IERQANFLGKIWPSHKG-RPGNFIQSRPE------PTAPP--------EPTAP
PAESFRFGE--TTPAPKQESKDRE--PLTSLKSLFGNDPLSQ
>gagC.syn6.3
MGARASVLKGEKLDKWERIRLRPGGKKQYRLKHLVWASRELERFALNPSLLETSEGCRQI
IKQLQPALKTGTEELRSLYNTIATLYCVHKGIKVQDTKEALDKVEEEQNKSQQKTQQAKA
ADE---KVSQNYPIVQNLQGQMVHQPLSPRTLNAWVKVIEEKGFNPEVIPMFTALSEGAT
PQDLNSMLNAVGGHQAAMQMLKDTINEEAAEWDRLHPVQAGPVAPGQIREPRGSDIAGTT
SSLQEQIAWMTGNPPVPVGDIYKRWIILGLNKIVRMYSPVSILDIKQGPKESFRDYVDRF
FKTLRAEQATQDVKNWMTETLLVQNANPDCKTILRALGPGATLEEMMTACQGVGGPSHKA
RVLAEAMSQ-ANNANIMMQRSNFKGPKRTVKCFNCGKEGHIAKNCRAPRKKGCWKCGREG
HQMKDC-IERQANFLGKIWPSNKG-RPGNFLQNRTE------PTAPPA-------EPTAP
PAESFRFEE--TTPAPKQELKDRE--PLTSLKSLFGSDPLLQ
>gagC.syn6.4
MGARASILRGEKLDKWEKIRLRPGGRKHYMLKHIVWASRELEGFALNPGLLETSEGCKQI
IKQLQPALQTGTEELRSLFNTVATLYCVHSGIEVRDTKEAVDKIEEEQNKIQQKTQQAKE
ADG---KVSQNYPIVQNSQGQMVHQAISPRTLNAWVKVIEEKAFSPEVIPMFTALSEGAT
PSDLNTMLNTIGGHQAAMQMLKDTINDEAAEWDRLHPVHAGPIAPGQMRDPRGSDIAGST
STLQEQIAWMTNNPPVPVGDIYKRWIIMGLNKIVRMYSPVSILDIKQGPKEPFRDYVDRF
FRTLRAEQATQEVKNWMTETLLVQNANPDCRTILKALGPGATLEEMMTACQGVGGPGHKA
RVLAEAMSQ-ANNINIMMQRNNFKGPKRIIKCFNCGKEGHIARNCKAPRKKGCWKCGKEG
HQMKDC-NERQANFLGKIWPSHKG-RPGNFLQNRP------------------EPTAP
PAESFRFEE--TTPTPKQEPKDRE--PLTSLKSLFGSDPSSQ
```

Fig. 9 cont'd-8

```
>gagC.syn6.5
MGARASILRGGKLDKWEKIRLRPGGKKRYMLKHLIWASRELERFALNPGLLETSDGCKQI
IQQLQPALKTGTEELKSLFNTVAVLYCVHKGIEVRDTKEAVDKIEEEQNKIQQKMQQQKV
TDG---KVSQNYPIVQNIQGQMVHQPISPRTLNAWVKVIEEKGFSPEVIPMFTALSEGAT
PSDLNTMLNTVGGHQAAMQMLKDTINEEAAEWDRTHPVHAGPVAPGQMREPRGSDIAGTT
STLQEQIGWMTNNPPIPVGEIYKRWIILGLNKIVRMYSPVSILDIKQGPKEPFRDYVDRF
FKALRAEQATQEVKGWMTDTLLVQNANPDCKTILKALGSGATLEEMMTACQGVGGPGHKA
RVLAEAMSQ-ANNTNIMMQKSNFKGPRRIVKCFNCGREGHIAKNCRAPRKKGCWKCGQEG
HQMKDC-TERQANFLGRIWPSHKG-RPGNFLQSRPE------PTAPL--------QPTAP
PAESFKFEE--TTPAPKQEQKDRE--PLTSLRSLFGNDPLSQ
>gagC.syn6.6
MGARASILRGGKLDTWEKIRLRPGGKKHYMLKHLVWASRELDRFALNPGLLETADGCKQI
IKQLHPALQTGTEEIKSLFNTVATLYCVHAGIEVRDTKEALDKIEEEQNKCQQKTQQAKE
ADK---KVSQNYPIVQNLQGQMVHQAISPRTLNAWVKVIEEKAFNPEIIPMFTALSDGAT
PQDLNTMLNTVGGHQAAMQMLKDTINEEAADWDRLHPVHAGPVAPGQLREPRGSDIAGTT
SNLQEQIAWMTSNPPIPVGDIYKRWIILGLNKIVRMYSPVSILDIKQGPKEPFRDYVDRF
FKVLRAEQATQDVKNWMTDTLLIQNANPDCKTILRALGPGASLEEMMTACQGVGGPSHKA
RVLAEAMSQ-TNSA-ILMQRSNFKGSKRIVKCFNCGKEGHLARNCRAPRKRGCWKCGKEG
HQMKDCTTERQANFLGKIWPSHKGGRPGNFLQNRPE------PTAPL--------EPTAP
PAESFGFGE--TTPAPKQEPKDRE--PLISLKSLFGSDPLSQ >gagM.syn1.1
MGARASILRGGKLDKWEKIRLRPGGKKHYMLKHLVWASRELERFALNPGLLETSEGCKQI
IKQLQPALQTGTEELRSLFNTVATLYCVHEKIEVRDTKEALDKIEEEQNKSQQKTQQAKA
ADG---KVSQNYPIVQNLQGQMVHQAISPRTLNAWVKVIEEKAFSPEVIPMFTALSEGAT
PQDLNTMLNTVGGHQAAMQMLKDTINEEAAEWDRLHPVHAGPIAPGQMREPRGSDIAGTT
STLQEQIAWMTSNPPIPVGEIYKRWIILGLNKIVRMYSPVSILDIRQGPKEPFRDYVDRF
FKTLRAEQATQDVKNWMTDTLLVQNANPDCKTILRALGPGATLEEMMTACQGVGGPSHKA
RVLAEAMSQ-ANNTNIMMQRSNFKGSKRIVKCFNCGKEGHIARNCRAPRKKGCWKCGKEG
HQMKDC-TERQANFLGKIWPSHKG-RPGNFLQSRPE------PTAPPA-------EPTAP
PAESFRFEE--TTPAPKQEPKDRE--PLTSLKSLFGSDPLSQ >gagM.syn3.1
---RASVLSGGKLDAWEKIRLRPGGKKKYKLKHIVWASRELERFAVNPGLLETSEGCRQI
LGQLQPSLQTGSEELRSLYNTVAVLYCVHQRIEVKDTKEALEKIEEEQNKSKKKAQQAAA
DTGNSSQVSQNYPIVQNLQGQMVHQAISPRTLNAWVKVIEEKAFSPEVIPMFTALSEGAT
PSDLNTMLNTIGGHQAAMQILKDTINEEAAEWDRLHPVHAGPIAPGQMREPRGSDIAGTT
STLQEQIGWMTNNPPIPVGEIYKRWIILGLDKIVRMYSPTSILDIRQGPKESFRDYVDRF
YKTLRAEQASQEVKNWMTETLLVQNANPDCKTILKALGPAATLEEMMTACQGVGGPSHKA
RILAEAMSQVTNSATIMMQRGNFRNQRKTVKCFNCGKEGHIAKNCRAPRKKGCWKCGKEG
HQMKDC-NERQANFLGKIWPSHKG-RPGNFLQSRP-----------------EPTAP
PEESFRFGEETTTPSQKQEPIDKELYPLASLKSLFGNDPLSQ
>gagM.syn3.2
MGARASILRGGKLDKWEKIRLRPGGKKHYMLKHLVWASRELERFALNPGLLETAEGCKQI
IKQLQPALKTGTEELKSLYNTVATLYCVHEKIEVRDTKEALDKLEEEQNKSQQKTQQAAA
GTGSSSKVSQNYPIVQNAQGQMVHQALSPRTLNAWVKVVEEKAFSPEVIPMFSALAEGAT
PQDLNTMLNTVGGHQAAMQMLKDTINEEAADWDRLHPVHAGPVAPGQMREPRGSDIAGST
STLQEQIAWMTSNPPIPVGDIYKRWIILGLNKIVRMYSPVSILDIKQGPKEPFRDYVDRF
FKTLRAEQATQDVKNWMTDTLLVQNANPDCKTILRALGPGASLEEMMTACQGVGGPGHKA
RVLAEAMSQ-ANNANIMMQRGNFKGQKR-IKCFNCGKEGHLARNCRAPRKKGCWKCGREG
HQMKDC-TERQANFLGRIWPSSKG-RPGNFPQSRP-----------------EPSAP
PAESFGFGE--TTPAPKQELKDRE--PLTSLKSLFGSDPLSQ
>gagM.syn3.3
MGARASVLSGGELDRWEKIRLRPGGKKKYRLKHLVWASRELEKFALNPGLLETSEGCKQI
MKQLQPALQTGTEELRSLFNTVATLYCVHQRIDVKDTKEALDKIEEEQNKIQQKTQQAKA
ADG---KVSQNYPIVQNIQGQMVHQPISPRTLNAWVKVVEEKGFNPEVIPMFSALSEGAT
```

Fig. 9 cont'd-9

```
PQDLNMMLNIVGGHQAAMQMLKETINEEAAEWDRVHPVHAGPIPPGQMREPRGSDIAGTT
SNLQEQIGWMTSNPPVPVGDIYKRWIVLGLNKIVRMYSPVSILDIRQGPKEPFRDYVDRF
FKVLRAEQATQEVKNWMTDTLLIQNANPDCKSILRALGPGATLEEMMTACQGVGGPSHKA
RVLAEAMSQ-TNSA-ILMQRSNFKGSKRIVKCFNCGKEGHIARNCRAPRKRGCWKCGQEG
HQMKDC-TERQVNFLGKIWPSNKG-RPGNFLQNRPE------PTAPPA-------EPTAP
PAESFRFEE--TTPAPKQEPKDRE--PLTSLRSLFGNDPSSQ

>gagM.syn4.1
MGARASVLSGGELDRWEKIRLRPGGKKKYKLKHIVWASRELERFAVNPGLLETSEGCRQI
LGQLQPSLQTGSEELRSLYNTVAVLYCVHQRIDVKDTKEALEKIEEEQNKSQQKTQQAKA
ADG---KVSQNYPIVQNAQGQMVHQAISPRTLNAWVKVIEEKGFSPEVIPMFSALAEGAT
PQDLNTMLNTIGGHQAAMQMLKDTINDEAAEWDRLHPVQAGPVAPGQIREPRGSDIAGTT
SNLQEQIGWMTSNPPIPVGDIYKRWIIMGLNKIVRMYSPTSILDIRQGPKESFRDYVDRF
FRTLRAEQASQEVKNWMTETLLVQNSNPDCKTILKALGPAATLEEMMTACQGVGGPGHKA
RVLAEAMSQ-VQQPNIMMQRGNFKGQKR-IKCFNCGREGHLARNCRAPRKKGCWKCGREG
HQMKDC-TESKANFLGKIWPSNKG-RPGNFLQSRP-----------------EPSAP
PAESFGFGEE-ITPSQKQEQKDKELYPLASLKSLFGNDPLSQ >gagM.syn4.2
MGARASVLSGGKLDAWEKIRLRPGGKKKYRLKHLVWASRELDRFALNPSLLETAEGCKQI
MKQLQPALKTGTEELKSLYNTVATLYCVHEKIDVRDTKEALDKIEEEQNKIQQKTQQAKE
ADG---KVSQNYPIVQNIQGQMVHQPISPRTLNAWVKVVEEKAFSPEVIPMFTALSDGAT
PQDLNSMLNAVGGHQAAMQILKDTINEEAADWDRLHPVHAGPVAPGQMREPRGSDIAGTT
STLQEQIGWMTNNPPIPVGEIYKRWIILGLNKIVRMYSPVSILDIKQGPKESFRDYVDRF
FKVLRAEQATQDVKNWMTDTLLIQNANPDCKSILRALGPGATLEEMMTACQGVGGPSHKA
RILAEAMSQVTNSATIMMQRGNFRNQRKTVKCFNCGKEGHLARNCKAPRKRGCWKCGKEG
HQMKEC-TERQANFLGKIWPSSKG-RPGNFPQSRP-----------------EPTAP
PEESFRFGEETTTPSQKQEPIDKELYPLASLRSLFGNDPSSQ >gagM.syn4.3
MGARASILRGGKLDKWEKIRLRPGGKKRYMLKHLIWASRELERFALNPGLLETAEGCQQI
IEQLQSTLKTGSEELKSLFNTVATLYCVHQRIEVKDTKEALDKVEEEQNKSKKKAQQAAA
DTGNSSQVSQNYPIVQNLQGQMVHQALSPRTLNAWVKVIEEKAFSPEIIPMFTALSEGAT
PSDLNTMLNTVGGHQAAMQMLKDTINEEAAEWDRVHPVHAGPIPPGQMREPRGSDIAGTT
SSLQEQIAWMTSNPPVPVGEIYKRWIVLGLNKIVRMYSPVSILDIRQGPKEPFRDYVDRF
FKTLRAEQASQDVKNWMTETLLVQNANPDCKTILRALGPGASLEEMMTACQGVGGPSHKA
RVLAEAMSQ-TNSA-ILMQRSNFKGSKRIVKCFNCGKEGHIARNCRAPRKRGCWKCGQEG
HQMKDC-NERQANFLGKIWPSHKG-RPGNFLQNRPE------PTAPP--------EPTAP
PAESFRFEE--TTPAPKQELKDRE--PLTSLKSLFGSDPLSQ >gagM.syn4.4
MGARASVLRGEKLDKWERIRLRPGGKKHYMLKHLVWASRELEKFALNPGLLETSEGCKQI
IKQLQPALQTGTEELRSLFNTVATLYCVHAGIEVRDTKEALDKIEEIQNKSQKTQQAAA
GTGSSSKVSQNYPIVQNLQGQMVHQPLSPRTLNAWVKVVEEKGFNPEVIPMFSALSEGAT
PQDLNMMLNIVGGHQAAMQMLKETINEEAAEWDRLHPVHAGPIAPGQMREPRGSDIAGST
STLQEQIAWMTGNPPVPVGDIYKRWIILGLNKIVKMYSPTSILDIKQGPKEPFRDYVDRF
YKTLRAEQATQEVKNWMTDTLLVQNANPDCKSILKALGTGATLEEMMSACQGVGGPAHKA
RVLAEAMSQ-ANNTNIMMQRSNFKGPKRIIKCFNCGKEGHIAKNCRAPRKKGCWKCGKEG
HQMKDC-TERQANFLGRIWPSSKG-RPGNFLQSRPE------PTAPPA-------EPTAP
PAESFKFEE--TTPAPKQEPKDRE--PLTSLRSLFGSDPLLQ >gagM.syn6.1
MGARASILSGGKLDAWEKIRLRPGGRKHYMLKHIVWASRELERFALNPGLLETAEGCQQI
IEQLQSTLKTGSEELKSLFNTVATLWCVHQRIEVKDTKEALDKLEEEQNKSQQKTQQAKA
ADG---KVSQNYPIVQNLQGQMVHQSISPRTLNAWVKAIEEKAFSPEVIPMFSALAEGAT
PQDLNTMLNTIGGHQAAMQILKDTINEEAAEWDRIHPVHAGPVAPGQMRDPRGSDIAGTT
SNLQEQIAWMTSNPPVPVGEIYKRWIILGLDKIVRMYSPVSILDIRQGPKEPFRDYVDRF
FKTLRAEQATQEVKGWMTDTLLVQNANPDCKTILKALGPGATLEEMMSACQGVGGPGHKA
```

Fig. 9 cont'd-10

```
RVLAEAMSQ-ANNTNIMMQKSNFKGPKRIIKCFNCGKEGHLARNCRAPRKKGCWKCGQEG
HQMKDC-TERQANFLGRIWPSHKG-RPGNFPQSRL-------------------EPTAP
PAESFGFGEE-IAPSPKQEPKEKELYPLTSLKSLFGNDPLSQ
>gagM.syn6.2
MGARASILRGGKLDWEKIRLRPGGKKKYKLKHIVWASRELEKFALNPGLLETSEGCRQI
LGQLQPSLQTGSEELKSLYNTVATLYCVHQRIDVKDTKEALEKIEEEQNKSQQKTQQAAA
DKG----VSQNYPIVQNLQGQMVHQAISPRTLNAWVKVIEEKAFSPEIIPMFTALSEGAT
PQDLTTMLNTVGGHQAAMQMLKETINDEAAEWDRLHPVHAGPVAPGQLREPRGSDIAGST
STLQEQIAWMTGNPPVPVGDIYKRWIVLGLNKIVRMYSPTSILDIRQGPKEPFRDYVDRF
YKTLRAEQASQDVKNWMTETLLVQNANPDCRTILKALGPAATLEEMMTACQGVGGPAHKA
RVLAEAMSQVTNPATIMMQRGNFRNQRKTVKCFNCGKEGHLAKNCRAPRKRGCWKCGKEG
HQMKDC-NERQANFLGKIWPSNKG-RPGNFLQNRT-------------------EPTAP
PAESFRFGEEKTTPSQKQEPIDKELYPLASLRSLFGNDPSLQ
>gagM.syn6.3
MGARASVLRGEKLDWERIRLRPGGKKRYMLKHLIWASRELERFALNPSLLETSEGCKQI
IQQLQPALKTGTEELRSLYNTVATLYCVHEKIEVRDTKEAVDKIEEEQNKSKKKAQQAAA
DTGNSSQVSQNYPIVQNIQGQMVHQALSPRTLNAWVKVVEEKGFNPEVIPMFSALSEGAT
PQDLNMMLNIVGGHQAAMQMLKDTINEEAAEWDRLHPVQAGPVAPGQMREPRGSDIAGTT
STLQEQITWMTSNPPIPVGEIYKRWIIMGLNKIVRMYSPVSILDIKQGPKESFRDYVDRF
FRTLRAEQASQEVKNWMTETLLIQNANPDCKTILRALGPAASLEEMMTACQGVGGPGHKA
RVLAEAMSQ-TNSA-ILMQRSNFKGSKRIVKCFNCGKEGHIARNCRAPRKKGCWRCGKEG
HQMKDC-TESKANFLGKIWPSHKG-RPGNFLQNRPEPTAPPEPTAPPAEPTAPPAEPTAP
PAESFKFEE--TTPAPKQELKDRE--PLISLKSLFGSDPLLQ
>gagM.syn6.4
MGARASILRGEKLDTWEKIRLRPGGKKQYRLKHIVWASRELDRFALNPSLLETAEGCKQI
IKQLHPALQTGTEELRSLFNTVATLYCVHAGIEVRDTKEALDKIEEEQNKIQQKTQQAKA
ADE---KVSQNYPIVQNMQGQMVHQPLSPRTLNAWVKVVEEKAFSPEVIPMFAALSEGAT
PSDLNTMLNTVGGHQAAMQMLKDTINDEAAEWDRLHPAQAGPIPPGQIREPRGSDIAGTT
STPQEQIGWMTNNPPIPVGEIYKRWIVLGLNKIVRMYSPISILDIRQGPKEPFRDYVDRF
FKALRAEQATQEVKGWMTETLLVQNSNPDCKTILRALGPGASLEEMMTACQGVGGPSHKA
RILAEAMSQ-ANS-NIMMQRSNFKGPKRIVKCFNCGKEGHIAKNCRAPRKKGCWKCGREG
HQMKDC-IERQANFLGKIWPSQKG-RPGNFLQSRP------------------EPSAP
PAESFRFGE--TTPAPKQEPKDRE--PLTSLRSLFGSDPLSQ
>gagM.syn6.5
MGARASVLSGGELDRWEKIRLRPGGKKKYRLKHLVWASRELERFAINPGLLETSDGCKQI
IKQLQPALQTGSEELRSLYNTIATLYCVHQKIEVKDTKEALDKIEEIQNKSKQKTQQAAA
GTGSSSKVSQNYPIVQNAQGQMVHQSLSPRTLNAWVKVIEEKGFNPEVIPMFTALSEGAT
PHDLNTMLNTVGGHQAAMQMLKETINEEAAEWDRVHPVHAGPIPPGQMREPRGSDIAGST
STLQEQIGWMTSNPPIPVGDIYKRWIILGLNKIVRMYSPSSILDIRQGPKESFRDYVDRF
FKCLRAEQATQEVKNWMTDTLLIQNANPDCKSILRALGPGATLEEMMTACQGVGGPGHKA
RILAEAMSQ-VQQPNIMMQRGNFKGQKR-IKCFNCGREGHIARNCKAPRKKGCWKCGKEG
HQMKDC-TERQVNFLGKIWPSYKG-RPGNFLQSRP-------------------EPTAP
PEESFRFGEETTTPSQKQETIDKELYPLASLKSLFGNDPSSQ
>gagM.syn6.6
MGARASVLSGGKLDAWERIRLRPGGKKHYMLKHLVWASRELERFAVNPGLLETSEGCKQI
MKQLQPALQTGTEELKSLYNTVAVLYCVHQRIEIKDTKEALDKIEEEQNCQQKTQQAKE
ADG---KVSQNYPIVQNLQGQMVHQPISPRTLNAWVKVIEEKGFSPEVIPMFTALSDGAT
PQDLNSMLNAVGGHQAAMQMLKDTINEEAADWDRLHPVHAGPIAPGQMREPRGSDIAGTT
SSLQEQIAWMTNNPPVPVGEIYRRWIILGLNKIVKMYSPTSILDIKQGPKEPFRDYVDRF
FKVLRAEQATQDVKNWMTDTLLVQNANPDCKSILKALGTGATLEEMMTACQGVGGPSHKA
RVLAEAMSQVTNSATIMMQKGNFRNQRKIVKCFNCGREGHLARNCKAPRKRGCWKCGKEG
HQMKEC-TERQANFLGKIWPSSKG-RPGNFPQSRP-------------------EPTAP
PAESFRFEE--TTPAPKQESKDRE--PLTSLKSLFGSDPSSQ
```

Fig. 10

\>ENV-B.syn1.1
MRVTGIRKNYQHLWRWGTMLLWRWGTMLLGMLMICSATEKLWVTVYYGVPVWKEATTTLF
CASDAKAYDTEVHNVWATHACVPTDPNPQEVVLENVTENFNMWKNNMVEQMHEDIISLWD
QSLKPCVKLTPLCVTLNCTDDVRNVT-NNATNTNSSW-GEPMEKGEIKNCSFNITTSIRD
KVQKEYALFYKLDVVPI-DNDSNNTN--------YRLISCNTSVITQACPKVSFEPIPIH
YCAPAGFAILKCNDKKFNGTGPCTNVSTVQCTHGIRPVVSTQLLLNGSLAEEEVVIRSEN
FTNNAKTIMVQLNVSVEINCTRPNNNTRKSIHIGPGRAFYTTGDIIGDIRQAHCNISRAQ
WNNTLKHIVEKLGKQFGNNKTIVFNHSSGGDPEIVMHSFNCGGEFFYCNSTKLFNSTWTR
N-NGTWTRN---DTERSNSTE---EHITLPCRIKQIINMWQEVGKAMYAPPIRGQIRCSS
NITGLLLTRDGGNDT-----SGTEIFRPGGGDMRDNWRSELYKYKVVKIEPLGVAPTKAK
RRVVQREKRAVG-IGAVFLGFLGAAGSTMGAASMTLTVQARQLLSGIVQQQNNLLRAIEA
QQHLLQLTVWGIKQLQARVLAVERYLRDQQLLGIWGCSGKLICTTAVPWNASWSNKSLNE
IWNNMTWMEWEKEIDNYTNLIYNLLEESQNQQEKNEQELLELDKWASLWNWFDISNWLWY
IKIFIMIVGGLVGLRIVFAVLSIVNRVRQGYSPLSFQTRLPAPRGPDRPEGIEEEGGERD
RDRSVRLVDGFLALIWDDLRSLCLFSYHRLRDLLLIVTRIVELLG-------RRGWEALK
YWWNLLQYWSQELKNSAVSLLNATAIAVAEGTDRVIEALQRACRAILHIPRRIRQGLERA
LL- \>ENV-B.syn3.1
MRVKETRKNYQHLWKWGTML--------LGMLMICSATEKLWVTVYYGVPVWRDANATLF
CASDAKAYDTEAHNVWATHACVPTDPNPQEVELKNVTENFNMWKNDMVEQMHEDIINLWD
QSLKPCVELTPLCVTLNCTDYVKNIT-NNATSTNSSW-GKPMEKGEIKFCSFNITTSIRN
KVQKQYALFYKLDIVPI-DNDNTS----------YRLISCNTSTITQACPKVTFEPIPIH
YCAPAGFAILKCNNKTFNGTGPCTNVSTVQCTHGIRPVISTQLLLNGSLAEEEVVIRSEN
FTNNAKTIMVQLNVSVEINCTRPNNNTRRSIPIGPGRVFYTTEDIIGDIRQAHCNISRAQ
WNNTLKHIVEKLGKQFGNNKTIVFNHSSGGDPEIVMHSFNCRGEFFYCKSTKLFNSTWTR
N-NGTWTRN---DTERSNSTE---EHITLPCRIKQIINMWQEVGKAMYAPPIKGQISCSS
NITGLLLTRDGGNDT-----SGTEIFRPGGGDMRDNWRSELYKYKVVRIEPLGVAPTEAK
RRVVQREKRAVG-IGAVFLGFLGAAGSTMGAASMTLTVQARLLLSGIVQQQSNLLRAIEA
QQHMLQLTVWGIKQLQARLLAVERYLGDQQLLGLWGCSGKLICTTTVPWNTSWSNKSLNE
IWDNMTWMQWEREIDNYTGLIYNLLEKSQNQQEKNEQELLELDKWASLWNWFDITNWLWY
IKIFIMIVGGLVGLRIVFTVLSIVNRVRKGYSPLSFQTRLPTPRGPDRPGGIEEEGGEQD
RDRSGPLVNGFLALIWVDLRSLFLFSYHRLRDLLLIVARIVELLG-------RRGWEILK
YWWNLLLYWSQELKNSAVSLLNATAIAVAEGTDRVIEVVQRAFRAILHIPRRIRQGFERA
LL- \>ENV-B.syn3.2
MRVTGIRKNYQHLWRWGTMLLWRWGTMLLGILMICSAAGKLWVTVYYGVPVWKEANTTLF
CASDAKAYDTEVHNVWATHACVPIDPNPQEVVLGNVTENFNMWKNNMVEQMHEDIISLWD
ESLKPCVKLTPICVTLNCTDDVRNVT-NNATNTNSSW-GEPMEKGEIKNCSFNITTSIRD
KVQKQYALFYKLDVVPI-DNDSNNTN--------YRLISCNTSVITQACPKISFEPIPIH
FCAPAGFAILKCNDKKFNGTGPCKNVSTVQCTHGIKPVVSTQLLLNGSLAEEEIVIRSEN
FTDNAKTIIVQLNESVVINCTRPNNNTRKSIHIGPGRAFYATGEIIGDIRQAHCNLSRAK
WNDTLKQIVIKLREQFG-NKTIVFNQSSGGDPEIVMHSFNCGGEFFYCNTTQLFNSTWTW
N-NSTW--N---NTKRSNDTE---EIITLPCRIKQIVNMWQKVGKAMYAPPIRGQIRCSS
NITGILLTRDGGNNNET---NRTETFRPGGGNMKDNWRSELYKYKVVKIEPLGIAPTKAR
RRVVQREKRAVGTIGAMFLGFLGAAGSTMGAASLTLTVQARQLLPGIVQQQNNLLKAIEA
QQHLLRLTVWGIKQLQARVLAVERYLRDQQLLGIWGCSGKIICTTAVPWNASWSNKSLDK
IWDNMTWMEWEKEIDNYTNLIYNLLEESQNQQEKNELELLELDKWANLWNWFDISNWLWY
IKIFIMIIGGLVGLRIVFAVLSIVNRVRQGYSPLSFQTRLPAPRGPDRPEGIEEEGGERD
RDRSVRLVDGFLALIWDDLRSLCLFLYHRLRDLLLIAARIVELLG-------RRGWEALK
YWWNLLQYWSQELKNSAISLLNATAVAVAEGTDRVIEALQRACRAILHIPRRIRQGLERL
LL- \>ENV-B.syn3.3
MRVKGIRKNCQHLWRWGIML--------LGMLMICSAAEQLWVTVYYGVPVWKEATTTLF
CASDAKAYDKEVHNVWATHASVPTDPNPQEVVLENVTENFNMWKNNMVDQMHEDIISLWD
QSLKPCVKLTPLCVTLNCTD-LRNATNGNDTNTTSSS-REMMGGGEMKNCSFNVTTSIRD
KVQKEYALFYKLDVIPI-DSRNNSNNSTE--YNSYRLINCNTSVITQACPKVSFEPIPIH

Fig. 10 cont'd-1

YCTPAGFAILKCKDKKFNGTGPCTKVSTVQCTHGIRPVVSTQLLLNGSLAEEEVIIRSEN
FTNNAKTIIVQLKEAVEINCTRPSNNTRKSIPIGPGRAFYTTGDIIGDIRKAHCNISRAN
WNNTLRQIVEKLGEQFGNNKTIIFKQSSGGDPEIVTHSFNCGGEFFYCNSTQLFNSTWNF
--NGTWNKN---FNNTWNNTEGTNDTITLPCRIKQIINRWQEVGKAMYAPPISGQIRCSS
NITGLILTRDGGNNGNET--NGTEIFRPGGGNMRDNWRSELYRYKVVKIEPLGVAPTKAK
RRVVQREKRAVG-IGALFLGFLGAAGSTMGAASITLTVQARQLLSGIVQQQNNLLRAIEA
QQHLLQLTVWGIKQLQARILAVERYLKDQQLLGIWGCSGKLICTTAVPWNTSWSNRSLNE
IWNNMTWMEWEREIDNYTSLIYTLIEESQNQQEKNEQELLALDKWASLWNWFSITNWLWY
IRIFIMIVGGLIGLRIVFAVLSVVNRVRQGYSPLSFQTHLPAQRGPDRPEGTEEEGGERD
RDRSGRLVDGFLAIIWVDLRSLCLFSYHRLRDLLLIVTRIVELLG-------RRGWEVLK
YWWNLLQYWIQELKNSAVSLFNAIAIAVAEGTDRIIEVVQRAYRAILHIPTRIRQGLERA
LL-

>ENV-B.syn4.1
MRVTGIRKNYQHLWRWGTMLLWRWGTMLLGILMICSAAGKLWVTVYYGVPVWKDATTTLF
CASDAKAYDTEVHNVWATHASVPTDPNPQEVVLENVTEDFNMWKNNMVDQMHEDIISLWD
QSLKPCVELTPLCVTLNCTDDVRNVT-NNATNTNSSW-GEPMEKGEIKFCSFNITTSIRN
KVQKQYALFYKLDVVPI-DNDSNNTN--------YRLISCNTSVITQACPKVTFEPIPIH
YCAPAGFAILKCNNKTFNGTGPCTKVSTVQCTHGIRPVVSTHLLLNGSLAEEEVIIRSEN
FTDNTKTIIVQLKEAVEINCTRPNNNTRKGIHIGPGRAFYTTGEIIGDIRQAHCNLSRAK
WNDTLKQIVIKLREQFG-NKTIIFNQSSGGDPEIVMHTFNCGGEFFYCNTTQLFNSTW--
-------QN---ETSGSINITDIGENITLPCRIKQIVNMWQKVGKAMYAPPIKGQISCSS
NITGLLLTRDGGNNGNET--NGTEIFRPGGGNMKDNWRSELYRYKVVKIEPLGVAPTRAK
RRVVQREKRAVT-LGAMFLGFLGAAGSTMGAASMTLTVQARLLLSGIVQQQSNLLRAIEA
QQHLLRLTVWGIKQLQARILAVERYLQDQQLLGIWGCSGKLICTTAVPWNASWSNKSQDE
IWNNMTWMQWEKEIDNYTGLIYTLLEESQIQQEKNEQELLELDKWASLWNWFDITNWLWY
IKIFIMIVGGLIGLRIVFTVLSIVNRVRKGYSPLSFQTHLPAPRGPDRPGGIEEEGGEQD
RDRSGPLVNGFLALIWVDLRSLFLFSYHRLRDLLLIVARIVELLG-------RRGWEVLK
YWWNLLQYWSQELKNSAISLLNATAVAVAEGTDRVIEALQRACRAILHIPRRIRQGLERL
LL- >ENV-B.syn4.2
MRVKGIRKNCQHLWRWGILL--------LGMLMICSAAEQLWVTVYYGVPVWRDANATLF
CASDAKAYDTEAHNVWATHACVPTDPNPQEVELKNVTENFNMWKNNMVEQMQEDIISLWD
QSLKPCVKLTPICVTLNCTDYVKNIT-NNATSTNSSW-GKPMEKGEIKNCSFNVTTSIRD
KVQKEYALFYRLDVVPI-DNDSNNNDSTNTNYTNYRLISCNTSTITQACPKVSFQPIPIH
YCAPAGFALLKCNDKKFNGTGPCKNVSTVQCTHGIKPVVSTQLLLNGSLAEEEIVIRSEN
FTNNAKTIIVQLNESVVINCTRPNNNTRKSIHIGPGRAFYATGDIIGDIRKAHCNISRAN
WNNTLRQIVEKLGEQFG-NKTIVFNQSSGGDVEIVMHSFNCGGEFFYCNSTQLFNSTWNF
--NGTWNKN---FNNTWNNTEGTNDTITLPCRIKQIINMWQGVGKAMYAPPISGQIRCSS
NITGLILTRDGGNN-NET--NRTETFRPGGGDMRDNWRSELYKYKVVKIEPLGIAPTKAR
RRVVQREKRAVGTIGAMFLGFLGTAGSTMGAASLTLTVQARLLLSGIVQQQNNLLKAIEA
QQHLLQLTVWGIKQLQARLLAVERYLGDQQLLGLWGCSGKLICTTTVPWNASWSNKSLDK
IWDNMTWMEWEREIDNYTGLIYNLLEKSQNQQEKNELELLELDKWANLWNWFDITKWLWY
IKIFIMIIGGLIGLRIVFAVLSVVNRVRQGYSPLSLQTRLPTQRGPDRPEGIAEEGGERD
RDRSGPLVDGFLAIIWVDLRSLCLFSYHHLRDLLLIVTRIVELLG-------RRGWEALK
YWWNLLLYWSQELKNSAVNLLNTTAIAVAEGTDRIIEVLQRIYRAFLHIPRRIRQGFERA
LL- >ENV-B.syn4.3
MRVKEIRKNYQHLWKWGTML--------LGMLMICSAAGNLWVTVYYGVPVWKEANTTLF
CASDAKAYETEVHNVWATHACVPIDPNPQEVVLGNVTENFNMGKNNMVEQMHEDIISLWD
ESLKPCVKLTPLCVTLNCTDELKNATFRSNTTTNSSW--EKMEKGEIKNCSFNITTNMRD
KMQKEYALFYKLDVIPI-DSRNNSNNSTE--YNSYRLINCNTSVITQACPKISFEPIPIH
YCTPAGFAILKCKDKKFNGKGPCTNVSTVQCTHGIRPVVSTQLLLNGSLAEKEVVIRSDN
FTNNAKTIMVQLNVSVEINCTRPNNNTRRSIPIGPGRVFYTTEDIIGDIRQAHCNISRAQ
WNNTLKHIVEKLGKQFGNNKTIVFNHSSGGDPEIVMHSFNCRGEFFYCKSTKLFNSTWTR

Fig. 10 cont'd-2

```
N-NGTWTRN---DTERSNSTE---EHITLPCRIKQIINMWQEVGKAMYAPPIRGQIRCSS
NITGILLTRDGGNDT-----SGTEIFRPGGGDMKDNWRSELYKYKVVRIEPLGVAPTEAK
RRVVQREKRAVG-IGAVFLGFLGAAGSTMGAAAVTLTVQARLLLSGIVQQQNNLLRAIEA
QQRLLQLTVWGIKQLQARVLAVERYLRDQQLLGIWGCSGKIICTTAVPWNTSWSNRSLNE
IWNNMTWMEWEKEIDNYTNLIYNLLEESQNQQEKNEQELLALDKWANLWNWFDISNWLWY
IKIFIIIVGGLVGLRIVFAVLSIVNRVRQGYSPLSFQTRLPAPRGPDRPEGIEEEGGERD
RDRSVRLVDGFLALIWDDLRSLCLFSYHRLRDLLLI----VELLG------RRGWEILK
YWWNLLQYWGQELKNSAVSLLNATAIAVAEGTDRVIEVVQRAYRAILHIPTRIRQGLERA
LL-
>ENV-B.syn4.4
MRVKETRKNYQHLWRWGIML--------LGMLMICSATEKLWVTVYYGVPVWKEATTTLF
CASDAKAYDKEVHNVWATHACVPTDPSPQEVVLENVTENFNMWKNDMVEQMHEDIINLWD
QSLKPCVRLTPLCVTLNCTN-VNVTNLKNETNTKSSSGGEKMEEGEMKNCSFNITTSIRD
KVQKQYALFYKLDVVPI-DNDNTS---------YRLISCNTSVIKQACPKVSFEPIPIH
FCAPAGFAILKCNDKKFNGTGPCTNVSTVQCTHGIRPVISTQLLLNGSLAEEEVVIRSEN
FTDNAKTIIVQLNETVEINCTRPSNNTRKSIPIGPGRAFYTTGDIIGDIRQAYCNISRAK
WNNTLKQIVTKLREQFGNNKTIIFKQSSGGDPEIVTHSFNCGGEFFYCNSTKLFNSTWTW
N-NSTW--N---NTKRSNDTE---EIITLPCRIKQIINRWQEVGKAMYAPPIEGQIRCLS
NITGLLLTRDGGTNNT----NTNETFRPGGGNMRDNWRSELYKYKVVQIEPLGVAPTKAK
RRVVQREKRAVG-IGALFLGFLGAAGSTMGAASITLTVQARQLLSGIVQQQRNLLRAIEA
QQHMLQLTVWGIKQLRARVLAVERYLKDQQLLGIWGCSGRLICTTNVPWNTSWSNKSLNE
IWDNMTWMQWEREIDNYTSLIYTLIEESQNQQEKNEQDLLALDKWASLWNWFSITNWLWY
IRIFIMIVGGLVGLRIVFTVISIVTRVRQGYSPLSFQTRLPTPRGPDRPEGTEEEGGERD
RDRSGRLVDGFLALFWDDLRSLCLFLYHRLRDLLLIAARIVELLG------RRGWELLK
YWWNLLQYWIQELKNSAVSLFNAIAIAVAEGTDWVIEISQRAFRAVLHIPVRIRQGLERA
LQ-
>ENV-B.syn6.1
MRVTGIRKNYQHLWRWGTMLLWRWGTMLLGILMICSAAGKLWVTVYYGVPVWKDATTTLF
CASDAKAYDTEAHNVWATHACVPIDPNPQEVVLENVTENFNAWKNNMVEQMHEDMISLWD
QSLQPCVRLTPLCVTLNCTDDVRN-----ATSTNSSW-GKPMEKGEIKNCSFNITTSIRD
KVQKQYALFYKLDVVPI-DNDSNNTN-------YRLISCNTSIITQACPKITFEPIPIH
YCTPAGFALLKCNDKKFNGTGPCTKVSTVQCTHGIRPVVSTHLLLNGSLAEEEVIIRSEN
FTNNAKTIMVQLNVSVEINCTRPSNNTRKSIHIGPGRAFYTTGDIIGDIRKAHCNISRAN
WNNTLRQIVEKLGEQFGNNKTIVFNHSSGGDLEIVTHSFICGGEFFYCNSTKLFNSTWTW
N-NSTW--N---NTKRSNDTE---EIITLPCRIKQIINMWQEVGKAMYAPPIRGKIRCSS
NITGLLLTRDGGTNNT----NTNETFRPGGGDMRDNWRNELYKYKVVRIEPLGIAPTEAK
RRVVQREKRAVG-IGAMFLGFLGTAGSTMGAASVALTVQARQLLPGIVQQQNNLLRAIDA
QQHLLQLTVWGIKQLQARILAVERYLKDQQLLGFWGCSGKLICTTNVPWNTSWSNKSYSQ
IWENMTWMEWEREINNYTGLIYNLLEKSQNQQEKNEQELLELDKWASLWSWFDISNWLWY
IKIFIIIVGGLVGLRIVFAVLSIINRVRQGYSPLSFQTHLPAPRGPDRPEGIAEEGGERD
RDRSGRLVNGFLALIWVDLRSLCLFSYHHLRDLLLI----VELLG------RRGWEVLK
YWWNLLLYWSQELKNSAISLLNATAVAVAEGTDRVIEALQRACRAILHIPRRIRQGLERL
LL-
>ENV-B.syn6.2
MRVKETRKNYQHLWKWGTML--------LGILMICSATENLWVTVYYGVPVWKEATTTLF
CASDAKAYDKEVHNVWATHACVPTDPNPQEVELKNVTENFNMWKNNMVEQMQEDIISLWD
QSLKPCVRLTPLCVTLNCTD-LRNATNGNDTNTTSSS-REMMGGGEMKNCSFNITTNIRD
KVQKEYALFYKLDIVPI-DNDNTN---------YRLISCNTSVVTQACPKVSFEPIPIH
FCAPAGFAILKCNDKKFNGKGPCTNVSTVQCTHGIRPVISTQLLLNGSLAEEEVVIRSEN
```

Fig. 10 cont'd-3

```
FTNNVKTIIVQLNETVEINCTRPNNNTRRSIPIGPGRVFYTTEDIIGDIRQAHCNLSRTQ
WNNTLKQIVTKLREQFG-NKTIIFNQSSGGDPEIVMHTFNCGGEFFYCNTTKLFNSTW--
---NDTTINR----TEGSNNTR----NITLPCRIKQIINLWQEVGKAMYAPPIQGQISCSS
NITGLLLTRDGGNN-NET--NRTETFRPGGGNMRDNWRSELYKYKVVKIEPLGVAPTKAK
RRVVQREKRAVG-IGALFLGFLGAAGSTMGAASVTLTVQARQLLSGIVQQRNNLLRAIEA
QQRMLQLTVWGIKQLRARVLAVERYLKDQQLMGIWGCSGKLICTTTVPWNASWSNKSLNE
IWDNMTWMEWEREIDNYTSLIYTLIEESQNQQEKNELELLELDKWASLWNWFSITNWLWY
IRLFIMIVGGLVGLRIVFTVISIVTRVRQGYSPLSFQTRLPTPRGPDRPGGIEEEGGEQD
RDRSIRLVDGFLALIWDDLRSLCLFSYHRLRDLLWI----VELLG------RRGWEALK
YLWNLLQYWSQELKKSAVSLFNATAIAVAEGTDWVIEVIQRAFRAFIHIPTRVRQGLERA
LQ-
>ENV-B.syn6.3
MRVKGIRKNCQHLWRWGILL--------LGMLMICSATEKLWVTVYYGVPVWKETTTTLF
CASDAKAYVAEKHNVWATHACVPTDPNPREVVMGNVTEEFNIWNNSMVEQMHEDIISLWE
QSLKPCVKLTPLCVSLKCTDL------KNDTNTNSSSGRMIMEKGEIKNCSFNITTGIRG
KVQ-EYSLFYKLDVVQM-DEDNTS---------YRLINCNTSVITQACPKVSFQPIPIH
YCAPAGFAILKCKDKKFNGTGSCKNVSTVQCTHGIRPVISTQLLLNGSLAEGEVVIRSEN
FTDNAKTIIVQLKDPVKINCTRPNNNTRKSIPIGPGRAFYATGDIIGDIRQAHCNISTTK
WNKTLGQVVKKLREQFK-NKTIVFKQSSGGDPEVVMHSFNCGGEFFYCNTSQLFNSTW--
---------N---STSLFNSTN---GTITLQCRIKQIINRWQEVGKAMYAPPIEGQIRCLS
NITGLLLVRDGGINVTNN--TGTEVFRPGGGDMRDNWRSELYKYKVIKIEPLGVAPTRAK
RRVVQREKRAVG-LGAMFLGFLGAAGSTMGAASITLTVQARQLLSGIVQQQRNLLRAIEA
QQHMLQLTVWGIKQLQARVLAVERYLQDQQLLGIWGCSGKLICTTTVPWNTSWSNKSLNQ
IWDNMTWMQWEKEIDNYTGLIYTLLEESQNQQEKNEHELLELDKWASLWNWFNITNWLWY
IKIFIMIGGLIGLRIVFAVLSIVNRVRQGYSPISFQTRLPAPRGPDRPDGIEEEGGDRD
RDRSGRLVDGFLTLIWVDLRSLCLFSYRRLRDLLLIAARIVELLG------HRGWEALK
YWWNLLQYWIQELKNSAVNLLNTTAIAVAEGTDRVIEVVQRAYRAILNIPTRIRQGFERA
LL-
>ENV-B.syn6.4
MRVKEIRKNCQRLWRWGTML--------LGMLMICSAAEQLWVTVYYGVPVWRDANATLF
CASDAKAYDTEVHNVWATHASVPTDPNPQEVVLGNVTENFNMWKNDMVEQMHEDVISLWD
QSLKPCVKLTPICVTLNCTDYVKNIT-NNATSTNSSW-GEPMEKGEIKNCSFNITTSMKD
KVQKTYALFYKLDVVPI-DNDSNNNDSTNTNYTNYRLISCNTSVIKQACPKVSFDPIPIH
YCTPAGFAILKCRDKKFNGTGPCKNVSTVQCTHGIRPVVPTQLLLNGSLAEEEIVIRSEN
FSDNAKTIIVHLNESVEINCTRLNNNTRKSIHMGPGRAFYATGEIIGDIRQAHCNISRAK
WNNTLKQIAIKLREQFGNNKTIIFKQSSGGDPEIVTHSFNCGGEFFYCNSTQLFNSTWNF
--NGTWNKN---FNNTWNNTEGTNDTITLPCRIKQIINMWQKVGKAMYAPPISGQIRCTS
NITGLLLTRDGGN---DT--SGTEIFRPGGGNMKDNWRSELYKYKVVQIEPLGVAPTEAK
RRVVQREKRAVG-IGAVFLGFLGAAGSTMGAAAVTLTVQARLLLSGIVQQQNNLLKAIEA
QQHLLRLTVWGIKQLQARLLAVERYLGDQQLLGLWGCSGKLICTTAVPWNTSWSNRSLNE
IWNNMTWMEWEKEIDNYTNLIYNLLEESQNQQEKNEKELLELDKWANLWNWFDISNWLWY
IRIFIMIVGGLIGLRIVFIVLSVVNRVRQGYSPLSLQTRLPTQRGPDRPEGTEEEGGERD
RDTSGRLVDGFLAIIWVDLRSLFLFSYHRLRDLLLIVTRIVELLG------RRGWEILK
YWWNLLQYWGQELKNSAVSLLNATAITVAEGTDRVIEVLQRAGRAILHIPTRIRQGLERI
LL-
>ENV-B.syn6.5
MRVKGIRRNYQHLWRWGIML--------LGMLMICSATEQLWVTVYYGVPVWKEANTTLF
CASDAKAYKTEAHNVWATHASVPTDPNPQEIVLENVTENFNMWKNNMAEQMHEDIINLWD
QSLKPCVELTPLCVTLNCTDELKNATFRSNTTTNSSW--EKMEKGEIKNCSFNVTTSIRD
KMQKEYALFYRLDVVPI-DNDNTS---------YRLISCNTSVITQACPKISFEPIPIH
YCVPAGFAILKCNNKTFNGTGPCTNVSTVQCTHGIKPVVSTQLLLNGSLAEEDVVIRSEN
FTDNTKTIIVQLKEAVEINCTRPNNNTRKGIHIGPGRAFYTTGEIIGNIRQAHCNLSRAK
WNDTLKQIVIKLREQFG-NKTIVFNQSSGGDVEIVMHSFNCGGEFFYCNTTQLFNSTW--
---NANDIRN---VTRGSNRTTGGNDTLILPCRIKQIVNMWQEVGKAMYAPPIKGQIKCSS
```

Fig. 10 cont'd-4

```
NITGLLLTRDGGNNGNET--NGTEIFRPGGGDMRNNWRSELYKYKVVRIEPLGVAPTKAR
RRVVQREKRAVT-LGAMFLGFLGAAGSTMGAASMTLTVQARLLLSGIVQQQSNLLRAIEA
QQRLLQLTVWGIKQLQARILAIERYLKDQQLLGIWGCSGKIICTTAVPWNASWSNKSQDE
IWNNMTWMQWEREIDNYTGLIYNLIEESQNQQEKNEQELLALDKWANLWNWFDITKWLWY
IKIFIMIVGGLIGLRIVFTVLSIVNRVRKGYSPLSFQTRLPAQRGPDRPEGIEEEGGERD
RDRSGPLVDGFLAIFWVDLRSLFLFSYRHLRDLLLIVARIVELLG------RRGWELLK
YWWNLLQYWSQELKSSAVSLLNATAIAVAEGTDRILEVLQRAYRAILHIPVRIRQGLERA
LL-
>ENV-B.syn6.6
MRVKGIRKNYQHLWRWGMML--------FGMLMICSAAGNLWVTVYYGVPVWREATTTLF
CASDAKAYETEVHNVWATHACVPTDPSPQEVVLENVTEDFNMWKNNMVDQMHEDIISLWD
ESLKPCVKLTPLCVTLNCTDDVRNVT-NNATNTNSSW-GEPMEKGEIKFCSFNITTSIRN
KVQKQYALFYKLDVIPI-DSRNNSNNSTE--YNSYRLINCNSSTITQACPKVTFEPIPIH
YCAPAGFAILKCNNKKFNGTGPCNNVSTVQCTHGIRPVVSTQLLLNGSLAEKEVVIRSDN
FTNNAKTIIVQLNESVVINCTRPNNNTRKRISMGPGRVYYTTGEIIGDIRRAHCNISRAQ
WNNTLKHIVEKLGKQFGNNKTI-FNHSSGGDPEIVMHSFNCRGEFFYCKSTKLFNSTWTR
N-NGTWTRN---DTERSNSTE---EHITLPCRIKQIINMWQGVGKAMYAPPIRGQIRCSS
NITGLILTRDGGNNDT----RGTEIFRPGGGDMKDNWRSELYRYKVVKIEPLGIAPTKAK
RRVVQREKRAVGTIGAMFLGFLGTAGSTMGAASLTLTVQARLLLSGIVQQQNNLLRAIEA
QQHLLQLTVWGIKQLQAKVLAVERYLRDQQLLGIWGCSGRLICTTNVPWNASWSNKSLDK
IWNNMTWMEWDREINNYTSLIYSLIEESQNQQEKNEQDLLALDKWASLWNWFDITNWLWY
IKIFIMVVGGLVGLRIIFAVLSIVNKVRQGYSPLSLQTHLPARRGPDRPEGIEGEGGERD
RDRSVRLVDGFLALFWDDLRSLCLFLYHRLRDLLLIVTRTVELLG------RRGWEALK
YCWNLLQYWSQELKNSAVSLFNAIAIAVAEGTDRIIEVVQRICRAIRHIPRRIRQGFERA
LL- >ENV-C.syn1.1
MRVRGIQRNWPQWWIWGILG--------FWMLMICNVVGNLWVTVYYGVPVWKEAKTTLF
CASDAKAYEKEVHNVWATHACVPTDPNPQEIVLENVTENFNMWKNDMVDQMHEDIISLWD
QSLKPCVKLTPLCVTLNCTDVKVNATSNGTTTYNNSI-DS--MNGEIKNCSFNTTTEIRD
KKQKVYALFYRLDIVPL-DNNSSE---------YRLINCNTSTITQACPKVSFDPIPIH
YCAPAGYAILKCNNKTFNGTGPCNNVSTVQCTHGIKPVVSTQLLLNGSLAEEEIIIRSEN
LTNNAKTIIVHLNESVEIVCTRPNNNTRKSIRIGPGQTFYATGDIIGDIRQAHCNISEKQ
WDQTLYRVSEKLKEHFP-NKTIKFAPSSGGDLEITTHSFNCRGEFFYCNTSKLFNSTY--
--NSTQMHN---DTGS--NST-----ITLPCRIKQIINMWQEVGRAMYAPPIAGNITCKS
NITGLLLTRDGGTNN-----NNTETFRPGGGDMRDNWRSELYKYKVVEIKPLGIAPTKAK
RRVVEREKRAVG-IGAVFLGFLGAAGSTMGAASITLTVQARQLLSGIVQQQSNLLRAIEA
QQHMLQLTVWGIKQLQTRVLAIERYLKDQQLLGIWGCSGKLICTTAVPWNSSWSNKSQTD
IWDNMTWMQWDREISNYTDTIYRLLEDSQNQQEKNEKDLLALDSWKNLWNWFDITNWLWY
IKIFIMIVGGLIGLRIIFAVLSIVNRVRQGYSPLSFQTLTPNPRGPDRLGRIEEEGGEQD
RDRSIRLVSGFLALAWDDLRSLCLFSYHRLRDFILVTARAVELLGRSSLRGLQRGWEALK
YLGSLVQYWGLELKKSAISLLDTIAIAVAEGTDRIIELIQRICRAIRNIPRRIRQGFEAA
LL- >ENV-C.syn3.1
MRVMGIQRNCQQWWIWGSLG--------FWMLMIYNVMGNLWVTVYYGVPVWKEAKTTLF
CASDAKAYDTEVHNVWATYACVPTDPNPQEMVLENVTENFNMWKNNMVDQMHEDIISLWD
QSLKPCVKMTPLCVTLNCSNAKKD---------NTTI-DNE-MKGEIKNCSFNITTELRD
KKKQVYALFYKLDIVPL-NSNSSE---------YRLINCNTSAITQACPKVSFDPIPIH
YCAPAGYAILKCNNETFNGTGPCNNVSTVQCTHGIRPVVSTQLLLNGSLAEKEIIIRSEN
LTDNVKTIIVHLNESVEINCTRPNNNTRRSIRIGPGQAFYATGEIIGDIRQAYCNISGEK
WNETLQRVGKKLKEHFP-NKTIKFAPSSGGDLEITTHSFNCRREFFYCNTSGLFNGTY--
--NGNGTYN---GTGTDTNST-----ITIPCRIKQIINMWQEVGRAMYAPPIEGNITCKS
NITGLLLVRDGGTENNTET-NNTETFRPGGGDMRDNWRSELYRYRVVEIKPLGIAPTKAK
RRVVERGKRAVG-IGAVFLGFLGVAGSTMGAASITLTVQARQVLSGIVQQQSNLLRAIEA
QQHLLQLTVWGIKQLQTRVLAIERYLKDQQLLGIWGYSGKLICTTAVPWNSSWSNRSQED
```

Fig. 10 cont'd-5

```
IWNNMTWMQWDREINNYTNTIYRLLEDSQNQQEKNEQDLLALDSWKNLWNWFDITNWLWY
IRIFIMIVGGLIGLRIIFAVLSIVNRVRQGYSPLSLQTLTPNPRELDRLGRIEEGGGEQD
RDRSIRLVSGFLALAWDDLRSLCLFSYHRLRDFILIAARAAELLGRSSLKGLQRGWEILK
YLGSLIQYWGLELKKSAINLLDTIAIVVAEGTDRIIELIQRICRAICNIPRRIRQGFEAA
LQ-
>ENV-C.syn3.2
MRVRGILRNWQQWWIWGILG--------FWMLMICNVVGNLWVTVYYGVPVWREAKTTLF
CASDAKAYEREVHNVWATHACVPTDPNPQELVLENVTENFNMWKNDMVDQMHQDIISLWD
ESLKPCVKLTPLCVTLKCVNVTKNS--NATVNSNATV-NNNTMGEEIKNCSFNATTEIRD
KKQNVYALFYRLDIVPL-NENNDNSS--------YRLINCNTSTITQACPKVTFDPIPIH
YCTPAGYAILKCNDKTFNGTPCHNVSTVQCTHGIKPVISTQLLLNGSLAEEEIIIRSEN
LTNNVKTIIVHLNKSVEIVCTRPGNNTRKSVRIGPGQTFYATGDIIGDIRQAHCNISRTA
WNKTLQEVGKKLAEHFP-NKTIEFKPSSGGDLEVTTHSFNCRGEFFYCNTSKLFNSTYNS
TYNSTYNSN---STNSNSNST-----ITLQCRIKQIINMWQKVGRAIYAPPIAGNITCRS
NITGLLLTRDGGNNNDTGNNNDTEIFRPGGGDMKDNWRNELYKYKVVEVKPLGIAPTGAK
RRVVEREKRAVG-LGAVFLGFLGAAGSTMGAASMTLTVQARQLLSGIVQQQNNLLRAIEA
QQHMWQVTVWGIKQLQARVLALERYLKDQQLLGLWGCSGKLICTTNVPWNSSWSNKSLTD
IWENMTWMQWDKEISNYTDTIYRLLEVSQNQQEKNEKDLLALDSWNNLWNWFSITKWLWY
IKIFIMIVGGLIGLRIIFGVLSIVKRVRQGYSPLSFQTLTPNPRGPDRLGRIEEEGGEQD
KDRSIRLVNGFLALAWDDLRNLCLFSYHQLRDFILIVARAVELLGHSSLRGLQRGWEALK
YLGSLVQYWGLELKRSAISLLDTTAIAVAEGTDRIIEVIQRICRAIRNIPTRIRQGFEAA
LLQ
>ENV-C.syn3.3
MRVRGIQRNWPQWWIWGILG--------FWMIIICRVVGNLWVTVYYGVPVWTEAKATLF
CASDAKAYEKEVHNVWATHSCVPTDPNPQEIVLGNVTENFNMWENDMVDQMHEDVISLWD
QSLKPCVKLTPLCVTLNCT--------NANVTVNATSDGS--IKEEIKNCSFNTTTEIRD
KKQKVYALFYRPDIVPLSGSNSSE----------YILINCNTSTVTQACPKVSFEPIPIH
YCAPASYAILKCNNKTFNGTPCQNVSTVQCTHGIKPVVSTQLLLNGSLAEGEIIIRSEN
LTNNAKTIIVHLNESIEIVCTRPNNNTRKSIRIGPGQTFFATGDIIGNIRQAHCNISEEK
WNKTLQEVSRKLREHFP-NKTIIFNSSSGGDLEITTHSFNCGGEFFYCNTTKLFNDS---
--------------ALSAFNKTS--NETITLPCRIKQIINMWQGVGRAMYAPPIAGNITCNS
SITGLLLTRDGGT-------NNTEIFRPGGGNMKDNWRSELYKYKVVEIKPLGVAPTEAK
RRVVEREKRAVG-IGAVLLGFLGAAGSTMGAASITLTAQARQLLSGIVQQQSNLLKAIEA
QQHMLQLTVWGIKQLQARVLAIERYLQDQQLLGIWGCSGKLICTTTVPWNSSWSNKSQTD
IWDNMTWMQWDREISNYTNTIYRLLEESQNQQEQNEKDLLALDKWQNLWSWFSITNWLWY
IKIFIIIVGGLIGLRIILGVLSIVRRVRQGYSPLSFQTLIPNPRGPDRLGGIEEEGGEQD
RDRSVRLVSGFLSLAWDDLRSLCLFCYHRLRDFILVTARAVELLGRSSLRGLQKGWEALK
YLGNLVQYWGLELKKSAISLLDTIAIAVAEGTDRIIEFIQRICRAIRNIPRRIRQGLEAA
LQ-
>ENV-C.syn4.1
MRVRGILRNYQQWWIWGSLG--------FWMLMIYNVGGNLWVTVYYGVPVWKEAKTTLF
CASDAKAYDTEVHNVWATHACVPTDPDPQEIVLENVTENFNMWENDMVDQMHEDIISLWD
ESLKPCVKLTPLCVTLKCTNVTST---GNTTRGNNTS-EN---REEMKNCSFNTTTEIRD
KKQKVYALFYKPDVVPL-KENSSE----------YILINCNTSTVTQACPKVSFDPIPIH
YCAPAGFAILKCNNKTFNGTPCNNVSTVQCTHGIKPVVSTQLLLNGSLAEEEIIIRSEN
LTDNAKTIIVHLNESIEIVCTRPGNNTRKSIRIGPGQAFYATGDIIGDIRQAYCNISKAT
WNKTLQEVGKELAKHFP-NKTINFNSSSGGDLEITTHSFNCGGEFFYCNTTKLFNNSL--
--------------LNNTADNST---STITLQCRIKQIINMWQGVGQAMYAPPIAGNITCKS
NITGLLLLRDGGDTST----NGTEIFRPGGGNMKDNWRSELYKYKVVEVKPLGIAPTGAK
RRVVEREKRAVG-IGAVLLGFLGAAGSTMGAASITLTAQARQVLSGTVQQQSNLLRAVEA
QQHMLQLTVWGIKQLQTRVLAIERYLKDQQLLGIWGCSGKLICTTNVPWNSSWSNKSQEE
IWENMTWMQWDREISNYTGTIYRLLEESQNQQEKNEQDLLALDSWKNLWNWFDISNWLWY
IKIFIIIVGGLIGLRIIFGVLSIVKRVRQGYSPLSFQTLIPNPRGPDRLERIEEEGGEQD
RGRSIRLVSGFLAIAWDDLRSLCLFSYHQLRDFILIAVRAVELLGHSSLRGLQRGWEALK
YLGSLVQYWGLELKRSAISLLDTIAIVVAEGTDRIIEFIQRICRAIRNIPTRIRQGFEAA
LQ-
```

Fig. 10 cont'd-6

```
>ENV-C.syn4.2
MRVMGIQRNCQQWWIWGILG--------FWILMICNVMGNLWVTVYYGVPVWKEAKATLF
CASDAKAYEKEVHNIWATHACVPTDPNPQELVLENVTENFNMWDNDMVDQMHQDIISLWD
QSLKPCVKLAPLCVTLNCTNATVTATRNGSDIMNTTS-ND----GEMKNCSFNVTTELRD
KKKKEYALFYRLDIVPL-NEGSGNANQNNSNYSDYRLINCNTSAITQACPKVTFDPIPIH
YCTPAGYAILKCNDKTFNGTGPCHNVSTVQCTHGIRPVVSTQLLLNGSLAEGEIMIRSEN
LTNNAKTIIVHLNKSVEIVCTRPNNNTRKSVRIGPGQTFYATNDIIGDIRQAHCNISEEK
WNKTLQQVGKKLAEHFP-NKTIEFKPSSGGDLEVTTHSFNCRGEFFYCNTSGLFNGTF--
--DGT-------ESNSTSNAT-----ITIPCRIKQIINMWQKVGRAIYAPPIAGNITCRS
NITGLLLVRDGGNDNKT---NDTETFRPGGGDMRDNWRSELYKYKVVEVKPLGVAPTKAK
RRVVQREKRAVG-IGAVFLGFLGVAGSTMGAASMTLTVQARQVLSGIVQQQSNLLRAIEA
QQHLLQLTVWGIKQLQARVLALERYLRDQQLLGMWGCSGKLICTTAVPWNSSWSNKSQED
IWGNMTWMQWDKEISNYTNTIYRLLEDSQNQQERNEKDLLALDSWKNLWSWFDITNWLWY
IKIFIMIIGGLIGLRIIFAVLSIVNRVRQGYSPLSLQTLTPNPRGPDRLGRIEEEGGEQD
KDRSIRLVNGFLALAWDDLRNLCLFSYHRLRDFILIVARAVELLGRNSLRGLQRGWETLK
YLGSLIQYWGLELKKSAISLLDTTAIAVAEGTDRIIELIQRICRAICNIPRRIRQGLEAA
LQ-
>ENV-C.syn4.3
MRVRGIQRNWPQWWIWGILG--------FWMIIICRVVGNLWVTVYYGVPVWREAKTTLF
CASNAKAYEKEVHNVWATHACVPTDPNPQEIVLGNVTENFNMWKNDMVDQMHEDVISLWD
QSLKPCVKMTPLCVTLNCTDVKVNATSNGTTTYNNSI-DS--MNGEIKNCSFNTTTELRD
KKQKAYALFYRPDIVPLPGKDNSKDNSSEYEE--YILINCNSSTITQACPKVSFEPIPIH
YCAPASYAILKCNNETFNGTGPCKNVSTVQCTHGIKPVISTQLLLNGSLAEKEIIIRSEN
LTNNVKTIIVHLKESVEINCTRPNNNTRKSIRIGPGQTFYATGDIIGNIRQAHCNISREK
WNTTLKRVKEKLKEHFP-NKTIKFAPSSGGDLEITTHTFNCRGEFFYCNTSKLFNSTYV-
--NRTDMND---D--TGNNST-----ITLPCRIKQIINMWQEVGRAMYAPPIAGNITCNS
SITGLLLTRDGGNNT-----ENTETFRPGGGNMKDNWRNELYKYKVVEIKPLGVAPTEAK
RRVVEREKRAVG-LGAVFLGFLGAAGSTMGAASITLTVQARQLLSGIVQQQNNLLRAIEA
QQHMLQLAVWGIKQLQARVLAIERYLQDQQLLGIWGCSGKLICTTSVPWNSSWSNRSQED
IWNNMTWMQWDREISNYTDTIYRLLEVSQNQQEQNEKDLLALDKWQNLWSWFSITNWLWY
IRIFIMIVGGLIGLRIVFAVLSLVNRVRQGYSPLSFQTLTPSPRGPDRLGGIEEEGGEQD
RDRSIRLVSGFLSLAWDDLRSLCLFSYHRLRDFILIAARAAELLGRSSLRGLQRGWEILK
YLGSLAQYWGLELKKSAINLLDTIAIAVAEGTDRIIEVIQRICRAIYNIPRRIRQGFEAS
LL-
>ENV-C.syn4.4
MRVRGIPRNWQQWWIWGILG--------FWMLMICNVVGNLWVTVYYGVPVWTEAKTTLF
CASDAKAYEREVHNVWATYACVPTDPNPQEMVLENVTENFNMWKNDMVEQMHEDIISLWD
QGLKPCVKLTPLCVTLNCSNAKKD--------NTTI-DNE-MKGEIKNCSFNITTELRD
KKQQVYALFYKLDIVPL-NSNSSE---------YRLINCNTSTITQACPKVNFDPIPIH
YCAPAGYAILKCNNKTFNGTGPCQNVSTVQCTHRIKPVVSTQLLINGSLAEGEIIIRSEN
LTDNVKTIIVHLNESVEIVCTRPNNNTRKSMRIGPGQTFYATGEIIGDIRQAHCNISKEK
WNNTLQEVREKLREHFP-NKTIKFAPHSGGDPEITTHSFNCRGEFFYCNTSQLFNSTY--
--NSTQMHN---DTGS--NST-----ITLPCKIKQIINMWQGVGRAMYAPPIEGNITCTS
NITGLLLTRDGGT-------NNTEIFRPGGGDMRNNWRSELYKYKVVEIKPLGIAPTKAK
RRVVERGKRAVG-IGAVLFGFLGAAGSTMGAASIALTAQARQLLSGIVQQQSNLLKAIEA
QQHMWQVTVWGIKQLQARVLAMERYLKDQQLLGLWGCSGKLICTTTVPWNSSWSNKSQTD
IWDNMTWMQWDREINNYTNTIYKLLEDSQNQQEKNEKDLLALDSWNNLWNWFSITKWLWY
IKIFIMIVGGLIGLRIILGVLSIVRRVRQGYSPLSFQTLTPNPRELDRLGRIEEGGGEQD
RDRSVRLVSGFLALAWDDLRSLCLFCYHRLRDFILVTARAVELLGRSSLKGLQRGWEALK
YLGNLVQYWGLELKKSAISLFDTIAITVAEGTDRIIELVQRICRAIRNIPRRIRQGFEAA
LL-
>ENV-C.syn6.1
MRVRGIQRNWPQWWIWGILG--------FWIIIMCRVMGNMWVTVYYGVPVWREAKTTLF
CASDAKGYEKEVHNAWATHACVPTGPNPQEMVLENVTENFNMWKNNMVDQMHEDIINLWD
QSLKPCVRLTPLCVTLKCVNVTKNS--NATVNSNATV-NNNTMGEEIKNCSFNATTEIRD
KKQKAYALFYRPDIVPL-NENSSSENNSSE----YILINCNTSTITQACPKVSFDPIPIH
YCAPASYAILKCNNETFNGTGPCQNVSTVQCTHGIKPVISTQLLLNGSLAEEDIIIRSEN
```

Fig. 10 cont'd-7

```
LTNNAKTIIVHLNQSVEIVCTRPGNNTRKSMRIGPGQTFYATNDIIGNIRQAHCNISEGK
WNETLLRVKKKLEEHFP-NKTIKFEPSSGGDLEITTHTFNCRGEFFYCDTSTLFNHTY--
---VSAYMNNTDVSADRKNDTQ-SNSTITLPCRIRQIINMWQEVGRAIYAPPIAGNITCRS
NITGLLLVRDGGNTT-----NSTETFRPEGGNMKDNWRSELYKYKVVEIRPLGIAPTGAK
RRVVEREKRAVG-IGAVFLGFLGVAGSTMGAASMTLTVQARQVLSGVVQQQSNLLQAIEA
QQHLLQLTVWGIKQLQTRVLALERYLRDQQLLGIWGCSGKIICTTAVPWNTSWSNKSQED
IWNNMTWMQWDREINNYTNTIYKLLEESQNQQEKNEQDLLALDSWNSLWNWFSITKWLWY
IRIFIIIVGSLIGLRIIFGVLSIVKRVRQGYSPLLSQTLTPNPREPDRLGRIEEGGGEQD
RDRSVRLVNGFLALVWDDLRSLCLFCYHRLRDFILVTARVVELLGRSSLRGLQKGWEALK
YLGSLVQYWGLELKKSAINLLDTIAIAVGEGTDRIIEVIQRICRAIYNIPRRIRQGFEAS
LL-
>ENV-C.syn6.2
MRVRGILRNYQQWWIWGSLG--------FWMLMIYNVGGNLWVTVYYGVPVWTDAKTTLF
CASDAKAYDKEVHNVWATHACVPTDPNPQELVLENVTENFNMWKNDMVNQMHEDIISLWD
ESLKPCVKLTPLCVTLNCTNATVTATRNGSDIMNTTS-ND----GEMKNCSFNITTELRD
KKRKEYALFYRLDIVPL-DENNSSEKSSENSSEYYRLINCNTSAITQACPKVTFDPIPLH
YCAPAGYAILKCKDKTFNGTGPCSNVSTVQCTHGIKPVVSTRLLLNGSLAEGEIIIRSEN
LTNNVKTIIVHLKEPVEINCTRPNNNTRESIRIGPGQTFYATGDIIGDIRQAHCNISREK
WNKTLQEVGKKLAEHFP-NKTIKFAPHSGGDLEITMHSFNCRGEFFYCNTSGLFNGTY--
---MPTYMPN---GTESNSNST-----ITIPCRIKQIINMWQEVGRAMYAPPIEGNITCNS
NITGLLLVRDGGINKT----NNTETFRPGGGDMRNNWRSELYKYKVVEIKPLGVAPTEAK
RRVVEREKRA-A-LGAMFLGFLGAAGSNMGAASITLTAQARQLLSGIVQQRSNLLRAIEA
QQHLLQLTVWGVKQLQARVLAMERYLKDQQLLGLWGCSGKLICTTSVPWNSSWSNRSQEE
IWNNMTWMEWDREISNYTNTIYRLLEDSQNQQEKNEKDLLALDSWKNLWSWFDITNWLWY
IKIFIMIIGGLIGLRIVFAVLSIVNRVRQGYSPLSFQTLTPSPRGPDRLGRIEEEGGEQD
KDRSVRLVSGFLSLAWDDLRSLCLFSYHRLRDLILIAARAVELLGHSSLRGLQRGWEILK
YLGSLAQYWGLELKRSAISLLDTIAITVAEGTDRIIEIIQRICRAICNIPRRIRQGFETA
LL-
>ENV-C.syn6.3
MRVMGILRNCQQWWIWGVLG--------FWMLMICNVVGNLWVTVYYGVPVWKEAKTTLF
CASNAKAYEREVHNIWATHACVPTDPNPQEMVLKNVTENFNMWKNDMVDQMHEDVISLWD
QSLKPCVKLAPLCVTLNCTNVTVNDTLHQNFT------------DMKNCSFNVTTELRD
KKQKVYALFYRLDVVPL-GDNNSS----------YRLINCNTSTIAQACPKVNFDPIPIH
YCTPAGYAILKCNDKTFNGTGPCKNVSTVQCTHEIKPVVSTQLLLNGSLAEEGIIIRSEN
LTDNAKTIIVHLNESVEINCTRPGNNTRQSIRIGPGQAFYATGAIIGDIRQAHCNISKDE
WEKTLKRVSEKLKEHFP-NKTIEFKPSSGGDLEVTTHSFNCRREFFYCNTSKLFNSTY--
---NSTQMHN---DTGS--NST-----ITLPCKIKQIINMWQGVGQAMYAPPIKGNITCKS
NITGILLTRDGGNLT-----NGTETFRPGGGDMKDNWRSELYRYRVVEIKPLGIAPTKAK
RRVVQREKRAVG-IGALFLGFLGTAGSTMGAASLTLTVQARQLLSSIVQQQSNLLRAIEA
QQHMLQLTIWGIKQLQTRVLAVERYLKDQQLLGMWGCSGKLICTTAVPWNASWSNKSQEE
IWGNMTWMQWDREISNYTDIIYRLLEESQNQQERNEKDLLALDSWNNLWNWFNITNWLWY
IKIFIMIVGGVIGLRIIFAVLSLVNRVRQGYSPLSFQTLTPNPRELDRLGRIEEEGGEQG
RDRSIRLVNGFLAIAWDDLRSLCLFSYRRLRDFILIAARAAELLGRSSLRGLQRGWETLK
YLGSLIQYWGLELKKSAISLFDTIAIAVAEGTDRIIELIQRICRAIRNIPRRIRQGLEAA
LQ-
>ENV-C.syn6.4
MRVMGIQRNCQQWWIWGILG--------FWMLMIYNVVGNLWVTIYYGVPVWKEAKATLF
CASDAKAYDTEVHNVWATHACVPTDPDPQEMVLGNVTENFNMWKNDMADQMHEDIISLWD
QGLKPCVKLTPLCVTLHCTN------TNITNENRTI-GDKLNE-EMKNCSFNTTTELRD
KKQQVYALFYKPDVVPL-NGGEHNETGE------YILINCNSSTITQACPKVSFEPIPIH
YCAPAGFAILKCNNKTFNGTGPCHNVSTVQCTHGIRPVVSTQLLLNGSLAEEEIIIRSEN
LTDNVKTIIVHLNKSVEIVCTRPNNNTRKSIRIGPGQTFFATNDIIGDIRQAYCNISAEK
WNKTLERVEEKLKEHFP-NKTIKFNSSSGGDLEITTHSFNCRGEFFYCNTSNLFNGTY--
---HGTQSTN---ST----NST-----ITLQCRIKQIINMWQKVGRAMYAPPIAGNITCKS
NITGLLLLRDGGTEN-----NDTETFRPGGGNMRDNWRSELYKYKVVEVKPLGIAPTTAK
RRVVERDKRAVG-IGAVLLGFLGAAGSTMGAASMALTVQARQLLSGIVQQQSNLLRAVEA
```

Fig. 10 cont'd-8

QQHMLQLTVWGIKQLQARVLALERYLKDQQLLGIWGCSGRLICTTAVPWNSSWSNKTQGE
IWENMTWMQWDKEINNYTNTIYRLLEESQTQQEQNEKDLLALDSWKNLWNWFDITKWLWY
IKIFIMVVGGLIGLRIIFAVLSIVNSVRQGYSPLSLQTLTPNPRGPDRLERIEEEGGEQD
RNRSIRLVNGFLALAWDDLRSLCLFSYHHLRDFILVTARAVELLGRSSLKGLQRGWEALK
YLGNLVQYWGLELKKSAISLLDTTAIAVAEGTDRIIELVQRICRAILNIPTRIRQGFEAA
LQ-
>ENV-C.syn6.5
MRVRGIPRNWPQWWTWGILG--------FWMIIICRVVGNLWVTVYYGVPVWTEAKTTLF
CASDAKAYEREVHNVWATHSCVPTDPNPQEIVLGNVTENFNMWENDMVDQMHQDIISLWD
QSLKPCVKMTPLCVTLNCSNAKKD---------NTTI-DNE-MKGEIKNCSFNITTEIRD
KKQKVHALFYRLDIVPL-NEGSGNANQNNSNYSDYRLINCNTSTVTQACPKVTFDPIPIH
YCAPARYAILKCNNNTFNGTGPCNNVSTVQCTHGIKPVVSTQLLLSGSLAEEEIVIRSEN
LTNNAKIIIVHLNESVEIVCTRPNNNTRRSIRIGPGQTFYATGEIIGDIRQAHCNISAKQ
WNTTLERVKEKLREHFP-NKTIKFEPHSGGDPEITTHSFNCGGEFFYCNTSQLFNSTY--
---NSTYMSN---NTGENSNET-----ITLPCRIKQIINMWQQVGRAMYAPPIAGNITCNS
SITGLLLTRDGGNNNDTGNNNDTEIFRPGGGDMRDNWRSELYKYKVVELKPLGIAPTEAK
RRVVKREKRAVG-IGAVLFGFLGAAGSTMGAASIALTAQARQVLSGIVQQQNNLLRAIEA
QQHVLQLTVWGIKQLQTRVLAIERYLKDQQLLSLWGCSGKLICTTTVPWNSSWSNKSLTD
IWDNMTWMQWDREISNYTGTIYRLLEDSQSQQEKNEKDLLELDKWNNLWNWFDISNWLWY
IKIFIIIVGGLIGLRIIFAVLSIINRVRQGYSPLLFQTLTPNPRGLDRLGRIEEEGGEQD
KDRSIRLVNGFLALAWEDLRSLCLFSYHQLRDFILIVARAVELLG------RRGWEALK
YLGNLVLYWGLELKKSAVSLLDTIAIAVAGGTDRIIEVVQRICRAIRNIPTRIRQGLEAA
LL-
>ENV-C.syn6.6
MRVRGILRNWQQWWIWGILG--------FWMVMICNVMGNLWVTVYYGVPVWQEAKTTLF
CASDAKAYEKEVHNVWATHACVPTDPSPQEIVLENVTENFNMWKNDMVEQMHEDIISIWD
QSLKPCVTLTPLCVTLNCTDVKVNATSNGTTTYNNSI-DS--MNGEIKNCSFNTTTEIRD
KKKQVYALFYKLDIVPL-NSNSSE----------YRLINCNTSAVTQACPKVSWDPIPIH
YCAPAGYAILKCNNKTFNGTGPCTNVSTVQCTHRIKPVVTTQLLLNGSLAEKEIIIRSEN
LTNNIKTIIVHLNESIEIVCTRPNNNTRKSVRIGPGQTFFATGDIIGDIRKAHCNISEDK
WNETLQRVGKKLVEHFP-NKTIKFAPSSGGDLEVTTHSFNCKGEFFYCNTTKLFD-----
--------------DSERINTTT---TTIILPCRIKQFINMWQGVGRAMYAPPIAGNITCTS
NITGLLLTRDGGT-------NNTEIFRPGGGNMKDNWRNELYKYKVVEVKPLGVAPTKAK
RRVVEREKRAVG-LGAVFLGFLGAAGSTMGAASITLTVQARQLLFGIVQQQSNLLKAIEA
QQHMWQVTVWGIKQLQARVLAIERYLQDQQLLGIWGCSGKLICTTNVPWNSSWSNKSQTD
IWDNMTWMQWDKEISNYTDTIYRLLEVSQNQQEENEKDLLALDKWQNLWNWFSITNWLWY
IRIFIMIVGGLIGLRIILGVLSIVRRVRQGYSPLSFQTLIPNPRGPDRLGGIEEEGGEQD
RDRSIRLVSGFLALAWDDLRNLCLFSYHRLRDFILIVVRAVELLGRNSLRGLQRGWEALK
YLGSLGQYWGLEIKKSAISLLDTIAIVVAEGTDRIIEFIQRFCRAIRNLPRRIRQGFEAA
LL-
>ENV-M.syn1.1
MRVTGIRKNYQHLWRWGTMLLWRWGTMLLGMLMICSAAGNLWVTVYYGVPVWKEATTTLF
CASDAKAYDTEVHNVWATHACVPTDPNPQEVVLENVTENFNMWKNNMVEQMHEDIISLWD
QSLKPCVKLTPLCVTLNCTDDVRNVT-NNATNTNSSW-GEPMEKGEIKNCSFNITTSIRD
KVQKEYALFYKLDVVPI-DNDSNNTN--------YRLISCNTSVITQACPKVSFEPIPIH
YCAPAGFAILKCNDKKFNGTGPCTNVSTVQCTHGIKPVVSTQLLLNGSLAEEEVVIRSEN
FTNNAKTIIVQLNESVEINCTRPNNNTRKSIRIGPGQTFYATGDIIGDIRQAHCNISRAQ
WNNTLKHIVEKLGKQFGNNKTIVFNHSSGGDPEIVMHSFNCGGEFFYCNTTKLFNSTWTR
N-NGTWTRN---DTERSNSTE---EHITLPCRIKQIINMWQEVGKAMYAPPIRGQIRCSS
NITGLLLTRDGGNDT-----SGTEIFRPGGGDMRDNWRSELYKYKVVKIEPLGVAPTKAK
RRVVQREKRAVG-IGAVFLGFLGAAGSTMGAASITLTVQARQLLSGIVQQQNNLLRAIEA
QQHLLQLTVWGIKQLQARVLAVERYLKDQQLLGIWGCSGKLICTTAVPWNSSWSNKSLNE
IWNNMTWMEWEREIDNYTGLIYTLIEESQNQQEKNEQELLELDKWASLWNWFDISNWLWY
IKIFIMIVGGLIGLRIVFAVLSIVNRVRQGYSPLSFQTRLPAPRGPDRPEGIEEEGGERD
RDRSIRLVSGFLALAWDDLRSLCLFSYHRLRDLLLIVTRIVELLG-------RRGWEALK

Fig. 10 cont'd-9

```
YWWNLLQYWSQELKNSAVSLLNATAIAVAEGTDRVIEALQRACRAILHIPRRIRQGLERA
LL-
>ENV-M.syn3.1
MRVRGIQRNWPQWWIWGILG--------FWMLMICNVVGNLWVTVYYGVPVWKEAKTTLF
CASDAKAYEKEVHNVWATYACVPTDPNPQEIHLENVTEEFNMWKNDMVDQMHEDIISLWD
QSLKPCVQLTPLCVTLNCTN-VNVTNLKNETNTKSSSGGEKMEEGEMKNCSFNITTSIRD
KVQKEYALFYKLDVVPI-DNDSNNTN--------YRLISCNTSVITQACPKVTFEPIPIH
YCTPAGFAILKCKDKKFNGTGPCKNVSTVQCTHGIKPVISTQLLLNGSLAEEEIIIRSEN
ITNNAKTIIVQLNESVEINCTRPGNNTRKSVRIGPGQTFYATGEIIGDIRQAHCNLSRAK
WNDTLKQIVIKLREQFG-NKTIVFNQSSGGDPEIVMHSFNCGGEFFYCNTTQLFNSTW--
---------N---STSLFNSTN---GTITLQCRIKQIINMWQEVGKAMYAPPIEGNITCKS
NITGLLLVRDGGT---EP--NDTETFRPGGGNMKDNWRSELYKYKVVKIEPLGVAPTKAK
RRVVQREKRAVGTIGAMFLGFLGAAGSTMGAASMTLTVQARLLLSGIVQQQNNLLRAIEA
QQHLLQLTVWGIKQLQARILAVERYLKDQQLLGLWGCSGKLICTTAVPWNTSWSNKSQTD
IWDNMTWMEWEREIDNYTGLIYTLIEESQNQQEKNEQELLELDKWASLWNWFDITKWLWY
IKIFIMIVGGLVGLRIVFAVLSIVNRVRKGYSPLSFQTLTPNPRGPDRLGRIEEEGGEQD
RDRSIRLVSGFLALAWDDLRSLCLFSYHQLRDFILIVARAVELLGRSSLRGLQRGWEALK
YLGSLVQYWGLELKKSAISLLDTIAIAVAEGTDRIIEVIQRICRAIRNIPRRIRQGFERA
LL-
>ENV-M.syn3.2
MRVTGIRKNYQHLWRWGTMLLWRWGTMLLGILMICSAAGKLWVTVYYGVPVWRDAETTLF
CASDAKAHETEVHNIWATHACVPTDPNPQEVVLGNVTENFNMWKNNMVEQMHEDIISLWD
ESLKPCVKLTPICVTLNCTDDVRNVT-NNATNTNSSW-GEPMEKGEIKNCSFNMTTELRD
KKQKVHALFYKLDIVPL-NSNSSE----------YRLINCNTSAITQACPKVSFEPIPIH
YCAPAGFAILKCNDKKFNGTGPCTNVSTVQCTHGIRPVVSTQLLLNGSLAEEEVVIRSEN
FTNNAKTIMVQLNVSVEINCTRPNNNTRKSIHIGPGRAFYTTGDIIGDIRQAHCNISRAQ
WNNTLKHIVEKLGKQFGNNKTIVFNHSSGGDPEITTHSFNCGGEFFYCNSTKLFNSTWTR
N-NGTWTRN---DTERSNSTE---EHITLPCRIKQIVNMWQRVGQAMYAPPIRGQIRCSS
NITGLLLTRDGGNDT-----SGTEIFRPGGGDMRNNWRNELYKYKVVRIEPLGVAPTRAK
RRVVEREKRAVG-LGAVFLGFLGAAGSTMGAASLTLTVQARQVLSGIVQQQSNLLKAIEA
QQHLLKLTVWGIKQLQARVLAVERYLRDQQLLGIWGCSGKLICTTTVPWNASWSNKSLNE
IWNNMTWMEWEKEIDNYTNLIYNLLEESQNQQEKNEQDLLALDKWANLWNWFDISNWLWY
IKIFIIIVGGLIGLRIVFAVLSIINRVRQGYSPLSLQTLIPNPRGPDRPGGIEEEGGEQG
RDRSIRLVNGFLALAWDDLRNLCLFSYHRLRDLLLIVTRIVELLG-------RRGWEALK
YWWNLLQYWSQELKNSAISLLNATAVAVAEGTDRVIEALQRACRAILHIPRRIRQGLERL
LL-
>ENV-M.syn3.3
MRVKETRKNYQHLWKWGTML--------LGMLMICSAAEQLWVTVYYGVPVWKEATTTLF
CASDAKAYDTEVHNVWATHACVPTDPSPQEVVLENVTENFNMWKNDMVEQMHTDIISLWD
QSLKPCVKLTPLCVTLNCTDYVKNIT-NNATSTNSSW-GKPMEKGEIKNCSFNITTSIRN
KVQKQYALFYKLDIVPI-DNDNTS----------YRLINCNTSTITQACPKVSFDPIPIH
YCAPAGYAILKCNNKTFNGTGPCNNVSTVQCTHGIKPVVSTQLLLNGSLAEGEIIIRSEN
LTNNAKTIIVHLNKSVEINCTRPSNNTRKSIRIGPGQAFYATGDIIGDIRKAHCNISGTK
WNHTLEQVMEELKKHFP-NKTIKFNSSSGGDLEITTHSFNCRGEFFYCNTSGLFNSTW--
--NDTTINR----TEGSNNTR----NITLPCRIKQIINMWQGVGRAMYAPPIAGNITCKS
NITGILLTRDGGNNN-----STNETFRPGGGDMRDNWRSELYKYKVVEIKPLGIAPTKAK
RRVVEREKRAVG-IGAVFLGFLGTAGSTMGAASITLTVQARQLLSGIVQQQSNLLRAIEA
QQHMLQLTVWGIKQLQTRVLAIERYLKDQQLLGIWGCSGKLICTTNVPWNSSWSNKSQSE
IWDNMTWMQWDREISNYTDTIYRLLEDSQNQQEKNEKDLLALDSWKNLWNWFDITNWLWY
IRIFIMIVGGLIGLRIIFAVLSIVNRVRQGYSPLSFQTRLPAPRGPDRPEGIEEEGGERD
RDRSVRLVDGFLALIWDDLRSLCLFSYHRLRDFILIAARTVELLGHSSLKGLRLGWEGLK
YLWNLLQYWIQELKNSAVSLLNATAIAVAEGTDRVIEVVQRAYRAILHIPTRIRQGLERA
LL-
```

Fig. 10 cont'd-10

```
>ENV-M.syn4.1
MRVKETRKNYQHLWKWGTML--------LGMLMICSAAEQLWVTVYYGVPVWKEATTTLF
CASDAKAHETEVHNIWATHACVPTDPNPQEVVLGNVTENFNMWKNDMVEQMHTDIISLWD
QSLKPCVELTPLCVTLHCTDL------GNATNT--------MEKGEIKNCSFNMTTELRD
KKQKVYALFYRLDIVPI-DNDNTS----------YRLINCNTSVIKQACPKVTFEPIPIH
YCTPAGFAILKCNDKNFNGTGPCKNVSTVQCTHGIRPVVSTQLLLNGSLAEKEIIIRSEN
LTDNAKTIIVHLNKSVEINCTRPSNNTRKSVRIGPGQTFYATGDIIGDIRQAHCNISRAK
WNNTLKQIVTKLREQFK-NKTIVFNQSSGGDLEITTHSFNCRGEFFYCNTTQLFNSTW--
--------KN---DTEVSNNTK-GNDTITLPCRIKQIVNMWQEVGRAMYAPPIEGNITCNS
NITGILLTRDGGNNGNET--NGTEIFRPGGGNMRDNWRNELYKYKVVEIKPLGVAPTEAK
RRVVEREKRAVG-IGAVFLGFLGAAGSTMGAASITLTVQARQLLTGIVQQQSNLLRAIEA
QQHMLQLTVWGIKQLQTRVLAIERYLKDQQLLGLWGCSGKLICTTAVPWNSSWSNKTYND
IWDNMTWMQWDREISNYTDTIYRLLEDSQNQQEKNEKDLLALDSWKNLWNWFDITNWLWY
IKIFIMIVGGLIGLRIIFAVLSIVNRVRQGYSPLSFQTLTPNPRGPDRPGGIEEEGGEQG
RDRSIRLVNGFLALAWDDLRNLCLFSYHQLRDFILIVARAVELLGRSSLRGLQRGWEALK
YLGSLVQYWGLELKKSAISLLDTIAIAVAEGTDRVIEVVQRAYRAILHIPTRIRQGLERL
LL-
>ENV-M.syn4.2
MRVRGIQRNWPQWWIWGILG--------FWMLMICNVVGNLWVTVYYGVPVWKEAKTTLF
CASDAKAYEKEVHNVWATHACVPTDPSPQEVVLENVTENFDMWKNNMVEQMQEDVISLWD
QSLKPCVKLAPLCVTLNCTDYVKNIT-NNATSTNSSW-GKPMEKGEIKFCSFNITTSIRN
KVQKQYALFYKLDVVQM-DEDNTS----------YRLISCNTSTITQACPKVTFDPIPIH
YCAPAGFAILKCNNKTFNGTGPCTNVSTVQCTHGIKPVVSTQLLLNGSLAEEEIIIRSEN
LTNNAKTIIVHLNESVEIVCTRPNNNTRKSIHIGPGRAFYATGEIIGDIRQAHCNLSRAK
WNDTLKQIVIKLREQFG-NKTIIFNQSSGGDPEITTHSFNCGGEFFYCNSTQLFNSTWNF
--NGTWNKN---FNNTWNNTEGTNDTITLPCKIKQIINMWQRVGQAMYAPPISGQIRCSS
NITGLILTRDGGN---DT--SGTEIFRPGGGDMRDNWRSELYKYKVVKIEPLGVAPTKAK
RRVVQREKRAVG-IGALFLGFLGAAGSTMGAASMTLTVQARQLLSGIVQQQSNLLKAIEA
QQHLLQLTVWGIKQLQARILAVERYLKDQQLLGIWGCSGKLICTTTVPWNASWSNKSLNE
IWDNMTWMEWEREIDNYTGLIYNLIEESQTQQEKNEQELLELDKWASLWNWFDITKWLWY
IKIFIMIIGGLIGLRIVFTVLSIVNRVRKGYSPLSFQTLTHHQREPDRPERIEEGGGEQD
RDRSGRLVDGFLAIIWVDLRSLCLFSYHRLRDLLLIVTRIVELLG------RRGWEVLK
YWWNLLQYWSQELKNSAVSLLNATAIAVAEGTDRIIEVIQRICRAIRNIPRRIRQGLERA
LL-
>ENV-M.syn4.3
MRVKETQMNWPNLWKWGTLI--------LGLVIICSASDNLWVTVYYGVPVWKDAETTLF
CASDAKAYDTEVHNVWATYACVPTDPNPQEIHLENVTEEFNMWKNDMVDQMHEDIISLWD
ESLKPCVKLTPLCVTLNCTDDVRNVT-NNATNTNSSW-GEPMEKGEIKNCSFNITTSIRD
KVQKEYALFYKLDVVPI-DNDSNNTN--------YRLISCNTSVITQACPKVSFEPIPIH
YCAPAGYAILKCNDKKFNGTGPCNNVSTVQCTHGIKPVVTTQLLLNGSLAEGEIIIRSEN
ITNNAKTIIVQLNESVVINCTRPNNNTRKSIRIGPGQAFYATGDIIGNIRQAHCNISRAN
WNNTLRQIVEKLGEQFGNNKTIVFNHSSGGDPEIVTHSFNCAGEFFYCNTTKLFNSTWTR
N-NGTWTRN---DTERSNSTE---EHITLPCRIKQIINMWQEVGKAMYAPPIRGQIRCSS
NITGLLLTRDGGNNN-----STNETFRPGGGNMKDNWRSELYKYKVVQIEPLGIAPTKAK
RRVVEREKRAVG-LGAVFLGFLGTAGSTMGAASLTLTVQARQVLSGIVQQQRNLLRAIEA
QQHLLKLTVWGIKQLQARVLAIERYLQDQQLLGMWGCSGKLICTTNVPWNSSWSNKSQTD
IWDNMTWLQWDKEISNYTSLIYTLIEESQNQQEKNEQDLLALDKWASLWSWFDISNWLWY
IKIFIIIVGGLIGLRIVFAVLSIINRVRQGYSPLSLQTLIPNPRGPDRLGRIEEEGGEQD
RDRSIRLVSGFLALAWDDLRSLCIFSYHRLRDFILIAARTVELLGHSSLKGLRLGWEGLK
YLGNLLLYWGQELKNSAINLLDTIAIAVAGWTDRVIEIGQRAGRAILNIPRRIRQGFERA
LL-
>ENV-M.syn4.4
MRVTGIRKNYQHLWRWGTMLLWRWGTMLLGILMICSAAGKLWVTVYYGVPVWRDADTTLF
CASDAKAYDTEAHNVWATHASVPTDPNPQEIVLENVTENFNMWKNNMVEQMHEDIISLWD
QSLKPCVQLTPLCVTLNCTN-VNVTNLKNETNTKSSSGGEKMEEGEMKNCSFNITTEIRD
KKQKVHALFYKLDIVPL-NSNSSE----------YRLINCNTSAITQACPKVSFDPIPIH
```

Fig. 10 cont'd-11

```
YCTPAGYAILKCNNKKFNGTGPCKNVSSVQCTHGIKPVISTQLLLNGSLAEEEVVIRSEN
FTNNAKTIMVQLNVSVEINCTRPNNNTRRSIPIGPGRAFYTTGDIIGDIRKAHCNISRAQ
WNNTLKHIVEKLGKQFGNNKTIIFKPSSGGDPEIVMHSFNCGGEFFYCNTSGLFNSTW--
---------N---STSLFNSTN---GTITLQCRIKQIINMWQGVGRAMYAPPIAGNITCKS
NITGLLLVRDGGT---EP--NDTETFRPGGGDMKDNWRSELYKYKVVRIEPLGVAPTRAK
RRVVEREKRAIG-LGAMFLGFLGAAGSTMGAASVTLTVQARLLLSGIVQQQNNLLRAIEA
QQHLLRLTVWGIKQLQARVLAVERYLRDQQLLGIWGCSGKIICTTAVPWNTSWSNRSLNE
IWNNMTWMEWEKEIDNYTNLIYNLLEESQNQQEKNEQELLALDKWANLWNWFDISNWLWY
IRIFIMIVGGLVGLRIVFAVLSIVKRVRQGYSPLSFQTRLPAPRGPDRPEGIEEEGGERD
RDRSVRLVDGFLALIWDDLRSLCLFSYHHLRDLLLIVARIVELLG-------RRGWEALK
YWWNLLQYWIQELKNSAISLLNATAVAVAEGTDRVIEALQRACRAILHIPRRIRQGFEAA
LL-
>ENV-M.syn6.1
MRVMGIQRNCQQWWIWGILG--------FWMLMICNVMGNLWVTVYYGVPVWKEANTTLF
CASDAKAYEREVHNVWATHASVPTDPNPQEVVLENVTEDFNMWKNNMVEQMQEDVISLWD
QSLQPCVKLTPLCVTLNCTD-LRNATNGNDTNTTSSS-REMMGGGEMKNCSFNITTEIRD
KKQKVYALFYKLDVVPI-DNDSNNTN--------YRLISCNTSAVTQACPKVTFDPIPIH
YCTPAGFAILKCRDKKFNGTGPCNNVSTVQCTHGIKPVVTTQLLLNGSLAEEEIVIRSEN
FTDNAKTIIVQLKEAVEINCTRPNNNTRKGIHIGPGRAFYATGEIIGDIRQAHCNVSRSE
WNKTLQQVATQLRKHF--NKTIIFNSSSGGDLEITTHSFNCRGEFFYCNTSGLFNSTW--
---NDTTINR----TEGSNNTR----NITLPCRIKQFINMWQEVGRAMYAPPIAGNITCRS
NITGLLLTRDGGNNGNET--NGTEIFRPGGGDMRNNWRSELYKYKVVEIKPLGIAPTKAR
RRVVQREKRAVG-IGAVFLGFLSAAGSTMGAASITLTVQARQLLTGIVQQQSNLLKAIEA
QQHMLQLTVWGVKQLQARVLAVERYLRDQQLLGIWGCSGRLICTTAVPWNTSWSNKSLNE
IWDNMTWMEWEREIDNYTSLIYTLIEESQNQQEKNEQELLELDKWANLWNWFSITNWLWY
IRIFIMIVGGLIGLRIIFGVLSIVKRVRQGYSPLSFQTRLPAPRGPDRPEGIEEEGGERD
RDRSGRLVDGFLALIWDDLRSLCLFSYHRLRDLILIAARIVELLGHSSLKGLRLGWEALK
YLWNLLLYWGQELKNSAISLLNTTAIVVAEGTDRVIEVLQRAGRAILNIPRRIRQGFEAA
LL-
>ENV-M.syn6.2
MRVTGIRKNYQHLWRWGTMLLWRWGTMLLGILMICSAAGKLWVTVYYGVPVWREAKTTLF
CASDAKAYEKEVHNVWATYACVPTDPNPQEMVLENVTENFNMWKNNMVDQMHEDIISLWD
ESLKPCVKLTPLCVTLHCTDL------GNATNT--------MEKGEIKNCSFNTTTEIRD
KKQKVHALFYRLDVVPI-DNDNTS----------YTLINCNTSVITQACPKVTFEPIPIH
YCAPAGFAILKCNNKKFNGTGPCTNVSTVQCTHGIRPVVSTQLLLNGSLAEGEIIIRSEN
LTDNAKTIIVHLNESVEIVCTRPNNNTRKSVRIGPGQTFYATGAIIGDIRQAYCNISRAK
WNNTLKQIVTKLREQFGNNKTIIFKPPSGGDLEITMHHFNCRGEFFYCNTTQLFNSTWNF
--NGTWNKN---FNNTWNNTEGTNDTITLPCKIKQIINMWQGVGRAMYAPPISGQIRCSS
NITGLLLTRDGGT------NNTEIFRPGGGNMRDNWRSELYKYKVVKIEPLGVAPTKAK
RRVVQREKRAVG-IGALFLGFLGAAGSTMGAASMTLTVQARQVLSGIVQQQRNLLRAIEA
QQHLLQLTVWGIKQLQARILAVERYLKDQKFLGLWGCSGKIICTTAVPWNASWSNKSLDD
IWNNMTWMQWEREIDNYTGLIYSLIEESQTQQEKNEQELLQLDKWASLWNWFDITNWLWY
IRLFIMIVGGLVGLRIVFTVLSIVNRVRKGYSPLSFQTLTHHQREPDRPERIEEGGGEQG
RDRSVRLVSGFLALFWDDLRSLCLFCYHRLRDFILIAARTVELLGHSSLKGLRRGWEGLK
YLWNLLQYWIQELKNSAISLLNATAVAVAEGTDRVIEALQRACRAILHIPRRIRQGLERL
LL-
>ENV-M.syn6.3
MRVRGIQRNWPQWWIWGILG--------FWMIIICRVVGNLWVTVYYGVPVWKDAETTLF
CASDAKSYETEAHNIWATHACVPTDPSPQEVVLGNVTENFNMWKNDMVEQMHEDIISLWD
QSLKPCVELTPLCVTLNCTDDVRNVT-NNATNTNSSW-GEPMEKGEIKNCSFNITTSIRN
KVQKQYALFYKLDVVQI-DDNNSTNTS-------YRLINCNTSAITQACPKVSFDPIPIH
YCAPAGYAILKCNNKTFNGTGPCHNVSTVQCTHGIRPVISTQLLLNGSLAEEEVVIRSEN
FTNNAKTIMVQLNVSVEINCTRPNNNTRKSIHIGPGRAFYTTGDIIGDIRQAHCNISRAQ
WNNTLKHIVEKLGKQFGNNKTIIFKPSSGGDPEIVMHSFNCRGEFFYCNTSKLFNSTWTR
N-NGTWTRN---DTERSNSTE---EHITLPCRIKQIINMWQRVGQAMYAPPIAGNITCNS
SITGLLLTRDGGN---DT--SGTEIFRPGGGNIKDNWRSELYKYKVVQIEPLGVAPTRAK
```

Fig. 10 cont'd-12

```
RRVVEREKRAVG-IGAMIFGFLGAAGSTMGAASMALTVQARQLLSGIVQQQSNLLMAIEA
QQHLLKLTVWGIKQLRARVLAVERYLKDQQLLGIWGCSGKHICTTNVPWNSSWSNKSLDE
IWNNMTWIEWEREINNYTGLIYNLLEKSQNQQEKNEQDLLALDKWASLWSWFDISNWLWY
IKIFIIIVGGLIGLRIVFAVLSLVNRVRQGYSPLSLQTLLPTPRGPDRPEGTEEEGGEQG
RDRSIRLVSGFLALAWDDLRSLCRFSYHRLRDFILIVARTVELLGRSSLKGLRLGWEGLK
YLGNLLLYWGQELKISAISLLDTTAIAVAGWTDRVIEIGQRLCRAIRNIPRRIRQGAERA
LQ-
>ENV-M.syn6.4
MRVKETQMNWPNLWKWGTLI--------LGLVIICSASDNLWVTVYYGVPVWRDADTTLF
CASDAKAHETEVHNVWATHACVPTDPNPQEIHLENVTEEFNMWKNNMVEQMHTDIISLWD
QSLKPCVRLTPLCVTLNCTDELKNATFRSNTTTNSSW--EKMERGEIKNCSFNITTSIRD
KVQKEYALFYKLDIVPL-NSNSSE---------YRLINCNTSVIKQACPKISFDPIPIH
YCAPAGFAILKCKDKKFNGTGPCQNVSTVQCTHRIKPVVSTQFLLNGSLAEEDIIIRSEN
ITNNAKTIIVQLNESVVINCTRPNNNTRRSIPIGPGRVFYTTEDIIGDIRQAHCNLSRAK
WNDTLKQIVIKLREQFG-NKTIVFNQSSGGDLEIVMHSFNCGGEFFYCNSTQLFNSTWF-
--NSTW------STEGSNNTE-GSDTITLPCRIKQIVNMWQGVGKAMYAPPIRGQIRCSS
NITGILLTRDGGTNGT----NETETFRPGGGNMKDNWRSELYRYKVVKIEPLGIAPTKAK
RRVVEREKRAIG-LGAMFLGFLGTAGSTMGAASLTLTVQARQLMSGIVQQQNNLLRAIEA
QQHMLKLTVWGIKQLQARVLALERYLKDQQLLGLWGCSGKLICTTTVPWNSSWSNKSQTD
IWDNMTWMQWDREISNYTNTIYRLLEDSQNQQEKNEKDLLALDSWKNLWNWFDITKWLWY
IKIFIMIVGGLIGLKIVFAVLSIINRVRQGYSPLSFQTLIPNPRGPDRPGGIEEEGGEQD
RDRSIRLVNGFLALIWVDLRSLFLFSYHRLRDLLLIVTRIVELLG-------RRGWEALK
YWWNLLQYWSQELKNSAINLLDTIAIAVAEGTDRIIEVIQRICRAIRNIPTRIRQGLERA
LL-
>ENV-M.syn6.5
MRVKGIRKNYQHLWKWGTML--------LGMLMICSATEKLWVTVYYGVPVWKEATTTLF
CASDAKAYDTEVHNVWATYACVPTDPNPQELVLENVTENFDMWKNNMVEQMHEDIINLWD
QSLKPCVKLTPICVTLNCTDYVKNIT-NNATSTNSSW-GKPMEKGEIKNCSFNMTTELRD
KKQKVYSLFYKLDVVQM-DEDNTS---------YRLISCNTSVITQACPKISFEPIPIH
YCTPAGYAILKCNDKNFNGTGPCKNVSSVQCTHGIKPVISTQLLLNGSLAEEEIIIRSEN
LTNNVKTIIVHLNKSVEINCTRPSNNTRTSIRIGPGQAFYATGDIIGDIRKAHCNISRAN
WNNTLRQIVEKLGEQFGNNKTIVFNHSSGGDPEITTHSFNCGGEFFYCNTTKLFNSTWTW
N-NSTW--N---NTKRSNDTE---EIITLPCRIKQIINMWQEVGKAMYAPPIQGVIRCES
NITGLILTRDGGNNN-----STNETFRPGGGDMRDNWRSELYKYKVVRIEPLGVAPTEAK
RRVVQREKRAVGTIGAMFLGFLGAAGSTMGAASVTLTVQARLLLSGIVQQQNNLLKAIEA
QQHLLRLTVWGIKQLQARVLAIERYLQDQQLLGIWGCSGKLICTTNVPWNTSWSNRSLNE
IWNNMTWMEWEKEIDNYTNLIYNLLEESQIQQEKNEQELLALDKWANLWNWFDISNWLWY
IRIFIIIVGGLVGLRIVFAVLSIVNKVRQGYSPLSFQTHLPAQRGPDRPEGIEEGGGEQD
RDRSVRLVDGFLAIIWVDLRSLCLFSYHHLRDLLLIVARIVELLG-------RRGWEVLK
YWWNLLKYWSQELKNSAVSLLNATAIAVAEGTDRIIELIQRICRAICNIPRRIRQGFERA
LL-
>ENV-M.syn6.6
MRVKETRKNYQHLWRWGIML--------LGMLMICSAAEQLWVTVYYGVPVWKEAKTTLF
CASNAKAYDTEAHNVWATHACIPTDPNPQEIVLENVTESFNMWKNDMVDQMHEDVISLWD
QSLKPCVQLTPLCVTLNCTN-VNVTNLKNETNTKSSSGGEKMEEGEMKNCSFNVTTELRD
KKKKEYALFYRLDIVPL-NEGNNSNSSY------YRLINCNTSTITQACPKVSFEPIPIH
FCAPAGFAILKCNDKKFNGTGPCKNVSTVQCTHGIKPVVSTQLLLNGSLAEKEIIIRSEN
LTNNAKIIIVQLNESVEINCTRPGNNTRKSIRIGPGQTFYATGDIIGNIRQAHCNISRTQ
WNNTLKQIAIKLREQFG-NKTIIFNQSSGGDPEIVTHSFNCGGEFFYCKSTKLFNSTW--
---------N---STSLFNSTN---GTITLQCRIKQIINRWQEVGKAMYAPPIEGNITCKS
NITGLLLVRDGGINVTNN--TGTEVFRPGGGDMKDNWRNELYKYKVVEIKPLGVAPTRAR
RRVVEREKRAVG-LGAVFLGFLGAAGSTMGAAAVTLTVQARQLLFGIVQQQSNLLRAIEA
QQRMLQLTVWGIKQLQTRVLAIERYLKDQQLLGMWGCSGKLICTTAVPWNSSWSNKTYND
IWDNMTWLQWDKEISNYTDTIYRLLEESQNQQERNEKDLLELDKWASLWNWFNITNWLWY
IKIFIMIIGGLIGLRIIFAVLSIVNRVRQGYSPLSFQTLTPNPRGPDRLGRIEEEGGEQD
KDRSIRLVNGFSALIWDDLRNLCLFSYHQLRDFILVTARAVELLGRSSLRGLQRGWEALK
YLGSLVQYWGLELKKSAISLLDTIAIAVANWTDRVIEVVQRAYRAILHIPTRIRQGFEAA
LQ-
```

Fig. 10 cont'd-13

```
>POL-B.syn1.1
FFRENLAFPQGKAREFSSEQTRANSPTRR--------------ELQVWGRDNNSLSEAGA
DR----QGTVS-FSFPQITLWQRPLVTIKIGGQLKEALLDTGADDTVLEEMNLPGRWKPK
MIGGIGGFIKVRQYDQIPIEICGHKAIGTVLVGPTPVNIIGRNLLTQIGCTLNFPISPIE
TVPVKLKPGMDGPKVKQWPLTEEKIKALVEICTEMEKEGKISKIGPENPYNTPVFAIKKK
DSTKWRKLVDFRELNKRTQDFWEVQLGIPHPAGLKKKKSVTVLDVGDAYFSVPLDKDFRK
YTAFTIPSINNETPGIRYQYNVLPQGWKGSPAIFQSSMTKILEPFRKQNPDIVIYQYMDD
LYVGSDLEIGQHRTKIEELRQHLLRWGFTTPDKKHQKEPPFLWMGYELHPDKWTVQPIVL
PEKDSWTVNDIQKLVGKLNWASQIYAGIKVKQLCKLLRGTKALTEVIPLTEEAELELAEN
REILKEPVHGVYYDPSKDLIAEIQKQGQGQWTYQIYQEPFKNLKTGKYARMRGAHTNDVK
QLTEAVQKIATESIVIWGKTPKFKLPIQKETWETWWTEYWQATWIPEWEFVNTPPLVKLW
YQLEKEPIVGAETFYVDGAANRETKLGKAGYVTDRGRQKVVSLTDTTNQKTELQAIHLAL
QDSGLEVNIVTDSQYALGIIQAQPDKSESELVSQIIEQLIKKEKVYLAWVPAHKGIGGNE
QVDKLVSAGIRKVLFLDGIDKAQEEHEKYHSNWRAMASDFNLPPVVAKEIVASCDKCQLK
GEAMHGQVDCSPGIWQLDCTHLEGKIILVAVHVASGYIEAEVIPAETGQETAYFLLKLAG
RWPVKTIHTDNGSNFTSTTVKAACWWAGIKQEFGIPYNPQSQGVVESMNKELKKIIGQVR
DQAEHLKTAVQMAVFIHNFKRKGGIGGYSAGERIVDIIATDIQTKELQKQITKIQNFRVY
YRDSRDPLWKGPAKLLWKGEGAVVIQDNSDIKVVPRRKAKIIRDYGKQMAGDDCVASRQD
ED-
>POL-B.syn3.1
FFRENLAFPQGKAREFPSEQTRANSPTSR--------------ELQVWGGDNNSLSEAGD
DR----QGTVS-FSFPQITLWQRPIVTIKIGGQQKEALLDTGADDTVLEEMNLPGRWKPK
IIGGIGGFIKVKQYDQILIEICGHKAIGTVLVGPTPANIIGRNLLTQIGCTLNFPISPIE
TVPVRLKPGMDGPKVKQWPLTEEKIKALIEICTELENEGKISKIGPENPYNTPVFAIKKK
DGTKWRKLVDFRELNKRTQDFWEVQLGIPHPAGLKKKKSVTVLDVGDAYFSVPLDKEFRK
YTAFTIPSINNETPGIRYQYNVLPQGWKGSPSIFQSSMTKILEPFRKQNPEIVIYQYMDD
LYVGSDLEIEQHRTKIEELRQHLLKWGFYTPDKKHQKEPPFLWMGYELHPDKWTVQPIVL
PEKDSWTVNDIQKLVGKLNWASQIYAGIKVKQLCRLLRGTKALTEVVPLTEEAELELAEN
REILKEPVHGVYYDPSKDLVAEIQKQGLGQWTYQIYQEPYKNLKTGKYAKMRGAHTNDVK
QLTEAVQKIATESIVIWGKTPKFRLPIQKETWEAWWMEYWQATWIPEWEFVNTPPLVKLW
YQLEKEPIVGAETFYVDGAANRDTKLGKAGYVTDRGRQKVVSLTDTTNQKTELQAIHLAL
QDSGLEVNIVTDSQYAIGIIQAQPDRSESELVSQIIEQLIKKEKVYLAWVPAHKGIGGNE
QVDKLVSSGIRKVLFLDGIDKAQEDHEKYHSNWKAMASDFNLPPVVAKEIVACCDKCQLK
GEAMHGQVDCSPGIWQLDCTHLEGKVILVAVHVASGYIEAEVIPAETGQETAYFILKLAG
RWPVTTIHTDNGSNFTSTAVKAACWWAGIKQEFGIPYNPQSQGVVESINKELKKIIKQVR
DQAEHLKTAVQMAVFVHNFKRKGGIGGYSAGERMIDIIATDIQTTELQKQITKLQNFRVY
FRDSRDPLWKGPAKLLWKGEGAVVIQDNSEIKVVPRRKAKIIRDYGKQMAGDDCVASRQD
ED-
>POL-B.syn3.2
FFREDLAFLQGKAREFSSEQTRANSPTRG--------------ELQVWGRDNNSLSEAGA
DR----QGTVS-LSFPQITLWQRPLVTVKIGGQLKEALLDTGADDTVLEEMSLPGRWKPK
MIGGIGGFIKVRQYDQILVEICGHKAIGTVLIGPTPVNIIGRDLLTQIGCTLNFPISPID
TVPVKLKPGMDGPKVKQWPLTEEKIKALVEICTEMEKEGKISKIGPENPYNTPIFAIKKK
DSTKWRKLVDFRELNRRTQDFWEVQLGIPHPAGLKQKKSVTVLDVGDAYFSVPLDEDFRK
YTAFTIPSTNNETPGIRYQYNVLPQGWKGSPAIFQSSMTRILEPFRKQNPDLVIYQYMDD
LYVGSDLEIGQHRTKIEELREHLLKWGFTTPDKKHQKEPPFLWMGYELHPDKWTVQPIML
PEKDSWTVNDIQKLVGKLNWASQIYPGIKVKQLCKLLRGAKALTEVIPLTKEAELELAEN
REILKEPVHGAYYDPSKDLIAEIQKQGQGQWTYQIYQDPFKNLKTGKYARMRGAHTNDVR
QLTEAVQKITTESIVIWGKIPKFKLPIQKETWETWWTEYWQATWIPEWEFVNTPPLVKLW
YQLEKEPIIGAETFYVDGAANRETKLGKAGYVTNKGRQKVVSITDTTNQKTELQAILLAL
QDSGLEVNIVTDSQYAIGIIQAQPDKSESELVSQIIEELIKKEKVYLTWVPAHKGIGGNE
QIDKLVSAGIRKVLFLDGIDQAQEEHEKYHSNWRAMASDFNIPPVVAKEIVASCDKCQLK
GEAIHGQVDCSPGIWQLDCTHLEGKIILVAVHVASGYIEAEIIPTETGQETAYFLLKLAG
RWPVKTVHTDNGSNFTSTTVKAACWWAGVKQEFGIPYNPQSQGVVESMNNELKKIIGQIR
DQAEHLKTAVQMAVFIHNFKRKGGIGGYSAGERIVDIIATDIQTKELQKQITKIQNFRVY
YRDNRDPLWKGPAKLLWKGEGAVVIQENSDIKVVPRRKVKIIRDYGKQMAGDDCVASGQD
ED-
```

Fig. 10 cont'd-14

```
>POL-B.syn3.3
FFREDLAFPQGEAREFSSEQTRANSPTRR--------------ELQVWGRDSNSLSEAGA
DR----QGTVS-FNFPQITLWQRPLVTIKIGGQLKEALLDTGADDTVLEDMNLPGKWKPK
MIGGIGGFIKVRQYDQIPIEICGHKAVGTVLVGPTPVNIIGRNLLTQLGCTLNFPISPIE
TVPVKLKPGMDGPKVKQWPLTEEKIKALVEICTELEKEGKISKIGPENPYNTPVFAIKKK
DSTKWRKVVDFRELNKKTQDFWEVQLGIPHPSGLKKKKSVTVLDVGDAYFSVPLDKDFRK
YTAFTIPSVNNETPGVRYQYNVLPQGWKGSPAIFQCSMTKILEPFRKQNPDIVIYQYMDD
LYVGSDLEIGQHRAKIEELRQHLLRWGFTTPDKKHQNEPPFLWMGYELHPDKWTVQPIEL
PEKDSWTVNDIQKLVGKLNWASQIYPGIKVRQLCKLLRGTKALTEVIPLTEEAELELAEN
REILREPVHGVYYDPTKDLIAEIQKQEQGQWTYQIYQEPFKNLKTGKYARTRGAHTNDVK
QLTEAVQKVATESIVIWGKTPKFKLPIQKETWEAWWTEYWQATWIPEWEFVNTPPLVKLW
YQLEKEPIEGAETFYVDGASNRETKLGKAGYVTNRGRQKVVPLTDTTNQKTELQAIYLAL
QDSGSEVNIVTDSQYALGIIQAQPDKSESELVNQIIEQLIKKEKIYLAWVPAHKGIGGNE
QVDKLVSAGIRKILFLDGIDKAQEEHEKYHNNWRAMASDFNLPPIVAKEIVASCDKCQLK
GEAIHGQVDCSPGIWQLDCTHLEGKVILVAVHVASGYIEAEVIPAETGQETAYFILKLAG
RWPVKTIHTDNGSNFTSATVKAACWWAGIKQEFGIPYNPQSQGVVESMNKELKKIIGQVR
DQAEHLKTAVQMAVFIHNFKRKGGIGEYSAGERIIDIIATDIQTRELQKQITKIQNFRVY
YRDSRDPLWKGPAKLLWKGEGAVVIQDNSDIKVVPRRKAKIIRDYGKQMAGDDCVAGRQD
ED- >POL-B.syn4.1
FFRENLAFPQGEAREFSSEQNRANSPTRR--------------ELQVWGGDNNSLSEAGA
DR----QGTVS-LSFPQITLWQRPLVTIRIGGQLKEALLDTGADDTVLEEMSLPGRWKPK
MIGGIGGFIKVRQYDQILIEICGHKAIGTVLIGPTPVNIIGRNLLTQLGCTLNFPISPID
TVPVKLKPGMDGPKVKQWPLTEEKIKALVEICTEMEKEGKISKIGPENPYNTPIFAIKKK
DSTKWRKLVDFRELNRRTQDFWEVQLGIPHPSGLKKKKSVTVLDVGDAYFSVPLDKDFRK
YTAFTIPSINNETPGVRYQYNVLPQGWKGSPAIFQSSMTKILEPFRKQNPDMVIYQYMDD
LYVGSDLEIGQHRTKIEELRQHLLRWGLTTPDKKHQKEPPFLWMGYELHPDKWTVQPIKL
PEKDSWTVNDIQKLVGKLNWASQIYAGIKVRQLCKLLRGAKALTEVIPLTAEAELELAEN
REILREPVHGVYYDPSKDLIAEIQKQGQGQWTYQIYQDPFKNLKTGKYAKMRGAHTNDVK
QLTEAVQKVATESIVIWGKTPKFRLPIQKETWEAWWTEYWQATWIPEWEFVNTPPLVKLW
YQLEKEPIEGAETFYVDGAANRDTKLGKAGYVTDRGRQKVVSLTDTTNQKTELQAIHLAL
QDSGLEVNIVTDSQYALGIIQAQPDKSESELVSQIIEELIKKEKVYLAWVPAHKGIGGNE
QIDKLVSAGIRRVLFLDGIDQAQEEHEKYHSNWRAMASDFNLPPIVAKEIVASCDKCQLK
GEAIHGQVDCSPGIWQLDCTHLEGKIILVAVHVASGYIEAEVIPAETGQETAYFLLKLAG
RWPVKTIHTDNGSNFTSTTVKAACWWAGIKQEFGIPYNPQSQGVVESMNKELKKIIEQVR
DQAEHLKTAVQMAVFIHNFKRKGGIGEYSAGERIIDIIATDIQTRELQKQITKIQNFRVY
YRDNRDPLWKGPAKLLWKGEGAVVIQDNSDIKVVPRRKAKIIRDYGKQMAGDDCVAGRQD
ED- >POL-B.syn4.2
FFRENLAFPQGKAREFPSEQTRANSPTSR--------------ELQVWGRDNNSLSEAGD
DR----QGTVS-FSFPQITLWQRPLVTVKIGGQLKEALLDTGADDTVLEEMNLPGRWKPK
MIGGIGGFIKVRQYDQIPIEICGHKAVGTVLVGPTPVNIIGRDLLTQIGCTLNFPISPIE
TVPVKLKPGMDGPKVKQWPLTEEKIKALIEICTELENEGKISKIGPENPYNTPVFAIKKK
DGTKWRKLVDFRELNKRTQDFWEVQLGIPHPAGLKQKKSVTVLDVGDAYFSVPLDKEFRK
YTAFTIPSTNNETPGIRYQYNVLPQGWKGSPAIFQCSMTKILEPFRKQNPDLVIYQYMDD
LYVGSDLEIEQHRTKIEELREHLLKWGFTTPDKKHQNEPPFLWMGYELHPDKWTVQPIML
PEKDSWTVNDIQKLVGKLNWASQIYAGIKVKQLCKLLRGTKALTEVVPLTEEAELELAEN
REILKVPVHGVYYDPSKDLVAEIQKQGLGQWTYQIYQEPFKNLKTGKYARTRGAHTNDVR
QLTEAVQKIATESIVIWGKTPKFKLPIQKETWEAWWMEYWQATWIPEWEFVNTPPLVKLW
YQLEKEPIVGAETFYVDGAANRETKLGKAGYVTDKGRQKVVPLTDTTNQKTELQAINLAL
QDSGSEVNIVTDSQYAIGIIQAQPDRSESELVSQIIEQLINKEKVYLAWVPAHKGIGGNE
QVDKLVSSGIRKVLFLDGIDKAQEDHEKYHSNWRAMGDFNLPPVVAKEIVACCDKCQLK
GEAMHGQVDCSPGIWQLDCTHLEGKVILVAVHVASGYIEAEVIPAETGQETAYFILKLAG
RWPVKTVHTDNGSNFISTTVKAACWWAGVKQEFGIPYNPQSQGVVESMNNELKKIIGQVR
DQAEHLKTAVQMAVFVHNFKRKGGIGGYTAGERIVDIIASDIQTKELQKQITKIQNFRVY
```

Fig. 10 cont'd-15

```
YRDSRDPIWKGPAKLLWKGEGAVVIQDNSEIKVVPRRKAKIIRDYGKQMAGDDCVASRQN
ED-
>POL-B.syn4.3
FFREDLAFLQGKAREFSSEQTRANSPTRR--------------ELQVWGRDNNSPSEAGA
DR----QGTVS-FNFPQITLWQRPIVTIKIGGQLKEALLDTGADDTVLEDMNLPGKWKPK
MIGGIGGFIKVRQYDQILVEICGHKAIGTVLVGPTPANIIGRNLLTQIGCTLNFPISPIE
TVPVKLKSGMDGPKVKQWPLTEEKIKALIEICTEMEKEGKISKIGPENPYNTPVFAIKKK
DSTKWRKLVDFRELNKRTQDFWEVQLGIPHPSGLKKKKSVTVLDVGDAYFSVPLDEDFRK
YTAFTIPSVNNETPGIRYQYNVLPQGWKGSPAIFQSSMTRILEPFRKQNPDIVIYQYMDD
LYVGSDLEIGQHRAKIEELRQHLLRWGFTTPDKKHQKEPPFLWMGYELHPDKWTVQPIEL
PEKDSWTVNDIQKLVGKLNWASQIYPGIKVRQLCKLLRGTKALTEVIPLTEEAELELAEN
REILKEPVHGVYYDPSKELIAEIQKQEQGQWTYQIYQEPFKNLKTGKYARMRGTHTNDVK
QLTEAVQKITTESIVIWGRTPKFKLPIQKETWESWWTEYWQATWIPEWEFVNTPPLVKLW
YQLEREPIAGAETFYVDGASNRETKLGKAGYVTNRGRQKVVSLPDTTNQKTELQAIYLAL
QDSGLEVNIVTDSQYAIGIIQAQPDKSESELVNQIIEQLIKKEKIYLAWVPAHKGIGGNE
QVDKLVSNGIRKILFLDGIDKAQDEHEKYHSNWKAMASDFNLPPVVAKEIVACCDKCQLK
GEAMHGQVDCSPGIWQLDCTHLEGKIILVAVHVASGYIEAEVIPAETGQETAYFLLKLAG
RWPVKIIHTDNGSNFTSTAVKAACWWAGIKQEFGIPYNPQSQGVVESINKELKKIIKQVR
DQAEHLKTAVQMAVFIHNFKRKGGIGGYSAGERMIDIIATDIQTTELQKQITKLQNFRVY
FRDSRDPLWKGPAKLLWKGEGAVVIQDNNDIKVVPRRKVKIIRDYGKQMAGDDCVASGQD
ED-
>POL-B.syn4.4
FFREDLAFPQGKARELSSEQTRANSPTRG--------------ELQVWGRDSNSLSEAGA
DR----PGTVS-FSFPQITLWQRPLVTIKIGGQQKEALLDTGADDTVLEEINLPGRWKPK
IIGGIGGFIKVKQYDQIPIEICGHKVIGTVLVGPTPANIIGRNLLTQLGCTLNFPISPIE
TVPVRLKPGMDGPKVKQWPLTEEKIKALVEICTELEKEGKISKIGPENPYNTPVFAIKKK
DSTKWRKVVDFRELNKKTQDFWEVQLGIPHPAGLKKKKSVTVLDVGDAYFSVPLDENFRK
YTAFTIPSINNETPGIRYQYNVLPQGWKGSPSIFQSSMTKILEPFRKQNPEIVIYQYMDD
LYVGSDLELGQHRTKIEELRQHLLKWGFYTPDKKHQKEPPFLWMGYELHPDKWTVQPIVL
PEKDSWTVNDIQKLVGKLNWASQIYPGIKVKQLCRLLRGAKALTEVIPLTKEAELELAEN
REILKEPVHGAYYDPTKDLIAEIQKQGEGQWTYQIYQEPYKNLKTGKYARMRGAHTNDVK
QLTETVQKITTESIVIWGKIPKFKLPIQKETWETWWTEYWQATWIPEWEFVNTPPLVKLW
YQLEKEPIIGAETFYVDGAASRETKLGKAGYVTNKGRQKVVSITDTTNQKTELQAILLAL
QDSGLEVNIVTDSQYAIGIIQAQPDKSESEIVSQIIEQLIKKEKVYLTWVPAHKGIGGNE
QVDKLVSAGIRKVLFLDGIDKAQEEHEKYHNNWRAMASDFNIPPVVAKEIVASCDKCQLK
GEAMHGQVDCSPGIWQLDCTHLEGKVILVAVHVASGYIEAEIIPTETGQETAYFILKLAG
RWPVTTIHTDNGSNFTSATVKAACWWAGVKQEFGIPYNPQSQGVIESMNKELKKIIGQIR
DQAEHLKTAVQMAVFIHNFKRKGGIGGYSAGERIVDIIATDIQTKELQNQITKIQNFRVY
YRDSRDPLWKGPAKLLWKGEGAVVIQENSDIKVVPRRKVKIIRDYGKQMAGDDCVASRQD
ED-
>POL-B.syn6.1
FFREDLAFPQGEAREFCSEQTRANSPATR--------------ELQVWGRDNTSLSEAGA
DR----PGTVS-FSFPQITLWQRPIVTVKIEGQLKEALLDTGADDTVLEEMNLPGKWKPK
MIGGIGGFIKVRQYDQVSIEICGHKAIGTVLVGPTPANIIGRNLLTQIGCTLNFPISPIE
TVPVKLKPGMDGPKVKQWPLTEEKIKALVEICTELEKEGKISKIGPENPYNTPVFAIKKK
DSTKWRKVVDFRELNKRTQDFWEVQLGIPHPSGLKKKKSVTVLDVGDAYFSVPLDENFRK
YTAFTIPSINNETPGIRYQYNVLPQGWKGSPAIFQSSMTKILEPFRKQNPDIIIYQYMDD
LYVGSDLEIGQHRAKIEELRQHLLKWGFTTPDKKHQKEPPFLWMGYELHPDKWTVQPIEL
PEKDSWTVNDIQKLVGKLNWASQIYAGIKVKELCKLLRGTKALTEVVPLTEEAELELAEN
REILKEPVHGVYYDPSKDLIAELQKQGQGQWTYQIYQEPYKNLKTGKYARTRGAHTNDVR
QLTEAVQKIATEGIVIWGKTPKFKLPIQKETWEAWWTEYWQATWIPEWEFVNTPPLVKLW
YQLEKEPILGAETFYVDGASNRETKLGKAGYVTDRGRQKVVSLTDTTNQKTELQAINLAL
QDSGLEVNIVTDSQYALGIIQAQPDRSESELVSQIIEQLINKEKVYLAWVPAHKGIGGNE
QVDKLVSTGIRRVLFLDGIDKAQEEHEKYHSNWRAMASDFNLPPIVAKEIVASCDKCQLK
GEAIHGQVDCSPGIWQLDCTHLEGKVILVAVHVASGYIEAEVIPAETGQETAYFILKLAG
```

Fig. 10 cont'd-16

```
RWPVKTIHTDNGSNFTSTTVKAACWWAGIKQEFGIPYNPQSQGVVESMNKELKKIIEQVR
DQAEHLKTAVQMAVFVHNFKRKGGIGEYSAGERIVDIIATDIQTKELQKHITKIQNFRVY
YRDSRDPLWKGPAKLLWKGEGAVVIQDNSEIKVVPRRKAKIIRDYGKQMAGDDCVASRQD
ED-
>POL-B.syn6.2
FFREDLAFPQGKARELSSEQTRANSPTSPTRG----------ELQVWGRDSNSLSEAGA
DR----QGPVS-FSFPQITLWQRPIVTIKIGGQLKEALLDTGADDTVLEDMNLPGRWKPK
MIGGIGGFIKVKQYDEILVEICGHKAIGTVLIGPTPVNIIGRNLLTQLGCTLNFPISPIE
TVPVKLKSGMDGPKVKQWPLTEEKIKALVEICTELEKEGKISKIGPENPYNTPIFAIKKK
DSTKWRKLVDFRELNKRTQDFWEVQLGIPHPAGLKKKKSVTVLDVGDAYFSVPLDKDFRK
YTAFTIPSVNNETPGIRYQYNVLPQGWKGSPAIFQCSMTKILEPFRKQNPDMVIYQYMDD
LYVGSDLEIGQHRIKIEELREHLLKWGFTTPDKKHQNEPPFLWMGYELHPDKWTVQPIVL
PEKDSWTVNDIQKLVGKLNWASQIYPGIKVRQLCKLLRGTKALTEVIPLTEEAELELAEN
REILREPVHGVYYDPTKDLIAEIQKQGQGQWTYQIYQEPFKNLKTGKYARMRGAHTNDVK
QLTEAVQKITTESIVIWGKIPKFRLPIQKETWEAWWIEYWQATWIPEWEFVNTPPLVKLW
YQLEREPIAGAETFYVDGAANRETKLGKAGYVTNRGRQKVVSITDTTNQKTELQAILLAL
QDSGLEVNIVTDSQYALGIIQAQPDKSESELVNQIIEQLIKKEKIYLAWVPAHKGIGGNE
QIDKLVSAGIRKVLFLDGIDKAQDEHEKYHSNWRAMAGDFNLPPVVAKEIVACCDKCQLK
GEAMHGQVDCSPGIWQLDCTHLEGKIILVAVHVASGYIEAEVIPAETGQETAYFLLKLAG
RWPVTTIHTDNGSNFTSATVKAACWWAGVKQEFGIPYNPQSQGVIESMNKELKKIIGQVR
DQAEHLKTAVQMAVFIHNFKRKGGIGEYSAGERIIDIIATDIQTKELQKQITKIQNFRVY
YRDSRDPIWKGPAKLLWKGEGAVVIQDNSEIKVVPRRKAKIIRDYGKQMAGDDCVAGRQD
ED-
>POL-B.syn6.3
FFRENLAFPQGEAREFSSEQTRANSPTRG-------------ELQVWGRDSNSLSEAGD
DR----QGTVS-FSFPQITLWQRPLVTIKIGGQQKEALLDTGADDTVLEEMNLPGRWKPK
IIGGIGGFIKVTQYDQIPIEICGHKAVGTVLVGPTPVNIIGRDLLTQIGCTLNFPISPIE
TVPVKLKSGMDGPKVKQWPLTEEKIKALIEICTEMEKEGKISKIGPENPYNTPVFAIKKK
DGTKWRKLVDFRELNKKTQDFWEVQLGIPHPAGLKQKKSVTVLDVGDAYFSVPLDREFRK
YTAFTIPSLNNETPGIRYQYNVLPQGWKGSPSIFQSSMTKILEPFRKQNPDLVIYQYMDD
LYVGSDLELGQHRTKIEELRQHLLKWGFYTPDKKHQKEPPFLWMGYELHPDKWTVQPIKL
PEKDSWTVNDIQKLVGKLNWASQIYPGIKVKQLCRLLRGAKALTEVVPLTKEAELELAEN
REILKEPVHGAYYDPTKDLIAEVQKQELGQWTYQIYQEPFKNLKTGKYARMKGAHTNDVK
QLTETVQKITTESIVIWGKTPKFRLPIQKETWESWWTEYWQATWIPEWEFVNTPPLVKLW
YQLEKEPITGAETFYVDGAANRETKIGKAGYVTDKGRQKVVSLPDTTNQKTELQAIHLAL
QDSGSEVNIVTDSQYAIGIIQAQPDRSESEVVNQIIEQLIKKEKVYLAWVPAHKGIGGNE
QVDKLVSNGIRKILFLDGIDKAQEEHERYHSNWKAMASDFNLPPVVAKEIVACCDKCQLK
GEAIHGQVDCSPGIWQLDCTHLEGKVILVAVHVASGYIEAEVIPAETGQETAYFILKLAG
RWPVKIIHTDNGSNFTSTAVKAACWWAGIKQEFGIPYNPQSQGVVESINKELKKIIKQVR
DQAEHLKTAVQMAVFIHNFKRKGGIGGYSAGERIIDIIASDIQTKELQNQITKIQNFRVY
YRDSRDPVWKGPAKLLWKGEGAVVIQDNSDIKVVPRRKAKIIRDYGKQMAGDDCVASRQN
ED-
>POL-B.syn6.4
FFRENLAFPQRKAREFSSEQTRANSPTRR-------------ELQVWGGDNNSLSEAGA
DR----QGTVS-LSFPQITLWQRPLVTIKVGGQLKEALLDTGADDTVLEEINLPGRWKPK
MIGGIGGFIKVRQYDQILVEICGHKAIGTVLVGPTPVNIIGRNLLTQIGCTLNFPISPIE
TVPVKLKPGMDGPKVKQWPLTEEKIKALVEICTEMEKEGKISKIGPENPYNTPIFAIKKK
DSTKWRKLVDFRELNRRTQDFWEVQLGIPHPAGLKKKKSVTVLDVGDAYFSVPLDEDFRK
YTAFTIPSINNETPGVRYQYNVLPQGWKGSPAIFQASMTKILEPFRKQNPDIVIYQYMDD
LYVGSDLEIGQHRIKIEELRQHLLRWGLTTPDKKHQKEPPFLWMGYELHPDKWTVQPIML
PEKDSWTVNDIQKLVGKLNWASQIYAGIKVRQLCKLLRGAKALTEVIPLTAEAELELAEN
REILKVPVHGVYYDPSKELIAEIQKQEQGQWTYQIYQDPFKNLKTGKYARMRGTHTNDVR
QLTEAVQKITTESIVIWGKIPKFKLPIQKETWETWWTEYWQATWIPEWEFVNTPPLVKLW
YQLEKEPIIGAETFYVDGAASRETKLGKAGYVTDRGRQKVISLTDTTNQKTELQAIHLAL
QDSGVEVNIVTDSQYALGIIQAQPDKSESEIVSQIIEQLIKKEKVYLTWVPAHKGIGGNE
```

Fig. 10 cont'd-17

QVDKLVSTGIRKVLFLDGIDQAQEEHEKYHSNWRTMASDFNLPPIVAKEIVASCDKCQLK
GEAMHGQVDCSPGIWQLDCTHLEGKVILVAVHVASGYIEAEVIPAETGQETAYFLLKLAG
RWPVKTIHTDNGPNFISTTVKAACWWAGIKQEFGIPYNPQSQGVVESMNNELKKIIGQVR
EQAEHLKTAVQMAVFIHNFKRKGGIGGYSAGERMIDIIATDIQTTELQKQITKLQNFRVY
FRDSRDPLWKGPAKLLWKGEGAVVIQENSDIKVVPRRKAKIIRDYGKQMAGDDCVAGRQD
ED-
>POL-B.syn6.5
FFRENLAFPQGKAREFPSEQTRANSPTSR-------------ELQVWGRDNNSLSEAGA
NR----QGTVS-FSFPQITLWQRPLVTVKIGGQLKEALLDTGADDTVLEDMDLPGRWKPK
MIGGIGGFIKVRQYDQIPIEICGHKVIGTVLVGPTPANIIGRNLLTQIGCTLNFPISPIE
TVPVRLKPGMDGPKVKQWPLTEEKIKALVEICTELEKEGKISKIGPENPYNTPVFAIKKK
DSTKWRKLVDFRELNKKTQDFWEVQLGIPHPSGLKKKKSVTVLDVGDAYFSVPLDKEFRK
YTAFTIPSTNNETPGIRYQYNVLPQGWKGSPAIFQASMTKILEPFRKQNPEIVIYQYMDD
LYVGSDLEIEQHRTKIEELRQHLLRWGFTTPDKKHQKEPPFLWMGYELHPDKWTVQPIVL
PDKDSWTVNDIQKLVGKLNWASQIYPGIKIRQLCKLLRGAKALTEVIPLTKEAELELAEN
REILKEPVHGVYYDPSKDLIAEIQKQGEGQWTYQIYQEPFKNLKTGKYAKMRGAHTNDVK
QLTEAVQKVATESIVIWGKTPKFKLPIQKETWEAWWMEYWQATWIPEWEFVNTPPLVKLW
YQLEKEPIEGAETFYVDGAANRDTKLGKAGYVTNKGRQKVVTLTDTTNQKTELQAIHLAL
QDSGLEVNIVTDSQYALGIIQAQPDKSESEIVNQIIEQLIKKEKVYLAWVPAHKGIGGNE
QVDKLVSSGIRKVLFLDGIDKAQEDHEKYHSNWRAMANDFNLPPVVAKEIVACCDKCQLK
GEAMHGQVDCSPGIWQLDCTHLEGKVILVAVHVASGYIEAEVIPAETGQETAYFILKLAG
RWPVKTVHTDNGSNFTSNTVKAACWWAGIKQEFGIPYNPQSQGVVESMNKQLKQIIGQVR
DQAEHLKTAVQMAVFIHNFKRKGGIGGYTAGERIVDIIATDIQTRELQKQITKIQNFRVY
YRDSREPLWKGPAKLLWKGEGAVVIQDNSDIKVVPRRKAKIIRDYGKQMAGDDCVASGQD
ED-
>POL-B.syn6.6
FFREDLAFLQGKAREFSSEQTRAISPTRR-------------ELQVWGRDNNSPSEAGA
DR----QGTVS-FNFPQITLWQRPLVTIRIGGQLKEALLDTGADDTVLEEMSLPGRWKPK
MIGGIGGFIKVRQYDQILIEICGHKAVGTVLIGPTPVNIIGRNLLTQIGCTLNFPISPID
TVPVKLKPGMDGPKVKQWPLTEEKIKALIEICTELENEGKISKIGPENPYNTPIFAIKKK
DSTKWRKLVDFRELNKRTQDFWEVQLGIPHPSGLKKKKSVTVLDVGDAYFSIPLDEDFRK
YTAFTIPSINNETPGTRYQYNVLPQGWKGSPAIFQSSMTRILEPFRKQNPDIVIYQYVDD
LYVGSDLEIGQHRTKIEELREHLLRWGFTTPDKKHQKEPPFLWMGYELHPDKWTVQPITL
PEKDSWTVNDIQKLVGKLNWASQIYAGIKVKQLCKLLRGTKSLTEVVPLTAEAELELAEN
REILKEPVHGAYYDPSKDLVAEIQKQGLGQWTYQIYQEPFKNLKTGKYAKMRGTHTNDVK
QLTEAVQKIATESIVIWGRTPKFKLPIQKETWDAWWTEYWQATWIPEWEFVNTPPLVKLW
YQLEKEPIVGAETFYVDGAANRETRLGKAGYVTDRGRQKVVPLTDTTNQKTELQAIYLAL
QDSGLEVNIVTDSQYALGIIQAQPDKSESELVSQIIEELIKKEKVYLAWVPAHKGIGGNE
QVDKLVSAGIRRVLFLDGIDKAQEEHEKYHNNWRAMASDFNIPPVVAKEIVASCDKCQLK
GEAIHGQVDCSPGIWQLDCTHLEGKIILVAVHVASGYIEAEIIPTETGQETAYFLLKLAG
RWPVKTIHTDNGRNFTSNSVKAACWWAGIKQEFGIPYNPQSQGVVESMNRELKKIIGQIR
DQAEHLKTAVQMAVFIHNFKRKGGIGGYSAGERIVDIIASDIQTKELQKQITKIQNFRVY
YRDNRDPLWKGPAKLLWKGEGAVVIQDNNDIKVVPRRKVKIIRDYGKQMAGDDCVASRQD
ED- >POL-C.syn1.1
FFRENLAFPQGEAREFPSEQTRANSPTSRANSPTSR-------ELQV--RGDNPRSEAGA
ER----QGT---LNFPQITLWQRPLVSIKVGGQIKEALLDTGADDTVLEEINLPGKWKPK
MIGGIGGFIKVRQYDQILIEICGKKAIGTVLVGPTPVNIIGRNMLTQLGCTLNFPISPIE
TVPVKLKPGMDGPKVKQWPLTEEKIKALTAICEEMEKEGKITKIGPENPYNTPVFAIKKK
DSTKWRKLVDFRELNKRTQDFWEVQLGIPHPAGLKKKKSVTVLDVGDAYFSVPLDEGFRK
YTAFTIPSINNETPGIRYQYNVLPQGWKGSPAIFQSSMTKILEPFRAQNPEIVIYQYMDD
LYVGSDLEIGQHRAKIEELREHLLRWGFTTPDKKHQKEPPFLWMGYELHPDKWTVQPIQL
PEKDSWTVNDIQKLVGKLNWASQIYPGIKVRQLCKLLRGAKALTDIVPLTEEAELELAEN
REILKEPVHGVYYDPSKDLIAEIQKQGHDQWTYQIYQEPFKNLKTGKYAKMRTAHTNDVK

Fig. 10 cont'd-18

```
QLTEAVQKIAMESIVIWGKTPKFRLPIQKETWETWWTDYWQATWIPEWEFVNTPPLVKLW
YQLEKEPIAGAETFYVDGAANRETKIGKAGYVTDRGRQKIVSLTETTNQKTELQAIQLAL
QDSGSEVNIVTDSQYALGIIQAPDKSESELVNQIIEQLIKKERVYLSWVPAHKGIGGNE
QVDKLVSSGIRKVLFLDGIDKAQEEHEKYHSNWRAMASEFNLPPIVAKEIVASCDKCQLK
GEAIHGQVDCSPGIWQLDCTHLEGKIILVAVHVASGYIEAEVIPAETGQETAYYILKLAG
RWPVKVIHTDNGSNFTSAAVKAACWWAGIQQEFGIPYNPQSQGVVESMNKELKKIIGQVR
DQAEHLKTAVQMAVFIHNFKRKGGIGGYSAGERIIDIIATDIQTKELQKQIIKIQNFRVY
YRDSRDPIWKGPAKLLWKGEGAVVIQDNSDIKVVPRRKVKIIKDYGKQMAGADCVAGRQD
EDQ
>POL-C.syn3.1
FFRENLAFPQGEAREFPPEQTRANSPT-RANSPTSR-------KLQV--RGDNPCSEAGA
ER----QGT---FNFPQITLWQRPLVTIKVGGQVKEALLDTGADDTVLEEINLPGKWKPK
MIGGIGGFIKVRQYDQIVIEICGKKAIGTVLIGPTPVNIIGRNMLTQLGCTLNFPISPIE
TVPVKLKPGMDGPKIKQWPLTEEKIKALTAICDEMEKEGKIEKIGPENPYNTPIFAIKKK
DSTKWRKLVDFKELNKRTQDFWEVQLGIPHPAGLKKKRSVTVLDVGDAYFSVPLDESFRK
YTAFTIPSINNETPGIRYQYNVLPQGWKGSPAIFQSSMTRILEPFRAKNPEIVIYQYMDD
LYIGSDLEIGQHRAKVEELREHLLRWGFTTPDKKHQKEPPFLWMGYELHPDKWTVQPIQL
PEKDSWTVNDIQRLVGKLNWASQIYPGIKVRQLCKLLRGTKALTDIVPLTEEAELELAEN
REILKEPVHGVYYDPSKDLIAEIQKQGDDQWTYQIYQESFKNLKTGKYAKMRSAHTNDVK
QLTEAVQKIALESIVIWGKAPKFRLPIQKETWEIWWTDYWQATWIPDWEFVNTPPLVKLW
YQLEKEPIAGAETFYVDGAANRETKIGKAGYVTDRGRQKVVTLTETTNQKTELQAIQLAL
QDSGLEVNIVTDSQYALGIIQAPDKSESELVNQIIEELIKKERVYLSWVPAHKGIGENE
QVDKLVSNGIRKVLFLDGIDKAQEEHEKYHSNWRAMANEFNLPPVVAKEIVASCDKCQLK
GEAIHGQVDCSPGMWQLDCTHLEGKVILVAVHVASGYVEAEVIPAETGQETAYFILKLAG
RWPVKIIHTDNGSNFTSNAVKAACWWAGIQQEFGIPYNPQSQGVVESMNKELKKIIGQVR
EQAEHLKTAVQMAVFIHNFKRRGGIGGYSAGERIIDIIASDIQTKELQKQITKIQNFRVY
YRDSRDPVWKGPAKLLWKGEGAVVIQDNGDIKVVPRRKAKIIKDYGKQMAGDDCVAGRQD
EDQ
>POL-C.syn3.2
FFRENLAFQQGEAREFPSEQTRANSPTSRANSPTSRTNSPTSRELQV--RGDNPRSEAGV
ER----QGT---LNFPQITLWQRPLVSIKVGGQIKEALLDTGADDTVLEDINLPGKWKPR
MIGGIGGFIKVRQYDQIPIEICGKKAIGTVLVGPTPVNIIRRNMLTQLRCTLNFPISPIK
TVPVKLKPGMDGPKVKQWPLTEEKIKALTEICEEMEKEGKITKIGPENPYNTPVFAIKKK
DSTKWRKLVDFRELNKRTQDFWEVQLGIPHPSGLKKKKSVTVLDVEDAYFSVPLDEGFRK
YTAFTIPSTNNETPGIRYQYNVLPQGWKGSPAIFQCSMTKILEPFRTQNPDIVIYQYMDD
LYVGSDLEIGQHRAKIEELRAHLLKWGLTTPDKKHQKEPPFLWMGYELHPDKWTVQPIKL
PEKDSWTVNDIQKIVGKLNWASQIYPGIKVQLCKLLRGAKALTDIIPLTEEAELELAEN
REILKEPVHGAYYDPSKDLVAEIQKQGHDQWTYQIYQEPYKNLKTGKYAKMRTAHTNDVR
QLTEAVQKIAQESIVIWGKTPKFRLPIQKETWETWWTDYWQATWIPEWEFINTPPLVKLW
YQLEKEPIVGAETFYVDGAANRETKMGKAGYVTDKGRQKIVSLTETTNQKAELQAIQLAL
QDSGPEVNIVTDSQYALGIIQAPDRSESELVNQIIEQLINKERIYLSWVPAHKGIGGNE
QVDKLVSSGIRKVLFLDGIDKAQEDHEKYHNNWRAMASDFNLPPIVAREIVASCDKCQLK
GEAMHGQVDCSPGVWQLDCTHLEGKIILVAVHVASGYMEAEVIPAETGQETAYYILKLAG
RWPVKVIHTDNGSNFTSTAVKAACWWAGIKQEFGIPYNPQSQGVVEAMNKELKKIIEQVR
DQAEHLKTAVQMAVLIHNFKRKGGIGGYSAGERIVDIIATDIQTRELQKQIIQIQNFRVY
YRDSRDPIWKGPAKLLWKGEGAVVIQDNSDIKVVPRRKVKIIKDYGKQMAGADCVASRQD
ED-
>POL-C.syn3.3
FFRENLAFPQGKAREFPSEQARANSPTSRANSPTSR-------ELQV--RRDNPRSEAGA
ER----QGT---LNCPQITLWQRPLVSIKIGGQTREALLDTGADDTVLEEISLPGKWKPK
MIGGIGGFIKVRQYDQILIEICGKKAIGSVLVGPTPVNIIGRNLLTQLGCTLNFPISPIE
TIPVKLKPGMDGPRVKQWPLTEEKIKALTAICEEMEKEGKISKIGPENPYNTPIFAIKKK
DSTKWRKLVDFRELNKRTQDFWEIQLGIPHPAGLKKKKSVTVLDVGDAYFSVPLDEDFRK
YTAFTIPSINNATPGIRYQYNVLPQGWKGSPSIFQSSMTKILEPFRAQNPEIVIYQYMDD
LYVGSDLEIEQHRAKIEELREHLLKWGFTTPDKKHQKEPPFLWMGCELHPDKWTVQPIQL
```

Fig. 10 cont'd-19

```
PEKESWTVNDIQKLVGKLNWASQIYAGIKVKQLCRLLRGAKALTDIVPLTAEAELELAEN
REILREPVHGVYYDPSKELIAEIQKQGQDQWTYQIYQEPFKNLKTGKYAKRRTAHTNDVK
QLAEAVQKIAMESIVIWGKIPKFRLPIQKETWEAWWTDYWQATWIPEWEFVNTPPLVKLW
YQLEKDPIAGVETFYVDGAANRETKLGKAGYVTDRGRQKIVSLSETTNQKTELHAIQLAL
QDSGSEVNIVTDSQYALRIIQAQPDKSESEIVNQIIEQLIKKERVYLAWVPAHKGIGENE
QVDKLVSKGIRKVLFLDGIEKAQEEHERYHSNWRAMASEFNLPPIVAKEIVASCDKCQLK
GEATHGQVDCSPGIWQLDCTHLEGKVIIVAVHVASGYIEAEVIPAETGQETAYFLLKLAG
RWPVKTIHTDNGSNFTSAAVKAACWWAGIHQEFGIPYNPQSQGVVESMNKELKKIIGQVR
DQAEHLKTAVLMAVFIHNFKRKGGIGDYSAGERIIDIIATDIQTKELQKQIIKIQNFRVY
YRDNRDPIWKGPAKLLWKGEGAVVLQDNSDIKVIPRRKAKIIRDYGKQMAGADCVAGRQD
ENQ

>POL-C.syn4.1
FFRENLAFPQGKAREFPSEQARANSPTSRANSPTSR-------ELQV--RRDNPRSEAGA
ER----QGT---LNLPQITLWQRPLVSIKVGGQIKEALLDTGADDTVLEDINLPGKWKPK
MIGGIGGFIKVRQYDQIPIEICGKKAIGTVLVGPTPVNIIGRNMLTQLGCTLNFPISPIE
TIPVKLKPGMDGPKVKQWPLTEEKIKALTEICKEMEKEGKIEKIGPENPYNTPVFAIKKK
DSTKWRKLVDFRELNKRTQDFWEVQLGIPHPSGLKKKKSVTVLDVEDAYFSVPLDENFRK
YTAFTIPSVNNETPGIRYQYNVLPQGWKGSPAIFQCSMTKILEPFRTQNPEIVIYQYMDD
LYVGSDLEIGQHRAKIEKLREHLLKWGFTTPDKKHQKEPPFLWMGYELHPDKWTVQPIKL
PEKDSWTVNDIQRLVGKLNWASQIYAGIKVRQLCKLLRGAKALTDIVPLTKEAELELAEN
REILKEPVHGVYYDPSKELIAEIQKQGQDQWTYQIYQEPFKNLKTGKYAKRRTAHTNDVK
QLAEAVQKITMESIVIWGRTPKFRLPIQKETWEAWWTDYWQATWIPEWEFVNTPPLVKLW
YQLEKEPIAEAETFYVDGAANRETKMGKAGYVTDKGRQKIVSLTETTNQKTELHAIQLAL
QDSGPEVNIVTDSQYALGIIQAQPDKSESELVSQIIEQLINKERIYLSWVPAHKGIGGNE
QVDKLVSKGIRKVLFLDGIDKAQEEHERYHSNWRAMANEFNLPPIVAREIVASCDKCQLK
GEAIHGQVDCSPGVWQLDCTHLEGKIILVAVHVASGYVEAEVIPAETGQETAYFLLKLAG
RWPVKTIHTDNGSNFTSAAVKAACWWAGVQQEFGIPYNPQSQGVVESMNKELKKIIGQIR
DQAEHLKTAVQMAVFIHNFKRKGGIGDYSAGERIIDIIATDIQTRELQKQIIQIQNFRVY
YRDSRDPVWKGPAKLLWKGEGAVVLQDNSDIKVVPRRKVKIIKDYGKQMAGADCVAGRQD
ENQ
>POL-C.syn4.2
FFRENLAFPEGEAREFPSEQTRANSPT-RANSPTSR-------KLQV--RGDNPRSEAGV
ER----QGT---LNFPQITLWQRPLVSIKIGGQTREALLDTGADDTVLEEIKLPGNWKPK
MIGGIGGFIKVRQYDQILIEICGKKAIGTVLIGPTPVNIIGRNLLTQLGCTLNFPISPIK
TVPVKLKPGMDGPKVKQWPLSEEKIKALTEICEEMEKEGKISKIGPENPYNTPVFAIKKK
DSTKWRKLVDFRELNKRTQDFWEIQLGIPHPAGLKKKKSVTVLDVGDAYFSVPLDEDFRK
YTAFTIPSINNATPGIRYQYNVLPQGWKGSPSIFQSSMTKILEPFRAKNPEIVIYQYMDD
LYVGSDLEIGQHRAKVEELREHLLKWGLTTPDKKHQKEPPFLWMGYELHPDKWTVQPIQL
PDKDSWTVNDIQKLVGKLNWASQIYPGIKVQLCKLLRGTKALTDIVPLTAEAELELAEN
REILREPVHGVYYDPSKDLVAEIQKQGNDQWTYQIYQEPYKNLKTGKYAKMRSAHTNDVK
QLTEAVQKIALESIVIWGKAPKFRLPIQKETWEIWWTDYWQATWIPDWEFVNTPPLVKLW
YQLEKDPIAGVETFYVDGAANRETKLGKAGYVTDRGRQKIVSLSETTNQKTELQAIQLAL
QDSGLEVNIVTDSQYALGIIQAQPDKSESELVNQIIEELIKKEKVYLSWVPAHKGIGENE
QVDKLVSSGIRKVLFLDGIEKAQEEHEKYHNNWRAMASEFNLPPIVAKEIVASCDKCQLK
GEATHGQVDCSPGMWQLDCTHLEGKIIIVAVHVASGYLEAEVIPAETGQDTAYYILKLAG
RWPVKVIHTDNGTNFTSAAVKAACWWAGIQQEFGIPYNPQSQGVVESMNKELKKIIGQVR
EQAEHLKTAVLMAVFIHNFKRKGGIGEYSAGERIIDMIATDIQTKELQNQITKIQNFRVY
YRDSRDPIWKGPAKLLWKGEGAVVIQDNGDIKVVPRRKVKIIRDYGKQMAGDDCVAGRQD
EDQ
>POL-C.syn4.3
FFRENLAFPQGEAREFPPEQTRANSPTSRTNSPTSR-------ELQV--RGDNPHSEAGA
ERQGTLQGT---LNCPQITLWQRPLVSIRVGGQIKEALLDTGADDTVLEEISLPGKWKPK
MIGGIGGFIKVRQYDQIVIEICGKKAIGSVLVGPTPVNIIRRNMLTQLRCTLNFPISSIE
TVPVKLKPGMDGPRVKQWPLTEEKIKALTAICEEMEKEGKITKIGPDNPYNTPVFAIKKK
```

Fig. 10 cont'd-20

```
DSTKWRKLVDFKELNKRTQDFWEVQLGIPHPAGLKRKKSVTVLDVGDAYFSVPLDEGFRK
YTAFTIPSTNNETPGIRYQYNVLPQGWKGSPAIFQSSMIKILEPFRAQNPDIVIYQYMDD
LYIGSDLEIGQHRAKIEELRAHLLKWGFTTPDKKHQKEPPFLWMGCELHPDKWTVQPIQL
PEKESWTVNDIQRLVGKLNWASQIYSGIKVRQLCKLLRGVKALTDIVPLTEEAELELAEN
REILKETVHGAYYDPSKDLIAEIQKQGHDQWTYQIYQEPFKNLKTGKYAKMRTAHTNDIK
QLTEAVQKIAMESIVIWGKTPKFRLPIQKETWETWWTDYWQATWIPEWEFINTPPLVKLW
YQLEKEPIVGAETFYVDGAANRDTKLGKAGYITDRGRQKVVTLTETTNQKAELQAIQLAL
QDSGSKVNIVTDSQYALGIIQAQPDRSESELVNQIIEQLIKKERVYLSWVPAHKGIGGNE
QIDKLVSSGIRRVLFLDGIDKAQEDHEKYHSNWRAMASDFNLPPIVAKEIIASCDKCQLK
GEAMHGQVDCSPGIWQLDCTHLEGKVIIVAVHVASGYIEAEVIPAETGQETAYYILKLAG
RWPVKIIHTDNGSNFTSNAVKAACWWAGIHQEFGIPYNPQSQGVVEAMNKELKKIIGQVR
DQAEHLKTAVLMAVFIHNFKRRGGIGGYSAGERIIDIIASDIQTKELQKQITKIQNFRVY
YRDSRDPIWKGPAKLLWKGEGAVVIQDNSDIKVIPRRKAKIIKDYGKQMAGADCVAGGQD
EN-
>POL-C.syn4.4
FFRENLAFQQGEAREFPSEQTRAISPTSR--------------ELQV--RGDNPCSEAGA
ER----QGT---FNFPQITLWQRPLVTIKVGGQVKEALLDTGADDTVLEEINLPGKWKPR
MIGGIGGFIKVRQYEQILIEICGKRAIGTVLVGPTPINIIGRNMLTQIGCTLNFPISPIE
TVPVKLKPGMDGPKIKQWPLTEEKIKALTAICDEMEKEGKITKIGPENPYNTPIFAIKKK
DSTKWRKLVDFRELNKRTQDFWEVQLGIPHPAGLKKKRSVTVLDVGDAYFSVPLDESFRK
YTAFTIPSINNETPGIRYQYNVLPQGWKGSPAIFQSSMTRILEPFRAQNPEIVIYQYMDD
LYVGSDLEIEQHRAKIEELREHLLRWGFTTPDKKHQKEPPFLWMGYELHPDKWTVQPIQL
PEKDSWTVNDIQKIVGKLNWASQIYPGIKVRQLCRLLRGAKALTDIIPLTEEAELELAEN
REILKEPVHGAYYDPSKDLIAEIQKQGDDQWTYQIYQESFKNLKTGKYAKMRTAHTNDVR
QLTEAVQKIAQESIVIWGKIPKFRLPIQKDTWETWWTDYWQATWIPDWEFVNTPPLVKLW
YQLEKEPIAGAETFYVDGAANRETKIGKAGYVTDRGRQKVITLTETTNQKTELQAIHLAL
QDSGSEVNIVTDSQYALRIIQAQPDKSESEIVNQIIEQLINKERVYLSWVPAHKGIGGNE
QVDKLVSNGIRKVLFLDGIDKAQEEHEKYHSNWRAMASEFNLPPVVAKEIVASCDKCQQK
GEAIHGQVDCSPRIWQLDCTHLEGKVILVAVHVASGYMEAEVIPAETGQETAYFILKLAG
RWPVKVIHTDNGSNFTSTAVKAACWWAGIKQEFGIPYNPQSQGVVESMNKELKKIIEQVR
DQAEHLKTAVQMAVLIHNFKRKGGIGGYSAGERIVDIIATDIQTKELQKQIIKIQNFRVY
YRDNRDPIWKGPAKLLWKGEGAVVIQDNSEIKVVPRRKAKIIRDYGKQMAGADCVASRQD
ED-
>POL-C.syn6.1
FFRENLAFPQGKAREFPSEQTRAISPTSR--------------ELQV--RGNNPRSEAGA
ER----QGT---LNLPQITLWQRPLVSIKIGGQTREALLDTGADDTVLEEIKLPGNWKPK
MIGGIGGFIKVRQYDQILIEICGKRAIGTVLVGPTPVNIIGRNMLTQIGCTLNFPISSIE
TVPVKLKPGMDGPKVKQWPLTEEKIKALTEICEEMEKEGKITKIGPDNPYNTPVFAIKKK
DSTKWRKLVDFKELNKRTQDFWEVQLGIPHPAGLKKNKSVTVLDVGDAYFSVPLDESFRK
YTAFTIPSINNETPGIRYQYNVLPQGWKGSPAIFQSSMTRILEPFRAQNPDIVIYQYMDD
LYVGSDLEIEQHRAKIEELREHLLRWGFTTPDKKHQKEPPFLWMGCELHPDKWTVQPIQL
PEKDSWTVNDIQKLVGKLNWASQIYSGIKVRQLCKLLRGVKALTDIVPLTKEAELELAEN
REILREPVHGVYYDPAKDLIAEIQKQGQDQWTYQIYQEPFKNLKTGKYAKRRTAHTNDVK
QLTEAVQKIATESIVIWGKIPKFRLPIQKDTWETWWTDYWQATWIPDWEFVNTPPLVKLW
YQLEKEPIAEAETFYVDGAASRETKMGKAGYVTDRGRQKVITLTETTNQKTELQAIKLAL
QDSGSEVNVVTDSQYALGIIQAQPDKSESEIVNQIIEQLINKERVYLSWVPAHKGIGGNE
QVDKLVSRGIRKVLFLDGIDKAQDEHEKYHSNWRAMASEFNLPPIVAREIVASCDKCQLK
GEATHGQVDCSPGIWQLDCTHLEGKIILVAVHVASGYIEAEVIPTETGQETAYYILKLAG
RWPVKIIHTDNGSNFTSSAVKAACWWAGIQQEFGIPYNPQSQGVVESMNKELKKIIGQVG
DQAEHLKTAVQMAVFIHNFKRRGGIGGYSAGERIIDIIATDIQTRELQKQIIKIQNFQVY
YRDSRDPIWKGPAKLLWKGEGAVVIQDNSEIKVVPRRKVKIIKDYGKQMAGADCMASRQD
ED-
>POL-C.syn6.2
FFRENLAFPQGEARELPSEQTRANGPTSR--------------ELQV--RGDNPCSEAGA
ER----QGT---FNFPQITLWQRPLVTIKVGGQVKEALLDTGADDTVLEEINLPGKWKPK
```

Fig. 10 cont'd-21

```
MIGGIGGFIKVRQYDQIPIEICGKRAIGTVLVGPTPINIIGRNMLTQLGCTLNFPISPIE
TVPVQLKPGMDGPRVKQWPLTEEKIKALTEICKEMEKEGKISKIGPENPYNTPIFAIKKK
DSTKWRKLVDFRELNKRTQDFWEVQLGIPHPAGLKKKRSVTVLDVGDAYFSVPLDEDFRK
YTAFTIPSINNETPGVRYQYNVLPQGWKGSPSIFQSSMTKILEPFRTQNPEIVIYQYMDD
LYIGSDLEIGQHREKIEELREHLLKWGFTTPDKKHQKEPPFLWMGYELHPDKWTVQPIKL
PEKDSWTVNDIQRLVGKLNWASQIYAGIKVRQLCKLLKGAKALTDIVTLTEEAELELAEN
REILKEPVYGVYYDPSKDLVAEIQKQGNDQWTYQIYQESFKNLKTGKYAKMRTAHTNDIK
QLTEAVQKIAQESIVIWGKTPKFRLPIQKETWEAWWTDYWQATWIPDWEFVNTPPLVKLW
YQLEKEPMAGVETFYVDGAANRETKIGKAGYVTDRGRQKVVTITETTNQKTELQAIYLAL
QDSGSKVNIVTDSQYALGIIQAQPDKSESELVSQIIEQLINKEKIYLSWVPAHKGIGGNE
QVDKLVSSGIRKVLFLDGIDKAQEDHERYHSNWRAMASDFNLPPIVAKEIVASCDQCQLK
GEAMHGQVDCSPGMWQLDCTHLEGKIIIVAVHVASGYIEAEVISAETGQETAYYILKLAG
RWPVKVVHTDNGSNFTSAAVKAACWWAGVQQEFGIPYNPQSQGVVESMNKELKRIIGQVR
DQAEHLKTAVQMAVFIHNFKRKGGIGGYSAGERIIDMIATDIQTKELQKQIIQIQNFRVY
YRDSRDPIWKGPAKLLWKGEGAVVIQDKGDIKVVPRRKAKTIRDYGKQMAGADCMAGRQD
EDQ
>POL-C.syn6.3
FFREDLAFPQGEARKFPPEQTRANSPTSRANSPTSR------KLQV--RGDNPRSEAGV
ER----QGT---LNFPQITLWQRPLVSIKVGGQIREALLDTGADDTVLEEMSLPGKWKPK
MIGGIGGFIKVKQYEQILIEICGKKAIGSVLVGPTPVNIIGRNLLTQLGCTLNFPISPIE
TVPVKLKPGMDGPKVKQWPLTEEKIKALTAICDEMEKEGKITKIGPENPYNTPVFAIKKK
DSTKWRKLVDFKELNKRTQDFWEVQLGIPHPAGLKKKKSVTVLDVGDAYFSVPLDENFRK
YTAFTIPSRNNETPGIRYQYNVLPQGWKGSPAIFQASMTKILEPFRAKNPEIVIYQYMDD
LYVGSDLEIGQHRAKIEELRDHLLKWGFTTPDKKHQKEPPFLWMGYELHPDKWTVQPIEL
PEKDSWTVNDIQKLVGKLNWASQIYPGIQVKQLCKLLRGAKALTDVVPLTEEAELELAEN
REILKEPVHGAYYDPSKDLIAEIQKQGHDQWTYQIYQEPYKNLKTGKYAKRRAAHTNDVK
QLTEAVQKIAMESIVIWGKTPKFRLPIQKETWETWWTEYWQATWIPEWEFVNTPPLVKLW
YQLEKEPIAGAETFYVDGAANRETKMGKAGYITDRGRQKIISLTETTNQKTELHAIQLAL
QDSGSEANIVTDSQYALGIIQAQPDRSESELVNQIIEQLIKKERVYLAWVPAHKGIGENE
QVDKLVSSGIRKILFLDGIDKAQEEHEKYHSNWKAMASEFNLPPVVAREIVASCDKCQLK
GEAMHGQVDCSPRIWQLDCTHLERKVILVAVHVASGYMEAEVIPAETGQETAYFILKLAG
RWPVKVIHTDNGSNFTSNAVKAACWWAGIHQEFGIPYNPQSQGVVESMNKELKKIIEQVR
DQAEHLKTAVQMAVLIHNFKRKGGIGGYTAGERIIDIIATDIQTKELQNQITKIQNFRVY
YRDNRDPIWKGPAKLLWKGEGAVVLQDNSDIKVVPRRKVKIIRDYGKQMAGADCVAGRQD
ED-
>POL-C.syn6.4
FFRKNLAFPQGEAREFPPEQTRANSPTSR-------------ELQV--RGDNPLSEAGA
ERQGTLQGT---LNCPQITLWQRPLVSIKVGGQIKEALLDTGADDTVLEEISLPGKWKPK
MIGGIGGFIKVRQYDQIVIEICGKKAIGAVLVGPTPVNIIRRNMLTQLRCTLNFPISPIK
TVPVKLKPGMDGPKVKQWPLSEEKIKALTAICEDMEKEGKITKIGPENPYNTPIFAIKKK
DSTKWRKLVDFRELNKRTQDFWEVQLGIPHPSGLKKKKSVTVLDVEDAYFSVPLDEGFRK
YTAFTIPSINNATPGIRYQYNVLPQGWKGSPAIFQSSMTKILEPFRTKNPDIVIYQYMDD
LYVGSDLEIGQHRAKIEKLREHLLRWGLTTPDKKHQKEPPFLWMGYELHPDKWTVQPIQL
PDKDSWTVNDIQKLVGKLNWASQIYAGIKVQLCRLLRGAKALTDIIPLTEEAELELAEN
REILKEPVHGAYYDPSKDLIAEIQKQGQGQWTYQIYQEPYKNLKTGKYAKMRTAHTNDVK
QLAEAVQKITMESIVIWGRTPKFRLPIQKETWETWWTDYWQATWIPEWEFINTPPLVKLW
YQLEKEPIVGAETFYVDGAANRETKLGKAGYVTDKGRQKIVSLTETTNQKTELQAIHLAL
QDSGSEVNIVTDSQYALRIIQAQPDKSESELVNQIIEQLINKERIYLSWVPAHKGIGGNE
QVDKLVSNGIRKVLFLDGIEKAQEEHERYHSNWRAMANEFNLPPIVAREIVASCDCQIK
GEAMHGQVDCSPGVWQLDCTHLEGKVILVAVHVASGYVEAEVIPAETGQEAAYFILKLAG
RWPVKTIHTDNGSNFTSTAVKAACWWAGIKQEFGIPYNPQSQGVVESMNKELKKIIGQVR
DQAEHLKTAVQMAVLIHNFKRKGGIGDYSAGERIIDIIATDMQTKELQKQIIKVQNFRVY
YRDSRDPIWKGPAKLLWKGEGAVVIQDNGDIKVVPRRKVKIIKDYGRQMAGADCVASRQD
ED-
```

Fig. 10 cont'd-22

```
>POL-C.syn6.5
FFRENLAFPEGEAREFPSEQARANSPTSR--------------ELQV--RRDNPRSEAGA
EG----QGT---LNFPQITLWQRPLVSIRVGGQIKEALLDTGADDTVLEEINLPGRWKPK
MIGGIGGFIKVRQYDQITIEICGKKAIGTVLVGPTPINIIGRNMLTQIGCTLNFPISPIE
TVPVKLKPGMDGPKIKQWPLTEEKIKALKAICEEMEKEGKIEKIGPENPYNTPVFAIKKK
DSTKWRKLVDFRELNKRTQDFWEIQLGIPHPAGLKRKKSVTVLDVGDAYFSVPLYEDFRK
YTAFTIPSVNNETPGIRYQYNVLPQGWKGSPAIFQCSMTKILEPFRAQNPEIVIYQYMDD
LYVGSDLEIGQHRAKVEELREHLLKWGLTTPDKKHQKEPPFLWMGYELHPDKWTVQPIQL
PEKESWTVNDIQKIVGKLNWASQIYPGIKVRQLCRLLRGAKALTDIVPLTAEAELELAEN
REILKEPVHGVYYDPSKELIAEIQKQGDDQWTYQIYQEPFKNLKTGKYAKMRSAHTNDVK
QLTEAVQKIALESIVIWGKAPKFRLPIQKETWEIWWTDYWQATWIPEWEFINTPPLVKLW
YQLEKEPIAGVETFYVDGAANRDTKIGKAGYVTDRGRQKIVSLSETTNQKTELQAIQLAL
QDSGLEVNIVTDSQYALGIIQAQPDNSESELVNQIIEELIKKERVYLSWVPAHKGIGGNE
QVDKLVSKGIRKVLFLDGIDKAQEEHEKYHNNWRAMASDFNLPPVVAKEIVACCDKCQLK
GEAIHGQVDCSPGIWQLDCTHLEGKVIIVAVHVASGYLEAEVIPAETGQETAYFLLKLAG
RWPVKVIHTDNGPNFTSAAVKAACWWAGINQEFGIPYNPQSQGVVESMNKELKKIIGQVR
EQAEHLKTAVQMAVFIHNFKRKGGIGGYSAGERIVDIIATDIQTKELQNQIIKIQNFRVY
YRDSRDPIWKGPAKLLWKGEGAVVIQENSDIKVVPRRKAKIIKDYGKQMAGDDCVAGRQD
EDQ
>POL-C.syn6.6
FFRENLAFQQGEAREFPSEQTRANSPT-RANSPTSRTNSPTSRELQV--RGDNPHSEAGA
ER----QGS---LNFPQITLWQRPLVTIKIGGQLKEALLDTGADDTVLEDINLPGKWKPR
MIGGIGGFIKVRQYEQIPIEICGKKAIGTVLIGPTPVNIIGRNLLTQLGCTLNFPISPIE
TIPVKLKPGMDGPKVKQWPLTEEKIKALTAICEEMEKEGKITKIGPDNPYNTPVFAIKKK
DSTKWRKLVDFRELNKRTQDFWEVQLGIPHPAGLKKKKSVTVLDVGDAYFSVPLDKDFRK
YTAFTIPSTNNETPGIRYQYNVLPQGWKGSPAIFQSSMIKILEPFRAKNPELVIYQYMDD
LYVGSDLEIMQHRAKIEELRAHLLKWGFTTPDKKHQKEPPFLWMGYELHPDKWTVQPIVL
PEKDSWTVNDIQKLVGKLNWASQIYPGIKVKQLCKLLRGTKALTDIVPLTEEAELELAEN
REILKETVHGAYYDPSKDLIAEIQKQGYDQWTYQIYQEPFKNLKTGKYAKKRTAHTNDVR
QLTEAVQKIAIESIVIWGKTPKFRLPIQKETWETWWADYWQATWIPEWEFVNTPPLVKLW
YQLEKDPIAGAETFYVDGAANRETKKGKAGYVTDKGRQKVVTLTETTNQKAELQAIQLAL
QDSGPEVNIVTDSQYALRIIQAQPDKSESGLVNQIIEQLIKKEKVYLSWVPAHKGIGGNE
QIDKLVSSGIRRVLFLDGIDKAQEDHEKYHSNWRAMAGEFNLPPVVAKEIVASCDCQQK
GEAIHGQVDCSPGIWQLDCTHLEGKIILVAVHVASGYIEAEVIPAETGQDTAYYILKLAG
RWPVKVIHTDNGTNFTSAAVKAACWWASIQQEFGIPYNPQSQGVVEAMNKELKKIIGQIR
DQAEHLKTAVLMAVFIHNFKRKGGIGEYSAGERIIDIIASDIQTKELQKQITKIQNFRVY
YRDSRDPVWKGPAKLLWKGEGAVVIQDNSDIKVIPRRKAKIIRDYGKQMAGADCVAGGQD
ED-
>POL-M.syn1.1
FFRENLAFPQGEAREFPSEQTRANSPTSRANSPTSR-------ELQV--RGDNPRSEAGA
ER----QGT---LNFPQITLWQRPLVTIKIGGQLKEALLDTGADDTVLEDINLPGKWKPK
MIGGIGGFIKVRQYDQILIEICGKKAIGTVLVGPTPVNIIGRNMLTQIGCTLNFPISPIE
TVPVKLKPGMDGPKVKQWPLTEEKIKALTEICTEMEKEGKISKIGPENPYNTPVFAIKKK
DSTKWRKLVDFRELNKRTQDFWEVQLGIPHPAGLKKKKSVTVLDVGDAYFSVPLDESFRK
YTAFTIPSINNETPGIRYQYNVLPQGWKGSPAIFQSSMTKILEPFRKQNPDIVIYQYMDD
LYVGSDLEIGQHRAKIEELREHLLKWGFTTPDKKHQKEPPFLWMGYELHPDKWTVQPIQL
PEKDSWTVNDIQKLVGKLNWASQIYPGIKVQLCKLLRGAKALTDIVPLTEEAELELAEN
REILKEPVHGVYYDPSKDLIAEIQKQGQDQWTYQIYQEPFKNLKTGKYAKMRTAHTNDVK
QLTEAVQKIATESIVIWGKTPKFRLPIQKETWETWWTDYWQATWIPEWEFVNTPPLVKLW
YQLEKEPIVGAETFYVDGAANRETKLGKAGYVTDRGRQKVVSLTETTNQKTELQAIQLAL
QDSGSEVNIVTDSQYALGIIQAQPDKSESELVNQIIEQLIKKEKVYLSWVPAHKGIGGNE
QVDKLVSSGIRKVLFLDGIDKAQEEHEKYHSNWRAMASDFNLPPIVAKEIVASCDKCQLK
GEAMHGQVDCSPGIWQLDCTHLEGKVILVAVHVASGYIEAEVIPAETGQETAYFILKLAG
RWPVKVIHTDNGSNFTSAAVKAACWWAGIQQEFGIPYNPQSQGVVESMNKELKKIIGQVR
DQAEHLKTAVQMAVFIHNFKRKGGIGGYSAGERIIDIIATDIQTKELQKQITKIQNFRVY
```

Fig. 10 cont'd-23

```
YRDSRDPIWKGPAKLLWKGEGAVVIQDNSDIKVVPRRKAKIIRDYGKQMAGDDCVAGRQD
EDQ
>POL-M.syn3.1
FFRENLAFPQGEAREFPSEQTRANSPTSRANSPTSR-------ELQV--RGDNPRSEAGA
ER----QGT---LNFPQITLWQRPLVSIKVGGQIKEALLDTGADDTVLEEINLPGKWKPK
MIGGIGGFIKVRQYDQIPIEICGKRAIGTVLVGPTPINIIGRNMLTQLGCTLNFPISPIK
TVPVKLKPGMDGPKVKQWPLTEEKIKALTAICEEMEKEGKITKIGPENPYNTPVFAIKKK
DGTKWRKLVDFRELNKRTQDFWEVQLGIPHPSGLKKKKSVSVLDVGDAYFSVPLDESFRK
YTAFTIPSINNETPGIRYCYNVLPQGWKGSPAIFQCSMTKILEPFRAQNPEIVIYQYMDD
LYIGSDLEIGQHRAKIEELREHLLRWGFTTPDKKHQKEPPFLWMGCELHPDKWTVQPIQL
PEKDSWTVNDIQKIVGKLNWASQIYPGIKVRQLCKLLRGAKALTDIVPLTEEAELELAEN
REILREPVHGVYYDPSKDLVAEIQKQGQDQWTYQIYQEPFKNLKTGKYAKMRTAHTNDVK
QLTEAVQKIALESIVIWGKIPKFRLPIQKETWEAWWMEYWQATWIPEWEFINTPPLVKLW
YQLEKEPIAGAETFYVDGAANRETKIGKAGYVTDRGRQKIVSLTETTNQKAELQAIQLAL
QDSGPEVNIVTDSQYALGIIQAHPDKSESELVNQIIEQLIKKERVYLSWVPAHKGIGENE
QVDKLVSNGIRKILFLDGIDKAQEEHEKYHSNWRAMASEFNLPPIVAKEIVASCNKCQLK
GEALHGQVDCSPGMWQLDCTHLEGKVILVAVHVASGYMEAEVIPAETGQETAYYILKLAG
RWPVKVVHTDNGSNFTSTAVKAACWWAGIQQEFGIPYNPQSQGVIESMNKELKKIIGQIR
DQAEHLKTAVQMAVFIHNFKRKGGIGEYSAGERIIDIIATDIQTRELQKQIIKIQNFRVY
YRDSRDPIWKGPAKLLWKGEGAVVLQDNSDIKVVPRRKVKIIKDYGKQMAGADCVAGRQD
ENQ
>POL-M.syn3.2
FFRENLAFQQGEARKFSSEQTGANSPTSR--------------ELRV-RRGDNPLSEAGA
ER----RGTVPSLSFPQITLWQRPLVTVKIGGQLIEALLDTGADDTVLEDINLPGKWKPR
MIGGIGGFIKVKQYDQILIEICGKKAIGTVLVGPTPVNIIGRNMLTQIGCTLNFPISPID
TVPVTLKPGMDGPKIKQWPLTEEKIKALTEICTEMEKEGKISRIGPENPYNTPIFAIKKK
DSTKWRKLVDFRELNKKTQDFWEVQLGIPHPAGLKKKRSVTVLDVGDAYFSVPLDKDFRK
YTAFTIPSTNNETPGIRYQYNVLPQGWKGSPSIFQSSMTRILEPFRAKNPEIVIYQYMDD
LYVGSDLEIEQHRTKIEELRQHLLRWGLTTPDKKHQKEPPFLWMGYELHPDRWTVQPIEL
PEKESWTVNDIQKLVGKLNWASQIYAGIKVKQLCKLLRGTKALTEVVPLTEEAELELEEN
REILKDPVHGAYYDPSKDLIAEIQKQGHDQWTYQIYQEQYKNLKTGKYARKRSAHTNDVR
QLTEAVQKIATESIVIWGKTPKFRLPIQRETWETWWTDYWQATWIPEWEFVNTPPLVKLW
YQLEKDPIAGVETFYVDGASNRETKKGKAGYVTDKGRQKVVSLTETTNQKTELHAIHLAL
QDSGSEVNIVTDSQYALGIIQAQPDRSESELVNQIIEELIKKEKVYLSWVPAHKGIGGNE
QVDKLVSSGIRKVLFLDRIDKAQEEHERYHSNWRTMASDFNLPPIVAKEIVANCDKCQLK
GEAMHGQVDCSPGIWQIDCTHLEGKVIIVAVHVASGYIEAEVIPAETGQETAYFLLKLAG
RWPVKVIHTDNGSNFTSAAVKAACWWANVTQEFGIPYNPQSQGVVESMNKELKKIIGQVR
EQAEHLKTAVQMAVLIHNFKRKGGIGGYSAGERIIDIIASDIQTKELQKQIIKVQNFRVY
YRDSRDPVWKGPAKLLWKGEGAVVIQDNSDIKVVPRRKVKIIRDYGKQMAGDDCVAGRQD
EDQ
>POL-M.syn3.3
FFREDLAFPQGKAREFSSEQTRANSPTRR--------------ELQVWGRDNNSLSEAGA
DR----QGTVS-FSFPQITLWQRPLVTIKIGGQLKEALLDTGADDTVLEEMNLPGRWKPK
MIGGIGGFIKVRQYDQILIEICGHKAIGTVLIGPTPVNIIGRNLLTQIGCTLNFPISPIE
TVPVKLKPGMDGPRVKQWPLTEEKIKALVEICTEMEKEGKISKIGPENPYNTPVFAIKKK
DSTRWRKLVDFRELNKRTQDFWEIQLGIPHPAGLKKKKSVTVLDVGDAYFSVPLDEGFRK
YTAFTIPSVNNETPGVRYQYNVLPQGWKGSPAIFQSSMTKILEPFRKQNPDIVIYQYMDD
LYVGSDLEIGQHRTKIEELREHLLKWGFTTPDKKHQNEPPFLWMGYELHPDKWTVQPIVL
PEKDSWTVNDLQKLVGKLNWASQIYPGIKVKQLCRLLRGAKALTEVIPLTKEAELELAEN
REILKEPVHGVYYDPSKELIAEIQKQGQGQWTYQIYQEPYKNLKTGKYARMRGAHTNDVK
QLTEVVQKIAMESIVIWGKTPKFKLPIQKETWETWWTEYWQATWIPDWEFVNTPPLVKLW
YQLEKEPIVGAETFYVDGAANRETKLGKAGYVTDRGRQKVVSLTDTTNQKTELQAIHLAL
QDSGLEVNIVTDSQYAIGIIQAQPDKSESELVSQIIEQLIKKEKVYLAWVPAHKGIGGNE
QVDKLVSAGIRKVLFLDGIDKAQEDHEKYHNNWRAMASDFNLPPVVAKEIVASCDKCQLK
```

Fig. 10 cont'd-24

GEAIHGQVDCSPGIWQLDCTHLEGKIILVAVHVASGYLEAEVIPAETGQETAYFILKLAG
RWPVKTIHTDNGSNFTSTTVKAACWWAGIKQEFGIPYNPQSQGVVESINKELKKIIGQVR
DQAEHLKTAVLMAVFIHNFKRRGGIGGYSAGERIVDIIATDIQTKELQKQITKIQNFRVY
YRDSRDPLWKGPAKLLWKGEGAVVIQDNSEIKVVPRRKAKIIRDYGKQMAGDDCVASRQD
ED-
>POL-M.syn4.1
FFRENLAFQQGEARKFSSEQTRANSPTRG--------------ELQVWGRDNNPLSEAGA
ER----RGTVPSLSFPQITLWQRPLVTVKIGGQLIEALLDTGADDTVLEDINLPGKWKPK
MIGGIGGFIKVKQYDQILIEICGKKAIGTVLVGPTPVNIIGRNMLTQIGCTLNFPISPID
TVPVTLKPGMDGPRIKQWPLTEEKIKALTEICKEMEEEGKISKIGPENPYNTPIFAIKKK
NSTRWRKLVDFRELNKKTQDFWEVQLGIPHPAGLKRKKSVTVLDVEDAYFSVPLDESFRK
YTAFTIPSINNETPGVRYQYNVLPQGWKGSPAIFQCSMTKILEPFRIKNPEMVIYQYMDD
LYVGSDLEIGQHRIKIEELRAHLLSWGFTTPDKKHQKDPPFLWMGYELHPDRWTVQPIEL
PEKDSWTVNDIQKLVEKLNWASQIYSGIKVRQLCRLLRGAKALTDIVPLTEEAELELAEN
REILKEPVHGAYYDPSKDLVAEIQKQGQDQWTYQIYQEPFKNLKTGKYARKRSAHTNDVK
QLTEVVQKIATESIVIWGKTPKFRLPIQRETWETWWTEYWQATWIPEWEFVNTPPLVKLW
YQLEKDPIAGVETFYVDGAASRETKLGKAGYVTDRGRQKVVSLTETTNQKTELHAIHLAL
QDSGSEVNIVTDSQYVLGIIQAQPDRSESELVNQIIEELIKKEKVYLSWVPAHKGIGGNE
QVDKLVSSGIRKVLFLNGIDKAQEEHERYHSNWRTMASDFNLPPIVAKEIVANCDKCQLK
GEAMHGQVDCSPGVWQLDCTHLEGKVIIVAVHVASGYIEAEVIPAETGQEAAYFILKLAG
RWPVKVVHTDNGSNFTSAAVKAACWWANVRQEFGIPYNPQSQGVVESMNNELKKIIGQIR
DQAEHLKTAVLMAVFIHNFKRKGGIGEYSAGERIIDIIATDIQTRELQKQITKIQNFRVY
FRDSRDPIWKGPAKLLWKGEGAVVIQDNSEIKVVPRRKVKIIRDYGKQMAGDDCVAGRQD
EN-
>POL-M.syn4.2
FFRENLAFPQGEAREFPSEQARANSPTSRANSPTSR-------DLWDGGRDNLP-SEAGA
ER----QGT---LNFPQITLWQRPLVTVRIGGQLREALLDTGADDTVLEDIDLPGKWKPK
IIGGIGGFIKVRQYEQIPIEICGHKAIGTVLVGPTPINIIGRNMLTQLGCTLNFPISPIK
TVPVKLKPGMDGPRVKQWPLTEEKIKALTAICEEMEKEGKITKIGPENPYNTPVFAIKKK
DSTRWRKLVDFRELNRRTQDFWEVQLGIPHPAGLKKKRSVTVLDVGDAYFSVPLDEGFRK
YTAFTIPSVNNETPGIRYQYNVLPQGWKGSPSIFQSSMTRILEPFRAKNPEIVIYQYIDD
LYVRSDLEIGQHRAKIEELREHLLRWGFTTPDKKHQKEPPFLWMGCELHPDKWTVQPIQL
PEKDSWTINDIQKLVGKLNWASQIYPGIKVRQLCKLLRGTKALTDIVTLTEEAELELAEN
REILKDPVHGVYYDPSKELIAEIQKQGDDQWTYQIYQEQYKNLKTGKYAKRRTAHTNDVR
QLTEAVQKIALESIVIWGKIPKFRLPIQKETWEAWWMEYWQATWIPEWEYVNTPPLVKLW
YQLEKEPIIGAETFYVDGAANRETKLGKAGYVTNRGRQKVVSLTDTTNQKTELQAIQLAL
QDSGSEVNVVTDSQYALGIIQAHPDKSESELVNQIIEQLIKKERVYLSWVPAHKGIGGNE
QVDKLVSAGIRKVLFLDGIDKAQEDHERYHSNWRAMASDFNLPPVVAKEIVASCNKCQLK
GEAIHGQVDCSPGIWQLDCTHLEGKIIIVAVHVASGYMEAEVIPAETGQETAYFILKLAG
RWPVKIIHTDNGSNFTSATVKAACWWANVTQEFGIPYNPQSQGVVESINKELKKIIGQVR
DQAEHLRTAVQMAVFIHNFKRRGGIGGYSAGERIVDIIATDIQTKELQKQITKIQKFRVY
YRDSRDPLWKGPAKLLWKGEGAVVIQDNSDIKVIPRRKAKIIKDYGKQMAGADCVAGRQD
EDQ
>POL-M.syn4.3
FFRENLAFPQGKAREFPSEQTRANSPTSRANSPTSR-------ELQV--RGDNPRSEAGA
ER----QGT---FNFPQITLWQRPLVSIKVGGQIKEALLDTGADDTVLEEINLPGKWKPR
MIGGIGGFIKVRQYDQILIEICGKRAIGTVLVGPTPANIIGRNLLTQLGCTLNFPISPIE
TVPVKLKPGMDGPKIKQWPLTEEKIKALTEICTEMEKEGKISKIGPENPYNTPIFAIKKK
DSTKWRKLVDFKELNKRTQDFWEVQLGIPHPSGLKKKKSVTVLDVGDAYFSVPLDEDFRK
YTAFTIPSTNNETPGIRYQYNVLPQGWKGSPAIFQASMTKILEPFRAQNPEIVIYQYMDD
LYVGSDLEIEQHRAKVEELREHLLKWGFTTPDKKHQNEPPFLWMGYELHPDKWTVQPIKL
PEKESWTVNDIQKLVGKLNWASQIYPGIKVKQLCRLLRGTKALTEVIPLTKEAELELAEN
REILREPVHGVYYDPTKDLIAEIQKQGHDQWTYQIYQEPHKNLKTGKYAKMRTAHTNDVK
QLAEAVQKIAMESIVIWGKIPKFKLPIQKETWETWWTDYWQATWIPDWEFVNTPPLVKLW

Fig. 10 cont'd-25

```
YQLEKEPIAGAETFYVDGAANRETKIGKAGYVTDRGRQKIVSLTETTNQKAELQAIQLAL
QDSGPEVNIVTDSQYALGIIQAQPDKSESEIVNQIIEKLIEKDKVYLSWVPAHKGIGGNE
QIDKLVSNGIRKVLFLDGIEKAQEEHEKYHSNWRAMASEFNLPPIVAKEIVASCDKCQLK
GEATHGQVDCSPGMWQLDCTHLEGKIILVAVHVASGYIEAEVIPTETGQETAYYILKLAG
RWPVKVIHTDNGSNFTSTAVKAACWWAGIQQEFGIPYNPQGQGVVESMNKELKKIIGQVR
EQAEHLKTAVQMAVLIHNFKRKGGIGGYSAGERIIDIIASDIQTKELQKQIIKVQNFRVY
YRDSRDPIWKGPAKLLWKGEGAVVLQDNSDIKVVPRRKVKIIKDYGKQMAGADCVASRQD
EN-
>POL-M.syn4.4
FFREDLAFPQGKAREFSSEQTRANSPTRR--------------ELQVWGRDNNSLSEAGA
DR----QGTVS-FSFPQITLWQRPLVTIKIGGQLKEALLDTGADDTVLEEMNLPGRWKPK
MIGGIGGFIKVRQYDQIPIEICGKKAIGTVLIGPTPVNIIGRNLLTQIGCTLNFPISPIE
TIPVKLKPGMDGPKVKQWPLTEEKIKALVEICTEMEKEGKISRIGPENPYNTPVFAIKKK
DGTKWRKLVDFRELNKRTQDFWEIQLGIPHPAGLKKKKSVSVLDVGDAYFSVPLDKDFRK
YTAFTIPSINNETPGIRYCYNVLPQGWKGSPAIFQSSMTKILEPFRKQNPDIVIYQYMDD
LYIGSDLEIGQHRTKIEELRQHLLRWGLTTPDKKHQNEPPFLWMGYELHPDKWTVQPIVL
PEKDSWTVNDLQKLVGKLNWASQIYAGIKVKQLCKLLRGAKALTEVVPLTEEAELELEEN
REILKEPVHGVYYDPSKDLIAEIQKQGQGQWTYQIYQEPYKNLKTGKYARMRGAHTNDVK
QLTEAVQKIAQECIVIWGKTPKFKLPIQKETWETWWMDYWQATWIPEWEFINTPPLVKLW
YQLEKEPIVGAETFYVDGASNRETKKGKAGYVTDKGRQKVVTLTETTNQKTELQAIHLAL
QDSGLEVNIVTDSQYAIGIIQAQPDKSESELVSQIIEQLIKKEKVYLAWVPAHKGIGGNE
QVDKLVSNGIRKILFLDGIDKAQEEHEKYHNNWRAMASDFNIPPVVAKEIVACCDKCQLK
GEALHGQVDCSPRIWQLDCTHLEGKVILVAVHVASGYLEAEVIPAETGQETAYFLLKLAG
RWPVKTIHTDNGSNFTSTTVKAACWWAGIKQEFGIPYNPQSQGVIESMNKELKKIIEQVR
DQAEHLKTAVQMAVFVHNFKRKGGIGDYSAGERIIDIISTDIQTRELQKQIIKIQNFRVY
YRDSRDPVWKGPAKLLWKGEGAVVIQDNNEIKVVPRRKAKIIRDYGKQMAGDDCVASRQD
ED-
>POL-M.syn6.1
FFREDLAFPQGEARKFPSEQTRANSPTRG--------------ELQVWGRDNNSLSEAGD
DR----QGTVS-FNLPQITLWQRPLVTVRIGGQLIEALLDTGADDTVLEDMNLPGKWKPK
MIGGIGGFIKVRQYEQIPIEICGHKAIGTVLIGPTPVNIIGRNLLTQIGCTLNFPISPID
TVPVTLKPGMDGPKIKQWPLTEEKIKALTEICTEMEKEGKISRIGPENPYNTPVFAIKKK
NSTRWRKLVDFRELNKRTQDFCEVQLGIPHPAGLKKKRSVTVLDVGDAYFSVPLDENFRK
YTAFTIPSINNETPGVRYQYNVLPQGWKGSPAIFQASMTKILEPFRTKNPELVIYQYMDD
LYVGSDLEIEQHRTKIEELRAHLLSWGFTTPDKKHQKEPPFLWMGYELHPDKWTVQPIEL
PEKDSWTVNDIQKIVGKLNWASQIYPGIKVRQLCRLLRGTKALTDIVPLTAEAELELAEN
REILREPVHGVYYDPSKELIAEIQKQGHDQWTYQIYQDPFKNLKTGKYARKRSAHTNDVR
QLTEAVQKITTESIVIWGKTPKFRLPIQRETWEAWWMEYWQATWIPEWEFINTPPLVKLW
YQLEKDPIVGAETFYVDGAASRETKLGKAGYVTNKGRQKVVSLNETTNQKTELHAIHLAL
QDSGSEANIVTDSQYALGIIQAQPDRSESEVVNQIIEELIKKEKVYLSWVPAHKGIGGNE
QVDKLVSSGIRKVLFLDGIDKAQEDHERYHSNWRTMASDFNLPPIVAREIVASCDKCQQK
GEAMHGQVDCGPGIWQLDCTHLERKVILVAVHVASGYIEAEVIPAETGQETAYFVLKLAG
RWPVKVIHTDNGSNFTSAAVKAACWWANVTQEFGIPYNPQSQGVVESMNNELKKIIGQVR
EQAEHLKTAVLMAVFIHNFKRKRGIGGYSAGERIVDIIASDIQTKELQNQITKIQNFRVY
FRDSRDPIWKGPAKLLWKGEGAVVIQDNNDIKVVPRRKVKIIRDYGKQMAGDDCVAGRQD
EN-
>POL-M.syn6.2
FFREDLAFQQGEARKFSSEQTRANSPTSR--------------ELRVWG-GDNTLSETGA
ER----QGT---LNFPQITLWQRPLVTIKVGGQIEALLDTGADDTVLEDINLPGKWKPR
MIGGIGGFIKVRQYDQIPIEICGKKAIGSVLGPTPVNIIGRNMLTQLGCTLNFPISPIK
TVPVKLKPGMDGPKVKQWPLSEEKIKALTAICDEMEKEGKITKIGPDNPYNTPVFAIKKK
DGTKWRKLVDFKELNKRTQDFWEIQLGIPHPAGLKKKKSVSVLDVGDAYFSVPLDESFRK
YTAFTIPSLNNETPGIRYCYNVLPQGWKGSPAIFQSSMTKILEPFRAQNPEIVIYQYIDD
LYVRSDLEIGQHRAKIEELREHLLKWGLTTPDKKHQKEPPFLWMGYELHPDRWTVQPIQL
```

Fig. 10 cont'd-26

```
PDKDSWTVNDLQKLVGKLNWASQIYPGIRVKQLCKLLKGAKALTDIVTLTEEAELELAEN
REILKNPVHGVYYDPAKDLIAEIQKQGNDQWTYQIYQEPHKNLKTGKYAKMRTAHTNDVK
QLTEVVQKIAMESIVIWGKVPKFRLPIQKETWETWWTDYWQATWIPDWEFVNTPPLVKLW
YQLEKEPIAGAETFYVDGAANRETKMGKAGYVTDRGRQKVVSLTETTNQKTELQAIQLAL
QDSGPEVNIVTDSQYAIGIIQAQPDKSESEIVNQIIEQLIKKERVYLSWVPAHKGIGENE
QVDKLVSTGIRRVLFLDGIDKAQEEHERYHSNWRAMASEFNLPPIVAKEIVASCDQCQLK
GEAMHGQVDCSPGVWQLDCTHLEGKIILVAVHVASGYMEAEVIPAETGQETAYFILKLAA
RWPVKVIHTDNGPNFTSATVKAACWWANITQEFGIPYNPQGQGVVESMNKELKKIIKQVR
DQAEHLKTAVQMAVLIHNFKRKGGIGGYSAGERIIDIIASDIQTKELQKQIIKIQNFQVY
YRDSRDPIWKGPAKLLWKGEGAVVLQDNSDIKVVPRRKVKIIKDYGKQMAGADCVAGGQD
ED-
>POL-M.syn6.3
FFRENLAFPQGKAREFPSEQTRAISPTSR-------------ELQVWGGDNNSLSEAGA
ER----QGTVS-FSFPQITLWQRPIVTIKIGGQLREALLDTGADDTVLEEMNLPGRWKPK
MIGGIGGFIKVKQYDNILIEICGHKAVGTVLVGPTPANIIGRNLLTQLGCTLNFPISPIE
TVPVKLKPGIDGPKVQWPLTEEKIKALVEICTEMEKEGKISKIGPENPYNTPIFAIKKK
DSTRWRKLVDFRELNRRTQDFWEVQLGIPHPAGLKRKKSVTVLDVGDAYFSVPLDKEFRK
YTAFTIPSINNETPGIRYQYNVLPQGWKGSPSIFQSSMTKILEPFRIKNPEMVIYQYMDD
LYIGSDLEIGQHRIKIEELREHLLKWGFTTPDKKHQKEPPFLWMGCELHPDKWTVQPIML
PEKDSWTVNDIQKLVGKLNWASQIYAGIKVRQLCKLLRGTKALTEVVPLTEEAELELAEN
REILKEPVHGAYYDPSKDLIAEVQKQGQDQWTYQIYQEPFKNLKTGKYAKKRSAHTNDVK
QLTEAVQKIALESIVIWGKAPKFRLPIQKETWEAWWTEYWQATWVPEWEFVNTPPLVKLW
YQLETEPIAGAETYYVDGAANRETKLGKAGYVTNRGRQKVVSLTDTTNQKTELQAIHLAL
QDSGLEVNIVTDSQYALGIIHAQPDKSESELVNQIIEQLINKERIYLSWVPAHKGIGENE
QVDKLVSKGIRKVLFLDGIEKAQEEHEKYHSNWKAMASEFNLPPVVAKEIVACCDKCQLK
GEALHGQVDCSPGMWQLDCTHLEGKIIIVAVHVASGYIEAEVIPTETGQETAYFLLKLAG
RWPVKTIHTDNGSNFTSTTVKAACWWAGIKQEFGIPYNPQSQGVVESINKELKKIIGQIR
DQAEHLKTAVLMAVFIHNFKRKGGIGGYTAGERIVDIIATDIQTKELQKQITKVQNFRVY
YRDSREPLWKGPAKLLWKGEGAVVIQDNNEIKVVPRRKAKILRDYGKQMAGADCVASRQD
EN-
>POL-M.syn6.4
FFRENLAFQQGEAREFSSEQTRTNSPTSR-------------ELWDGGRDNLP-SEAGA
ER----RGTVPSLSFPQITLWQRPLVTVKIGGQLKEALLDTGADDTVLEEINLPGKWKPK
LIGGIGGFIKVRQYDQILIEICGKKAIGTVLVGPTPINIIGRNMLTQIGCTLNFPISPIE
TIPVKLKPGMDGPRVKQWPLTEEKIKALIEICTEMEKEGKISRVGPENPYNTPIFAIKKK
NSNRWRKLVDFRELNKRTQDFWEVQLGIPHPGGLKKKKSVTILDVGDAYFSVPLDEDFRK
YTAFTIPSINNATPGIRYQYNVLPQGWKGSPAIFQCSMTKILEPFRKQNPEIIIYQYMDD
LYVRSDLEIGQHRTKIEELRQHLLKWGFYTPDKKHQKEPPFLWMGYELHPDKWTVQPIKL
PEKESWTVNDIQKLVEKLNWASQIYPGIKVQLCRLLRGAKALTEVIPLTEEAELELEEN
REILKDPVHGVYYDPTKDLIAEIQKQGDDQWTYQIYQEPYKNLKTGKYAKRRTAHTNDVR
QLTEVVQKVATESIVIWGKIPKFKLPIQKETWEIWWTDYWQATWIPEWEFVNTPHLVKLW
YQLEKEPIIGAETFYVDGASNRETKKGKAGYVTDRGRQKIVSLTETTNQKAELQAIQLAL
QDSGSEVNIVTDSQYALGIIQAHPDKSESELVSQIIEQLIKKEKVYLAWVPAHKGIGGNE
QIDKLVSNGIRKILFLDGIDKAQEEHEKYHNNWRAMASDFNLPPVVAKEIVASCNKCQLK
GEAIHGQVDCSPRIWQLDCTHLEGKVIMVAVHVASGYVEAEVIPAETGQDTAYFILKLAG
RWPVKVVHTDNGSNFTSAAFKAACWWANVQQEFGIPYNPQSQGVVEAMNKELKKIIEQVR
DQAEHLKTAVQMAVFVHNFKRKGGIGDYSAGERIIDIIATDIQTRELQKQIIKIQNFRVY
YRDNRDPIWKGPAKLLWKGEGAVVIQDNSDIKVIPRRKAKIIRDYGKQMAGDDCMAGRQD
EDQ
>POL-M.syn6.5
FFREDLAFLQGKAREFSSEQTRANSPTRR-------------ELQVWGRDSNSLSEAGA
DR----QGTVS-FNFPQITLWQRPLVTIKIGGQLKEALLDTGADDTVLEDIDLPGKWKPK
IIGGIGGFIKVKQYDQILIEICGKRAIGTVLVGPTPVNIIGRNILTQIGCTLNFPISPID
TVPVKLKPGMDGPRIKQWPLTEEKIKALTEICKEMEEGKISKIGPENPYNTPVFAIKKK
```

Fig. 10 cont'd-27

```
DSTKWRKVVDFRELNKGTQDFWEVQLGIPHPAGLKQKKSVTVLDVEDAYFSVPLDKDFRK
YTAFTIPSVNNETPGIRYQYNVLPQGWKGSPAIFQSSMTRILEPFRKQNPDIVIYQYMDD
LYVGSDLEIGQHRTKVEELRQHLLRWGFTTPDKKHQKDPPFLWMGYELHPDKWTVQPIVL
PEKDSWTINDIQKLVGKLNWASQIYSGIKVRQLCKCLRGTKALTEVIPLTKEAELELAEN
KEILKEPVHGVYYDPSKDLVAEIQKQGQGQWTYQIYQEQYKNLKTGKYARMRGAHTNDVK
QLAEAVQKIATESIVIWGKIPKFRLPIQRETWETWWTEYWQATWIPEWEYVNTPPLVKLW
YQLEKEPIVGAETFYVDGAANRDTKLGKAGYVTDRGRQKVVPLTDTTNQKTELQAINLAL
QDSGSKVNIVTDSQYVLGIIQAQPDRSESEIVNQIIEKLIEKDKVYLSWVPAHKGIGGNE
QVDKLVSAGIRKVLFLDGIDKAQDEHEKYHSNWRAMASDFNLPPVIAKEIVASCDKCQLK
GEATHGQVDCSPGIWQLDCTHLEGKVIIVAVHVASGYIEAEVISAETGQETAYYILKLAG
RWPVKIIHTDNGSNFTSTAVKAACWWAGIQQEFGIPYSPQSQGVVESMNKQLKQIIGQVR
DQAEQLKTAVQMAVFIHNFKRKGGIGEYSAGERIIDIISTDIQTRELQKQITKIQNFRVY
YRDSRDPVWKGPAKLLWKGEGAVVIQDNSEIKVVPRRKAKIIRHYGKQMAGDDCVASRQD
EDQ
>POL-M.syn6.6
FFRENLAFPQGEAREFPSEQARANSPTSRANSPTSR-------ELQV--RGDNPRSEAGA
ERQGTLQGT---LNCPQITLWQRPLVSIKVGGQVKEALLDTGADDTVLEEMSLPGKWKPK
MVGGIGGFIKVRQYDQILVEICGHKAIGTVLVGPTPVNIIRRNMLTQLRCTLNFPISPIE
TVPVTLKPGMDGPKVRQWPLTEEKIKALTAICEEMEKEGKITKIGPENPYNTPVFAIRKK
DSTKWRKLVDFRELNKKTQDFWEVQLGIPHPSGLKKKKSVTVLDVGDAYFSVPLDEGFRK
YTAFTIPSTNNETPGIRYQYNVLPQGWKGSPAIFQSSMIKILEPFRAKNPEIVIYQYMDD
LYVGSDLEIGQHRAKVEELREHLLRWGFTTPDKKHQNEPPFLWMGYELHPDKWTVQPIQL
PEKDSWTVNDIQRLVGKLNWASQIYAGIKVQLCKLLRGAKALTDIVPLTEEAELELAEN
REILKTPVHGVYYDPSKDLIAEIQKQGQDQWSYQIYQEPFKNLKTGKYARTRGAHTNDVR
QLTEAVQKIAQECIVIWGKTPKFKLPIQKDTWETWWMDYWQATWIPKWEFVNTPPLVKLW
YQLEKDPIAGVETFYVDGAANRETKIGKAGYVTDKGRQKVVTLTETTNQKTELHAIYLAL
QDSGSEVNVVTDSQYALGIIQAQPDRSESELVNQIIEKLIGKDKVYLSWVPAHKGIGENE
QVDKLVSNGIRKVLFLDGIDKAQEDHEKYHSNWRAMANEFNLPPIVAKEIVANCDKCQLK
GEAMHGQVDCSPGIWQIDCTHLEGKVILVAVHVASGYLEAEVIPAETGQEAAYFILKLAG
RWPVKTVHTDNGSNFTSNAVKAACWWANVRQEFGIPYNPQSQGVIESMNKELKKIIGQVR
DQAEHLRTAVQMAVFIHNFKRRGGIGGYSAGERMIDIIATDIQTTELQKQITKIQKFRVY
YRDSRDPLWKGPAKLLWKGEGAVVIQENSDIKVVPRRKAKIIKDYGKQVAGADCVAGRQD
EDQ
```

Fig. 11

This plot is alignment independent, based on splintering all M group proteins, (database and CHAVI, one sequence per person) into all possible 9-mers, attending to their frequencies, and then looking for matches and near matches in each vaccine antigen or cocktail with the database

| Vaccine | subset | Off-by0 | Off-by1 | Off-by2 | (<3,>1) | unique | absent | rare < 3 |
|---|---|---|---|---|---|---|---|---|
| ConSgp160 | Total | 0.2628 | 0.5301 | 0.7267 | 9 | 12 | 45 | 66 |
| ConSgp160 | B | 0.2682 | 0.5344 | 0.7223 | 2 | 8 | 45 | |
| ConSgp160 | C | 0.2526 | 0.5214 | 0.7302 | 1 | 0 | 45 | |
| ConSgp160 | N | 0.2662 | 0.5332 | 0.7283 | 7 | 4 | 45 | |
| Mos.3 | Total | 0.4485 | 0.7032 | 0.8358 | 15 | 164 | 8 | 179 |
| Mos.3 | B | 0.4749 | 0.7319 | 0.8576 | 3 | 40 | 8 | |
| Mos.3 | C | 0.4809 | 0.7363 | 0.8498 | 8 | 65 | 8 | |
| Mos.3 | N | 0.3868 | 0.6383 | 0.7970 | 11 | 59 | 8 | |
| Nat.1.acute | Total | 0.2258 | 0.4598 | 0.6458 | 125 | 0 | 0 | 125 |
| Nat.1.acute | B | 0.3190 | 0.5803 | 0.7482 | 125 | 0 | 0 | |
| Nat.1.acute | C | 0.1589 | 0.3781 | 0.5726 | 0 | 0 | 0 | |
| Nat.1.acute | N | 0.1815 | 0.3979 | 0.5968 | 0 | 0 | 0 | |
| Nat.3.acute | Total | 0.3673 | 0.6449 | 0.8036 | 164 | 252 | 0 | 416 |
| Nat.3.acute | B | 0.3765 | 0.6483 | 0.8045 | 130 | 0 | 0 | |
| Nat.3.acute | C | 0.3940 | 0.6840 | 0.8307 | 19 | 102 | 0 | |
| Nat.3.acute | N | 0.3311 | 0.6036 | 0.7766 | 21 | 150 | 0 | |

ConSgp160

Mos.3

Nat.1.acute

Nat.3.acute

Alignment positions (reordered by coverage ranking)

up to 7/9 match  
up to 8/9 match  
exact match  
total 9-mers  
Upper bound: 3 ant Con S Mos.3

Nat.1

Nat.3

Env alignment position    0 1 2 3 4 5 6 7 8 9

■ B clade

Fig. 17

Coverage of the HIV database plus CHAVI sequences (N = 2020)

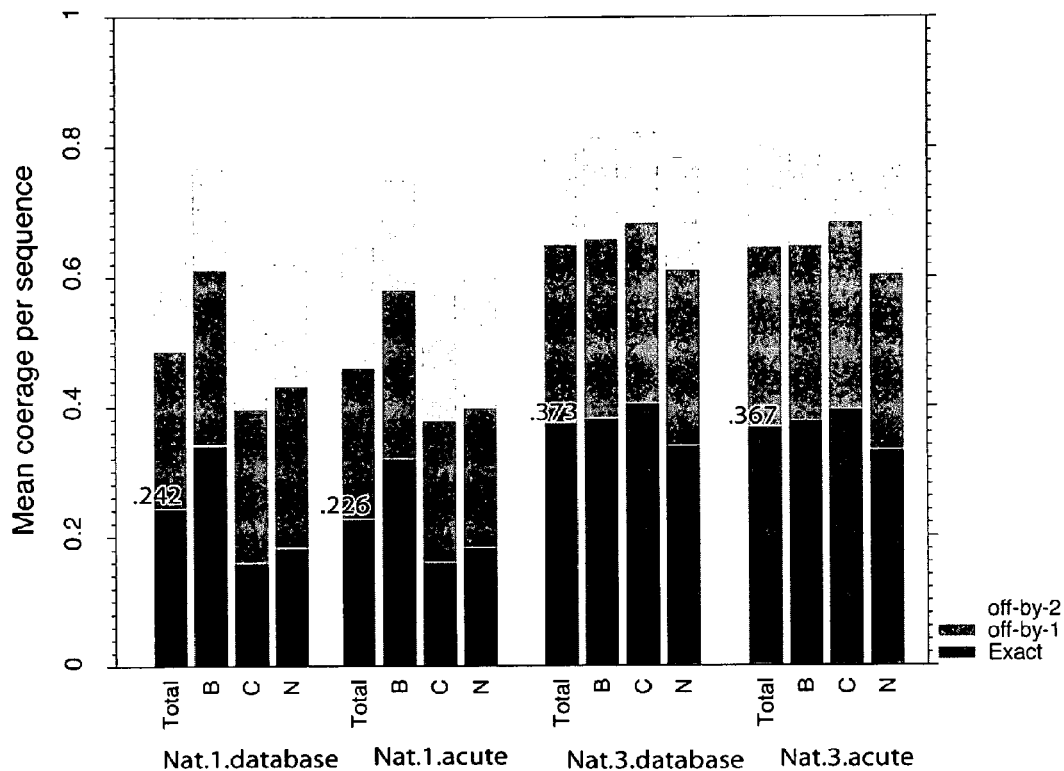

Nat.3.database

Option 1:
B YU2* -- 1986, USA
C DU467, South Africa,
A ML170 -- 1986 Kenya

Optimal for the set
after requiring inclusion
of one each of subtype
A, B and C.

Nat.3.acute

Option 2:
B 1059*
C 0393
A R66201FPB

Optimal for the set
after requiring inclusion
of one each of subtype
A, B and C as well as
restricting antigen selection
to SGA sequences sampled
during acute infection.

Fig. 18
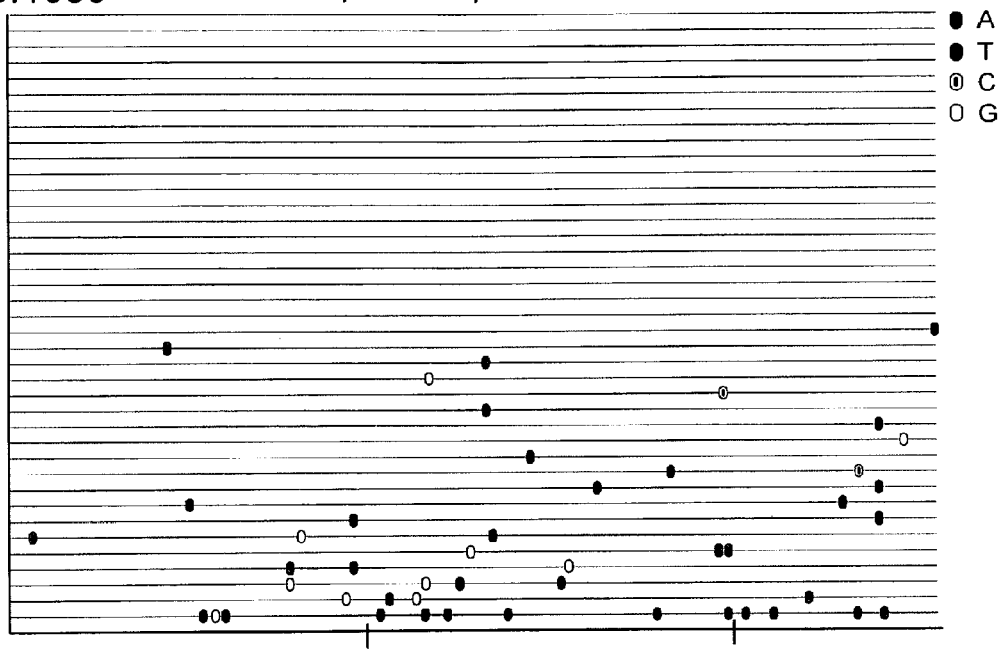
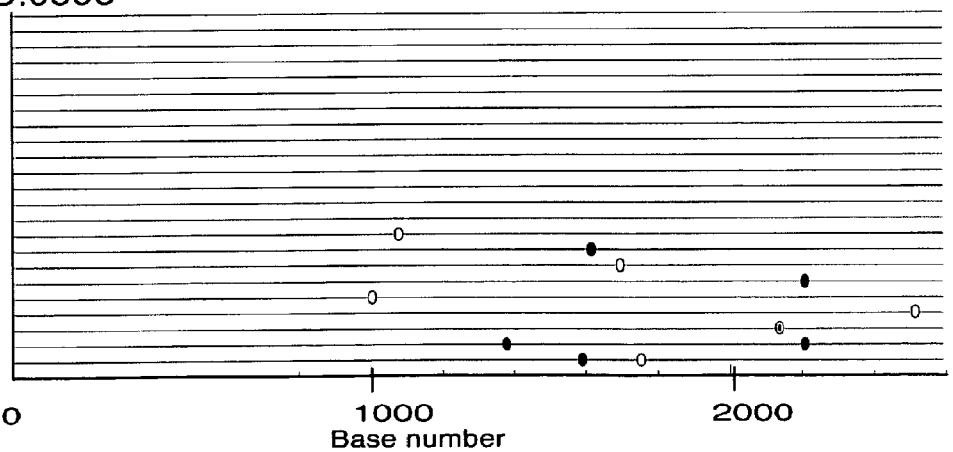

Proposed vaccine mosaic coverage of Gag and Env

Fig. 21

>nefM_4.1Dmyr
MAAKWSKSSIVGWPAVRERMRRAEPAADGVGAVSRDLEKHGAITSSNTAATNADCAWLEAQEE
DSEVGFPVRPHVPLRPMTYKAAVDLSHFLKEQGGLEGLIYSQKRQDILDLWVYHTQGYFPDWQN
YTPGPGIRYPLTFGWCFKLVPVDPREVEEANKGENNCLLHPMSQHGMDDPEKEVLMWKFDSRLA
FHHMAREKHPEFYKDC >nefM_4.2Dmyr
MAAKWSKRSIVGWPAIRERMRRTEPAAEGVGAASQDLDKYGALTSSNTAQTNPDCAWLEAQEE
EEVGFPVRPQVPVRPMTYKGALDLSHFLKEKGGLDGLIYSRKRQEILDLWVYNTQGYFPDWQNY
TPGPGVRYPLTFGWCYKLVPVDPEEVEKANEGENNSLLHPMSLHGMEDPEREVLKWKFDSRLAL
KHRARELHPEFYKDC >nefM_4.3Dmyr
MAANWSKSSIVGWPEIRERIRRTDPAAEGVGAASRDLERHGAITSSNTATTNAACAWLEAQEDEE
VGFPVRPQVPLRPMTFKGAFDLGFFLKEKGGLEGLIYSKKRQDILDLWVYNTQGFFPDWQNYTPG
PGTRFPLTFGWCFELVPVDPKEVEEANEGENNCLLHPICQHGMDDEEREVLMWKFDSSLARRHLA
REKHPEYYKDC >nefM_4.4Dmyr
MASKWSKSSIVGWPQVRERIRQTPPAAEGVGAVSQDLDKHGAVTSSNTAANNADCAWLQAQEE
EEEVGFPVKPQVPLRPMTYKGAFDLSFFLKEKGGLDGLIYSKKRQEILDLWVYHTQGFFPDWHNY
TPGPGTRYPLCFGWCFKLVPMDPAEVEEATEGENNSLLHPICQHGMEDEDREVLVWRFDSSLARR
HIARELHPEYYKDC >Gag-M4.1Dmyr
MAARASVLSGGELDRWEKIRLRPGGKKKYKLKHIVWASRELERFAVNPGLLETSEGCRQILGQLQ
PSLQTGSEELRSLYNTVAVLYCVHQRIDVKDTKEALEKIEEEQNKSQQKTQQAKAADGKVSQNYP
IVQNAQGQMVHQAISPRTLNAWVKVIEEKGFSPEVIPMFSALAEGATPQDLNTMLNTIGGHQAAM
QMLKDTINDEAAEWDRLHPVQAGPVAPGQIREPRGSDIAGTTSNLQEQIGWMTSNPPIPVGDIYKR
WIIMGLNKIVRMYSPTSILDIRQGPKESFRDYVDRFFRTLRAEQASQEVKNWMTETLLVQNSNPDC
KTILKALGPAATLEEMMTACQGVGGPGHKARVLAEAMSQVQQPNIMMQRGNFKGQKRIKCFNC
GREGHLARNCRAPRKKGCWKCGREGHQMKDCTESKANFLGKIWPSNKGRPGNFLQSRPEPSAPP
AESFGFGEEITPSQKQEQKDKELYPLASLKSLFGNDPLSQ >Gag_M4.2 Dmyr
MAARASVLSGGKLDAWEKIRLRPGGKKKYRLKHLVWASRELDRFALNPSLLETAEGCKQIMKQL
QPALKTGTEELKSLYNTVATLYCVHEKIDVRDTKEALDKIEEEQNKIQQKTQQAKEADGKVSQNY
PIVQNIQGQMVHQPISPRTLNAWVKVVEEKAFSPEVIPMFTALSDGATPQDLNSMLNAVGGHQAA
MQILKDTINEEAADWDRLHPVHAGPVAPGQMREPRGSDIAGTTSTLQEQIGWMTNNPPIPVGEIYK
RWIILGLNKIVRMYSPVSILDIKQGPKESFRDYVDRFFKVLRAEQATQDVKNWMTDTLLIQNANPD
CKSILRALGPGATLEEMMTACQGVGGPSHKARILAEAMSQVTNSATIMMQRGNFRNQRKTVKCF
NCGKEGHLARNCKAPRKRGCWKCGKEGHQMKECTERQANFLGKIWPSSKGRPGNFPQSRPEPTA
PPEESFRFGEETTTPSQKQEPIDKELYPLASLRSLFGNDPSSQAS

Fig. 21 cont'd-1

>Gag_M4.3 Dmyr
MAARASILRGGKLDKWEKIRLRPGGKKRYMLKHLIWASRELERFALNPGLLETAEGCQQIIEQLQS
TLKTGSEELKSLFNTVATLYCVHQRIEVKDTKEALDKVEEEQNKSKKKAQQAAADTGNSSQVSQ
NYPIVQNLQGQMVHQALSPRTLNAWVKVIEEKAFSPEIIPMFTALSEGATPSDLNTMLNTVGGHQ
AAMQMLKDTINEEAAEWDRVHPVHAGPIPPGQMREPRGSDIAGTTSSLQEQIAWMTSNPPVPVGE
IYKRWIVLGLNKIVRMYSPVSILDIRQGPKEPFRDYVDRFFKTLRAEQASQDVKNWMTETLLVQN
ANPDCKTILRALGPGASLEEMMTACQGVGGPSHKARVLAEAMSQTNSAILMQRSNFKGSKRIVKC
FNCGKEGHIARNCRAPRKRGCWKCGQEGHQMKDCNERQANFLGKIWPSHKGRPGNFLQNRPEPT
APPEPTAPPAESFRFEETTPAPKQELKDREPLTSLKSLFGSDPLSQAS >Gag_M4.4 Dmyr
MAARASVLRGEKLDKWERIRLRPGGKKHYMLKHLVWASRELEKFALNPGLLETSEGCKQIIKQL
QPALQTGTEELRSLFNTVATLYCVHAGIEVRDTKEALDKIEEIQNKSKQKTQQAAAGTGSSSKVSQ
NYPIVQNLQGQMVHQPLSPRTLNAWVKVVEEKGFNPEVIPMFSALSEGATPQDLNMMLNIVGGH
QAAMQMLKETINEEAAEWDRLHPVHAGPIAPGQMREPRGSDIAGSTSTLQEQIAWMTGNPPVPV
GDIYKRWIILGLNKIVKMYSPTSILDIKQGPKEPFRDYVDRFYKTLRAEQATQEVKNWMTDTLLVQ
NANPDCKSILKALGTGATLEEMMSACQGVGGPAHKARVLAEAMSQANNTNIMMQRSNFKGPKRI
IKCFNCGKEGHIAKNCRAPRKKGCWKCGKEGHQMKDCTERQANFLGRIWPSSKGRPGNFLQSRP
EPTAPPAEPTAPPAESFKFEETTPAPKQEPKDREPLTSLRSLFGSDPLLQAS >M_mos_3_1 (M_mos_Env_3_1)
MRVKGIRKNYQHLWRWGTMLLGMLMICSAAEQLWVTVYYGVPVWRDAETTLFCASDAKAYER
EVHNVWATHACVPTDPNPQEIVLENVTEEFNMWKNNMVDQMHEDIISLWDESLKPCVKLTPLCV
TLNCTDVNVTKTNSTSWGMMEKGEIKNCSFNMTTELRDKKQKVYALFYKLDIVPLEENDTISNST
YRLINCNTSAITQACPKVTFEPIPIHYCTPAGFAILKCNDKKFNGTGPCKNVSTVQCTHGIRPVVTTQ
LLLNGSLAEEEIIIRSENLTNNAKTIIVQLNESVVINCTRPNNNTRKSIRIGPGQTFYATGDIIGNIRQA
HCNISREKWINTTRDVRKKLQEHFNKTIIFNSSSGGDLEITTHSFNCRGEFFYCNTSKLFNSVWGNS
SNVTKVNGTKVKETITLPCKIKQIINMWQEVGRAMYAPPIAGNITCKSNITGLLLVRDGGNVTNNT
EIFRPGGGNMKDNWRSELYKYKVVEIKPLGIAPTKAKRRVVEREKRAVGLGAVFLGFLGAAGST
MGAASMTLTVQARQLLSGIVQQQSNLLRAIEAQQHMLQLTVWGIKQLQARILAVERYLRDQQLL
GIWGCSGKLICTTNVPWNSSWSNKSLDEIWNNMTWMQWEKEIDNYTSLIYTLIEESQNQQEKNEQ
DLLALDKWANLWNWFDISNWLWYIRIFIMIVGGLIGLRIVFAVLSIVNRVRKGYSPLSFQTLTPNPR
GPDRLGRIEEEGGEQDKDRSIRLVNGFLALAWDDLRNLCLFSYHRLRDLLLIVTRIVELLGRRGWE
ALKYLWNLLQYWIQELKNSAVSLLNATAIAVAEGTDRVIEVVQRACRAILHIPRRIRQGLERALL >M_mos_3_2 (M_mos_Env_3_2)
MRVKETQMNWPNLWKWGTLILGLVIICSASDNLWVTVYYGVPVWKEATTTLFCASDAKAYDTE
VHNVWATYACVPTDPNPQEVVLGNVTENFNMWKNNMVEQMHEDIISLWDQSLKPCVRLTPLCV
TLNCSNANTTNTNSTEEIKNCSFNITTSIRDKVQKEYALFYKLDVVPIDNDNTSYRLISCNTSVITQA
CPKVSFEPIPIHYCAPAGFAILKCKDKKFNGTGPCTNVSTVQCTHGIRPVVSTQLLLNGSLAEEEVVI
RSENFTNNAKTIIVHLNKSVEINCTRPNNNTRKSIHIGPGRAFYATGEIIGDIRQAHCNISRAKWNNT
LKQIVKKLKEQFNKTIIFNQSSGGDPEITTHSFNCGGEFFYCNTSGLFNSTWNSTATQESNNTELNG
NITLPCRIKQIVNMWQEVGKAMYAPPIRGQIRCSSNITGLILTRDGGNNNSTNETFRPGGGDMRDN
WRSELYKYKVVKIEPLGVAPTKAKRRVVQREKRAVGTIGAMFLGFLGAAGSTMGAASLTLTVQA
RLLLSGIVQQQNNLLRAIEAQQHLLQLTVWGIKQLQARVLAVERYLKDQQLLGIWGCSGKLICTT
TVPWNTSWSNKSLNEIWDNMTWMEWEREIDNYTGLIYTLLEESQNQQEKNEQELLELDKWASL
WNWFDITKWLWYIKIFIMIVGGLVGLRIVFTVLSIVNRVRQGYSPLSFQTHLPAPRGPDRPEGIEEE
GGERDRDRSGRLVDGFLAIIWVDLRSLCLFSYHQLRDFILIAARTVELLGHSSLKGLRRGWEALKY
WWNLLQYWSQELKNSAISLLNTTAJVVAEGTDRIIEVLQRAGRAILHIPTRIRQGLERLLL

Fig. 21 cont'd-2

>M_mos_3_3 (M_mos_Env_3_3)
MRVRGIQRNWPQWWIWGILGFWMLMICNVVGNLWVTVYYGVPVWKEAKTTLFCASDAKAYEK
EVHNVWATHACVPTDPSPQEVVLENVTENFNMWKNDMVDQMHEDVISLWDQSLKPCVKLTHL
CVTLNCTNATNTNYNNSTNVTSSMIGEMKNCSFNITTEIRDKSRKEYALFYRLDIVPLNEQNSSEY
RLINCNTSTITQACPKVSFDPIPIHYCAPAGYAILKCNNKTFNGTGPCNNVSTVQCTHGIKPVVSTQL
LLNGSLAEGEIIIRSENLTDNAKTIIVHLNESVEIVCTRPNNNTRKSVRIGPGQAFYATGDIIGDIRQA
HCNLSRTQWNNTLKQIVTKLREQFGNKTIVFNQSSGGDPEIVMHSFNCGGEFFYCNTTQLFNSTWE
NSNITQPLTLNRTKGPNDTITLPCRIKQIINMWQGVGRAMYAPPIEGLIKCSSNITGLLLTRDGGNNS
ETKTTETFRPGGGNMRDNWRNELYKYKVVQIEPLGVAPTRAKRRVVEREKRAVGIGAVFLGFLG
TAGSTMGAASITLTVQARQVLSGIVQQQSNLLKAIEAQQHLLKLTVWGIKQLQTRVLAIERYLKD
QQLLGLWGCSGKLICTTAVPWNSSWSNKSQTDIWDNMTWMQWDREISNYTDTIYRLLEDSQNQ
QEKNEKDLLALDSWKNLWNWFDITNWLWYIKIFIIIVGGLIGLRIIFAVLSIVNRCRQGYSPLSLQTL
IPNPRGPDRLGGIEEEGGEQDRDRSIRLVSGFLALAWDDLRSLCLFSYHRLRDFILIVARAVELLGRS
SLRGLQRGWEALKYLGSLVQYWGLELKKSAISLLDTIAIAVAEGTDRIIEVIQRICRAIRNIPRRIRQ
GFEAALL

Fig. 22

| HVI number | Gene name | Nef | Myristylation signal mutated |
|---|---|---|---|
| HV13236 | M.con_Nef01_Dmyr.WLV | Group M (2001) consensus | Yes |
| HV13319 | nefM_4.1Dmyr.wlv | Mosaic No. 1 | Yes |
| HV13231 | nefM_4.2Dmyr.wlv | Mosaic No. 2 | Yes |
| HV13230 | nefM_4.3Dmyr.wlv | Mosaic No. 3 | Yes |
| HV13232 | nefM_4.4Dmyr.wlv | Mosaic No. 4 | Yes |
| HV10001 | No inser | | |

All five constructs were cloned into HV10001 (WLV001AM DNA vaccine plasmid.

M.con_Nef01_Dmyr.WLV (657nt.)(hv13236), 67% GC
XhoI
CTCGAGAAGAAAATGGCGGCCAAGTGGTCGAAGAGCTCCATCGTCGGGTGGCCGGCGGTCCGGGAG
CGCATCCGGCGGACGCACCCCGCGGCCGAGGGGGTCGGCGCGGTCTCGCAAGACCTCGACAAGC
ACGGGGCGATCACGTCGAGCAACACCGCCGCGAACAACCCCGACTGCGCGTGGCTGGAGGCCCA
GGAGGAAGAGGAAGAGGTCGGCTTCCCGGTCCGCCCGCAAGTGCCGCTCAGGCCGATGACGTAC
AAGGCGGCCCTCGACCTCTCGCACTTCCTGAAAGAGAAGGGTGGCCTGGAGGGGCTCATCTACT
CGAAGAAGAGGCAGGAGATCCTCGACCTGTGGGTCTACCACACCCAGGGCTACTTCCCGGACTG
GCAGAACTACACGCCAGGCCCGGGAATCCGCTACCCGCTGACCTTCGGGTGGTGCTTCAAGCTC
GTCCCCGTCGACCCGGAGGAGGTCGAGGAAGCCAACGAGGGCGAGAACAACAGCCTCCTGCACC
CGATGTGCCAGCACGGGATGGAGGACGAGGAGCGCGAGGTGCTGATGTGGAAGTTCGACTCGCG
CCTGGCCCTGCGCCACATCGCCCGGGAGCTCCACCCGGAGTACTACAAGGACTGCTGATAAGCTA
GCGGATCCTGATCA
NheI BamHI BclI MAAKWSKSSIVGWPAVRERIRRTHPAAEGVGAVSQDLDKHGAITSSNTAANNPDCAWLEAQEEE
EEVGFPVRPQVPLRPMTYKAALDLSHFLKEKGGLEGLIYSKKRQEILDLWVYHTQGYFPDWQNY
TPGPGIRYPLTFGWCFKLVPVDPEEVEEANEGENNSLLHPMCQHGMEDEEREVLMWKFDSRLAL
RHIARELHPEYYKDC_

>HV13236 in hv10001, 3953nt.
AAATGGGGGCGCTGAGGTCTGCCTCGTGAAGAAGGTGTTGCTGACTCATACCAGGCCTGAATCGCCCCATCATCCAG
CCAGAAAGTGAGGGAGCCACGGTTGATGAGAGCTTTGTTGTAGGTGGACCAGTTGGTGATTTTGAACTTTTGCTTTG
CCACGGAACGGTCTGCGTTGTCGGGAAGATGCGTGATCTGATCCTTCAACTCAGCAAAAGTTCGATTTATTCAACAA
AGCCGCCGTCCCGTCAAGTCAGCGTAATGCTCTGCCAGTGTTACAACCAATTAACCAATTCTGCGTTCAAAATGGTA
TGCGTTTTGACACATCCACTATATATCCGTGTCGTTCTGTCCACTCCTGAATCCCATTCCAGAAATTCTCTAGCGAT
TCCAGAAGTTTCTCAGAGTCGGAAAGTTGACCAGACATTACGAACTGGCACAGATGGTCATAACCTGAAGGAAGATC
TGATTGCTTAACTGCTTCAGTTAAGACCGACGCGCTCGTCGTATAACAGATGCGATGATGCAGACCAATCAACATGG
CACCTGCCATTGCTACCTGTACAGTCAAGGATGGTAGAAATGTTGTCGGTCCTTGCACACGAATATTACGCCATTTG
CCTGCATATTCAAACAGCTCTTCTACGATAAGGGCACAAATCGCATCGTGGAACGTTTGGGCTTCTACCGATTTAGC
AGTTTGATACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTTCCACTCA
CCGGTTGTCCATTCATGGCTGAACTCTGCTTCCTCTGTTGACATGACACACATCATCTCAATATCCGAATACGGACC
ATCAGTCTGACGACCAAGAGAGCCATAAACACCAATAGCCTTAACATCATCCCCATATTTATCCAATATTCGTTCCT
TAATTTCATGAACAATCTTCATTCTTTCTTCTCTAGTCATTATTATTGGTCCGTTCATAACACCCCTTGTATTACTG
TTTATGTAAGCAGACAGTTTTATTGTTCATGATGATATATTTTTATCTTGTGCAATGTAACATCAGAGATTTTGAGA
CACAACGTGGCTTTCCCCGGCCCATGACCAAAATCCCTTAACGTGAGTTTTCGTTCCACTGAGCGTCAGACCCCGTA
GAAAAGATCAAAGGATCTTCTTGAGATCCTTTTTTTCTGCGCGTAATCTGCTGCTTGCAAACAAAAAAACCACCGCT

Mosaic and Group M nef_Dmyr-Patent.doc

Fig. 22 cont'd-1

```
ACCAGCGGTGGTTTGTTTGCCGGATCAAGAGCTACCAACTCTTTTTCCGAAGGTAACTGGCTTCAGCAGAGCGCAGA
TACCAAATACTGTTCTTCTAGTGTAGCCGTAGTTAGGCCACCACTTCAAGAACTCTGTAGCACCGCCTACATACCTC
GCTCTGCTAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACGACCTACA
CCGAACTGAGATACCTACAGCGTGAGCTATGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGGAAACGCCTGGTATCTTTATAGTCCTGT
CGGGTTTCGCCACCTCTGACTTGAGCGTCGATTTTTGTGATGCTCGTCAGGGGGGCGGAGCCTATGGAAAAACGCCA
GCAACGCGGCCTTTTTACGGTTCCTGGCCTTTTGCTGGCCTTTTGCTCACATGTTCTTTCCTGCGTTATCCCCTGAT
TCTGTGGATAACCGTATTACCGCCTTTGAGTGAGCTGATACCGCTCGCCGCAGCCGAACGACCGAGCGCAGCGAGTC
AGTGAGCGAGGAAGCGGAAGAGCGCCTGATGCGGTATTTTCTCCTTACGCATCTGTGCGGTATTTCACACCGCATAT
GGTGCACTCTCAGTACAATCTGCTCTGATGCCGCATAGTTAAGCCAGTATCTGCTCCCTGCTTGTGTGTTGGAGGTC
GCTGAGTAGTGCGCGAGCAAAATTTAAGCTACAACAAGGCAAGGCTTGACCGACAATTGCATGAAGAATCTGCTTAG
GGTTAGGCGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTATTGACTA
GTTATTAATAGTAATCAATTACGGGGTCATTAGTTCATAGCCCATATATGGAGTTCCGCGTTACATAACTTACGGTA
AATGGCCCGCCTGGCTGACCGCCCAACGACCCCCGCCCATTGACGTCAATAATGACGTATGTTCCCATAGTAACGCC
AATAGGGACTTTCCATTGACGTCAATGGGTGGAGTATTTACGGTAAACTGCCCACTTGGCAGTACATCAAGTGTATC
ATATGCCAAGTCCGCCCCCTATTGACGTCAATGACGGTAAATGGCCCGCCTGGCATTATGCCCAGTACATGACCTTA
CGGGACTTTCCTACTTGGCAGTACATCTACGTATTAGTCATCGCTATTACCATGGTGATGCGGTTTTGGCAGTACAT
CAATGGGCGTGGATAGCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATGGGCGGTAGGCGTGTA
CGGTGGGAGGTCTATATAAGCAGAGCTCGTTTAGTGAACCGTCAGATCGCCTGGAGACGCCATCCACGCTGTTTTGA
CCTCCATAGAAGACACCGGGACCGATCCAGCCTCCGCGGGCGCGCGTCGACGGGCGACGCGAAACTTGGGCCCACTC
GAGAAGAAAATGGCGGCCAAGTGGTCGAAGAGCTCCATCGTCGGGTGGCCGGCGGTCCGGGAGCGCATCCGGCGGAC
GCACCCCGCGGCCGAGGGGGTCGGCGCGGTCTCGCAAGACCTCGACAAGCACGGGCGATCACGTCGAGCAACACCG
CCGCGAACAACCCCGACTGCGCGTGGCTGGAGGCCCAGGAGGAAGAGGAAGAGGTCGGCTTCCCGGTCCGCCCGCAA
GTGCCGCTCAGGCCGATGACGTACAAGGCGGCCCTCGACCTCTCGCACTTCCTGAAAGAGAAGGGTGGCCTGGAGGG
GCTCATCTACTCGAAGAAGAGGCAGGAGATCCTCGACCTGTGGGTCTACCACACCCAGGGCTACTTCCCGGACTGGC
AGAACTACACGCCAGGCCCGGGAATCCGCTACCCGCTGACCTTCGGGTGGTGCTTCAAGCTCGTCCCCGTCGACCCG
GAGGAGGTCGAGGAAGCCAACGAGGGCGAGAACAACAGCCTCCTGCACCCGATGTGCCAGCACGGGATGGAGGACGA
GGAGCGCGAGGTGCTGATGTGGAAGTTCGACTCGCGCCTGGCCTTCCACCATCGCCCGGGAGCTCCACCCGGAGT
ACTACAAGGACTGCTGATAAGCTAGCGGATCCTGATCAGCCTCGACTGTGCCTTCTAGTTGCCAGCCATCTGTTGTT
TGCCCCTCCCCCGTGCCTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGCAGGACAGCAAGGGGGAGGATTGGGAAG
ACAATAGCAGGCATGCTGGGGAATTT
```

| | | | | | |
|---|---|---|---|---|---|
| Thursday, August 2, 2007 | | ApaI | GGGCCC | 3485 3541 3678 | |
| | | 1 Site | | 3679 3691 | |
| Sequence 0 Length : 3953 | | 3075 | | BglI | GCCNNNNNGGC |
| | | ApaLI | GTGCAC | 4 Sites | |
| AatII | GACGTC | 2 Sites | | 2475 2597 2668 | |
| 4 Sites | | 1583 2081 | | 3320 | |
| 2510 2563 2646 | | AvaI | CYCGRG | BglII | AGATCT |
| 2832 | | 3 Sites | | 1 Site | |
| AccI | GTMKAC | 3078 3482 3676 | | 458 | |
| 3 Sites | | BamHI | GGATCC | Bsp1286 | GDGCHC |
| 3050 3433 3535 | | 1 Site | | 8 Sites | |
| AflIII | ACRYGT | 3723 | | 652 1587 2085 | |
| 1 Site | | BanI | GGYRCC | 2953 3075 3114 | |
| 1897 | | 3 Sites | | 3391 | |
| AluI | AGCT | 538 2850 3807 | | 3685 | |
| 13 Sites | | BanII | GRGCYC | BspHI | TCATGA |
| 109 633 1340 | | 5 Sites | | 2 Sites | |
| 1597 1643 1733 | | 2953 3075 3114 | | 1007 1105 | |
| 1959 | | 3391 3685 | | BspNI | CCWGG |
| 2184 2951 3112 | | BclI | TGATCA | 13 Sites | |
| 3524 3683 3717 | | 1 Site | | 52 1738 1751 | |
| AlwNI | CAGNNNCTG | 3729 | | 1872 2475 2668 | |
| 2 Sites | | BcnI | CCSGG | 2977 | |
| 1488 2129 | | 12 Sites | | 3270 3381 3444 | |
| AosII | GRCGYC | 1173 1521 3021 | | 3478 3657 3801 | |
| 5 Sites | | 3139 3298 3457 | | BssHII | GCGCGC |
| 2507 2560 2643 | | 3484 | | 1 Site | |
| 2829 2963 | | | | 3045 | |

Mosaic and Group M nef_Dmyr-Patent.doc

Fig. 22 cont'd-2

```
BstNI    CCWGG                    55      771     1175        25 Sites
13 Sites                       1423    1857    1875                52    1172    1520
     52    1738    1751         1886                           1738    1751    1872
1872    2475    2668              2268    2469    2662         2475
2977                            3073    3096    3128              2668    2977    3020
   3270    3381    3444         3168                           3138    3270    3297
3478    3657    3801               3267    3323    3342        3381
Cfr10I    RCCGGY                3379    3481    3660              3444    3456    3478
2 Sites                         HgiAI    GWGCWC                3483    3484    3540
    847    3128                 5 Sites                        3657
CfrI    YGGCCR                      1587    2085    2953          3677    3678    3690
4 Sites                         3114    3685                   3801
    769    3094    3126         BhaI    GCGC                   NaeI    GCCGGC
3166                            19 Sites                       1 Site
ClaI    ATCGAT                      11    496    1273             3130
1 Site                          1382    1556    1656           NciI    CCSGG
   2287                         1723                           12 Sites
DdeI    CTNAG                      1993    2026    2169            1172    1520    3020
12 Sites                        2249    3045    3047           3138    1297    3456
     12    204    397           3145                           3483
   711    787    1214    1623      3183    3255    3625           3484    3540    3677
   2088    2158    2229         3655    3667                   3678    3690
3318    3861                    HincII    GTYRAC               NcoI    CCATGG
DpnI    GATC                    5 Sites                        1 Site
13 Sites                            413    886    2369            2745
    190    195    460           3051    3536                   NdeI    CATATG
1239    1247    1258            HinfI    GANTC                 2 Sites
1333                            15 Sites                           2076    2619
   2972    3028    3216             43    59    357            NheI    GCTAGC
3417    3725    3731            383    401    725    779       1 Site
DraIII    CACNNNGTG                 807    1527    1923           3717
1 Site                          1998    2222    2795           NlaIII    CATG
   1161                         3487                           14 Sites
Eco47I    GGWCC                 3648                               538    762    864
7 Sites                         HinPI    GCGC                  892    1011    1105    1181
    122    586    919           19 Sites                           1901    2219    2349
1048    3021    3133                9    494    1271          2367    2689    2749
3298                            1380    1554    1654           3942
EcoRII    CCWGG                 1721                           NlaIV    GGNNCC
13 Sites                           1991    2024    2167        9 Sites
     50    1736    1749         2247    3043    3045               92    540    1830
1870    2473    2666            3143                           1869    2852    3023
2975                               3181    3253    3623        3073
   3268    3379    3442         3653    3665                      3725    3809
3476    3655    3799            HpaII    CCGG                  NruI    TCGCGA
EcoRV    GATATC                 16 Sites                       1 Site
1 Site                              848    1172    1329           2257
   2294                         1519    1545    1692           NsiI    ATGCAT
Fnu4HI    GCNGC                 3019                           1 Site
20 Sites                           3129    3137    3149           796
    234    769    1283          3297    3456    3483           Nsp7524I    RCATGY
1489    1492    1557            3540                           2 Sites
1700                               3677    3690                    1901    3942
   1855    1973    1976         MaeI    CTAG                   NspBII    CMGCKG
1994    2110    2250            7 Sites                        6 Sites
2279                                378    801    1034             1314    1559    2281
   2282    3094    3166         1404    2385    3718           3039    3165    3500
3235    3315    3340            3751                           RsaI    GTAC
FnuDII    CGCG                  MaeII    ACGT                  11 Sites
17 Sites                        12 Sites                           559    2093    2263
    494    1273    1854             669    1160    1196        2330    2604    2684
2169    2257    2281            2306    2507    2519           2717
2445                            2560                               2768    2925    3333
   3039    3045    3047            2643    2724    2829        3696
3062    3165    3183            3219    3330                   RsrII    CGGWCCG
3237                            MaeIII    GTNAC                2 Sites
   3255    3625    3653         8 Sites                           3134    3299
HaeII    RGCGCY                     270    1134    1361        SacI    GAGCTC
3 Sites                         1477    1540    2446           3 Sites
     12    1657    2027         2533                               2953    3114    3685
HaeIII    GGCC                  2882                           SacII    CCGCGG
20 Sites                        MvaI    CCNGG                  3 Sites
```

Mosaic and Group M nef_Dmyr-Patent.doc

Fig. 22 cont'd-3

```
        2282      3040      3166           1 Site                      SinI      GGWCC
Sall              GTCGAC                     3696                      7 Sites
2 Sites                                    ScrFI     CCNGG                 123       587       920
        3049      3534                     25 Sites                     1049      3022      3134
Sau3A             GATC                          52      1172      1520   3299
13 Sites                                      1738      1751      1872  SmaI      CCCGGG
         188       193       458             2475                      2 Sites
        1237      1245      1256             2668      2977      3020       3484      3678
        1331                                  3138      3270      3297  SnaBI     TACGTA
        2970      3026      3214             3381                      1 Site
        3415      3723      3729             3444      3456      3478       2725
Sau96A            GGNCC                       3483      3484      3540  SpeI      ACTAGT
17 Sites                                      3657                      1 Site
         123       587       920             3677      3678      3690       2384
        1049      1174      2266             3801                      SphI      GCATGC
        2468                                SdnI      GDGCHC            1 Site
        2661      3022      3071            8 Sites                          3942
        3072      3134      3266                 652      1587      2085  SspI      AATATT
        3299                                  2953      3075      3114  2 Sites
        3341      3480      3659             3391                           603       991
ScaI              AGTACT                       3685                      StuI      AGGCCT
1 Site
          55
StyI              CCWWGG
1 Site
        2745
TaqI              TCGA
15 Sites
         216      1799      2287
        3050      3079      3105
        3199
        3222      3346      3399
        3421      3535      3550
        3646
        3738
XhoI              CTCGAG
1 Site
        3078
XhoII             RGATCY
5 Sites
         458      1245      1256
        3415      3723
XmaI              CCCGGG
2 Sites
        3482      3676
XmaIII            CGGCCG
1 Site
        3166
XmnI              GAANNNNTTC
1 Site
         811
Following enzymes have no
sites
AccIII    AflII     Asp718
AsuII     AvrII     BalI
BbeI      BspMII    BstEII
BstXI     DraI
Eco47III
EcoO109   EcoRI     EspI
FspI      HindIII   HpaI
XpnI      MluI      MstI
NarI      NotI      OxaNI
PflMI     PpuMI     PssI
PstI      PvuI      PvuII
SfiI      SplI      Tth111I
XbaI      XcaI
```

Mosaic and Group M nef_Dmyr-Patent.doc

Fig. 22 cont'd-4 nefM_4.1Dmyr (hv13225 in), (663nt.), GC=67%
CTCGAGAAGAAAATGGCGGCCAAGTGGTCGAAGAGCTCCATCGTCGGGTGGCCGGCGGTCCGGGAGAGGA
TGCGGAGGGCGGAGCCGGCGGCCGACGGGGTCGGGGCGGTCTCGCGGGACCTGGAGAAGCACGGGGCGAT
CACGTCGAGCAACACCGCCGCGACGAACGCGGACTGCGCGTGGCTGGAGGCCCAGGAGGAGGACTCGGAG
GTCGGCTTCCCGGTCCGGCCGCACGTCCCGCTCCGGCCGATGACGTACAAGGCGGCCGTCGACCTCTCCC
ACTTCCTGAAAGAGCAGGGGGGCCTGGAGGGGCTCATCTACTCGCAGAAGAGGCAGGACATCCTCGACCT
GTGGGTCTACCACACCCAGGGCTACTTCCCGGACTGGCAGAACTACACGCCAGGCCCGGGAATCCGCTAC
CCGCTGACCTTCGGGTGGTGCTTCAAGCTCGTCCCCGTGGACCCGCGGGAGGTCGAGGAAGCCAACAAGG
GGGAGAACAACTGCCTCCTGCACCCGATGTCGCAGCACGGGATGGACGACCCGGAGAAGGAGGTGCTGAT
GTGGAAGTTCGACTCGCGGCTGGCGTTCCACCACATGGCCCGCGAGAAGCACCCGGAGTTCTACAAGGAC
TGCTGATAAGCTAGCTGATCAGGATCCACGCGT MAAKWSKSSIVGWPAVRERMRRAEPAADGVGAVSRDLEKHGAITSSNTAATNADCAWLEAQEEDSEVGFP
VRPHVPLRPMTYKAAVDLSHFLKEQGGLEGLIYSQKRQDILDLWVYHTQGYFPDWQNYTPGPGIRYPLTF
GWCFKLVPVDPREVEEANKGENNCLLHPMSQHGMDDPEKEVLMWKFDSRLAFHHMAREKHPEFYKDC HV13319 (nefM_4.1Dmyr.wlv), 3918nt.
AAATGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA Mosaic and CON nef_Dmyr_final.doc

Fig. 22 cont'd-5

```
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGAGAAGAAAATGGCGGCCAAGTGGTCGAA
GAGCTCCATCGTCGGGTGGCCGGCGGTCCGGGAGAGGATGCGGAGGGCGGAGCCGGCGGCCGACGGGGTC
GGGGCGGTCTCGCGGGACCTGGAGAAGCACGGGGCGATCACGTCGAGCAACACCGCCGCGACGAACGCGG
ACTGCGCGTGGCTGGAGGCCCAGGAGGAGGACTCGGAGGTCGGCTTCCCGGTCCGGCCGCACGTCCCGCT
CCGGCCGATGACGTACAAGGCGGCCGTCGACCTCTCCCACTTCCTGAAAGAGCAGGGGGGCCTGGAGGGG
CTCATCTACTCGCAGAAGAGGCAGGACATCCTCGACCTGTGGGTCTACCACACCCAGGGCTACTTCCCGG
ACTGGCAGAACTACACGCCAGGCCCGGGAATCCGCTACCCGCTGACCTTCGGGTGGTGCTTCAAGCTCGT
CCCCGTGGACCCGCGGGAGGTCGAGGAAGCCAACAAGGGGGAGAACAACTGCCTCCTGCACCCGATGTCG
CAGCACGGGATGGACGACCCGGAGAAGGAGGTGCTGATGTGGAAGTTCGACTCGCGGCTGGCGTTCCACC
ACATGGCCCGCGAGAAGCACCCGGAGTTCTACAAGGACTGCTGATAAGCTAGCTGATCAGCCTCGACTGT
GCCTTCTAGTTGCCAGCCATCTGTTGTTTGCCCCTCCCCGTGCCTTCCTTGACCCTGGAAGGTGCCACT
CCCACTGTCCTTTCCTAATAAAATGAGGAAATTGCATCGCATTGTCTGAGTAGGTGTCATTCTATTCTGG
GGGGTGGGGTGGGGCAGGACAGCAAGGGGGAGGATTGGGAAGACAATAGCAGGCATGCTGGGAATTT
```

| | | | | | |
|---|---|---|---|---|---|
| Thursday, August 2, 2007 | | 2953 3085 3362 | | 3169 3241 3352 | |
| | | BclI TGATCA | | 3415 3449 3766 | |
| Sequence 0 Length : 3918 | | 1 Site | | Cfr10I RCCGGY | |
| | | 3694 | | 3 Sites | |
| AatII GACGTC | | BcnI CCSGG | | 847 3099 3132 | |
| 4 Sites | | 10 Sites | | CfrI YGGCCR | |
| 2510 2563 2646 | | 1173 1521 3021 | | 7 Sites | |
| 2832 | | 3110 3269 3428 | | 769 3065 3097 | |
| AccI GTMKAC | | 3455 | | 3137 3274 3292 | |
| 2 Sites | | 3456 3590 3662 | | 3311 | |
| 3317 3404 | | BglI GCCNNNNNGGC | | ClaI ATCGAT | |
| AflIII ACRYGT | | 3 Sites | | 1 Site | |
| 1 Site | | 2475 2597 2668 | | 2287 | |
| 1897 | | BglII AGATCT | | DdeI CTNAG | |
| AluI AGCT | | 1 Site | | 11 Sites | |
| 13 Sites | | 458 | | 12 204 397 | |
| 109 633 1340 | | Bsp1286 GDGCHC | | 711 787 1214 1623 | |
| 1597 1643 1733 | | 6 Sites | | 2088 2158 2229 | |
| 1959 | | 652 1587 2085 | | 3826 | |
| 2184 2951 3083 | | 2953 3085 3362 | | DpnI GATC | |
| 3495 3688 3692 | | BspHI TCATGA | | 11 Sites | |
| AlwNI CAGNNNCTG | | 2 Sites | | 190 195 460 | |
| 2 Sites | | 1007 1105 | | 1239 1247 1258 | |
| 1488 2129 | | BspNI CCWGG | | 1333 | |
| AosII GRCGYC | | 13 Sites | | 2972 3028 3187 | |
| 5 Sites | | 52 1738 1751 | | 3696 | |
| 2507 2560 2643 | | 1872 2475 2668 | | DraIII CACNNNGTG | |
| 2829 2983 | | 2977 | | 1 Site | |
| ApaLI GTGCAC | | 3169 3241 3352 | | 1161 | |
| 2 Sites | | 3415 3449 3766 | | Eco47I GGWCC | |
| 1563 2081 | | BssHII GCGCGC | | 9 Sites | |
| AvaI CYCGRG | | 1 Site | | 122 586 919 | |
| 1 Site | | 3045 | | 1048 3021 3104 | |
| 3453 | | BstNI CCWGG | | 3164 | |
| BanI GGYRCC | | 13 Sites | | 3269 3506 | |
| 3 Sites | | 52 1738 1751 | | EcoO109 RGGNCCY | |
| 538 2850 3772 | | 1872 2475 2668 | | 2 Sites | |
| BanII GRGCYC | | 2977 | | 3165 3348 | |
| 3 Sites | | | | EcoRII CCWGG | |

Mosaic and CON nef_Dmyr_final.doc

Fig. 22 cont'd-6

```
13 Sites                          9      494     1271      NlaIV     GGNNCC
      50     1736    1749     1380    1554    1654         11 Sites
1870    2473    2666          1721                               92     540    1830
2975                              1991    2024    2167     1869    2852    3023
    3167    3239    3350      2247    3043    3045         3131
3413    3447    3764          3224                             3166    3349    3509
EcoRV    GATATC               HpaII    CCGG                3774
1 Site                        17 Sites                     NruI      TCGCGA
    2294                          848    1172    1329      1 Site
Fnu4HI   GCNGC                1519    1545    1692             2257
22 Sites                      3019                         NsiI      ATGCAT
     234     769    1283          3100    3108    3133     1 Site
1489    1492    1557          3268    3273    3291             796
1700                          3427                         Nsp7524I  RCATGY
    1855    1973    1976          3454    3589    3661     2 Sites
1994    2110    2250          MaeI      CTAG                   1901    3907
2279                          7 Sites                      NspBII    CMGCKG
    2282    3065    3137          378     801    1034      6 Sites
3206    3277    3311          1404    2385    3689             1314    1559    2281
3571                          3716                         3039    3471    3513
    3625                      MaeII     ACGT               PflMI     CCANNNNNTGG
FnuDII   CGCG                 13 Sites                     1 Site
17 Sites                          669    1160    1196          3642
     494    1273    1854      2306    2507    2519         PpuMI     RGGWCCY
2169    2257    2281          2560                         1 Site
2445                              2643    2724    2829         3165
    3039    3045    3047      3190    3281    3301         PssI      RGGNCCY
3162    3208    3217          MaeIII    GTNAC              2 Sites
3226                          8 Sites                          3168    3351
    3513    3624    3650          270    1134    1361      RsaI      GTAC
HaeII    RGCGCY               1477    1540    2446         10 Sites
3 Sites                       2533                              559    2093    2263
      12    1657    2027          2882                     2330    2604    2684
HaeIII   GGCC                 MvaI      CCNGG              2717
20 Sites                      23 Sites                         2763    2925    3304
      55     771    1175           52    1172    1520      RsrII     CGGWCCG
1423    1857    1875          1738    1751    1872         2 Sites
1886                          2475                             3105    3270
    2268    2469    2662          2668    2977    3020     SacI      GAGCTC
3067    3099    3139          3109    3169    3241         2 Sites
3238                          3268                             2953    3085
    3276    3294    3313          3352    3415    3427     SacII     CCGCGG
3350    3452    3646          3449    3454    3455         3 Sites
HgiAI    GWGCWC               3585                             2282    3040    3514
4 Sites                           3661    3766             SalI      GTCGAC
    1587    2085    2953      NaeI      GCCGGC             1 Site
3085                          2 Sites                          3316
HhaI     GCGC                     3101    3134             Sau3A     GATC
14 Sites                      NciI      CCSGG              11 Sites
      11     496    1273      10 Sites                          188     193     458
1382    1556    1656              1172    1520    3020     1237    1245    1256
1723                          3109    3268    3427         1331
    1993    2026    2169      3454                             2970    3026    3185
2249    3045    3047              3455    3589    3661     3694
3226                          NcoI      CCATGG             Sau96A    GGNCC
HincII   GTYRAC               1 Site                       17 Sites
4 Sites                           2745                          123     587     920
     413     886    2369      NdeI      CATATG             1049    1174    2266
3318                          2 Sites                      2468
HinfI    GANTC                    2076    2619                 2661    3022    3105
16 Sites                      NheI      GCTAGC             3165    3237    3270
      43      59     357      1 Site                       3348
383     401     725     779       3688                         3451    3507    3645
    807    1527    1923       NlaIII    CATG               ScrFI     CCNGG
1998    2222    2795          15 Sites                     23 Sites
3250                              538     762     864           52    1172    1520
    3458    3619               892    1011    1109   1181  1738    1751    1872
HinPI    GCGC                     1901    2219    2349     2475
14 Sites                      2367    2689    2749             2668    2977    3020
                              3645                         3109    3169    3241
                                  3907                     3268

Mosaic and CON nef_Dmyr_final.doc
```

Fig. 22 cont'd-7

| | | | | | | | | |
|---|---|---|---|---|---|---|---|---|
| 3352 | 3415 | 3427 | | 3907 | | | 3453 | |
| 3449 | 3454 | 3455 | SspI | AATATT | | XmaIII | CGGCCG | |
| 3589 | | | 2 Sites | | | 4 Sites | | |
| 3661 | 3766 | | 603 | 991 | | 3137 | 3274 | 3292 |
| SdnI | GDGCHC | | StuI | AGGCCT | | 3311 | | |
| 6 Sites | | | 1 Site | | | XmnI | GAANNNNTTC | |
| 652 | 1587 | 2085 | 55 | | | 1 Site | | |
| 2953 | 3085 | 3362 | StyI | CCWWGG | | 811 | | |
| SinI | GGWCC | | 1 Site | | | | | |
| 9 Sites | | | 2745 | | | Following enzymes have no | | |
| 123 | 587 | 920 | TaqI | TCGA | | sites | | |
| 1049 | 3022 | 3105 | 11 Sites | | | AccIII | AflII | ApaI |
| 3165 | | | 216 | 1799 | 2287 | Asp718 | AsuII | AvrII |
| 3270 | 3507 | | 3050 | 3076 | 3193 | BalI | BamHI | BbeI |
| SmaI | CCCGGG | | 3317 | | | BspMII | BstEII | BstXI |
| 1 Site | | | 3392 | 3521 | 3617 | DraI | Eco47III | EcoRI |
| 3455 | | | 3703 | | | EspI | FspI | HindIII |
| SnaBI | TACGTA | | Tth111I | GACNNNGTC | | HpaI | KpnI | MluI |
| 1 Site | | | 1 Site | | | MstI | NarI | NotI |
| 2725 | | | 3145 | | | OxaNI | PstI | PvuI |
| SpeI | ACTAGT | | XhoII | RGATCY | | PvuII | ScaI | SfiI |
| 1 Site | | | 3 Sites | | | SplI | XbaI | XcaI |
| 2384 | | | 458 | 1245 | 1256 | XhoI | | |
| SphI | GCATGC | | XmaI | CCCGGG | | | | |
| 1 Site | | | 1 Site | | | | | | nefM_4.2Dmyr (654nt.) hv13231, GC=66%
ctcgagAAGAAA[ATG]GCGGCCAAGTGGTCGAAGCGGTCCATCGTCGGGTGGCCGGCGATCCGGGAGAGGA
TGCCGGAGGACGGAGCCGGCGGCCGAGGGGGTCGGGGCGGCGTCGCAGGACCTCGACAAATACGGGGCGCT
CACGTCGAGCAACACCGCCCAGACGAACCCGGACTGGCGCTGGCTGGAGGCCCAGGAGGAGGAAGAGGTC
GGCTTCCCGGTCCGGCCGCAAGTCCCAGTCAGGCCGATGACGTACAAGGGCGCCCTGGACCTCTCCCACT
TCCTGAAAGAGAAGGGGGGCCTGGACGGGCTCATCTACTCGCGGAAGAGGCAGGAGATCCTCGACCTGTG
GGTCTACAACACCCAGGGCTACTTCCCCGACTGGCAGAACTACACGCCAGGCCCCGGAGTGCGGTACCCG
CTGACCTTCGGGTGGTGCTACAAGCTCGTCCCCGTGGACCCGGAGGAGGTCGAGAAGGCCAACGAGGGGG
AGAACAACTCCCTCCTGCACCCGATGTCGCTCCACGGGATGGAGGACCCCGAGAGGGAGGTGCTGAAGTG
GAAGTTCGACTCGCGGCTGGCGCTCAAGCACCGGGCCCGGGAGCTCCACCCGGAGTTCTACAAGGACTGC
TGATAAGCTAGCGGATCCTGATCA MAAKWSKRSIVGWPAIRERMRRTEPAAEGVGAASQDLDKYGALTSSNTAQTNPDCAWLEAQEEEEVGFPV
RPQVPVRPMTYKGALDLSHFLKEKGGLDGLIYSRKRQEILDLWVYNTQGYFPDWQNYTPGPGVRYPLTFG
WCYKLVPVDPEEVEKANEGENNSLLHPMSLHGMEDPEREVLKWKFDSRLALKHRARELHPEFYKDC_

>HV13231 in hv10001 (nefM_4.2Dmyr.wlv), 3950nt.
AAATGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT Mosaic and CON nef_Dmyr_final.doc

Fig. 22 cont'd-8

```
ATTTATCCAATATTCGTTCCTTAATTTCATGAACAATCTTCATTCTTTCTTCTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGACGGGCGACGCGAAACTTGGGCCCACTC
GAGAAGAAAATGGCGGCCAAGTGGTCGAAGCGGTCCATCGTCGGGTGGCCGGCGATCCGGGAGAGGATGC
GGAGGACGGAGCCGGCGGCCGAGGGGGTCGGGGCGGCGTCGCAGGACCTCGACAAATACGGGGCGCTCAC
GTCGAGCAACACCGCCCAGACGAACCCGGACTGCGCGTGGCTGGAGGCCCAGGAGGAGGAAGAGGTCGGC
TTCCCGGTCCGGCCGCAAGTCCCAGTCAGGCCGATGACGTACAAGGGCGCCCTGGACCTCTCCCACTTCC
TGAAAGAGAAGGGGGGCCTGGACGGGCTCATCTACTCGCGGAAGAGGCAGGAGATCCTCGACCTGTGGGT
CTACAACACCCAGGGCTACTTCCCCGACTGGCAGAACTACACGCCAGGCCCCGGAGTGCGGTACCCGCTG
ACCTTCGGGTGGTGCTACAAGCTCGTCCCCGTGGACCCGGAGGAGGTCGAGAAGGCCAACGAGGGGGAGA
ACAACTCCCTCCTGCACCCGATGTCGCTCCACGGGATGGAGGACCCCGAGAGGGAGGTGCTGAAGTGGAA
GTTCGACTCGCGGCTGGCGCTCAAGCACCGGGCCCGGGAGCTCCACCCGGAGTTCTACAAGGACTGCTGA
TAAGCTAGCGGATCCTGATCAGCCTCGACTGTGCCTTCTAGTTGCCAGCCATCTGTTGTTTGCCCCTCCC
CCGTGCCTTCCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGGACAGCAAGGGGGAGGATTGG
GAAGACAATAGCAGGCATGCTGGGGAATTT
```

Thursday, August 2, 2007

Sequence 0   Length : 3950

| | | |
|---|---|---|
| AatII | GACGTC | |
| 4 Sites | | |
| 2510 | 2563 | 2646 |
| 2832 | | |
| AccI | GTMKAC | |
| 2 Sites | | |
| 3050 | 3430 | |

| | | |
|---|---|---|
| AflIII | ACRYGT | |
| 1 Site | | |
| 1897 | | |
| AluI | AGCT | |
| 12 Sites | | |
| 109 | 633 | 1340 |
| 1597 | 1643 | 1733 |
| 1959 | | |
| 2184 | 2951 | 3521 |
| 3680 | 3714 | |
| AlwNI | CAGNNNCTG | |

| | | |
|---|---|---|
| 2 Sites | | |
| 1488 | 2129 | |
| AosII | GRCGYC | |
| 7 Sites | | |
| 2507 | 2560 | 2643 |
| 2829 | 2983 | 3186 |
| 3337 | | |
| ApaI | GGGCCC | |
| 2 Sites | | |
| 3075 | 3674 | |
| ApaLI | GTGCAC | |

Mosaic and CON nef_Dmyr_final.doc

Fig. 22 cont'd-9

```
2 Sites                      ClaI      ATCGAT              3267      3302      3320
   1583      2081            1 Site                        3376      3478      3555
Asp718    GGTACC                2287                       3672
1 Site                       DdeI      CTNAG              HgiAI     GWGCWC
   3490                      11 Sites                      4 Sites
AvaI      CYCGRG                  12       204       397      1587      2085      2953
3 Sites                         711       787      1214      1623   3682
   3078      3615      3673     2088      2158      2229           HhaI      GCGC
BamHI     GGATCC                3858                              17 Sites
1 Site                       DpnI      GATC                      11       496      1273
   3720                      13 Sites                           1382      1556      1656
BanI      GGYRCC                190       195       460         1723
5 Sites                        1239      1247      1258           1993      2026      2169
    538      2850      3336    1333                              2249      3045      3047
3490      3804                  2972      3028      3135        3215
BanII     CRGCYC                3414      3722      3728           3255      3339      3659
5 Sites                      DraIII    CACNNNGTG                HincII    GTYRAC
   2953      3075      3388   1 Site                            4 Sites
3674      3682                  1161                               413       886      2369
BbeI      GGCGCC             Eco47I    GGWCC                    3051
1 Site                       11 Sites                           HinfI     GANTC
   3340                         122       586       919         14 Sites
BclI      TGATCA                1048      3021      3111            43        59       357
1 Site                          3193                               383       401       725      779
   3726                         3295      3343      3532           807      1527      1923
BcnI      CCSGG                 3610                              1998      2222      2795
12 Sites                     Eco0109   RGGNCCY                   3645
   1173      1521      3021   4 Sites                          HinPI     GCGC
   3139      3247      3295      3194      3374      3477      17 Sites
   3482                         3611                                 9       494      1271
   3538      3670      3675   EcoRII    CCWGG                    1380      1554      1654
   3676      3688             13 Sites                           1721
BglI      GCCNNNNNGGC              50      1736      1749           1991      2024      2167
3 Sites                         1870      2473      2666          2247      3043      3045
   2475      2597      2668     2975                              3213
BglII     AGATCT                3268      3340      3376           3253      3337      3657
1 Site                          3439      3473      3796       HpaII     CCGG
    458                      EcoRV     GATATC                   18 Sites
Bsp1286   GDGCHC             1 Site                                848      1172      1329
8 Sites                         2294                              1519      1545      1692
    652      1587      2085  Fnu4HI    GCNGC                     3019
   2953      3075      3388  20 Sites                             3129      3137      3162
   3674                         234       769      1283          3246      3294      3299
   3682                         1489      1492      1557         3481
BspHI     TCATGA                1700                               3537      3668      3674
2 Sites                         1855      1973      1976         3687
   1007      1105               1994      2110      2250       KpnI      GGTACC
BspNI     CCWGG                 2279                             1 Site
13 Sites                        2282      3094      3166            3494
     52      1738      1751     3184      3303      3651       MaeI      CTAG
   1872      2475      2668  FnuDII    CGCG                     7 Sites
   2977                      14 Sites                              378       801      1034
   3270      3342      3378      494      1273      1854         1404      2385      3715
   3441      3475      3798     2169      2257      2281         3748
BssHII    GCGCGC                2445                           MaeII     ACGT
1 Site                          3039      3045      3047        12 Sites
   3045                         3062      3255      3398           669      1160      1196
BstNI     CCWGG                 3650                              2306      2507      2519
13 Sites                     HaeII     RGCGCY                    2560
     52      1738      1751   6 Sites                             2643      2724      2829
   1872      2475      2668        12      1657      2027        3219      3327
   2977                         3216      3340      3660      MaeIII    GTNAC
   3270      3342      3378  HaeIII    GGCC                      8 Sites
   3441      3475      3798  21 Sites                              270      1134      1361
Cfr10I    RCCGGY                  55       771      1175        1477      1540      2446
3 Sites                         1423      1857      1875        2533
    847      3128      3161     1886                              2882
CfrI      YGGCCR                2268      2469      2662      MvaI      CCNGG
5 Sites                         3073      3096      3128        25 Sites
    769      3094      3126     3168
   3166      3300
Mosaic and CON nef_Dmyr_final.doc
```

Fig. 22 cont'd-10

```
         52    1172    1520      PpuMI      RGGWCCY             11 Sites
1738    1751    1872             2 Sites                            123      587     920
2475                                 3194    3611                1049    3022    3112
    2668    2977    3020        PssI       RGGNCCY             3194
3138    3246    3270             4 Sites                            3296    3344    3533
3294                                 3197    3377    3480        3611
    3342    3378    3441        3614                            SmaI       CCCGGG
3475    3481    3537            RsaI       GTAC                  1 Site
3669                             11 Sites                           3675
    3674    3675    3687             559    2093    2263        SnaBI      TACGTA
3798                             2330    2604    2684            1 Site
NaeI       GCCGGC                2717                               2725
2 Sites                              2768    2925    3330       SpeI       ACTAGT
    3130    3163                 3492                            1 Site
NarI       GGCGCC                RsrII      CGGWCCG                 2384
1 Site                           1 Site                         SphI       GCATGC
    3337                             3296                        1 Site
NciI       CCSGG                 SacI       GAGCTC                  3939
12 Sites                         2 Sites                        SapI       AATATT
    1172    1520    3020             2953    3682                2 Sites
3138    3246    3294             SacII      CCGCGG                  603     991
3481                             2 Sites                        StuI       AGGCCT
    3537    3669    3674             2282    3040                1 Site
3675    3687                     SalI       GTCGAC                  55
NcoI       CCATGG                1 Site                         StyI       CCWWGG
1 Site                               3049                        1 Site
    2745                         Sau3A      GATC                    2745
NdeI       CATATG                13 Sites                       TaqI       TCGA
2 Sites                              188     193     458         12 Sites
    2076    2619                 1237    1245    1256                216    1799    2287
NheI       GCTAGC                1331                            3050    3079    3105
1 Site                               2970    3026    3133        3199
    3714                         3412    3720    3726                3222    3418    3547
NlaIII     CATG                  Sau96A     GGNCC                 3643    3735
14 Sites                         22 Sites                       XhoI       CTCGAG
    538     762     864              123     587     920         1 Site
892    1011    1109    1181     1049    1174    2266                3078
    1901    2219    2349        2468                            XhoII      RGATCY
2367    2689    2749                 2661    3022    3071        5 Sites
3939                             3072    3112    3194                458    1245    1256
NlaIV      GGNNCC                3266                            3412    3720
17 Sites                             3296    3344    3374       XmaI       CCCGGG
    92     540    1830          3477    3533    3611             1 Site
1869    2852    3023             3670                               3673
3073                                 3671                       XmaIII     CGGCCG
    3160    3338    3375        ScrFI      CCNGG                 2 Sites
3479    3492    3535             25 Sites                           3166    3300
3613                                  52    1172    1520        XmnI       GAANNNNTTC
    3672    3722    3806        1738    1751    1872             1 Site
NruI       TCGCGA                2475                               811
1 Site                               2668    2977    3020
    2257                         3138    3246    3270           Following enzymes have no
NsiI       ATGCAT                3294                           sites
1 Site                               3342    3378    3441       AccIII     AflII      AsuII
    796                         3475    3481    3537            AvrII      BalI       BspMII
Nsp7524I   RCATGY                3669                           BstEII     BstXI      DraI
2 Sites                              3674    3675    3687       Eco47III   EcoRI      EspI
    1901    3939                3798                            FspI       HindIII    HpaI
NspBII     CMGCKG                SdnI       GDGCHC              MluI       MstI       NotI
5 Sites                          8 Sites                        OxaNI      PstI       PvuI
    1314    1559    2281             652    1587    2085        PvuII      ScaI       SfiI
3039    3497                     2953    3075    3388           SplI       Tth111I    XbaI
PflMI      CCANNNNNTGG          3674                            XcaI
1 Site                               3682
    3605                         SinI       GGWCC
```

>nefM_4.3Dmyr(654nt.), hvl3230, GC=66%
ctcgagAAGAAAATGGCGGCCAACTGGTCGAAGAGCTCCATCGTCGGGTGGCCGGAGATCCGGGAGCGCA
TCCGGAGGACGGACCCGGCGGCCGAGGGGGTCGGGGCGGCCTCGCGGGACCTGGAGCGCCACGGGGCGAT Mosaic and CON nef_Dmyr_final.doc

Fig. 22 cont'd-11

```
CACGTCGAGCAACACCGCCACCACGAACGCGGCCTGCGCGTGGCTGGAGGCCCAGGAGGACGAGGAAGTC
GGCTTCCCGGTCCGGCCGCAAGTCCCGCTCAGGCCGATGACGTTCAAGGGGGCCTTCGACCTCGGCTTCT
TCCTGAAAGAGAAGGGGGGCCTGGAGGGGCTCATCTACTCGAAGAAGAGGCAGGACATCCTCGACCTGTG
GGTCTACAACACCCAGGGGTTCTTCCCGGACTGGCAGAACTACACGCCAGGCCCGGGAACCCGGTTCCCG
CTGACCTTCGGGTGGTGCTTCGAGCTCGTCCCCGTGGACCCGAAGGAGGTCGAGGAAGCCAACGAGGGGG
AGAACAACTGCCTCCTGCACCCGATCTGCCAGCACGGGATGGACGACGAGGAGCGCGAGGTGCTGATGTG
GAAGTTCGACTCGTCCCTGGCCCGGCGCCACCTCGCCCGGGAGAAGCACCCGGAGTACTACAAGGACTGC
TGATAAGCTAGCGGATCCTGATCA

MAANWSKSSIVGWPEIRERIRRTDPAAEGVGAASRDLERHGAITSSNTATTNAACAWLEAQEDEEVGFPV
RPQVPLRPMTFKGAFDLGFFLKEKGGLEGLIYSKKRQDILDLWVYNTQGFFPDWQNYTPGPGTRFPLTFG
WCFELVPVDPKEVEEANEGENNCLLHPICQHGMDDEEREVLMWKFDSSLARRHLAREKHPEYYKDC_

>hv13230 in hv10001 (nefM_4.3Dmyr.wlv)(3950nt.)
AAATGGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
```

Mosaic and CON nef_Dmyr_final.doc

Fig. 22 cont'd-12

```
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGACGGGCGACGCGAAACTTGGGCCCACTC
GAGAAGAAAATGGCGGCCAACTGGTCGAAGAGCTCCATCGTCGGGTGGCCGGAGATCCGGGAGCGCATCC
GGAGGACGGACCCGGCGGCCGAGGGGGTCGGGGCGGCCTCGCGGGACCTGGAGCGCCACGGGGCGATCAC
GTCGAGCAACACCGCCACCACGAACGCGGCCTGCGCGTGGCTGGAGGCCCAGGAGGACGAGGAAGTCGGC
TTCCCGGTCCGGCCGCAAGTCCCGCTCAGGCCGATGACGTTCAAGGGGGCCTTCGACCTCGGCTTCTTCC
TGAAAGAGAAGGGGGGCCTGGAGGGGCTCATCTACTCGAAGAAGAGGCAGGACATCCTCGACCTGTGGGT
CTACAACACCCAGGGGTTCTTCCCGGACTGGCAGAACTACACGCCAGGCCCGGGAACCCGGTTCCCGCTG
ACCTTCGGGTGGTGCTTCGAGCTCGTCCCCGTGGACCCGAAGGAGGTCGAGGAAGCCAACGAGGGGAGA
ACAACTGCCTCCTGCACCCGATCTGCCAGCACGGGATGGACGACGAGGAGCGCGAGGTGCTGATGTGGAA
GTTCGACTCGTCCCTGGCCCGGCGCCACCTCGCCCGGGAGAAGCACCCGGAGTACTACAAGGACTGCTGA
TAAGCTAGCGGATCCTGATCAGCCTCGACTGTGCCTTCTAGTTGCCAGCCATCTGTTGTTTGCCCCTCCC
CCGTGCCTTCCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGGACAGCAAGGGGGAGGATTGG
GAAGACAATAGCAGGCATGCTGGGGAATTT
```

Thursday, August 2, 2007

Sequence 0   Length : 3950

| | | | | | | | |
|---|---|---|---|---|---|---|---|
| AatII | GACGTC | | BanI | GGYRCC | | 52 | 1738 | 1751 |
| 4 Sites | | | 4 Sites | | | 1872 | 2475 | 2668 |
| 2510 | 2563 | 2646 | 538 | 2850 | 3661 | 2977 | | |
| 2832 | | | 3804 | | | 3198 | 3270 | 3378 |
| AccI | GTMKAC | | BanII | GRGCYC | | 3441 | 3475 | 3654 |
| 2 Sites | | | 5 Sites | | | 3798 | | |
| 3050 | 3430 | | 2953 | 3075 | 3114 | BssHII | GCGCGC | |
| AccIII | TCCGGA | | 3388 | 3523 | | 1 Site | | |
| 1 Site | | | BbeI | GGCGCC | | 3045 | | |
| 3148 | | | 1 Site | | | BstNI | CCWGG | |
| AflIII | ACRYGT | | 3665 | | | 14 Sites | | |
| 1 Site | | | BclI | TGATCA | | 52 | 1738 | 1751 |
| 1897 | | | 1 Site | | | 1872 | 2475 | 2668 |
| AluI | AGCT | | 3726 | | | 2977 | | |
| 12 Sites | | | BcnI | CCSGG | | 3198 | 3270 | 3378 |
| 109 | 633 | 1340 | 14 Sites | | | 3441 | 3475 | 3654 |
| 1597 | 1643 | 1733 | 1173 | 1521 | 3021 | 3798 | | |
| 1959 | | | 3139 | 3163 | 3295 | Cfr10I | RCCGGY | |
| 2184 | 2951 | 3112 | 3454 | | | 1 Site | | |
| 3521 | 3714 | | 3481 | 3482 | 3489 | 847 | | |
| AlwNI | CAGNNNCTG | | 3660 | 3675 | 3676 | CfrI | YGGCCR | |
| 2 Sites | | | 3688 | | | 5 Sites | | |
| 1488 | 2129 | | BglI | GCCNNNNNGGC | | 769 | 3094 | 3126 |
| AosII | GRCGYC | | 3 Sites | | | 3166 | 3300 | |
| 6 Sites | | | 2475 | 2597 | 2668 | ClaI | ATCGAT | |
| 2507 | 2560 | 2643 | BglII | AGATCT | | 1 Site | | |
| 2829 | 2983 | 3662 | 1 Site | | | 2287 | | |
| ApaI | GGGCCC | | 458 | | | DdeI | CTNAG | |
| 1 Site | | | Bsp1286 | GDGCHC | | 12 Sites | | |
| 3075 | | | 8 Sites | | | 12 | 204 | 397 |
| ApaLI | GTGCAC | | 652 | 1587 | 2085 | 711 | 787 | 1214 | 1623 |
| 2 Sites | | | 2953 | 3075 | 3114 | 2088 | 2158 | 2239 |
| 1583 | 2081 | | 3388 | | | 3315 | 3858 | |
| AvaI | CYCGRG | | 3523 | | | DpnI | GATC | |
| 3 Sites | | | BspHI | TCATGA | | 14 Sites | | |
| 3078 | 3479 | 3673 | 2 Sites | | | 190 | 195 | 460 |
| BamHI | GGATCC | | 1007 | 1105 | | 1239 | 1247 | 1258 |
| 1 Site | | | BspMII | TCCGGA | | 1333 | | |
| 3720 | | | 1 Site | | | 2972 | 3028 | 3135 |
| | | | 3148 | | | 3216 | 3591 | 3722 |
| | | | BspNI | CCWGG | | 3728 | | |
| | | | 14 Sites | | | DraIII | CACNNNGTG | |
| | | | | | | 1 Site | | |

Mosaic and CON nef_Dmyr_final.doc

Fig. 22 cont'd-13

```
      1161                    4 Sites                      3480     3481     3488
Eco47I      GGWCC              413      886     2369       3659     3674     3675
9 Sites                      3051                          3687
       122      586      919  HinfI      GANTC             NcoI       CCATGG
1048     3021     3157         14 Sites                    1 Site
3193                                43       59      357       2745
     3295     3532             383      401      725      779   NdeI      CATATG
EcoO109     RGGNCCY                807     1527     1923       2 Sites
3 Sites                        1998     2222     2795          2076     2619
      3194     1337     3374   3645                        NheI       GCTAGC
EcoRII      CCWGG              HinPI      GCGC             1 Site
14 Sites                       18 Sites                        3714
        50     1736     1749          9      494     1271  NlaIII     CATG
1870     2473     2666         1380     1554     1654      14 Sites
2975                           1721                            538      762      864
     3196     3268     3376        1991     2024     2167   892     1011     1109     1181
3439     3473     3652         2247     3043     3045      1901     2219     2349
3796                           3143                        2367     2689     2749
EcoRV       GATATC                 3203     3253     3620   3939
1 Site                         3662                        NlaIV      GGNNCC
      2294                     HpaII      CCGG             17 Sites
Fnu4HI      GCNGC              19 Sites                         92      540     1830
20 Sites                            848     1172     1329   1869     2852     3023
       234      769     1283   1519     1545     1692      3073
1489     1492     1557         3019                            3160     3195     3338
1700                               3129     3137     3149   3375     3485     3492
     1855     1973     1976    3162     3294     3299      3535
1994     2110     2250         3453                             3663     3722     3806
2279                               3480     3488     3659   NruI       TCGCGA
     2282     3094     3166    3674     3687               1 Site
3184     3247     3303         MaeI       CTAG                 2257
FnuDII      CGCG               7 Sites                     NsiI       ATGCAT
15 Sites                            378      801     1034   1 Site
       494     1273     1854   1404     2385     3715          796
2169     2257     2281         3748                        Nsp7524I    RCATGY
2445                           MaeII      ACGT             2 Sites
     3039     3045     3047    12 Sites                        1901     3939
3062     3191     3246              669     1160     1196   NspBII     CMGCKG
3255                           2306     2507     2519      5 Sites
     3622                      2560                             1314     1559     2281
HaeII       RGCGCY                 2643     2724     2829   3039     3497
5 Sites                        3219     3327               PpuMI      RGGWCCY
        12     1657     2027   MaeIII     GTNAC            1 Site
3206     3665                  8 Sites                         3194
HaeIII      GGCC                    270     1134     1361   PssI       RGGNCCY
23 Sites                       1477     1540     2446      3 Sites
        55      771     1175   2533                             3197     3340     3377
1423     1857     1875              2882                   RsaI       GTAC
1886                           MvaI       CCNGG            10 Sites
     2268     2469     2662    28 Sites                         559     2093     2263
3073     3096     3128                52     1172     1520  2330     2604     2684
3168                           1738     1751     1872      2717
     3186     3249     3267    2475                             2768     2925     3693
3302     3320     3339              2668     2977     3020  RsrII      CGGWCCG
3376                           3138     3162     3198      1 Site
     3478     3657             3270                            3296
HgiAI       GWGCWC                  3294     3378     3441  SacI       GAGCTC
5 Sites                        3453     3475     3480      3 Sites
      1587     2085     2953   3481                             2953     3114     3523
3114     3523                       3488     3654     3659  SacII      CCGCGG
HhaI        GCGC               3674     3675     3687      2 Sites
18 Sites                       3798                             2282     3040
        11      496     1273   NarI       GGCGCC           SalI       GTCGAC
1382     1556     1656         1 Site                      1 Site
1723                               3662                        3049
     1993     2026     2169    NciI       CCSGG            Sau3A      GATC
2249     3045     3047         14 Sites                    14 Sites
3145                                1172     1520     3020      168      193      458
     3205     3255     3622    3138     3162     3294      1237     1245     1256
3664                           3453                        1331
HincII      GTYRAC
Mosaic and CON nef_Dmyr_final.doc
```

Fig. 22 cont'd-14

| | | | | | | | | |
|---|---|---|---|---|---|---|---|---|
| 2970 | 3026 | 3133 | | 3523 | | 3343 | 3396 | 3418 |
| 3214 | 3589 | 3720 | SinI | GGWCC | | 3517 | 3547 | 3643 |
| 3726 | | | 9 Sites | | | 3735 | | |
| Sau96A | GGNCC | | 123 | 587 | 920 | XhoI | CTCGAG | |
| 20 Sites | | | 1049 | 3022 | 3158 | 1 Site | | |
| 123 | 587 | 920 | 3194 | | | 3078 | | |
| 1049 | 1174 | 2266 | 3296 | 3533 | | XhoII | RGATCY | |
| 2468 | | | SmaI | CCCGGG | | 5 Sites | | |
| 2661 | 3022 | 3071 | 2 Sites | | | 458 | 1245 | 1256 |
| 3072 | 3158 | 3194 | 3481 | 3675 | | 3133 | 3720 | |
| 3266 | | | SnaBI | TACGTA | | XmaI | CCCGGG | |
| 3296 | 3337 | 3374 | 1 Site | | | 2 Sites | | |
| 3477 | 3533 | 3656 | 2725 | | | 3479 | 3673 | |
| ScaI | AGTACT | | SpeI | ACTAGT | | XmaIII | CGGCCG | |
| 1 Site | | | 1 Site | | | 2 Sites | | |
| 3693 | | | 2384 | | | 3166 | 3300 | |
| ScrFI | CCNGG | | SphI | GCATGC | | XmnI | GAANNNNTTC | |
| 28 Sites | | | 1 Site | | | 1 Site | | |
| 52 | 1172 | 1520 | 3939 | | | 811 | | |
| 1738 | 1751 | 1872 | SspI | AATATT | | | | |
| 2475 | | | 2 Sites | | | Following enzymes have no | | |
| 2668 | 2977 | 3020 | 603 | 991 | | sites | | |
| 3138 | 3162 | 3198 | StuI | AGGCCT | | AflII | Asp718 | AsuII |
| 3270 | | | 1 Site | | | AvrII | BalI | BstEII |
| 3294 | 3378 | 3441 | 55 | | | BstXI | DraI | |
| 3453 | 3475 | 3480 | StyI | CCWWGG | | Eco47III | EcoRI | BspI |
| 3481 | | | 1 Site | | | FspI | | |
| 3488 | 3654 | 3659 | 2745 | | | HindIII | HpaI | KpnI |
| 3674 | 3675 | 3687 | TaqI | TCGA | | MluI | MstI | NaeI |
| 3798 | | | 14 Sites | | | NotI | OxaNI | PflMI |
| SdnI | GDGCHC | | 216 | 1799 | 2287 | PstI | PvuI | PvuII |
| 8 Sites | | | 3050 | 3079 | 3105 | SfiI | SplI | Tth111I |
| 652 | 1587 | 2085 | 3222 | | | XbaI | XcaI | |
| 2953 | 3075 | 3114 | | | | | | |
| 3388 | | | | | | | | | nefM_4.4Dmyr (657nt.) hv13232, GC=66%
ctcgagAAGAAAATGGCCTCCAAGTGGTCGAAGAGCTCCATCGTCGGGTGGCCGCAAGTCCGGGAGCGCA
TCCGGCAGACGCCCCCCGCGGCCGAGGGGGTCGGCGCGGTCTCGCAGGACCTCGACAAGCACGGGCGGT
CACGTCGAGCAACACCGCCGGAACAACGCGGACTGCGCGTGGCTGCAGGCCCAGGAGGAAGAGGAACAG
GTCGGCTTCCCGGTCAAGCCGCAAGTGCCGCTCAGGCCGATGACGTACAAGGGGGCCTTCGACCTCTCGT
TCTTCCTGAAAGAGAAGGGTGGCCTGGACGGGCTCATCTACTCGAAGAAGAGGCAGGAGATCCTCGACCT
GTGGGTCTACCACACCCAGGGGTTCTTCCCGGACTGGCACAACTACACGCCAGGCCCGGGAACCCGCTAC
CCGCTGTGCTTCGGGTGGTGCTTCAAGCTCGTCCCCATGGACCCGGCCGAGGTCGAGGAAGCCACCGAGG
GCGAGAACAACTCCCTCCTGCACCCGATCTGCCAGCACGGGATGGAGGACGAGGACCGCGAGGTGCTGGT
CTGGCGGTTCGACTCGTCCCTGGCCCGGCGCCACATCGCCCGGGAGCTCCACCCGGAGTACTACAAGGAC
TGCTGATAAGCTAGCGGATCCTGATCA MASKWSKSSIVGWPQVRERIRQTPPAAEGVGAVSQDLDKHGAVTSSNTAANNADCAWLQAQEEEEEVGFP
VKPQVPLRPMTYKGAFDLSFFLKEKGGLDGLIYSKKRQEILDLWVYHTQGFFPDWHNYTPGPGTRYPLCF
GWCFKLVPMDPAEVEEATEGENNSLLHPICQHGMEDEDREVLVWRFDSSLARRHIARELHPEYYKDC_

>HV13232 in hv10001 (nefM_4.4Dmyr.wlv), 3953nt.
AAATGGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
Mosaic and CON nef_Dmyr_final.doc

Fig. 22 cont'd-15

```
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGCGTCGACGGGCGACGCGAAACTTGGGCCCACTC
GAGAAGAAAATGGCCTCCAAGTGGTCGAAGAGCTCCATCGTCGGGTGGCCGCAAGTCCGGGAGCGCATCC
GGCAGACGCCCCCGCGGCCGAGGGGGTCGGCGCGGTCTCGCAGGACCTCGACAAGCACGGGCGGTCAC
GTCGAGCAACACCGCCGCGAACAACGCGGACTGCGCGTGGCTGCAGGCCCAGGAGGAAGAGGAAGAGGTC
GGCTTCCCGGTCAAGCCGCAAGTGCCGCTCAGGCCGATGACGTACAAGGGGCCTTCGACCTCTCGTTCT
TCCTGAAAGAGAAGGGTGGCCTGGACGGGCTCATCTACTCGAAGAAGAGGCAGGAGATCCTCGACCTGTG
GGTCTACCACACCCAGGGGTTCTTCCCGGACTGGCACAACTACACGCCAGGCCCGGGAACCCGCTACCCG
CTGTGCTTCGGGTGGTGCTTCAAGCTCGTCCCCATGGACCCGGCCGAGGTCGAGGAAGCCACCGAGGGCG
AGAACAACTCCCTCCTGCACCCGATCTGCCAGCACGGGATGGAGGACGAGGACCGCGAGGTGCTGGTCTG
GCGGTTCGACTCGTCCCTGGCCCGGCGCCACATCGCCCGGGAGCTCCACCCGGAGTACTACAAGGACTGC
TGATAAGCTAGCGGATCCTGATCAGCCTCGACTGTGCCTTCTAGTTGCCAGCCATCTGTTGTTTGCCCCT
CCCCCGTGCCTTCCTTGACCCTGGAAGGTGCCACTCCCACTGTCCTTTCCTAATAAAATGAGGAAATTGC
ATCGCATTGTCTGAGTAGGTGTCATTCTATTCTGGGGGGTGGGGTGGGCAGGACAGCAAGGGGAGGAT
TGGGAAGACAATAGCAGGCATGCTGGGGAATTT
```

THURSDAY, AUGUST 2, 2007  SEQUENCE 0  LENGTH : 3953
Mosaic and CON nef_Dmyr_final.doc

Fig. 22 cont'd-16

```
AATII     GACGTC                  3685                      1855      1973      1976
4 SITES                  BSPHI     TCATGA         1994      2110      2250
    2510      2563      2646      2 SITES                   2279
2832                         1007      1105                 2282      3129      3166
ACCI      GTMKAC         BSPNI     CCWGG          3235      3261      3306
2 SITES                  13 SITES                  3315
    3050      3433             52      1738      1751    FNUDII    CGCG
AFLIII    ACRYGT          1872      2475      2668     17 SITES
1 SITE                   2977                            494      1273      1854
    1897                     3270      3381      3444     2169      2257      2281
ALUI      AGCT            3478      3657      3801      2445
13 SITES                 BSSHII    GCGCGC                   3039      3045      3047
     109       633      1340    1 SITE                      3062      3165      3183
    1597      1643      1733        3045                    3237
    1959                 BSTNI     CCWGG                    3246      3255      3525
    2184      2951      3112   13 SITES                HAEII     RGCGCY
    3524      3683      3717       52      1738      1751    4 SITES
ALWNI     CAGNNNCTG       1872      2475      2668         12      1657      2027
2 SITES                  2977                            3668
    1488      2129             3270      3381      3444    HAEIII    GGCC
AOSII     GRCGYC          3478      3657      3801     21 SITES
7 SITES                  CFR10I    RCCGGY                 55       771      1175
    2507      2560      2643   1 SITE                     1423      1857      1875
    2829      2983      3156        847                     1886
3665                     CFRI      YGGCCR                 2268      2469      2662
APAI      GGGCCC         4 SITES                         3073      3093      3128
1 SITE                        769      3126      3166     3168
    3075                 3541                             3267      3323      3342
APALI     GTGCAC         CLAI      ATCGAT                3379      3481      3543
2 SITES                  1 SITE                          3660
    1583      2081             2287                    HGIAI     GWGCWC
AVAI      CYCGRG         DDEI      CTNAG                 5 SITES
3 SITES                  12 SITES                        1587      2085      2953
    3078      3482      3676        12       204       397    3114      3685
BAMHI     GGATCC              711       787      1214      1623   HHAI      GCGC
1 SITE                       2088      2158      2229   17 SITES
    3723                 3318      3861                       11       496      1273
BANI      GGYRCC         DPNI      GATC                  1382      1556      1656
4 SITES                  13 SITES                        1723
     538      2850      3664         190       195       460    1993      2026      2169
3807                         1239      1247      1258    2249      3045      3047
BANII     GRGCYC         1333                            3145
5 SITES                      2972      3028      3417    3183      3255      3667
    2953      3075      3114   3594      3725      3731   HINCII    GTYRAC
    3391      3685       DRAIII    CACNNNGTG             4 SITES
BBEI      GGCGCC         1 SITE                             413       886      2369
1 SITE                       1161                        3051
    3668                 EC047I    GGWCC                 HINFI     GANTC
BCLI      TGATCA         8 SITES                        14 SITES
1 SITE                        122       586       919       43        59       357
    3729                     1048      3021      3193    383       401       725       779
BCNI      CCSGG          3535                            807      1527      1923
13 SITES                     3619                        1998      2222      2795
    1173      1521      3021   ECO0109   RGGNCCY         3648
    3139      3298      3457   2 SITES                  HINPI     GCGC
    3484                      3194      3340           17 SITES
    3485      3541      3663   ECORII    CCWGG               9       494      1271
    3678      3679      3691   13 SITES                  1380      1554      1654
BGLI      GCCNNNNNGGC          50      1736      1749    1721
4 SITES                      1870      2473      2666    1991      2024      2167
    2475      2597      2668   2975                      2247      3043      3045
    3320                      3268      3379      3442    3143
BGLII     AGATCT              3476      3655      3799    3181      3253      3665
1 SITE                   ECORV     GATATC             HPAII     CCGG
     458                 1 SITE                        16 SITES
BSP1286   GDGCHC              2294                        848      1172      1329
8 SITES                  FNU4HI    GCNGC                 1519      1545      1692
     652      1587      2085   21 SITES                  3019
    2953      3075      3114        234       769      1283    3137      3149      3297
    3391                      1489      1492      1557    3456      3483      3540
Mosaic and CON nef_Dmyr_final.doc     1700                    3662
```

Fig. 22 cont'd-17

```
     3677      3690              1 SITE                            652      1587      2085
MAEI         CTAG                 796                             2953      3075      3114
7 SITES                          NSP7524I    RCATGY               3391
     378       801      1034     2 SITES                              3685
   1404      2385      3718          1901      3942               SINI         GGWCC
   3751                           NSPBII      CMGCKG              8 SITES
MAEII        ACGT                6 SITES                              123       587       920
12 SITES                             1314      1559      2281       1049      3022      3194
     669      1160      1196        3039      3165      3500        3536
   2306      2507      2519      PPUMI       RGGWCCY                  3620
   2560                           1 SITE                          SMAI         CCCGGG
   2643      2724      2829           3194                        2 SITES
   3219      3330                 PSSI        RGGNCCY                3484      3678
MAEIII       GTNAC                2 SITES                         SNABI        TACGTA
9 SITES                              3197      3343               1 SITE
     270      1134      1361     PSTI        CTGCAG                  2725
   1477      1540      2446      1 SITE                           SPEI         ACTAGT
   2533                              3265                         1 SITE
       2882      3215             RSAI        GTAC                   2384
MVAI         CCNGG                11 SITES                        SPHI         GCATGC
26 SITES                             559      2093      2263      1 SITE
      52      1172      1520       2330      2604      2684           3942
   1738      1751      1872        2717                           SSPI         AATATT
   2475                              2768      2925      3333     2 SITES
   2668      2977      3020        3696                               603       991
   3138      3270      3297      SACI        GAGCTC               STUI         AGGCCT
   3381                           3 SITES                         1 SITE
   3444      3456      3478          2953      3114      3685          55
   3483      3484      3540      SACII       CCGCGG               STYI         CCWWGG
   3657                            3 SITES                         2 SITES
   3662      3677      3678          2282      3040      3166        2745      3532
   3690      3801                 SALI        GTCGAC               TAQI         TCGA
NARI         GGCGCC               1 SITE                          14 SITES
1 SITE                               3049                             216      1799      2287
   3665                           SAU3A       GATC                 3050      3079      3105
NCII         CCSGG                13 SITES                         3199
13 SITES                             188       193       458        3222      3346      3399
   1172      1520      3020       1237      1245      1256         3421      3550      3646
   3138      3297      3456       1331                              3738
   3483                              2970      3026      3415     XHOI         CTCGAG
   3484      3540      3662       3592      3723      3729        1 SITE
   3677      3678      3690      SAU96A      GGNCC                    3078
NCOI         CCATGG              18 SITES                         XHOII        RGATCY
2 SITES                              123       587       920      5 SITES
   2745      3532                   1049      1174      2266          458      1245      1256
NDEI         CATATG                 2468                            3415      3723
2 SITES                              2661      3022      3071     XMAI         CCCGGG
   2076      2619                   3072      3194      3266      2 SITES
NHEI         GCTAGC                 3340                             3482      3676
1 SITE                               3480      3536      3620     XMAIII       CGGCCG
   3717                              3659                         2 SITES
NLAIII       CATG                 SCAI        AGTACT                 3166      3541
15 SITES                          1 SITE                          XMNI         GAANNNNTTC
     538       762       864          3696                        1 SITE
    892      1011      1109      1181      SCRFI      CCNGG           811
    1901      2219      2349      26 SITES
   2367      2689      2749           52      1172      1520      FOLLOWING ENZYMES HAVE NO
   3536                            1738      1751      1872       SITES
   3942                            2475                           ACCIII       AFLII        ASP718
NLAIV        GGNNCC                2668      2977      3020       ASUII        AVRII        BALI
13 SITES                           3138      3270      3297       BSPMII       BSTEII       BSTXI
      92       540      1830       3381                           DRAI         ECO47III     ECORI
   1869      2852      3023        3444      3456      3478       ESPI         FSPI         HINDIII
   3073                             3483      3484      3540      HPAI         KPNI         MLUI
   3341      3488      3538       3657                            MSTI         NAEI         NOTI
   3666      3725      3809        3662      3677      3678       OXANI        PFLMI        PVUI
NRUI         TCGCGA                3690      3801                 PVUII        RSRII        SFII
1 SITE                           SDNI         GDGCHC              SPLI         TTH111I      XBAI
   2257                          8 SITES                          XCAI
NSII         ATGCAT

Mosaic and CON nef_Dmyr_final.doc
```

Fig. 22 cont'd-18

Gag gene constructs:

| HVI number | Gene name | Gag | | Myristylation signal mutated |
|---|---|---|---|---|
| | | Group M | | |
| HV13234 | M.con_Gag01_Dmyr.wlv | (2001) | | Yes |
| HV13309 | Gag-M4.1 Dmyr.wlv | Mosaic | No. 1 | Yes |
| HV13316 | Gag_M4.2 Dmyr.wlv | Mosaic | No. 2 | Yes |
| HV13317 | Gag_M4.3 Dmyr.wlv | Mosaic | No. 3 | Yes |
| HV13318 | Gag_M4.4 Dmyr.wlv | Mosaic | No. 4 | Yes |

All five constructs were cloned into HV10001 (WLV001AM DNA vaccine plasmid.

M.con_Gag01_Dmyr
MAARASVLSGGKLDAWEKIRLRPGGKKKYRLKHLVWASRELERFALNPGLLETSEGCQQIIGQLQPALQT
GSEELRSLYNTVATLYCVHQRIEVKDTKEALEKIEEEQNKSQQKTQQAAADKGNSSKVSQNYPIVQNLQG
QMVHQAISPRTLNAWVKVIEEKAFSPEVIPMFSALSEGATPQDLNTMLNTVGGHQAAMQMLKDTINEEAA
EWDRLHPVHAGPIPPGQMREPRGSDIAGTTSTLQEQIAWMTSNPPIPVGEIYKRWIILGLNKIVRMYSPV
SILDIRQGPKEPFRDYVDRFFKTLRAEQATQDVKNWMTDTLLVQNANPDCKTILKALGPGATLEEMMTAC
QGVGGPSHKARVLAEAMSQVTNAAIMMQRGNFKGQRRIIKCFNCGKEGHIARNCRAPRKKGCWKCGKEGH
QMKDCTERQANFLGKIWPSNKGRPGNFLQSRPEPTAPPAESFGFGEEITPSPKQEPKDKEPPLASLKSLF
GNDPLSQ_

HV13234 (M.con_Gag01_Dmyr.wlv) (1527nt)

XhoI

CTCGAGAAGAAAATGGCGGCTCGCGCCTCGGTCCTCAGCGGGGGCAAGTTGGATGCGTGGAGAA
GATCCGCTTGAGGCCAGGAGGGAAGAAGAAGTACCGGCTCAAGCACCTGGTCTGGGCGAGCAGG
GAGCTGGAGCGCTTCGCGCTGAACCCGGGCCTGCTGGAGACATCCGAGGGCTGTCAGCAGATCA
TCGGGCAGCTTCAGCCAGCGCTCCAGACGGGCAGCGAGGAGCTGCGCTCGCTATACAACACGGT
AGCGACCCTCTACTGCGTGCACCAGCGGATCGAGGTCAAGGACACGAAGGAGGCTCTTGAGAAG
ATCGAGGAGGAGCAGAACAAGTCGCAGCAGAAGACCCAGCAGGCGGCGGCCGACAAGGGCAACT
CCTCAAAAGTATCTCAGAACTACCCGATCGTGCAGAACCTGCAGGGACAGATGGTCCACCAGGC
CATCAGCCCACGGACGCTTAACGCCTGGGTCAAGGTGATCGAGGAGAAGGCCTTCTCGCCGGAG
GTCATCCCCATGTTCTCGGCACTCTCCGAGGGAGCCACCCCGCAGGACCTGAACACGATGTTGA
ACACGGTCGGCGGGCACCAGGCGGCCATGCAGATGCTCAAGGATACCATCAACGAGGAGGCTGC
GGAGTGGGACCGCCTGCACCCAGTGCACGCGGGGCCCATCCCCCCGGGCCAGATGAGAGAGCCG
CGGGGATCGGACATCGCGGGCACGACCAGCACCTTGCAGGAGCAAATCGCCTGGATGACTAGCA
ACCCCCCGATCCCGGTCGGGGAGATCTACAAGCGGTGGATCATCCTCGGGTTGAACAAGATCGT
GCGGATGTACAGCCCTGTCTCAATCCTGGACATCCGGCAGGGGCCCAAGGAGCCCTTCCGCGAC
TACGTCGACCGGTTCTTCAAGACTCTCCGGGCGGAGCAGGCGACGCAGGACGTCAAGAACTGGA
TGACGGACACCTTGTTGGTCCAGAACGCTAACCCGGACTGCAAGACGATCCTGAAGGCTCTCGG
CCCGGGAGCGACCTTGGAGGAGATGATGACCGCGTGCCAGGGGGTCGGGGGACCCAGCCACAAG
GCGCGGGTCTTGGCCGAGGCGATGTCCCAGGTCACGAACGCCGCGATCATGATGCAGCGGGGGA
ACTTCAAGGGCCAGCGCCGGATCATCAAGTGCTTCAACTGCGGCAAGGAGGGCCACATCGCCCG
GAACTGCCGGGCCCCGCGGAAGAAGGGCTGCTGGAAGTGCGGAAAGGAGGGGCACCAGATGAAG
GACTGCACGGAGCGCCAGGCGAATTTCCTCGGGAAGATCTGGCCGTCCAACAAGGGGCGGCCAG
GGAACTTCCTGCAATCGCGGCCAGAGCCGACGGCCCCTCCCGCGGAGAGCTTCGGGTTCGGCGA

Fig. 22 cont'd-19

```
GGAGATCACGCCCAGCCCCAAGCAAGAGCCGAAGGACAAGGAGCCGCCCCTTGCGTCCCTCAAG
TCGCTCTTCGGCAACGACCCGCTCTCCCAATGATAAGCTAGCGGATCCTGATCA
                                NheI    BamHI  BclI
Cut with XhoI and NheI site for VSV subcloning.
>HV13234 in hv10001 (4,822bp)
AAATGGGGGCGCTGAGGTCTGCCTCGTGAAGAAGGTGTTGCTGACTCATACCAGGCCTGAATCGCCCCAT
CATCCAGCCAGAAAGTGAGGGAGCCACGGTTGATGAGAGCTTTGTTGTAGGTGGACCAGTTGGTGATTTT
GAACTTTTGCTTTGCCACGGAACGGTCTGCGTTGTCGGGAAGATGCGTGATCTGATCCTTCAACTCAGCA
AAAGTTCGATTTATTCAACAAAGCCGCCGTCCCGTCAAGTCAGCGTAATGCTCTGCCAGTGTTACAACCA
ATTAACCAATTCTGCGTTCAAAATGGTATGCGTTTTGACACATCCACTATATATCCGTGTCGTTCTGTCC
ACTCCTGAATCCCATTCCAGAAATTCTCTAGCGATTCCAGAAGTTTCTCAGAGTCGGAAAGTTGACCAGA
CATTACGAACTGGCACAGATGGTCATAACCTGAAGGAAGATCTGATTGCTTAACTGCTTCAGTTAAGACC
GACGCGCTCGTCGTATAACAGATGCGATGATGCAGACCAATCAACATGGCACCTGCCATTGCTACCTGTA
CAGTCAAGGATGGTAGAAATGTTGTCGGTCCTTGCACACGAATATTACGCCATTTGCCTGCATATTCAAA
CAGCTCTTCTACGATAAGGGCACAAATCGCATCGTGGAACGTTTGGGCTTCTACCGATTTAGCAGTTTGA
TACACTTTCTCTAAGTATCCACCTGAATCATAAATCGGCAAAATAGAGAAAAATTGACCATGTGTAAGCG
GCCAATCTGATTCCACCTGAGATGCATAATCTAGTAGAATCTCTTCGCTATCAAAATTCACTTCCACCTT
CCACTCACCGGTTGTCCATTCATGGCTGAACTCTGCTTCCTCTGTTGACATGACACACATCATCTCAATA
TCCGAATACGGACCATCAGTCTGACGACCAAGAGAGCCATAAACACCAATAGCCTTAACATCATCCCCAT
ATTTATCCAATATTCGTTCCTTAATTTCATGAACAATCTTCATTCTTTCTTCTAGTCATTATTATTGG
TCCGTTCATAACACCCCTTGTATTACTGTTTATGTAAGCAGACAGTTTTATTGTTCATGATGATATATTT
TTATCTTGTGCAATGTAACATCAGAGATTTTGAGACACAACGTGGCTTTCCCCGGCCCATGACCAAAATC
CCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCC
GGATCAAGAGCTACCAACTCTTTTTCCGAAGGTAACTGGCTTCAGCAGAGCGCAGATACCAAATACTGTT
CTTCTAGTGTAGCCGTAGTTAGGCCACCACTTCAAGAACTCTGTAGCACCGCCTACATACCTCGCTCTGC
TAATCCTGTTACCAGTGGCTGCTGCCAGTGGCGATAAGTCGTGTCTTACCGGGTTGGACTCAAGACGATA
GTTACCGGATAAGGCGCAGCGGTCGGGCTGAACGGGGGGTTCGTGCACACAGCCCAGCTTGGAGCGAACG
ACCTACACCGAACTGAGATACCTACAGCGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGC
CTGGTATCTTTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTTTGCTGGCCTT
TTGCTCACATGTTCTTTCCTGCGTTATCCCCTGATTCTGTGGATAACCGTATTACCGCCTTTGAGTGAGC
TGATACCGCTCGCCGCAGCCGAACGACCGAGCGCAGCGAGTCAGTGAGCGAGGAAGCGGAAGAGCGCCTG
ATGCGGTATTTTCTCCTTACGCATCTGTGCGGTATTTCACACCGCATATGGTGCACTCTCAGTACAATCT
GCTCTGATGCCGCATAGTTAAGCCAGTATCTGCTCCCTGCTTGTGTGTTGGAGGTCGCTGAGTAGTGCGC
GAGCAAAATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCATACGTT
GTATCTATATCATAATATGTACATTTATATTGGCTCATGTCCAATATGACCGCCATGTTGACATTGATTA
TTGACTAGTTATTAATAGTAATCAATTACGGGGTCATTAGTTCATAGCCCATATATGGAGTTCCGCGTTA
CATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACT
GCCCACTTGGCAGTACATCAAGTGTATCATATGCCAAGTCCGCCCCCTATTGACGTCAATGACGGTAAAT
GGCCCGCCTGGCATTATGCCCAGTACATGACCTTACGGGACTTTCCTACTTGGCAGTACATCTACGTATT
AGTCATCGCTATTACCATGGTGATGCGGTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACT
TTCCAAAATGTCGTAACAACTCCGCCCCATTGACGCAAATGGGCGGTAGGCGTGTACGGTGGGAGGTCTA
TATAAGCAGAGCTCGTTTAGTGAACCGTCAGATCGCCTGGAGACGCCATCCACGCTGTTTTGACCTCCAT
AGAAGACACCGGGACCGATCCAGCCTCCGCGGGCGCGTCGACGGGCGACGCGAAACTTGGGCCCACTC
GAGAAGAAAATGGCGGCTCGCGCCTCGGTCCTCAGCGGGGGCAAGTTGGATGCGTGGGAGAAGATCCGCT
TGAGGCCAGGAGGGAAGAAGAAGTACCGGCTCAAGCACCTGGTCTGGGCGAGCAGGGAGCTGGAGCGCTT
CGCGCTGAACCCGGGCCTGCTGGAGACATCCGAGGGCTGTCAGCAGATCATCGGGCAGCTTCAGCCAGCG
CTCCAGACGGGCAGCGAGGAGCTGCGCTCGCTATACAACACGGTAGCGACCCTCTACTGCGTGCACCAGC
```

Mosaic and Group M Gag_dmyr-patent.doc

Fig. 22 cont'd-20

```
GGATCGAGGTCAAGGACACGAAGGAGGCTCTTGAGAAGATCGAGGAGGAGCAGAACAAGTCGCAGCAGAA
GACCCAGCAGGCGGCGGCCGACAAGGGCAACTCCTCAAAAGTATCTCAGAACTACCCGATCGTGCAGAAC
CTGCAGGGACAGATGGTCCACCAGGCCATCAGCCCACGGACGCTTAACGCCTGGGTCAAGGTGATCGAGG
AGAAGGCCTTCTCGCCGGAGGTCATCCCCATGTTCTCGGCACTCTCCGAGGGAGCCACCCCGCAGGACCT
GAACACGATGTTGAACACGGTCGGCGGGCACCAGGCGGCCATGCAGATGCTCAAGGATACCATCAACGAG
GAGGCTGCGGAGTGGGACCGCCTGCACCCAGTGCACGCGGGGCCCATCCCCCCGGGCCAGATGAGAGAGC
CGCGGGGATCGGACATCGCGGGCACGACCAGCACCTTGCAGGAGCAAATCGCCTGGATGACTAGCAACCC
CCCGATCCCGGTCGGGGAGATCTACAAGCGGTGGATCATCCTCGGGTTGAACAAGATCGTGCGGATGTAC
AGCCCTGTCTCAATCCTGGACATCCGGCAGGGGCCCAAGGAGCCCTTCCGCGACTACGTCGACCGGTTCT
TCAAGACTCTCCGGGCGGACCAGGCGACGCAGGACGTCAAGAACTGGATGACGGACACCTTGTTGGTCCA
GAACGCTAACCCGGACTGCAAGACGATCCTGAAGCGCTCTCGGCCCGGGAGCGACCTTGGAGGAGATGATG
ACCGCGTGCCAGGGGGTCGGGGGACCCAGCCACAAGGCGCGGGTCTTGGCCGAGGCGATGTCCCAGGTCA
CGAACGCCGCGATCATGATGCAGCGGGGGAACTTCAAGGGCCAGCGCCGGATCATCAAGTGCTTCAACTG
CGGCAAGGAGGGCCACATCGCCCGGAACTGCCGGGCCCCGCGGAAGAAGGGCTGCTGGAAGTGCGGAAAG
GAGGGGCACCAGATGAAGGACTGCACGGAGCGCCAGGCGAATTTCCTCGGGAAGATCTGGCCGTCCAACA
AGGGGCGGCCAGGGAACTTCCTGCAATCGCGGCCAGAGCCGACGGCCCCTCCCGCGGAGAGCTTCGGGTT
CGGCGAGGAGATCACGCCCAGCCCCAAGCAAGAGCCGAAGGACAAGGAGCCGCCCCTTGCGTCCCTCAAG
TCGCTCTTCGGCAACGACCCGCTCTCCCAATGATAAGCTAGCGGATCCTGATCAGCCTCGACTGTGCCTT
CTAGTTGCCAGCCATCTGTTGTTTGCCCCTCCCCCGTGCCTTCCTTGACCCTGGAAGGTGCCACTCCCAC
TGTCCTTTCCTAATAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCTGGGGAATTT
```

Thursday, August 2, 2007

Sequence 0   Length : 4823

```
AatII       GACGTC
5 Sites
   2510     2563     2646
   2832     4027
AccI        GTMKAC
2 Sites
   3050     3979
AflIII      ACRYGT
1 Site
   1897
AluI        AGCT
14 Sites
   109      633      1340
   1597     1643     1733
   1959
   2184     2951     3209
   3278     3311     4471
   4587
AlwNI       CAGNNNCTG
4 Sites
   1488     2129     3500
   3638
AosII       GRCGYC
6 Sites
   2507     2560     2643
   2829     2983     4024
ApaI        GGGCCC
4 Sites
   3075     3754     3955
   4307
ApaLI       GTGCAC
4 Sites
   1583     2081     3351
   3741
AvaI        CYCGRG
6 Sites
   3078     3230     3761
   3891     4103     4386
BamHI       GGATCC
1 Site
   4593
```

```
BanI        GGYRCC
5 Sites
   538      2850     3667
   4345     4677
BanII       GRGCYC
6 Sites
   2953     3075     3754
   3955     3964     4307
BclI        TGATCA
1 Site
   4599
BcnI        CCSGG
14 Sites
   1173     1521     3021
   3232     3233     3763
   3764
   3859     4003     4072
   4105     4106     4293
   4303
BglI        GCCNNNNNGGC
3 Sites
   2475     2597     2668
BglII       AGATCT
3 Sites
   458      3868     4393
Bpp1286     GDGCHC
14 Sites
   652      1587     2085
   2953     3075     3355
   3670
   3745     3754     3804
   3955     3964     4307
   4348
BspHI       TCATGA
3 Sites
   1007     1105     4213
BspNI       CCWGG
19 Sites
   52       1738     1751
   1872     2475     2668
   2977
   3157     3189     3522
   3551     3672     3833
   3936
```

```
                  4140     4194     4374
   4420     4671
BssHII      GCGCGC
1 Site
   3045
BstNI       CCWGG
19 Sites
   52       1738     1751
   1872     2475     2668
   2977
   3157     3189     3522
   3551     3672     3833
   3936
   4140     4194     4374
   4420     4671
Cfr10I      RCCGGY
3 Sites
   847      3175     3982
CfrI        YGGCCR
7 Sites
   769      3445     3676
   4177     4398     4416
   4440
ClaI        ATCGAT
1 Site
   2287
DdeI        CTNAG
13 Sites
   12       204      397
   711      787      1214     1623
   2088     2158     2229
   3111     3475     4731
DpnI        GATC
27 Sites
   190      195      460
   1239     1247     1258
   1333
   2972     3028     3144
   3267     3363     3399
   3489
   3564     3788     3855
   3870     3885     3906
   4086
   4212     4251     4395
   4491     4595     4601
```

Mosaic and Group M Gag_dmyr-patent.doc

Fig. 22 cont'd-21

```
DraIII      CACNNNGTC            4179    4240    4282           52    1172    1520
2 Sites                          4305    4400    4418         1738    1751    1872
    1161    3740                 4442                         2475
Eco47I      GGWCC                4455                         2668    2977    3020
11 Sites                         HgiAI   GWGCWC               3157    3189    3231
     122     586     919         5 Sites                      3232
    1048    3021    3106             1587    2085    2953     3522    3551    3672
    3514                         3355    3745                 3762    3763    3833
    3634    3724    4054         HhaI    GCGC                 3858
    4151                         21 Sites                     3936    4002    4071
Eco47III    AGCGCT                    11     496    1273      4104    4105    4140
2 Sites                          1382    1556    1656         4194
    3216    3289                 1723                         4292    4302    4374
EcoO109     RGGNCCY              1993    2026    2169         4420    4671
5 Sites                          2249    3045    3047         NciI    CCSGG
    3635    3750    3951         3102                         14 Sites
    4152    4304                 3217    3224    3290         1172    1520    3020
EcoRII      CCWGG                3316    4169    4246         3231    3232    3762
19 Sites                         4372                         3763
      50    1736    1749         HincII  GTYRAC               3858    4002    4071
    1870    2473    2666         5 Sites                      4104    4105    4292
    2975                              413     886    2369     4302
    3155    3187    3520         3051    3980                 NcoI    CCATGG
    3549    3670    3831         HinfI   GANTC                1 Site
    3934                         14 Sites                     2745
    4138    4192    4372              43      59     357      NdeI    CATATG
    4418    4669                  383     401     725    779  2 Sites
EcoRV       GATATC                807    1527    1923         2076    2619
1 Site                           1998    2222    2795         NheI    GCTAGC
    2294                         3995                         1 Site
Fnu4HI      GCNGC                HinPI   GCGC                 4587
32 Sites                         21 Sites                     NlaIII  CATG
     234     769    1283              9     494    1271       17 Sites
    1489    1492    1557         1380    1554    1654             538     762     864
    1700                         1721                          892    1011    1109    1181
    1855    1973    1976         1991    2024    2167         1901    2219    2349
    1994    2110    2250         2247    3043    3045         2367    2689    2749
    2279                         3100                         3602
    2282    3094    3276         3215    3222    3288         3683    4217    4812
    3302    3312    3423         3314    4167    4244         NlaIV   GGNNCC
    3442                         4370                         24 Sites
    3445    3676    3715         HpaII   CCGG                     92     540    1830
    3780    4207    4221         20 Sites                     1869    2852    3023
    4271                          848    1172    1329         3073
    4322    4416    4440         1519    1545    1692         3623    3669    3726
    4530                         3019                         3751    3752    3952
FnuDII      CGCG                 3176    3231    3585         3953
23 Sites                         3762    3858    3944         3961    4153    4154
     494    1273    1854         3983                         4305    4306    4347
    2169    2257    2281         4001    4071    4104         4456
    2445                         4247    4292    4301         4528    4595    4679
    3039    3045    3047         MaeI    CTAG                 NruI    TCGCGA
    3062    3100    3222         8 Sites                      1 Site
    3747                          378     801    1034         2257
    3782    3798    3970         1404    2385    3841         NsiI    ATGCAT
    4134    4169    4209         4588                         1 Site
    4310                         4621                         796
    4439    4464                 MaeII   ACGT                 Nsp7524I RCATGY
HaeII       RGCGCY               12 Sites                     2 Sites
7 Sites                           669    1160    1196         1901    4812
      12    1657    2027         2306    2507    2519         NspBII  CMGCKG
    3218    3291    4247         2560                         10 Sites
    4373                         2643    2724    2829         1314    1559    2281
HaeIII      GGCC                 3976    4024                 3039    3115    3359
29 Sites                         MaeIII  GTNAC                3782
      55     771    1175         9 Sites                      4223    4310    4464
    1423    1857    1875          270    1134    1361         PpuMI   RGGWCCY
    1886                         1477    1540    2446         2 Sites
    2268    2469    2662         2533                         3635    4152
    3073    3155    3235         2882    4196                 PssI    RGGNCCY
    3447                         MvaI    CCNGG                5 Sites
    3525    3576    3678         33 Sites                     3638    3753    3954
    3752    3766    3953                                      4155    4307
    4102                                                      PstI    CTGCAG
Mosaic and Group M Gag_dmyr-patent.doc
```

Fig. 22 cont'd-22

```
1 Site                        2668    2977    3020       3975
   3505                       3157    3189    3231       XhoI      CTCGAG
PvuI       CGATCG             3232                       1 Site
1 Site                           3522    3551    3672       3078
   3490                          3762    3763    3833    XhoII     RGATCY
RsaI       GTAC                  3858                    7 Sites
11 Sites                         3936    4002    4071          458    1245    1256
      559    2093    2263       4104    4105    4140       3142    3868    4393
   2330    2604    2684         4194                       4593
   2717                           4292    4302    4374    XmaI      CCCGGG
   2768    2925    3174         4420    4671             3 Sites
   3918                       SdnI      GDGCHC              3230    3761    4103
SacI       GAGCTC             14 Sites                   XmaIII    CGGCCG
1 Site                             652    1587    2085   1 Site
   2953                          2953    3075    3355       3445
SacII      CCGCGG                3670                    XmnI      GAANNNNTTC
5 Sites                          3745    3754    3804   2 Sites
   2282    3040    3783         3955    3964    4307          811    3576
   4311    4465                 4348
SalI       GTCGAC            SinI       GGWCC           Following enzymes have no
2 sites                      11 Sites                   sites
   3049    3978                    123     587     920  AccIII    AflII     Asp718
Sau3A      GATC                 1049    3022    3107    AsuII     AvrII     BalI
27 Sites                        3515                    BbeI      BspMII    BstEII
      188     193     458        3635    3725    4055   BstXI     DraI      EcoRI
   1237    1245    1256         4152                    EspI      FspI      HindIII
   1331                       SmaI       CCCGGG         HpaI      KpnI      MluI
   2970    3026    3142       3 Sites                   MstI      NaeI      NarI
   3265    3361    3397          3232    3763    4105   NotI      OxaNI     PflMI
   3487                       SnaBI      TACGTA         PvuII     RsrII     ScaI
   3562    3786    3853       1 Site                    SfiI      SplI      XbaI
   3868    3883    3904          2725                   XcaI
   4084
   4210    4249    4393       SpeI       ACTAGT         1 Site
   4489    4593    4599       1 Site                       2953
Sau96A     GGNCC                 2384                   SnaBI     TACGTA
29 Sites                      SphI       GCATGC         1 Site
      123     587     920     1 Site                       2725
   1049    1174    2266          4812                   SpeI      ACTAGT
   2468                       SspI       AATATT         1 Site
   2661    3022    3071       2 Sites                      2384
   3072    3107    3233           603     991           SphI      GCATGC
   3515                       StuI       AGGCCT         1 Site
   3635    3725    3750       2 Sites                      4812
   3751    3764    3951            55    3576           Tth111I   GACNNNGTC
   3952                       StyI       CCWWGG         1 Site
   4055    4101    4152       3 Sites                      3975
   4238    4280    4303         2745    3955    4114    XhoI      CTCGAG
   4304                       TaqI       TCGA           1 Site
   4454                       10 Sites                     3078
ScrFI      CCNGG                   216    1799    2287  XmaIII    CGGCCG
33 Sites                        3050    3079    3364    1 Site
       52    1172    1520       3400                       3445
   1738    1751    1872          3565    3979    4608
   2475                       Tth111I    GACNNNGTC
                              1 Site
```

Gag-M4.1Dmyr
MAARASVLSGGELDRWEKIRLRPGGKKKYKLKHIVWASRELERFAVNPGLLETSEGCRQILGQL
QPSLQTGSEELRSLYNTVAVLYCVHQRIDVKDTKEALEKIEEEQNKSQQKTQQAKAADGKVSQN
YPIVQNAQGQMVHQAISPRTLNAWVKVIEEKGFSPEVIPMFSALAEGATPQDLNTMLNTIGGHQ
AAMQMLKDTINDEAAEWDRLHPVQAGPVAPGQIREPRGSDIAGTTSNLQEQIGWMTSNPPIPVG
DIYKRWIIMGLNKIVRMYSPTSILDIRQGPKESFRDYVDRFFRTLRAEQASQEVKNWMTETLLV
QNSNPDCKTILKALGPAATLEEMMTACQGVGGPGHKARVLAEAMSQVQQPNIMMQRGNFKGQKR
IKCFNCGREGHLARNCRAPRKKGCWKCGREGHQMKDCTESKANFLGKIWPSNKGRPGNFLQSRP
EPSAPPAESFGFGEEITPSQKQEQKDKELYPLASLKSLFGNDPLSQ Mosaic and Group M Gag_dmyr-patent.doc

Fig. 22 cont'd-23

HV13309 (Gag-M4.1Dmyr.wlv)
CTCGACAAGAAAATGGCGGCGCGCGCCTCGGTCCTTAGCGGGGGCGAGTTGGATCGGTG
GGAAAAGATCCGCTTGAGGCCAGGAGGGAAGAAGAAGTACAAGCTCAAGCACATCGTCT
GGGCGAGCAGAGAGCTCGAGCGGTTCGCGGTCAACCCGGGCCTGCTTGAGACATCGGAG
GGCTGTCGGCAAATCCTGGGGCAGCTTCAACCGTCCTTGCAAACGGGCAGCGAGGAGCT
GCGATCGCTATACAACACGGTAGCGGTCCTCTACTGCGTGCACCAGCGGATCGACGTCA
AGGACACGAAGGAGGCTCTTGAGAAGATTGAGGAAGAGCAGAACAAGTCGCAGCAGAAG
ACGCAGCAGGCGAAGGCCGCAGACGGCAAAGTATCTCAGAACTACCCGATCGTGCAGAA
CGCGCAGGGACAGATGGTCCACCAGGCCATCTCCCCACGGACGCTTAACGCCTGGGTCA
AAGTAATCGAGGAGAAGGGATTCAGCCCGGAAGTGATCCCCATGTTCTCGGCACTTGCG
GAGGGAGCCACCCCGCAGGACCTGAACACGATGTTGAACACCATCGGCGGGCACCAGGC
GGCCATGCAGATGCTTAAGGACACCATCAACGACGAGGCTGCGGAGTGGGACCGGCTTC
ACCCGGTGCAGGCGGGGCCCGTCGCGCCGGGCCAGATCAGAGAGCCGCGGGATCGGAC
ATCGCGGGAACCACCAGCAACTTGCAGGAGCAAATCGGGTGGATGACTTCGAACCCCCC
GATCCCGGTCGGGGACATCTACAAGAGATGGATCATCATGGGGTTGAACAAGATCGTGA
GGATGTACAGCCCGACCAGCATCCTGGACATCCGACAGGGACCGAAGGAGTCGTTCAGA
GACTACGTAGACCGGTTCTTCCGGACTCTCCGGGCGGAGCAGGCGTCGCAGGAGGTCAA
GAACTGGATGACGGAGACCTTGTTGGTCCAGAACTCGAACCCGGACTGCAAGACCATCC
TGAAGGCTCTCGGCCCGGCGGCGACGTTGGAAGAGATGATGACGGCGTGCCAGGGAGTC
GGGGGACCCGGCCACAAGGCGCGGGTCTTGGCCGAGGCGATGAGCCAGGTGCAGCAGCC
GAACATCATGATGCAGCGGGGCAACTTCAAGGGACAGAAGCGGATCAAGTGTTTCAACT
GTGGCAGGGAGGGACACCTCGCCAGGAACTGCCGGGCCCCGCGGAAGAAGGGCTGCTGG
AAGTGCGGAAGGGAGGGGCACCAAATGAAGGACTGCACGGAGTCGAAGGCGAATTTCCT
CGGGAAGATCTGGCCGTCCAACAAGGGGCGGCCAGGGAACTTTCTGCAAAGCCGGCCGG
AGCCGTCGGCCCCGCCGGCGGAGTCCTTTGGGTTCGGGGAGGAGATCACGCCCTCGCAG
AAGCAAGAGCAAAAGGACAAGGAGCTCTACCCTCTTGCGTCCCTCAAGTCGCTCTTCGGC
AACGACCCGCTTTCGCAATGATAAGCTAGCGGATCCTGATCAGGCGCGCC
                                NheI                     AscI HV13309 in HV10001, 4836bp
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGAACGTTTGGGCTTCTACCGATTTAGCAGTTGATACA
CTTTCTCTAAGTATCCACCTGAATCATAAATCGGCAAAATAGAGAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTAGTCATTATTATTGGTCCGTTCATAACACCCCTTGTATTACTGTTTATGTAAG
Mosaic and Group M Gag_dmyr-patent.doc

Fig. 22 cont'd-24

```
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGACGGGCGACGCGAAACTTGG
GCCCACTCGACAAGAAAATGGCGGCGCGCGCCTCGGTCCTTAGCGGGGCGAGTTGGAT
CGGTGGGAAAAGATCCGCTTGAGGCCAGGAGGGAAGAAGAAGTACAAGCTCAAGCACAT
CGTCTGGGCGAGCAGAGAGCTCGAGCGGTTCGCGGTCAACCCGGGCCTGCTTGAGACAT
CGGAGGGCTGTCGGCAAATCCTGGGGCAGCTTCAACCGTCCTTGCAAACGGGCAGCGAG
GAGCTGCGATCGCTATACAACACGGTAGCGGTCCTCTACTGCGTGCACCAGCGGATCGA
CGTCAAGGACACGAAGGAGGCTCTTGAGAAGATTGAGGAAGAGCAGAACAAGTCGCAGC
AGAAGACGCAGCAGGCGAAGGCCGCAGACGGCAAAGTATCTCAGAACTACCCGATCGTG
CAGAACGCGCAGGGACAGATGGTCCACCAGGCCATCTCCCCACGGACGCTTAACGCCTG
GGTCAAAGTAATCGAGGAGAAGGGATTCAGCCCGGAAGTGATCCCCATGTTCTCGGCAC
TTGCGGAGGGAGCCACCCCGCAGGACCTGAACACGATGTTGAACACCATCGGCGGGCAC
CAGGCGGCCATGCAGATGCTTAAGGACACCATCAACGACGAGGCTGCGGAGTGGGACCG
GCTTCACCCGGTGCAGGCGGGGCCCGTCGCGCCGGGCCAGATCAGAGAGCCGCGGGAT
CGGACATCGCGGGAACCACCAGCAACTTGCAGGAGCAAATCGGGTGGATGACTTCGAAC
CCCCGATCCCGGTCGGGGACATCTACAAGAGATGGATCATCATGGGGTTGAACAAGAT
CGTGAGGATGTACAGCCCGACCAGCATCCTGGACATCCGACAGGGACCGAAGGAGTCGT
TCAGAGACTACGTAGACCGGTTCTTCCGGACTCTCCGGGCGGAGCAGGCGTCGCAGGAG
```

Fig. 22 cont'd-25

```
GTCAAGAACTGGATGACGGAGACCTTGTTGGTCCAGAACTCGAACCCGGACTGCAAGAC
CATCCTGAAGGCTCTCGGCCCGGCGGCGACGTTGGAAGAGATGATGACGGCGTGCCAGG
GAGTCGGGGGACCCGGCCACAAGGCGCGGGTCTTGGCCGAGGCGATGAGCCAGGTGCAG
CAGCCGAACATCATGATGCAGCGGGGCAACTTCAAGGGACAGAAGCGGATCAAGTGTTT
CAACTGTGGCAGGGAGGGACACCTCGCCAGGAACTGCCGGGCCCCGCGGAAGAAGGGCT
GCTGGAAGTGCGGAAGGGAGGGGCACCAAATGAAGGACTGCACGGAGTCGAAGGCGAAT
TTCCTCGGGAAGATCTGGCCGTCCAACAAGGGGCGGCCAGGGAACTTTCTGCAAAGCCG
GCCGGAGCCGTCGGCCCCGCCGGCGGAGTCCTTTGGGTTCGGGGAGGAGATCACGCCCT
CGCAGAAGCAAGAGCAAAAGGACAAGGAGCTCTACCCTCTTGCGTCCCTCAAGTCGCTC
TTCGGCAACGACCCGCTTTCGCAATGATAAGCTAGCGGATCCTGATCAGGCGCGCCGAGCTCGC
TGATCAGCCTCGACTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATCGCA
TTGTCTGAGTAGGTGTCATTCTATTCTGGGGGTGGGGTGGGGCAGGACAGCAAGGGGGAGGAT
TGGGAAGACAATAGCAGGCATGCTGGGGAATTT
```

| Thursday, August 2, 2007 | 1 Site 4584 | 4185 4280 4408 4684 |
|---|---|---|
| Sequence 0 Length : 4836 | BanI GGYRCC 5 Sites | BssHII GCGCGC 4 Sites |
| AatII GACGTC 5 Sites | 538 2850 3658 4333 4690 | 3045 3098 3100 4599 |
| 2510 2563 2646 2832 3370 | BanII GRGCYC 7 Sites | BstNI CCWGG 18 Sites |
| AccI GTMKAC 2 Sites | 2953 3075 3211 3745 4295 4519 4608 | 52 1738 1751 1872 2475 2668 2977 |
| 3050 3970 | BclI TGATCA 2 Sites | 3157 3270 3513 3542 3663 3927 |
| AccIII TCCGGA 1 Site | 4590 4612 | 4131 |
| 3982 | BcnI CCSGG 14 Sites | 4185 4280 4408 4684 |
| AflII CTTAAG 1 Site | 1173 1521 3021 | BstXI CCANNNNNNTGG 1 Site |
| 3681 | 3232 3233 3577 3730 | 3926 |
| AflIII ACRYGT 1 Site | 3755 3850 3994 | Cfr10I RCCGGY 5 Sites |
| 1897 | 4063 4096 4148 4291 | 847 3718 3973 |
| AluI AGCT 16 Sites | BglI GCCNNNNNGGC 4 Sites | 4426 4448 |
| 109 633 1340 | 2475 2597 2668 4449 | CfrI YGGCCR 7 Sites |
| 1597 1643 1733 1959 | BglII AGATCT 2 Sites | 769 3667 4148 4168 4386 4404 |
| 2184 2951 3179 3209 3278 3311 | 458 4381 | 4428 |
| 4517 | Bsp1286 GDGCHC 13 Sites | ClaI ATCGAT 1 Site |
| 4578 4606 | 652 1587 2085 | 2287 |
| AlwNI CAGNNNCTG 4 Sites | 2953 3075 3211 3355 | DdeI CTNAG 13 Sites |
| 1488 2129 3629 4285 | 3661 3745 4295 4336 4519 4608 | 12 204 397 711 787 1214 1623 |
| AosII GRCGYC 7 Sites | BspHI TCATGA 3 Sites | 2088 2158 2229 3111 3466 4744 |
| 2507 2560 2643 2829 2983 3367 4005 | 1007 1105 4204 | DpnI GATC 26 Sites |
| ApaI GGGCCC 3 Sites | BspMII TCCGGA 1 Site | 190 195 460 1239 1247 1258 |
| 3075 3745 4295 | 3982 | 1333 |
| ApaLI GTGCAC 3 Sites | BspNI CCWGG 18 Sites | 2972 3028 3130 3144 3317 3363 |
| 1583 2081 3351 | 52 1738 1751 | 3480 |
| AsuII TTCGAA 1 Site | 1872 2475 2668 2977 | 3585 3762 3779 3846 3876 3897 |
| 3834 | 3157 3270 3513 | 4242 |
| AvaI CYCGRG 3 Sites | 3542 3663 3927 | 4383 4479 4586 4592 4614 |
| 3210 3230 4374 | 4131 | DraIII CACNNNGTG |
| BamHI GGATCC | | |

Mosaic and Group M Gag_dmyr-patent.doc

Fig. 22 cont'd-26

```
2 Sites                      21 Sites                       3513      3542      3576
    1161      3731               11       496      1273    3663      3729      3754
Eco47I    GGWCC               1382      1556      1656    3849
13 Sites                      1723                             3927      3993      4062
     122       586       919      1993      2026      2169    4095      4131      4147
    1048      3021      3106    2249      3045      3047    4185
    3337                          3098                          4280      4290      4408
    3505      3625      3715    3100      3102      3494    4684
    3941      4045      4142    3752      4160      4599    NaeI      GCCGGC
EcoO109    RGGNCCY             4601                          2 Sites
4 Sites                       HincII    GTYRAC                  4428      4450
    3626      3741      4143   5 Sites                       NciI      CCSGG
    4292                           413       886      2369   14 Sites
EcoRII    CCWGG                3051      3227                     1172      1520      3020
18 Sites                      HinfI    GANTC                    3231      3232      3576
      50      1736      1749  19 Sites                          3729
    1870      2473      2666       43        59       357       3754      3849      3993
    2975                          383       401       725   779 4062      4095      4147
    3155      3268      3511       807      1527      1923      4290
    3540      3661      3925      1998      2222      2795  NcoI      CCATGG
    4129                          3568                       1 Site
    4183      4278      4406      3951      3986      4135      2745
    4682                          4356      4455             NdeI      CATATG
EcoRV    GATATC                HinPI    GCGC                 2 Sites
1 Site                        21 Sites                          2076      2619
    2294                             9       494      1271  NheI      GCTAGC
Fnu4HI    GCNGC                   1380      1554      1654  1 Site
31 Sites                         1721                            4578
     234       769      1283      1991      2024      2167  NlaIII    CATG
    1489      1492      1557      2247      3043      3045  18 Sites
    1700                          3096                            538       762       864
    1855      1973      1976      3098      3100      3492      892      1011      1109      1181
    1994      2110      2250      3750      4158      4597      1901      2219      2349
    2279                          4599                          2367      2689      2749
    2282      3094      3276  HpaII    CCGG                     3593
    3302      3312      3423  23 Sites                          3674      3884      4208
    3435                           848      1172      1329      4825
    3448      3667      3706      1519      1545      1692  NlaIV    GGNNCC
    3771      4099      4191      3019                       23 Sites
    4194                          3231      3576      3719        92       540      1830
    4212      4310      4404      3729      3753      3849      1869      2852      3023
FnuDII    CGCG                    3974                          3073
21 Sites                          3983      3992      4062      3614      3660      3717
     494      1273      1854      4095      4147      4289      3742      3743      3794
    2169      2257      2281      4427                          3943
    2445                          4431      4449                4144      4145      4293
    3039      3045      3047  MaeI      CTAG                    4294      4335      4435
    3062      3098      3100  7 Sites                           4444
    3222                           378       801      1034      4586      4692
    3492      3750      3773      1404      2385      4579  NruI      TCGCGA
    3789      4160      4298      4634                       1 Site
    4599                       MaeII     ACGT                    2257
HaeII    RGCGCY                13 Sites                      NsiI      ATGCAT
3 Sites                            669      1160      1196   1 Site
      12      1657      2027      2306      2507      2519        796
HaeIII    GGCC                    2560                       Nsp7524I    RCATGY
26 Sites                          2643      2724      2829   2 Sites
      55       771      1175      3367      3967      4104      1901      4825
    1423      1857      1875  MaeIII    GTNAC                NspBII    CMGCKG
    1886                       8 Sites                       8 Sites
    2268      2469      2662       270      1134      1361      1314      1559      2281
    3073      3155      3235      1477      1540      2446      3039      3359      3773
    3447                          2533                          4214
    3516      3669      3743      2882                          4298
    3757      4093      4150  MvaI      CCNGG                PpuMI     RGGWCCY
    4170                      32 Sites                       2 Sites
    4293      4388      4406        52      1172      1520      3626      4143
    4430      4443              1738      1751      1872   PssI      RGGNCCY
HgiAI    GWGCWC                  2475                       4 Sites
7 Sites                           2668      2977      3020      3629      3744      4146
    1587      2085      2953      3157      3231      3232      4295
    3211      3355      4519      3270                      PvuI      CGATCG
    4608                                                     2 Sites
HhaI     GCGC                                                    3318      3481
Mosaic and Group M Gag_dmyr-patent.doc
```

Fig. 22 cont'd-27

```
RsaI      GTAC                ScrFI     CCNGG              603       991
11 Sites                      32 Sites                     StuI      AGGCCT
    559      2093      2263       52      1172      1520   1 Site
   2330      2604      2684     1738      1751      1872       55
   2717                          2475                      StyI      CCWWGG
   2768      2925      3174     2668      2977      3020   1 Site
   3909                          3157      3231      3232      2745
SacI      GAGCTC                 3270                      TaqI      TCGA
4 Sites                          3513      3542      3576  12 Sites
   2953      3211      4519     3663      3729      3754      216      1799      2287
   4608                          3849                         3050      3079      3211
SacII     CCGCGG                 3927      3993      4062     3364
4 Sites                          4095      4131      4147     3556      3834      4056
   2282      3040      3774     4185                          4359      4621
   4299                          4280      4290      4408  XhoI      CTCGAG
SalI      GTCGAC              SdnI      GDGCHC             1 Site
1 Site                        13 Sites                        3210
   3049                           652      1587      2085  XhoII     RGATCY
Sau3A     GATC                   2953      3075      3211  6 Sites
26 Sites                         3355                          458      1245      1256
    188       193       458     3661      3745      4295     3142      4381      4584
   1237      1245      1256     4336      4519      4608  XmaI      CCCGGG
   1331                        SinI      GGWCC             1 Site
   2970      3026      3128    13 Sites                       3230
   3142      3315      3361        123       587       920 XmaIII    CGGCCG
   3478                          1049      3022      3107  1 Site
   3583      3760      3777     3338                           4428
   3844      3874      3895     3506      3626      3716  XmnI      GAANNNNTTC
   4240                          3942      4046      4143  2 Sites
   4381      4477      4584   SmaI      CCCGGG                 811      3567
   4590      4612              1 Site
Sau96A    GGNCC                  3232                     Following enzymes have no
27 Sites                      SnaBI     TACGTA            sites
    123       587       920   2 Sites                     Asp718    AvrII     BalI
   1049      1174      2266     2725      3968            BbeI      BstEII    DraI
   2468                        SpeI      ACTAGT           Ecc47III  EcoRI     EspI
   2661      3022      3071    1 Site                     FspI      HindIII   HpaI
   3072      3107      3233     2384                      KpnI      MluI      MstI
   3338                        SphI      GCATGC           NarI      NotI      OxaNI
   3506      3626      3716    1 Site                     PflMI     PstI      PvuII
   3741      3742      3755     4825                      RsrII     ScaI      SfiI
   3942                        SspI      AATATT           SplI      Tth111I   XbaI
   4046      4092      4143    2 Sites                    XcaI
   4291      4292      4442
```

Gag_M4.2 Dmyr
MAARASVLSGGKLDAWEKIRLRPGGKKKYRLKHLVWASRELDRFALNPSLLETAEGCKQIMKQL
QPALKTGTEELKSLYNTVATLYCVHEKIDVRDTKEALDKIEEEQNKIQQKTQQAKEADGKVSQN
YPIVQNIQGQMVHQPISPRTLNAWVKVVEEKAFSPEVIPMFTALSDGATPQDLNSMLNAVGGHQ
AAMQILKDTINEEAADWDRLHPVHAGPVAPGQMREPRGSDIAGTTSTLQEQIGWMTNNPPIPVG
EIYKRWIILGLNKIVRMYSPVSILDIKQGPKESFRDYVDRFFKVLRAEQATQDVKNWMTDTLLI
QNANPDCKSILRALGPGATLEEMMTACQGVGGPSHKARILAEAMSQVTNSATIMMQRGNFRNQR
KTVKCFNCGKEGHLARNCKAPRKRGCWKCGKEGHQMKECTERQANFLGKIWPSSKGRPGNFPQS
RPEPTAPPEESFRFGEETTTPSQKQEPIDKELYPLASLRSLFGNDPSSQAS HV13316 (Gag_M4.2 Dmyr.wlv) cloned in to XhoI
GTCGAGAAGAAAATGGCGGCTCGCGCCTCGGTCCTTAGCGGGGGCAAGTTGGATGCGTGGGAAA
AGATCCGCTTGAGGCCAGGAGGGAAGAAGAAGTACCGGCTCAAGCACCTTGTCTGGGCGAGCAG
AGAGCTCGACCGGTTCGCGCTGAACCCGTCGCTGCTTGAGACAGCCGAGGGCTGCAAGCAAATC
ATGAAGCAGCTTCAACCGGCGTTGAAGACGGGCACGGAGGAGCTGAAGTCGCTATACAACACGG
TAGCGACGCTCTACTGCGTGCACGAGAAGATCGACGTCAGGGACACGAAGGAGGCTCTTGACAA Mosaic and Group M Gag_dmyr-patent.doc

Fig. 22 cont'd-28

```
GATTGAGGAAGAGCAGAACAAGATCCAGCAGAAGACGCAGCAGGCGAAGGAGGCAGACGGCAAA
GTATCTCAGAACTACCCGATCGTGCAGAACATCCAGGGACAGATGGTCCACCAGCCGATCTCCC
CACGGACGCTTAACGCCTGGGTCAAAGTAGTCGAGGAGAAGGCATTCAGCCCGGAAGTGATCCC
CATGTTCACTGCACTTAGCGACGGAGCCACCCCGCAGGACCTGAACAGCATGTTGAACGCCGTC
GGCGGGCACCAGGCGGCCATGCAGATCCTTAAGGACACCATCAACGAGGAGGCTGCGGACTGGG
ACCGGCTTCACCCGGTGCACGCGGGGCCCGTCGCGCCGGGCCAGATGAGAGAGCCGCGGGGATC
GGACATCGCGGGAACCACCAGCACCTTGCAGGAGCAAATCGGGTGGATGACTAACAACCCCCCG
ATCCCGGTCGGGGAGATCTACAAGAGATGGATCATCCTGGGGTTGAACAAGATCGTGAGGATGT
ACAGCCCAGTCAGCATCCTGGACATCAAGCAGGGACCGAAGGAGTCGTTCAGAGACTACGTCGA
CCGGTTCTTCAAAGTCCTCCGGGCGGAGCAGGCGACGCAGGACGTCAAGAACTGGATGACGGAC
ACCTTGTTGATCCAGAACGCGAACCCGGACTGCAAGTCGATCCTGCGGGCTCTCGGCCCGGGAG
CGACGTTGGAAGAGATGATGACGGCGTGCCAGGGAGTCGGGGGACCCTCGCACAAGGCGCGGAT
CTTGGCCGAGGCGATGTCACAAGTGACTAACAGCGCGACCATCATGATGCAGCGGGGCAACTTC
CGGAACCAGCGGAAGACGGTGAAGTGTTTCAACTGTGGCAAGGAGGGACACCTCGCCAGGAACT
GCAAGGCCCCGCGGAAGCGGGGCTGCTGGAAGTGCGGAAAGGAGGGGCACCAAATGAAGGAGTG
CACGGAGCGGCAGGCGAATTTCCTCGGGAAGATCTGGCCGTCCTCGAAGGGGCGGCCAGGGAAC
TTTCCGCAAAGCCGGCCGGAGCCGACGGCCCCGCCGGAGGAGTCCTTTCGGTTCGGGGAGGAGA
CGACCACGCCCTCGCAGAAGCAAGAGCCGATCGACAAGGAGCTCTACCCTCTTGCGTCCCTCCG
GTCGCTCTTCGGCAACGACCCGTCGTCGCAAGCGTCGTGATAAGCTAGCGGATCCGGCGCGCC
                                          NheI        AscI
>HV13316 in HV10001 4816bp
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
```

Mosaic and Group M Gag_dmyr-patent.doc

Fig. 22 cont'd-29

```
TGAGCGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGAGAAGAAAATGGCGGCTCGC
GCCTCGGTCCTTAGCGGGGGCAAGTTGGATGCGTGGGAAAAGATCCGCTTGAGGCCAGGAGGGA
AGAAGAAGTACCGGCTCAAGCACCTTGTCTGGGCGAGCAGAGAGCTCGACCGGTTCGCGCTGAA
CCCGTCGCTGCTTGAGACAGCCGAGGGCTGCAAGCAAATCATGAAGCAGCTTCAACCGGCGTTG
AAGACGGGCACGGAGGAGCTGAAGTCGCTATACAACACGGTAGCGACGCTCTACTGCGTGCACG
AGAAGATCGACGTCAGGGACACGAAGGAGGCTCTTGACAAGATTGAGGAAGAGCAGAACAAGAT
CCAGCAGAAGACGCAGCAGGCGAAGGAGGCAGACGGCAAAGTATCTCAGAACTACCCGATCGTG
CAGAACATCCAGGGACAGATGGTCCACCAGCCGATCTCCCCACGGACGCTTAACGCCTGGGTCA
AAGTAGTCGAGGAGAAGGCATTCAGCCCGGAAGTGATCCCCATGTTCACTGCACTTAGCGACGG
AGCCACCCCGCAGGACCTGAACAGCATGTTGAACGCCGTCGGCGGGCACCAGGCGGCCATGCAG
ATCCTTAAGGACACCATCAACGAGGAGGCTGCGGACTGGGACCGGCTTCACCCGGTGCACGCGG
GGCCCGTCGCGCCGGGCCAGATGAGAGAGCCGCGGGGATCGGACATCGCGGGAACCACCAGCAC
CTTGCAGGAGCAAATCGGGTGGATGACTAACAACCCCCGATCCCGGTCGGGGAGATCTACAAG
AGATGGATCATCCTGGGGTTGAACAAGATCGTGAGGATGTACAGCCCAGTCAGCATCCTGGACA
TCAAGCAGGGACCGAAGGAGTCGTTCAGAGACTACGTCGACCGGTTCTTCAAAGTCCTCCGGGC
GGAGCAGGCGACGCAGGACGTCAAGAACTGGATGACGGACACCTTGTTGATCCAGAACGCGAAC
CCGGACTGCAAGTCGATCCTGCGGGCTCTCGGCCCGGGAGCGACGTTGGAAGAGATGATGACGG
CGTGCCAGGGAGTCGGGGGACCCTCGCACAAGGCGCGGATCTTGGCCGAGGCGATGTCACAAGT
GACTAACAGCGCGACCATCATGATGCAGCGGGGCAACTTCCGGAACCAGCGGAAGACGGTGAAG
TGTTTCAACTGTGGCAAGGAGGGACACCTCGCCAGGAACTGCAAGGCCCCGCGGAAGCGGGGCT
GCTGGAAGTGCGGAAAGGAGGGGCACCAAATGAAGGAGTGCACGGAGCGGCAGGCGAATTTCCT
CGGGAAGATCTGGCCGTCCTCGAAGGGGCGGCCAGGGAACTTTCCGCAAAGCCGGCCGGAGCCG
ACGGCCCCGCCGGAGGAGTCCTTTCGGTTCGGGGAGGAGACGACCACGCCCTCGCAGAAGCAAG
AGCCGATCGACAAGGAGCTCTACCCTCTTGCGTCCCTCCGGTCGCTCTTCGGCAACGACCCGTC
GTCGCAAGCGTCGTGATAAGCTAGCGGATCCGGCGCGCCGAGCTCGCTGATCAGCCTCGACTGT
GCCTTCTAGTTGCCAGCCATCTGTTGTTTGCCCCTCCCCCGTGCCTTCCTTGACCCTGGAAGGT
GCCACTCCCACTGTCCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGGGAAGACAATAGCAG
GCATGCTGGGGAATTT
```

Thursday, August 2, 2007    Sequence 1   Length : 4816    AatII    GACGTC
                                                          6 Sites
Mosaic and Group M Gag_dmyr-patent.doc

Fig. 22 cont'd-30

```
    2510    2563    2646         3632    3707    3716         3596    3686    3912
 2832    3341    3989         4059    4313    4330         4113
AccI       GTMKAC            4499                          Eco0109    RGGNCCY
1 Site                          4588                       4 Sites
    3941                     BspHI      TCATGA                3597    3712    4114
AccIII     TCCGGA            4 Sites                       4269
1 Site                          1007    1105    3239       EcoRII     CCWGG
    4199                     4178                          17 Sites
AflII      CTTAAG            BspMII     TCCGGA                  50    1736    1749
1 Site                       1 Site                        1870    2473    2666
    3652                        4199                       2975
AflIII     ACRYGT            BspNI      CCWGG                 3126    3464    3511
1 Site                       17 Sites                      3632    3851    3896
    1897                         52    1738    1751        4100
AluI       AGCT              1872    2475    2668             4255    4383    4662
15 Sites                     2977                          EcoRV      GATATC
     109     633    1340        3128    3466    3513       1 Site
 1597    1643    1733        3634    3853    3898             2294
 1959                        4102                          Fnu4HI     GCNGC
    2184    2951    3180         4257    4385    4664      27 Sites
 3249    3282    4497        BssHII     GCGCGC                 234     769    1283
 4564                        2 Sites                       1489    1492    1557
    4586                         3045    4579              1700
AlwNI      CAGNNNCTG         BstNI      CCWGG                 1855    1973    1976
4 Sites                      17 Sites                      1994    2110    2250
    1488    2129    3600          52    1738    1751       2279
 4262                        1872    2475    2668             2282    3065    3208
AosII      GRCGYC            2977                          3228    3247    3406
7 Sites                          3128    3466    3513      3638
    2507    2560    2643     3634    3853    3898             3677    3742    4186
 2829    2983    3338        4102                          4287    4336    4381
 3986                            4257    4385    4664      FnuDII     CGCG
ApaI       GGGCCC            Cfr10I     RCCGGY             21 Sites
1 Site                       7 Sites                           494    1273    1854
    3716                         847    3146    3185       2169    2257    2281
ApaLI      GTGCAC            3255    3689    3944          2445
5 Sites                      4403                              3039    3045    3047
    1583    2081    3322     CfrI       YGGCCR             3071    3193    3709
 3703    4326                6 Sites                       3721
AvaI       CYCGRG                769    3638    4139           3744    3760    4027
2 Sites                      4363    4381    4405          4131    4171    4275
    4065    4351             ClaI       ATCGAT             4579
BamHI      GGATCC            1 Site                        HaeII      RGCGCY
1 Site                           2287                      3 Sites
    4570                     DdeI       CTNAG                   12    1657    2027
BanI       GGYRCC            14 Sites                      HaeIII     GGCC
5 Sites                          12     204     397        21 Sites
     538    2850    3629      711     787    1214    1623      55     771    1175
 4310    4670                    2088    2158    2229      1423    1857    1875
BanII      GRGCYC            3082    3437    3574          1886
6 Sites                      4724                              2268    2469    2662
    2953    3182    3716     DpnI       GATC               3126    3640    3714
 4059    4499    4588        28 Sites                      3728
BclI       TGATCA                190     195     460           4064    4141    4270
1 Site                       1239    1247    1258          4365    4383    4407
    4592                     1333                          4420
BcnI       CCSGG                 2972    3028    3115      HgiAI      GWGCWC
11 Sites                     3334    3391    3451          9 Sites
    1173    1521    3021     3490                              1587    2085    2953
 3548    3701    3726            3556    3649    3750      3182    3326    3707
 3821                        3817    3832    3847          4330
    3965    4034    4067     3868                              4499    4588
 4068                            4018    4048    4135      HhaI       GCGC
BglI       GCCNNNNNGGC       4360    4486    4572          20 Sites
3 Sites                      4594                               11     496    1273
    2475    2597    2668     DraIII     CACNNNGTG          1382    1556    1656
BglII      AGATCT            2 Sites                       1723
3 Sites                          1161    3702                 1993    2026    2169
     458    3830    4358     Eco47I     GGWCC              2249    3045    3047
Bsp1286    GDGCHC            11 Sites                      3073
15 Sites                         122     586     919          3195    3723    4131
     652    1587    2085     1048    3021    3077          4171    4579    4581
 2953    3182    3274        3476                          HincII     GTYRAC
 3326                                                      4 Sites
Mosaic and Group M Gag_dmyr-patent.doc
```

Fig. 22 cont'd-31

```
    413     886    2369         3964    4033    4066         3940
3942                            4067                        Sau3A    GATC
HinfI    GANTC                  NcoI    CCATGG              28 Sites
16 Sites                        1 Site                          188     193     458
     43      59     357             2745                    1237    1245    1256
383     401     725     779     NdeI    CATATG              1331
    807    1527    1923         2 Sites                         2970    3026    3113
1998    2222    2795                2076    2619             3332    3389    3449
3922                            NheI    GCTAGC              3488
   4106    4432                 1 Site                          3554    3647    3748
HinPI    GCGC                       4564                    3815    3830    3845
20 Sites                        NlaIII    CATG              3866
      9     494    1271         19 Sites                        4016    4046    4133
1380    1554    1654                538     762     864     4358    4434    4570
1721                            892    1011    1109    1181 4592
   1991    2024    2167             1901    2219    2349    Sau96A   GGNCC
2247    3043    3045            2367    2689    2749        21 Sites
3071                            3243                            123     587     920
   3193    3721    4129             3564    3612    3645    1049    1174    2266
4169    4577    4579            4182    4805                2468
HpaII    CCGG                   NlaIV    GGNNCC                 2661    3022    3078
25 Sites                        22 Sites                    3477    3597    3687
    848    1172    1329              92     540    1830     3712
1519    1545    1692            1869    2852    3023            3713    3726    3913
3019                            3585                        4063    4114    4269
   3147    3186    3256             3631    3688    3713    4419
3547    3690    3700            3714    3765    3914        ScrFI    CCNGG
3724                            4115                        28 Sites
   3820    3945    3963             4116    4204    4271         52    1172    1520
4033    4066    4200            4312    4412    4421        1738    1751    1872
4404                            4572                        2475
   4408    4426    4518         4672                            2668    2977    3020
4574                            NruI    TCGCGA             3128    3466    3513
MaeI    CTAG                    1 Site                      3547
7 Sites                             2257                        3634    3700    3725
    378     801    1034         NsiI    ATGCAT              3820    3853    3898
1404    2385    4565            1 Site                      3964
4614                                796                         4033    4066    4067
MaeII    ACGT                   Nsp7524I    RCATGY           4102    4257    4385
14 Sites                        3 Sites                     4664
    669    1160    1196             1901    3612    4805    SdnI    GDGCHC
2306    2507    2519            NspBII    CMGCKG            15 Sites
2560                            8 Sites                         652    1587    2085
   2643    2724    2829             1314    1559    2281    2953    3182    3274
3338    3938    3986            3039    3744    4188        3326
4075                            4209                            3632    3707    3716
MaeIII    GTNAC                 4275                        4059    4313    4330
10 Sites                        PpuMI    RGGWCCY             4499
    270    1134    1361         2 Sites                     4588
1477    1540    2446                3597    4114            SinI    GGWCC
2533                            PssI    RGGNCCY             11 Sites
   2882    4151    4158         4 Sites                         123     587     920
MvaI    CCNGG                       3600    3715    4117    1049    3022    3078
28 Sites                        4272                        3477
     52    1172    1520         PvuI    CGATCG                  3597    3687    3913
1738    1751    1872            2 Sites                     4114
2475                                3452    4487            SmaI    CCCGGG
   2668    2977    3020         RsaI    GTAC                1 Site
3128    3466    3513            11 Sites                        4067
3547                                559    2093    2263     SnaBI    TACGTA
   3634    3700    3725         2330    2604    2684        1 Site
3820    3853    3898            2717                            2725
3964                                2768    2925    3145    SpeI    ACTAGT
   4033    4066    4067         3880                        1 Site
4102    4257    4385            SacI    GAGCTC                  2384
4664                            4 Sites                     SphI    GCATGC
NaeI    GCCGGC                      2953    3182    4499    1 Site
1 Site                          4588                            4805
   4405                         SacII    CCGCGG             SspI    AATATT
NciI    CCSGG                   4 Sites                     2 Sites
11 Sites                            2282    3040    3745        603     991
   1172    1520    3020         4276                        StuI    AGGCCT
3547    3700    3725            SalI    GTCGAC              1 Site
3820                            1 Site                           55
Mosaic and Group M Gag_dmyr-patent.doc
```

Fig. 22 cont'd-32

```
StyI        CCWWGG              Tth111I     GACNNNGTC            1 Site
1 Site                          1 Site                              4065
   2745                            3937                          XmaIII      CGGCCG
TaqI        TCGA                XhoII       RGATCY               1 Site
12 Sites                        10 Sites                            4405
    216       1799      2287       458       1245      1256      XmnI        GAANNNNTTC
   3050       3182      3335      3113       3389      3647      3 Sites
   3527                            3830                             811       3538      4225
   3941       4045      4372      4133       4358      4570
   4487       4601                XmaI       CCCGGG
```

Need re-create XhoI site at the 5' end
Primer:
Gag-M2-4-fG/C:
GGGCGCCTCGAGAAGAAA<u>ATG</u>GCGGCTCG Gag_M4.3 Dmyr
MAARASILRGGKLDKWEKIRLRPGGKKRYMLKHLIWASRELERFALNPGLLETAEGCQQIIEQL
QSTLKTGSEELKSLFNTVATLYCVHQRIEVKDTKEALDKVEEEQNKSKKKAQQAAADTGNSSQV
SQNYPIVQNLQGQMVHQALSPRTLNAWVKVIEEKAFSPEIIPMFTALSEGATPSDLNTMLNTVG
GHQAAMQMLKDTINEEAAEWDRVHPVHAGPIPPGQMREPRGSDIAGTTSSLQEQIAWMTSNPPV
PVGEIYKRWIVLGLNKIVRMYSPVSILDIRQGPKEPFRDYVDRFFKTLRAEQASQDVKNWMTET
LLVQNANPDCKTILRALGPGASLEEMMTACQGVGGPSHKARVLAEAMSQTNSAILMQRSNFKGS
KRIVKCFNCGKEGHIARNCRAPRKRGCWKCGQEGHQMKDCNERQANFLGKIWPSHKGRPGNFLQ
NRPEPTAPPEPTAPPAESFRFEETTPAPKQELKDREPLTSLKSLFGSDPLSQAS HV13317 (Gag_M4.3 Dmyr.wlv)
GTCGAGAAGAAA<u>ATG</u>GCGGCTCGCGCCTCGATCCTTCGAGGGGGCAAGTTGGATAAGTGGGAAA
AGATCCGCTTGAGGCCAGGAGGGAAGAAGAGATACATGCTCAAGCACCTGATCTGGGCGAGCAG
AGAGCTGGAGCGGTTCGCGCTGAACCCGGGCCTGCTTGAGACAGCGGAGGGCTGTCAGCAAATC
ATCGAGCAGCTTCAAAGCACGCTGAAGACGGGCAGCGAGGAGCTGAAGTCGCTATTCAACACGG
TAGCGACCCTCTACTGCGTGCACCAGCGGATCGAGGTCAAGGACACGAAGGAGGCTCTTGACAA
GGTGGAGGAAGAGCAGAACAAGTCGAAGAAGAAGGCGCAGCAGGCGGCGGCCGACACCGGCAAC
TCCTCACAAGTATCTCAGAACTACCCGATCGTGCAGAACCTGCAGGGACAGATGGTCCACCAGG
CCCTCTCCCCACGGACGCTTA<u>ACGCCT</u>GGGTCAAAGTAATCGAGGAGAAGGCCTTCAGCCCGGA
AATCATCCCCATGTTCACAGCACTTTCCGAGGGAGCCACCCCGAGCGACCTGAACACGATGTTG
AACACCGTCGGCGGGCACCAGGCGGCCATGCAGATGCTTAAGGACACCATCAACGAGGAGGCTG
CGGAGTGGGACCGGGTGCACCCGGTGCACGCGGGGCCCATCCCACCGGGCCAGATGAGAGAGCC
GCGGGGATCGGACATCGCGGGAACCACCAGCAGCTTGCAGGAGCAAATCGCCTGGATGACTTCG
AACCCCCCGGTCCCGGTCGGGGAGATCTACAAGAGATGGATCGTCCTCGGGTTGAACAAGATCG
TGAGGATGTACAGCCCTGTGTCAATCCTGGACATCCGACAGGGACCGAAGGAGCCCTTCAGAGA
CTACGTCGACCGGTTCTTCAAGACTCTCCGGGCGGAGCAGGCGTCGCAGGACGTCAAGAACTGG
ATGACGGAGACCTTGTTGGTCCAGAACGCTAACCCGGACTGCAAGACCATCCTGCGCGCTCTCG
GCCCGGGAGCGTCCTTGGAAGAGATGATGACGGCGTGCCAGGGAGTCGGGGGACCCTCACACAA
GGCGCGGGTCTTGGCCGAGGCGATGAGCCAGACGAACTCCGCCATCCTCATGCAGCGGTCCAAC
TTCAAGGGAAGCAAGCGGATCGTCAAGTGTTTCAACTGTGGCAAGGAGGGACACATCGCCAGGA
ACTGCCGGGCCCCGCGGAAGCGAGGCTGCTGGAAGTGCGGACAGGAGGGGCACCAAATGAAGGA
CTGCAACGAGCGCCAGGCGAATTTCCTCGGGAAGATCTGGCCGTCCCACAAGGGGCGGCCAGGG
AACTTCCTTCAAAACCGGCCAGAGCCGACGGCCCCTCCCGAGCCGACCGCCCCGCCGGCGGAGT
CCTTTCGCTTCGAGGAGACCACGCCCGCCCCCAAGCAAGAGCTCAAGGACCGCGAGCCTCTTAC Mosaic and Group M Gag_dmyr-patent.doc
```

Fig. 22 cont'd-33

CTCCCTCAAGTCGCTCTTCGGCTCCGACCCGCTTTCGCAAGCGTCG*TGATAA*GCTAGCGGATCC
GGCGCGC
AscI                                                        NheI
Need re-create XhoI site at the 5' end

HV13317 in HV10001 4824bp
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG

Mosaic and Group M Gag_dmyr-patent.doc

Fig. 22 cont'd-34

ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGAGAAGAAAATGGCGGCTCGC
GCCTCGATCCTTCGAGGGGGCAAGTTGGATAAGTGGGAAAAGATCCGCTTGAGGCCAGGAGGGA
AGAAGAGATACATGCTCAAGCACCTGATCTGGGCGAGCAGAGAGCTGGAGCGGTTCGCGCTGAA
CCCGGGCCTGCTTGAGACAGCGGAGGGCTGTCAGCAAATCATCGAGCAGCTTCAAAGCACGCTG
AAGACGGGCAGCGAGGAGCTGAAGTCGCTATTCAACACGGTAGCGACCCTCTACTGCGTGCACC
AGCGGATCGAGGTCAAGGACACGAAGGAGGCTCTTGACAAGGTGGAGGAAGAGCAGAACAAGTC
GAAGAAGAAGGCGCAGCAGGCGGCGGCCGACACCGGCAACTCCTCACAAGTATCTCAGAACTAC
CCGATCGTGCAGAACCTGCAGGACAGATGGTCCACCAGGCCCTCTCCCCACGGACGCTTAACG
CCTGGGTCAAAGTAATCGAGGAGAAGGCCTTCAGCCCGGAAATCATCCCCATGTTCACAGCACT
TTCCGAGGGAGCCACCCCGAGCGACCTGAACACGATGTTGAACACCGTCGGCGGGCACCAGGCG
GCCATGCAGATGCTTAAGGACACCATCAACGAGGAGGCTGCGGAGTGGGACCGGGTGCACCCGG
TGCACGCGGGGCCCATCCCACCGGGCCAGATGAGAGAGCCGCGGGGATCGGACATCGCGGGAAC
CACCAGCAGCTTGCAGGAGCAAATCGCCTGGATGACTTCGAACCCCCCGGTCCCGGTCGGGGAG
ATCTACAAGAGATGGATCGTCCTCGGGTTGAACAAGATCGTGAGGATGTACAGCCCTGTGTCAA
TCCTGGACATCCGACAGGGACCGAAGGAGCCCTTCAGAGACTACGTCGACCGGTTCTTCAAGAC
TCTCCGGGCGGAGCAGGCGTCGCAGGACGTCAAGAACTGGATGACGGAGACCTTGTTGGTCCAG
AACGCTAACCCGGACTGCAAGACCATCCTGCGCGCTCTCGGCCCGGGAGCGTCCTTGGAAGAGA
TGATGACGGCGTGCCAGGGAGTCGGGGGACCCTCACACAAGGCGCGGGTCTTGGCCGAGGCGAT
GAGCCAGACGAACTCCGCCATCCTCATGCAGCGGTCCAACTTCAAGGGAAGCAAGCGGATCGTC
AAGTGTTTCAACTGTGGCAAGGAGGGACACATCGCCAGGAACTGCCGGGCCCCGCGGAAGCGAG
GCTGCTGGAAGTGCGGACAGGAGGGGCACCAAATGAAGGACTGCAACGAGCGCCAGGCGAATTT
CCTCGGGAAGATCTGGCCGTCCCACAAGGGGCGGCCAGGGAACTTCCTTCAAAACCGGCCAGAG
CCGACGGCCCCTCCCGAGCCGACCGCCCCGCCGGCGGAGTCCTTTCGCTTCGAGGAGACCACGC
CCGCCCCCAAGCAAGAGCTCAAGGACCGCGAGCCTCTTACCTCCCTCAAGTCGCTCTTCGGCTC
CGACCCGCTTTCGCAAGCGTCG*TGATAA*GCTAGC*GGATCC*GGCGCGCAGCTCGC*TGATCA*GCC
TCGACTGTGCCTTCTAGTTGCCAGCCATCTGTTGTTTGCCCCTCCCCCGTGCCTTCCTTGACCC
TGGAAGGTGCCACTCCCACTGTCCTTTCCTAATAAAATGAGGAAATTGCATCGCATTGTCTGAG
TAGGTGTCATTCTATTCTGGGGGGTGGGGTGGGGCAGGACAGCAAGGGGGAGGATTGGGAAGAC
AATAGCAGGCATGCTGGGGAATTT

Thursday, August 2, 2007                    2184    2951    3180        6 Sites
                                            3249    3282    3785           3201    3600    3862
Sequence 2    Length : 4824                 4497                           4074    4354    4429
                                            4573    4594                BamHI       GGATCC
AatII         GACGTC                     AlwNI      CAGNNNCTG           1 Site
5 Sites                                  4 Sites                           4579
  2510    2563    2646                      1488    2129    3471        BanI        GGYRCC
  2832    3998                              4265                        5 Sites
AccI          GTMKAC                     AosII      GRCGYC                  538    2850    3638
1 Site                                   7 Sites                           4313    4678
   3950                                     2507    2560    2643        BanII       GRGCYC
AflII         CTTAAG                        2829    2983    3985        6 Sites
1 Site                                      3995                           2953    3725    3935
   3661                                  ApaI       GGGCCC                 4275    4499    4596
AflIII        ACRYGT                     2 Sites                        BclI        TGATCA
1 Site                                      3725    4275                1 Site
   1897                                  ApaLI      GTGCAC                 4600
AluI          AGCT                       5 Sites                        BcnI        CCSGG
16 Sites                                    1583    2081    3322        16 Sites
   109    633    1340                       3703    3712                   1173    1521    3021
  1597    1643    1733                   AsuII      TTCGAA                 3203    3204    3557
  1959                                   1 Site                            3701
                                            3814
                                         AvaI       CYCGRG Mosaic and Group M Gag_dmyr-patent.doc

Fig. 22 cont'd-35

```
         3710    3735    3824           4602                          1587    2085    2953
3830     3974    4043             DraIII      CACNNNGTG        3326    3707    3716
4076                              2 Sites                      4499
     4077    4271                     1161    3711                 4596
BglI      GCCNNNNNGGC             Eco47I      GGWCC            HhaI        GCGC
4 Sites                           13 Sites                     22 Sites
    2475    2597    2668              122     586     919          11      496     1273
4447                              1048    3021    3485         1382    1556    1656
BglII     AGATCT                  3695                         1723
3 Sites                               3824    3921    4025         1993    2026    2169
     458     3839    4361         4122    4192    4502         2249    3045    3047
Bsp1286   GDGCHC                  EcoO109     RGGNCCY          3073
14 Sites                          4 Sites                          3195    3405    4064
     652    1587    2085              3495    3721    4123     4066    4140    4340
2953    3326    3641              4272                         4588
3707                              EcoRII      CCWGG                4590
     3716    3725    3935         18 Sites                     HincII      GTYRAC
4275    4316    4499                   50    1736    1749      4 Sites
4596                              1870    2473    2666             413     886    2369
BspHI     TCATGA                  2975                         3951
2 Sites                               3126    3491    3520     HinfI       GANTC
    1007    1105                  3641    3802    3905         16 Sites
BspNI     CCWGG                   4109                              43      59     357
18 Sites                              4258    4340    4386     383     401     725     779
      52    1738    1751          4670                             807    1527    1923
1872    2475    2668              EcoRV       GATATC           1998    2222    2795
2977                              1 Site                       3966
    3128    3493    3522              2294                         4115    4453
3643    3804    3907              Fnu4HI      GCNGC            HinPI       GCGC
4111                              28 Sites                     22 Sites
    4260    4342    4388              234     769    1283           9     494    1271
4672                              1489    1492    1557         1380    1554    1654
BssHII    GCGCGC                  1700                         1721
3 Sites                               1855    1973    1976         1991    2024    2167
    3045    4064    4588          1994    2110    2250         2247    3043    3045
BstNI     CCWGG                   2279                         3071
18 Sites                              2282    3065    3247         3193    3403    4062
      52    1738    1751          3273    3406    3413         4064    4138    4338
1872    2475    2668              3416                         4586
2977                                  3647    3686    3751         4588
    3128    3493    3522          3783    4189    4290         HpaII       CCGG
3643    3804    3907              4384                         23 Sites
4111                              FnuDII      CGCG                 848    1172    1329
    4260    4342    4388          21 Sites                     1519    1545    1692
4672                                   494    1273    1854     3019
Cfr10I    RCCGGY                  2169    2257    2281             3202    3425    3556
5 Sites                           2445                         3699    3709    3733
     847    3424    3953              3039    3045    3047     3823
4406    4446                      3071    3193    3718             3829    3954    3972
CfrI      YGGCCR                  3753                         4042    4075    4269
7 Sites                               3769    4064    4140     4407
     769    3416    3647          4278    4508    4588             4447    4583
4148    4366    4384              4590                         MaeI        CTAG
4408                              HaeII       RGCGCY           7 Sites
ClaI      ATCGAT                  4 Sites                           378     801    1034
1 Site                                12    1657    2027       1404    2385    4574
    2287                          4341                         4622
DdeI      CTNAG                   HaeIII      GGCC             MaeII       ACGT
12 Sites                          25 Sites                     12 Sites
      12     204     397               55     771    1175           669    1160    1196
711     787    1214    1623       1423    1857    1875         2306    2507    2519
2088    2158    2229              1886                         2560
3446    4732                          2268    2469    2662         2643    2724    2829
DpnI      GATC                    3126    3206    3418         3947    3995
22 Sites                          3496                         MaeIII      GTNAC
     190     195     460              3547    3649    3723     8 Sites
1239    1247    1258              3737    4073    4150             270    1134    1361
1333                              4273                         1477    1540    2446
    2972    3028    3079              4368    4386    4410     2533
3115    3163    3334              4423                             2882
3460                              HgiAI       GWGCWC           MvaI        CCNGG
    3759    3841    3856          8 Sites                      34 Sites
3877    4219    4363
4581
Mosaic and Group M Gag_dmyr-patent.doc
```

Fig. 22 cont'd-36

```
        52    1172    1520         1314    1559    2281         3823    3829    3907
  1738    1751    1872         3039    3220    3330         3973    4042    4075
  2475                          3753                          4076
  2668    2977    3020         4191    4278                 4111    4260    4270
  3128    3202    3203         PpuMI   RGGWCCY              4342    4388    4672
  3493                          1 Site                       SdnI    GDGCHC
  3522    3556    3643         4123                         14 Sites
  3700    3709    3734         PssI    RGGNCCY                652    1587    2085
  3804                          4 Sites                      2953    3326    3641
  3823    3829    3907         3498    3724    4126         3707
  3973    4042    4075         4275                         3716    3725    3935
  4076                          PstI    CTGCAG              4275    4316    4499
  4111    4260    4270         1 Site                       4596
  4342    4388    4672         3476                         SinI    GGWCC
NaeI    GCCGGC                  PvuI    CGATCG              13 Sites
1 Site                          1 Site                       123    587    920
  4448                          3461                        1049    3022    3486
NciI    CCSGG                   RsaI    GTAC                3696
16 Sites                        10 Sites                     3825    3922    4026
  1172    1520    3020          559    2093    2263         4123    4193    4503
  3202    3203    3556          2330    2604    2684        SmaI    CCCGGG
  3700                          2717                        2 Sites
  3709    3734    3823          2768    2925    3889         3203    4076
  3829    3973    4042         SacI    GAGCTC               SnaBI   TACGTA
  4075                          3 Sites                     1 Site
  4076    4270                  2953    4499    4596         2725
NcoI    CCATGG                  SacII   CCGCGG              SpeI    ACTAGT
1 Site                          4 Sites                     1 Site
  2745                          2282    3040    3754         2384
NdeI    CATATG                  4279                        SphI    GCATGC
2 Sites                         SalI    GTCGAC              1 Site
  2076    2619                  1 Site                       4813
NheI    GCTAGC                  3949                        SspI    AATATT
1 Site                          Sau3A   GATC                2 Sites
  4573                          22 Sites                     603    991
NlaIII  CATG                    188    193    458           StuI    AGGCCT
18 Sites                        1237    1245    1256        2 Sites
  538    762    864            1331                          55    3547
  892   1011   1109   1181     2970    3026    3077         StyI    CCWWGG
  1901   2219   2349            3113    3161    3332        2 Sites
  2367   2689   2749            3458                         2745    4085
  3150                          3757    3839    3854        TaqI    TCGA
  3573   3654   4188            3875    4217    4361        14 Sites
  4813                          4579                         216    1799    2287
NlaIV   GGNNCC                  4600                        3050    3076    3084
24 Sites                       Sau96A  GGNCC                3242
  92    540    1830            26 Sites                      3335    3391    3536
  1869   2852   3023             123    587    920          3814    3950    4466
  3594                          1049    1174    2266        4609
  3640   3697   3722            2468                        Tth111I GACNNNGTC
  3723   3774   3827            2661    3022    3204        1 Site
  3923                          3486    3495    3696         3946
  3932   4124   4125            3721                        XhoII   RGATCY
  4273   4274   4315            3722    3735    3825        7 Sites
  4424                          3922    4026    4072         458    1245    1256
  4542   4581   4680            4123                        3113    3839    4361
NruI    TCGCGA                  4193    4271    4272        4579
1 Site                          4422    4503                XmaI    CCCGGG
  2257                         ScrFI   CCNGG                2 Sites
NsiI    ATGCAT                  34 Sites                     3201    4074
1 Site                           52    1172    1520         XmaIII  CGGCCG
  796                           1738    1751    1872        1 Site
Nsp7524I RCATGY                 2475                         3416
3 Sites                         2668    2977    3020        XmnI    GAANNNNTTC
  1901   3150   4813            3128    3202    3203        2 Sites
NspBII  CMGCKG                  3493                         811    3547
9 Sites                         3522    3556    3643
                                3700    3709    3734
                                3804
```

Fig. 22 cont'd-37

Gag_M4.4 Dmyr
MAARASVLRGEKLDKWERIRLRPGGKKHYMLKHLVWASRELEKFALNPGLLETSEGCKQIIKQL
QPALQTGTEELRSLFNTVATLYCVHAGIEVRDTKEALDKIEEIQNKSKQKTQQAAAGTGSSSKV
SQNYPIVQNLQGQMVHQPLSPRTLNAWVKVVEEKGFNPEVIPMFSALSEGATPQDLNMMLNIVG
GHQAAMQMLKETINEEAAEWDRLHPVHAGPIAPGQMREPRGSDIAGSTSTLQEQIAWMTGNPPV
PVGDIYKRWIILGLNKIVKMYSPTSILDIKQGPKEPFRDYVDRFYKTLRAEQATQEVKNWMTDT
LLVQNANPDCKSILKALGTGATLEEMMSACQGVGGPAHKARVLAEAMSQANNTNIMMQRSNFKG
PKRIIKCFNCGKEGHIAKNCRAPRKKGCWKCGKEGHQMKDCTERQANFLGRIWPSSKGRPGNFL
QSRPEPTAPPAEPTAPPAESFKFEETTPAPKQEPKDREPLTSLRSLFGSDPLLQAS HV13318 (Gag_M4.4 Dmyr.wlv)
GTCGAGAAGAAA<u>ATG</u>GCGGCTCGCGCCTCGGTCCTTCGAGGGGAGAAGTTGGATAAGTGGGAAC
GGATCCGCTTGAGGCCAGGAGGGAAGAAGCACTACATGCTCAAGCACCTGGTCTGGGCGAGCAG
AGAGCTGGAGAAGTTCGCGCTGAACCCGGGCCTGCTTGAGACATCCGAGGGCTGTAAGCAAATC
ATCAAGCAGCTTCAACCAGCGCTCCAGACGGGCACCGAGGAGCTGCGCTCGCTATTCAACACGG
TAGCGACCCTCTACTGCGTGCACGCCGGAATCGAAGTTCGTGACACGAAGGAGGCTCTTGACAA
GATCGAGGAAATCCAGAACAAGTCGAAGCAGAAGACCCAGCAGGCGGCGGCCGGGACCGGCTCG
TCCTCAAAAGTATCTCAGAACTACCCGATCGTGCAGAACCTGCAGGGACAGATGGTCCACCAGC
CGCTCTCCCCACGGACGCTTA<u>ACGCCT</u>GGGTCAAAGTAGTCGAGGAGAAGGGGTTCAACCCGGA
AGTCATCCCCATGTTCTCGGCACTTTCCGAGGGAGCCACCCCGCAGGACCTGAACATGATGTTG
AACATCGTCGGCGGGCACCAGGCGGCCATGCAGATGCTTAAGGAGACCATCAACGAGGAGGCTG
CGGAGTGGGACCGCCTGCACCCGGTGCACGCGGGGCCCATCGCACCGGGCCAGATGAGAGAGCC
GCGGGGATCGGACATCGCGGGATCCACCAGCACCTTGCAGGAGCAAATCGCCTGGATGACTGGG
AACCCCCCGGTCCCGGTCGGGGACATCTACAAGAGATGGATCATCCTCGGGTTGAACAAGATCG
TGAAGATGTACAGCCCTACGTCAATCCTGGACATCAAGCAGGGCCCCAAGGAGCCCTTCAGAGA
CTACGTCGACCGGTTCTACAAGACTCTCCGGGCGGAGCAGGCGACGCAGGAGGTCAAGAACTGG
ATGACGGACACCTTGTTGGTCCAGAACGCTAACCCGGACTGCAAGAGCATCCTGAAGGCTCTCG
GCACGGGAGCGACCTTGGAAGAGATGATGTCCGCGTGCCAGGGAGTCGGGGGACCCGCGCACAA
GGCGCGGGTCTTGGCCGAGGCGATGTCCCAGGCCAACAACACGAACATCATGATGCAGCGGTCC
AACTTCAAGGGACCGAAGCGGATCATCAAGTGTTTCAACTGTGGCAAGGAGGGACACATCGCCA
AGAACTGCCGGGCCCCGCGGAAGAAGGGCTGCTGGAAGTGCGGAAAGGAGGGGCACCAAATGAA
GGACTGCACGGAGCGCCAGGCGAATTTCCTCGGGCGGATCTGGCCGTCCTCGAAGGGGCGGCCA
GGGAACTTCCTTCAATCGCGGCCAGAGCCGACGGCCCTCCCGCGGAGCCGACCGCCCCGCCGG
CGGAGTCCTTTAAGTTCGAGGAGACCACGCCCGCCCCAAGCAAGAGCCGAAGGACCGCGAGCC
TCTTACCTCCCTCCGGTCGCTCTTCGGCTCCGACCCGCTTCTGCAAGCGTCG<u>TGATAA</u>GCTAGC
GGATCCGGCGCGCC                                                             NheI
    AscI HV13318 in in HV10001 4831bp
AAATGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT Mosaic and Group M Gag_dmyr-patent.doc

Fig. 22 cont'd-38

```
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG
CAGACAGTTTTATTGTTCATGATGATATATTTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTTGTGATGCTCGTCAGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGCGGTAGG
CGTTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGAGAAGAAAATGGCGGCTCGC
GCCTCGGTCCTTCGAGGGGAGAAGTTGGATAAGTGGGAACGGATCCGCTTGAGGCCAGGAGGGA
AGAAGCACTACATGCTCAAGCACCTGGTCTGGGCGAGCAGAGAGCTGGAGAAGTTCGCGCTGAA
CCCGGGCCTGCTTGAGACATCCGAGGGCTGTAAGCAAATCATCAAGCAGCTTCAACCAGCGCTC
CAGACGGGCACCGAGGAGCTGCGCTCGCTATTCAACACGGTAGCGACCCTCTACTGCGTGCACG
CCGGAATCGAAGTTCGTGACACGAAGGAGGCTCTTGACAAGATCGAGGAAATCCAGAACAAGTC
GAAGCAGAAGACCCAGCAGGCGGCGGCCGGGACCGGCTCGTCCTCAAAAGTATCTCAGAACTAC
CCGATCGTGCAGAACCTGCAGGGACAGATGGTCCACCAGCCGCTCTCCCCACGGACGCTTAACG
CCTGGGTCAAAGTAGTCGAGGAGAAGGGGTTCAACCCGGAAGTCATCCCATGTTCTCGGCACT
TTCCGAGGGAGCCACCCCGCAGGACCTGAACATGATGTTGAACATCGTCGGCGGGCACCAGGCG
GCCATGCAGATGCTTAAGGAGACCATCAACGAGGAGGCTGCGGAGTGGGACCGCCTGCACCCGG
TGCACGCGGGGCCCATCGCACCGGGCCAGATGAGAGAGCCGCGGGGATCGGACATCGCGGGATC
```

Mosaic and Group M Gag_dmyr-patent.doc

```
CACCAGCACCTTGCAGGAGCAAATCGCCTGGATGACTGGGAACCCCCGGTCCCGGTCGGGGAC
ATCTACAAGAGATGGATCATCCTCGGGTTGAACAAGATCGTGAAGATGTACAGCCCTACGTCAA
TCCTGGACATCAAGCAGGGCCCCAAGGAGCCCTTCAGAGACTACGTCGACCGGTTCTACAAGAC
TCTCCGGGCGGAGCAGGCGACGCAGGAGGTCAAGAACTGGATGACGGACACCTTGTTGGTCCAG
AACGCTAACCCGGACTGCAAGAGCATCCTGAAGGCTCTCGGCACGGGAGCGACCTTGGAAGAGA
TGATGTCCGCGTGCCAGGGAGTCGGGGGACCCGCGCACAAGGCGCGGGTCTTGGCCGAGGCGAT
GTCCCAGGCCAACAACACGAACATCATGATGCAGCGGTCCAACTTCAAGGGACCGAAGCGGATC
ATCAAGTGTTTCAACTGTGGCAAGGAGGGACACATCGCCAAGAACTGCCGGGCCCCGCGGAAGA
AGGGCTGCTGGAAGTGCGGAAAGGAGGGGCACCAAATGAAGGACTGCACGGAGCGCCAGGCGAA
TTTCCTCGGGCGGATCTGGCCGTCCTCGAAGGGGCGGCCAGGGAACTTCCTTCAATCGCGGCCA
GAGCCGACGGCCCCTCCCGCGGAGCCGACCGCCCCGCCGGCGGAGTCCTTTAAGTTCGAGGAGA
CCACGCCCGCCCCCAAGCAAGAGCCGAAGGACCGCGAGCCTCTTACCTCCCTCCGGTCGCTCTT
CGGCTCCGACCCGCTTCTGCAAGCGTCG TGATAAGCTAGCGGATCCGGCGCGCCGAGCTCGCTG
ATCAGCCTCGACTGTGCCTTCTAGTTGCCAGCCATCTGTTGTTTGCCCCTCCCCCGTGCCTTCC
TTGACCCTGGAAGGTGCCACTCCCACTGTCCTTTCCTAATAAAATGAGGAAATTGCATCGCATT
GTCTGAGTAGGTGTCATTCTATTCTGGGGGGTGGGGTGGGGCAGGACAGCAAGGGGGAGGATTG
GGAAGACAATAGCAGGCATGCTGGGGAATTT
```

Primers:

HV1001-F2892
CCGCCCCATTGACGCAAATGG

HV1001-R3113
GCTGGCAACTAGAAGGCACAG
(+ strand: CTGTGCCTTCTAGTTGCCAGC

Thursday, August 2, 2007

Sequence 4   Length : 4831

| | | | | | | |
|---|---|---|---|---|---|---|
| AatII | GACGTC | ApaLI | GTGCAC | | BglII | AGATCT |
| 4 Sites | | 4 Sites | | | 1 Site | |
| 2510 | 2563 2646 | 1583 | 2081 3322 | | 458 | |
| 2832 | | 3712 | | | Bsp1286 | GDGCHC |
| AccI | GTMKAC | AvaI | CYCGRG | | 14 Sites | |
| 1 Site | | 3 Sites | | | 652 | 1587 2085 |
| 3950 | | 3201 | 3862 4357 | | 2953 | 3274 3326 |
| AflII | CTTAAG | BamHI | GGATCC | | 3641 | |
| 1 Site | | 3 Sites | | | 3716 | 3725 3925 |
| 3661 | | 3113 | 3772 4585 | | 3935 | 4278 4319 |
| AflIII | ACRYGT | BanI | GGYRCC | | 4603 | |
| 1 Site | | 6 Sites | | | BspHI | TCATGA |
| 1897 | | 538 | 2850 3271 | | 3 Sites | |
| AluI | AGCT | 3638 | 4316 4685 | | 1007 | 1105 4184 |
| 14 Sites | | BanII | GRGCYC | | BspNI | CCWGG |
| 109 | 633 1340 | 6 Sites | | | 18 Sites | |
| 1597 | 1643 1733 | 2953 | 3725 3925 | | 52 | 1738 1751 |
| 1959 | | 3935 | 4278 4603 | | 1872 | 2475 2668 |
| 2184 | 2951 3180 | BclI | TGATCA | | 2977 | |
| 3249 | 3282 4579 | 1 Site | | | 3128 | 3160 3522 |
| 4601 | | 4607 | | | 3643 | 3804 3907 |
| AlwNI | CAGNNNCTG | BcnI | CCSGG | | 4111 | |
| 4 Sites | | 14 Sites | | | 4165 | 4345 4391 |
| 1488 | 2129 3471 | 1173 | 1521 3021 | | 4679 | |
| 3609 | | 3203 | 3204 3421 | | BssHII | GCGCGC |
| AosII | GRCGYC | 3557 | | | 2 Sites | |
| 5 Sites | | 3710 | 3735 3824 | | 3045 | 4594 |
| 2507 | 2560 2643 | 3830 | 3974 4043 | | BstNI | CCWGG |
| 2829 | 2983 | 4274 | | | 18 Sites | |
| ApaI | GGGCCC | BglI | GCCNNNNNGGC | | 52 | 1738 1751 |
| 3 Sites | | 4 Sites | | | 1872 | 2475 2668 |
| | | 2475 | 2597 2668 | | 2977 | |
| | | 4453 | | | | |

Mosaic and Group M Gag_dmyr-patent.doc

Fig. 22 cont'd-40

```
           3128      3160      3522              2282      3065      3247       HpaII     CCGG
3643      3804      3907              3283      3413      3416                  23 Sites
4111                                  3496                                           848      1172      1329
     4165      4345      4391              3647      3686      3751             1519      1545      1692
4679                                  4192      4293      4387                  3019
Cfr10I    RCCGGY                      4411                                           3202      3329      3419
4 Sites                               FnuDII    CGCG                            3425      3556      3709
     847      3424      3953          23 Sites                                  3733
4452                                       494      1273      1854                   3823      3829      3954
CfrI      YGGCCR                      2169      2257      2281                  3972      4042      4272
7 Sites                               2445                                      4453
     769      3416      3647              3039      3045      3047                   4533      4589
4148      4369      4387              3071      3193      3718                  MaeI      CTAG
4411                                  3753                                      7 Sites
ClaI      ATCGAT                           3769      4105      4129                  378       801      1034
1 Site                                4140      4281      4410                  1404      2385      4580
     2287                             4435                                      4629
DdeI      CTNAG                            4514      4594                       MaeII     ACGT
12 Sites                              HaeII     RGCGCY                          12 Sites
      12       204       397          5 Sites                                        669      1160      1196
 711       787      1214      1623          12      1657      2027              2306      2507      2519
     2088      2158      2229         3262      4344                            2560
3446      4739                        HaeIII    GGCC                                 2643      2724      2829
DpnI      GATC                        24 Sites                                  3898      3947
20 Sites                                    55       771      1175              MaeIII    GTNAC
     190       195       460          1423      1857      1875                  9 Sites
1239      1247      1258              1886                                           270      1134      1361
1333                                       2268      2469      2662             1477      1540      2446
     2972      3028      3115         3126      3206      3418                  2533
3370      3460      3759              3649                                           2882      3343
3774                                       3723      3737      3923             MvaI      CCNGG
     3856      3877      4222         4150      4168      4276                  32 Sites
4366      4587      4609              4371                                            52      1172      1520
DraIII    CACNNNGTG                        4389      4413      4426             1738      1751      1872
2 Sites                               HgiAI     GWGCWC                          2475
     1161      3711                   6 Sites                                        2668      2977      3020
Eco47I    GGWCC                            1587      2085      2953             3128      3160      3202
16 Sites                              3326      3716      4603                  3203
     122       586       919          HhaI      GCGC                                 3420      3522      3556
1048      3021      3077              22 Sites                                  3643      3709      3734
3421                                       11       496      1273               3804
     3485      3605      3695         1382      1556      1656                       3823      3829      3907
3824      4025      4122              1723                                      3973      4042      4111
4195                                       1993      2026      2169             4165
     4209      4508                   2249      3045      3047                       4273      4345      4391
Eco47III  AGCGCT                      3073                                      4679
1 Site                                     3195      3261      3287             NaeI      GCCGGC
     3260                             4131      4140      4343                  1 Site
EcoO109   RGGNCCY                     4594                                           4454
6 Sites                                    4596                                 NciI      CCSGG
     3606      3721      3921         HincII    GTYRAC                          14 Sites
3922      4123      4275              4 Sites                                        1172      1520      3020
EcoRII    CCWGG                            413       886      2369              3202      3203      3420
18 Sites                              3951                                      3556
      50      1736      1749          HinfI     GANTC                                3709      3734      3823
1870      2473      2666              17 Sites                                  3829      3973      4042
2975                                        43        59       357      779     4273
     3126      3158      3520         383       401       725                   NcoI      CCATGG
3641      3802      3905                   807      1527      1923              1 Site
4109                                  1998      2222      2795                       2745
     4163      4343      4389         3332                                      NdeI      CATATG
4677                                       3966      4115      4459             2 Sites
EcoRV     GATATC                      HinPI     GCGC                                 2076      2619
1 Site                                22 Sites                                  NheI      GCTAGC
     2294                                   9       494      1271               1 Site
Fnu4HI    GCNGC                       1380      1554      1654                       4579
28 Sites                              1721                                      NlaIII    CATG
     234       769      1283               1991      2024      2167             19 Sites
1489      1492      1557              2247      3043      3045                       538       762       864
1700                                  3071                                      892      1011      1109      1181
     1855      1973      1976              3193      3259      3285                  1901      2219      2349
1994      2110      2250              4129      4138      4341                  2367      2689      2749
2279                                  4592                                      3150
                                      4594
Mosaic and Group M Gag_dmyr-patent.doc
```

Fig. 22 cont'd-41

```
     3573      3618      3654        1 Site                            4210      4509
4188      4820                            3949                    SmaI      CCCGGG
NlaIV     GGNNCC                      Sau3A     GATC              1 Site
31 Sites                              20 Sites                        3203
      92       540      1830              188       193       458  SnaBI     TACGTA
1869      2852      3023              1237      1245      1256    1 Site
3115                                  1331                            2725
    3273      3423      3594              2970      3026      3113  SpeI      ACTAGT
3640      3697      3722              3368      3458      3757    1 Site
3723                                  3772                            2384
    3774      3817      3827              3854      3875      4220  SphI      GCATGC
3923      3924      3932              4364      4585      4607    1 Site
4124                                  Sau96A    GGNCC                 4820
    4125      4211      4276          29 Sites                    SspI      AATATT
4277      4318      4427                   123       587       920  2 Sites
4439                                  1049      1174      2266         603       991
    4548      4587      4687          2468                        StuI      AGGCCT
NruI      TCGCGA                          2661      3022      3078  1 Site
1 Site                                3204      3422      3486           55
    2257                              3606                        StyI      CCWWGG
NsiI      ATGCAT                          3696      3721      3722  3 Sites
1 Site                                3735      3825      3921        2745      3926      4085
     796                              3922                        TaqI      TCGA
Nsp7524I  RCATGY                          4026      4123      4196  13 Sites
3 Sites                               4210      4274      4275          216      1799      2287
    1901      3150      4820          4425                        3050      3084      3335
NspBII    CMGCKG                          4509                    3371
8 Sites                               ScrFI     CCNGG                 3391      3536      3950
    1314      1559      2281          32 Sites                    4378      4472      4616
3039      3753      4194                    52      1172      1520  Tth111I   GACNNNGTC
4281                                  1738      1751      1872    1 Site
    4435                              2475                            3946
PpuMI     RGGWCCY                         2668      2977      3020  XhoII     RGATCY
2 Sites                               3128      3160      3202    7 Sites
    3606      4123                    3203                             458      1245      1256
PssI      RGGNCCY                         3420      3522      3556  3113      3772      4364
6 Sites                               3643      3709      3734    4585
    3609      3724      3924          3804                        XmaI      CCCGGG
3925      4126      4278                  3823      3829      3907  1 Site
PstI      CTGCAG                          3973      4042      4111      3201
1 Site                                4165                        XmaIII    CGGCCG
    3476                                  4273      4345      4391  1 Site
PvuI      CGATCG                      4679                            3416
1 Site                                SdnI      GDGCHC            XmnI      GAANNNNTTC
    3461                              14 Sites                    2 Sites
RsaI      GTAC                             652      1587      2085       811      3547
10 Sites                              2953      3274      3326
     559      2093      2263          3641                        Following enzymes have no
2330      2604      2684                  3716      3725      3925  sites
2717                                  3935      4278      4319    AccIII    Asp718    AsuII
    2768      2925      3889          4603                        AvrII     BalI      BbeI
SacI      GAGCTC                      SinI      GGWCC             BspMII    BstEII    BstXI
2 Sites                               16 Sites                    DraI      EcoRI     EspI
    2953      4603                         123       587       920  FspI      HindIII   HpaI
SacII     CCGCGG                      1049      3022      3078    KpnI      MluI      MstI
5 Sites                               3422                        NarI      NotI      OxaNI
    2282      3040      3754              3486      3606      3696  PflMI     PvuII     RsrII
4282      4436                        3825      4026      4123    ScaI      SfiI      SplI
SalI      GTCGAC                      4196                        XbaI      XcaI      XhoI
```

Primer below can be used for Gag-M4.1 through 4.4 to generate XhoI site:

Gag-M2-4-fG/C: GGGCGCCTCGAGAAGAAA<u>ATG</u>GCGGCTCG

WLV001AM (vector sequence), hv10001
AAATGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGACCA Mosaic and Group M Gag_dmyr-patent.doc

Fig. 22 cont'd-42

```
GTTGGTGATTTTGAACTTTTGCTTTGCCACGGAACGGTCTGCGTTGTCGGGAAGATGCGTGATC
TGATCCTTCAACTCAGCAAAAGTTCGATTTATTCAACAAAGCCGCCGTCCCGTCAAGTCAGCGT
AATGCTCTGCCAGTGTTACAACCAATTAACCAATTCTGCGTTCAAAATGGTATGCGTTTTGACA
CATCCACTATATATCCGTGTCGTTCTGTCCACTCCTGAATCCCATTCCAGAAATTCTCTAGCGA
TTCCAGAAGTTTCTCAGAGTCGGAAAGTTGACCAGACATTACGAACTGGCACAGATGGTCATAA
CCTGAAGGAAGATCTGATTGCTTAACTGCTTCAGTTAAGACCGACGCGCTCGTCGTATAACAGA
TGCGATGATGCAGACCAATCAACATGGCACCTGCCATTGCTACCTGTACAGTCAAGGATGGTAG
AAATGTTGTCGGTCCTTGCACACGAATATTACGCCATTTGCCTGCATATTCAAACAGCTCTTCT
ACGATAAGGGCACAAATCGCATCGTGGAACGTTTGGGCTTCTACCGATTTAGCAGTTTGATACA
CTTTCTCTAAGTATCCACCTGAATCATAAATCGGCAAAATAGAGAAAAATTGACCATGTGTAAG
CGGCCAATCTGATTCCACCTGAGATGCATAATCTAGTAGAATCTCTTCGCTATCAAAATTCACT
TCCACCTTCCACTCACCGGTTGTCCATTCATGGCTGAACTCTGCTTCCTCTGTTGACATGACAC
ACATCATCTCAATATCCGAATACGGACCATCAGTCTGACGACCAAGAGAGCCATAAACACCAAT
AGCCTTAACATCATCCCCATATTTATCCAATATTCGTTCCTTAATTTCATGAACAATCTTCATT
CTTTCTTCTCTAGTCATTATTATTGGTCCGTTCATAACACCCCTTGTATTACTGTTTATGTAAG
CAGACAGTTTTATTGTTCATGATGATATATTTTATCTTGTGCAATGTAACATCAGAGATTTTG
AGACACAACGTGGCTTTCCCCGGCCCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGCTAC
CAACTCTTTTTCCGAAGGTAACTGGCTTCAGCAGAGCGCAGATACCAAATACTGTTCTTCTAGT
GTAGCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCGCCACGCTT
CCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACT
TGAGCGTCGATTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCC
CTGATTCTGTGGATAACCGTATTACCGCCTTTGAGTGAGCTGATACCGCTCGCCGCAGCCGAAC
GACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCG
CATAGTTAAGCCAGTATCTGCTCCCTGCTTGTGTGTTGGAGGTCGCTGAGTAGTGCGCGAGCAA
AATTTAAGCTACAACAAGGCAAGGCTTGACCGACAATTGCATGAAGAATCTGCTTAGGGTTAGG
CGTTTGCGCTGCTTCGCGATGTACGGGCCAGATATAGCCGCGGCATCGATGATATCCATTGCA
TACGTTGTATCTATATCATAATATGTACATTTATATTGGCTCATGTCCAATATGACCGCCATGT
TGACATTGATTATTGACTAGTTATTAATAGTAATCAATTACGGGGTCATTAGTTCATAGCCCAT
ATATGGAGTTCCGCGTTACATAACTTACGGTAAATGGCCCGCCTGGCTGACCGCCCAACGACCC
CCGCCCATTGACGTCAATAATGACGTATGTTCCCATAGTAACGCCAATAGGGACTTTCCATTGA
CGTCAATGGGTGGAGTATTTACGGTAAACTGCCCACTTGGCAGTACATCAAGTGTATCATATGC
CAAGTCCGCCCCCTATTGACGTCAATGACGGTAAATGGCCCGCCTGGCATTATGCCCAGTACAT
GACCTTACGGGACTTTCCTACTTGGCAGTACATCTACGTATTAGTCATCGCTATTACCATGGTG
ATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATG
TCGTAACAACTCCGCCCCATTGACGCAAATGGGCGGTAGGCGTGTACGGTGGGAGGTCTATATA
AGCAGAGCTCGTTTAGTGAACCGTCAGATCGCCTGGAGACGCCATCCACGCTGTTTTGACCTCC
ATAGAAGACACCGGGACCGATCCAGCCTCCGCGGGCGCGCGTCGACGGGCGACGCGAAACTTGG
GCCCACTCGAGAGGCGCGCCGAGCTCGCTGATCAGCCTCGACTGTGCCTTCTAGTTGCCAGCCA
TCTGTTGTTTGCCCCTCCCCCGTGCCTTCCTTGACCCTGGAAGGTGCCACTCCCACTGTCCTTT
```

Mosaic and Group M Gag_dmyr-patent.doc

Fig. 22 cont'd-43

CCTAATAAAATGAGGAAATTGCATCGCATTGTCTGAGTAGGTGTCATTCTATTCTGGGGGGTGG
GGTGGGGCAGGACAGCAAGGGGGAGGATTGGGAAGACAATAGCAGGCATGCTGGGGAATTT

MOSAIC CLADE M HUMAN IMMUNODEFICIENCY VIRUS TYPE 1 (HIV-1) GAG IMMUNOGENS

This application is a divisional of U.S. application Ser. No. 12/737,761, filed Feb. 1, 2012, which is the U.S. national phase of International Application No. PCT/US2009/004664, filed 14 Aug. 2009, which designated the U.S. and is a continuation of U.S. application Ser. No. 12/192,015, filed 14 Aug. 2008, now U.S. Pat. No. 7,795,377 and a continuation-in-part of U.S. application Ser. No. 11/990,222, filed Feb. 8, 2008, now U.S. Pat. No. 8,119,140, which is the U.S. national phase of International Application No. PCT/US2006/032907, filed Aug. 23, 2006, which designated the U.S. and claims the benefit of U.S. Provisional Application No. 60/710,154, filed Aug. 23, 2005, and U.S. Provisional Application No. 60/739,413, filed Nov. 25, 2005. The entire contents of each of the above-identified applications are hereby incorporated herein by reference.

TECHNICAL FIELD

The present invention relates, in general, to an immunogenic composition (e.g., a vaccine) and, in particular, to a polyvalent immunogenic composition, such as a polyvalent HIV vaccine, and to methods of using same. The invention further relates to methods that use a genetic algorithm to create sets of polyvalent antigens suitable for use, for example, in vaccination strategies.

BACKGROUND

Designing an effective HIV vaccine is a many-faceted challenge. The vaccine preferably elicits an immune response capable of either preventing infection or, minimally, controlling viral replication if infection occurs, despite the failure of immune responses to natural infection to eliminate the virus (Nabel, Vaccine 20:1945-1947 (2002)) or to protect from superinfection (Altfeld et al, Nature 420:434-439 (2002)). Potent vaccines are needed, with optimized vectors, immunization protocols, and adjuvants (Nabel, Vaccine 20:1945-1947 (2002)), combined with antigens that can stimulate cross-reactive responses against the diverse spectrum of circulating viruses (Gaschen et al, Science 296:2354-2360 (2002), Korber et al, Br. Med. Bull. 58:19-42 (2001)). The problems that influenza vaccinologists have confronted for decades highlight the challenge posed by HIV-1: human influenza strains undergoing antigenic drift diverge from one another by around 1-2% per year, yet vaccine antigens often fail to elicit cross-reactive B-cell responses from one year to the next, requiring that contemporary strains be continuously monitored and vaccines be updated every few years (Korber et al, Br. Med. Bull. 58:19-42 (2001)). In contrast, co-circulating individual HIV-1 strains can differ from one another by 20% or more in relatively conserved proteins, and up to 35% in the Envelope protein (Gaschen et al, Science 296:2354-2360 (2002), Korber et al, Br. Med. Bull. 58:19-42 (2001)).

Different degrees of viral diversity in regional HIV-1 epidemics provide a potentially useful hierarchy for vaccine design strategies. Some geographic regions recapitulate global diversity, with a majority of known HIV-1 subtypes, or clades, co-circulating (e.g., the Democratic Republic of the Congo (Mokili & Korber, J. Neurovirol 11(Suppl. 1):66-75 (2005)); others are dominated by two subtypes and their recombinants (e.g., Uganda (Barugahare et al, J. Virol. 79:4132-4139 (2005)), and others by a single subtype (e.g., South Africa (Williamson et al, AIDS Res. Hum. Retroviruses 19:133-144 (2003)). Even areas with predominantly single-subtype epidemics must address extensive within-clade diversity (Williamson et al, AIDS Res. Hum. Retroviruses 19:133-44 (2003)) but, since international travel can be expected to further blur geographic distinctions, all nations would benefit from a global vaccine.

Presented herein is the design of polyvalent vaccine antigen sets focusing on T lymphocyte responses, optimized for either the common B and C subtypes, or all HIV-1 variants in global circulation [the HIV-1 Main (M) group]. Cytotoxic T-lymphocytes (CTL) directly kill infected, virus-producing host cells, recognizing them via viral protein fragments (epitopes) presented on infected cell surfaces by human leukocyte antigen (HLA) molecules. Helper T-cell responses control varied aspects of the immune response through the release of cytokines. Both are likely to be crucial for an HIV-1 vaccine: CTL responses have been implicated in slowing disease progression (Oxenius et al, J. Infect. Dis. 189:1199-208 (2004)); vaccine-elicited cellular immune responses in nonhuman primates help control pathogenic SIV or SHIV, reducing the likelihood of disease after challenge (Barouch et al, Science 290:486-92 (2000)); and experimental depletion of CD8+ T-cells results in increased viremia in SIV infected rhesus macaques Schmitz et al, Science 283:857-60 (1999)). Furthermore, CTL escape mutations are associated with disease progression (Barouch et al, J. Virol. 77:7367-75 (2003)), thus vaccine-stimulated memory responses that block potential escape routes may be valuable.

The highly variable Env protein is the primary target for neutralizing antibodies against HIV; since immune protection will likely require both B-cell and T-cell responses (Moore and Burton, Nat. Med. 10:769-71 (2004)), Env vaccine antigens will also need to be optimized separately to elicit antibody responses. T-cell-directed vaccine components, in contrast, can target the more conserved proteins, but even the most conserved HIV-1 proteins are diverse enough that variation is an issue. Artificial central-sequence vaccine approaches (e.g., consensus sequences, in which every amino acid is found in a plurality of sequences, or maximum likelihood reconstructions of ancestral sequences (Gaschen et al, Science 296:2354-60 (2002), Gao et al, J. Virol. 79:1154-63 (2005), Doria-Rose et al, J. Virol. 79:11214-24 (2005), Weaver et al, J. Virol., in press)) are promising; nevertheless, even centralized strains provide limited coverage of HIV-1 variants, and consensus-based reagents fail to detect many autologous T-cell responses (Altfeld et al, J. Virol. 77:7330-40 (2003)).

Single amino acid changes can allow an epitope to escape T-cell surveillance; since many T-cell epitopes differ between HIV-1 strains at one or more positions, potential responses to any single vaccine antigen are limited. Whether a particular mutation results in escape depends upon the specific epitope/T-cell combination, although some changes broadly affect between-subtype cross-reactivity (Norris et al, AIDS Res. Hum. Retroviruses 20:315-25 (2004)). Including multiple variants in a polyvalent vaccine could enable responses to a broader range of circulating variants, and could also prime the immune system against common escape mutants (Jones et al, J. Exp. Med. 200:1243-56 (2004)). Escape from one T-cell receptor may create a variant that is susceptible to another (Allen et al, J. Virol. 79:12952-60 (2005), Feeney et al, J. Immunol. 174:7524-30 (2005)), so stimulating polyclonal responses to epitope variants may be beneficial (Killian et al, Aids 19:887-96 (2005)). Escape mutations that inhibit processing (Milicic et al, J. Immunol. 175:4618-26 (2005)) or HLA binding (Ammaranond et al, AIDS Res. Hum. Retroviruses 21:395-7 (2005)) cannot be directly countered by a T-cell with a different specificity, but responses to overlapping epitopes may block even some of these escape routes.

The present invention relates to a polyvalent vaccine comprising several "mosaic" proteins (or genes encoding these proteins). The candidate vaccine antigens can be cocktails of k composite proteins (k being the number of sequence variants in the cocktail), optimized to include the maximum number of potential T-cell epitopes in an input set of viral proteins. The mosaics are generated from natural sequences: they resemble natural proteins and include the most common forms of potential epitopes. Since CD8+ epitopes are contiguous and typically nine amino-acids long, sets of mosaics can be scored by "coverage" of nonamers (9-mers) in the natural sequences (fragments of similar lengths are also well represented). 9-Mers not found at least three times can be excluded. This strategy provides the level of diversity coverage achieved by a massively polyvalent multiple-peptide vaccine but with important advantages: it allows vaccine delivery as intact proteins or genes, excludes low-frequency or unnatural epitopes that are not relevant to circulating strains, and its intact protein antigens are more likely to be processed as in a natural infection.

SUMMARY OF THE INVENTION

In general, the present invention relates to an immunogenic composition. More specifically, the invention relates to a polyvalent immunogenic composition (e.g., an HIV vaccine), and to methods of using same. The invention further relates to methods that involve the use of a genetic algorithm to design sets of polyvalent antigens suitable for use as vaccines.

Objects and advantages of the present invention will be clear from the description that follows.

BRIEF DESCRIPTION OF THE DRAWINGS

In FIGS. 1A, 1C and 1E, the scores for each consecutive 9-mer are plotted in their natural order to show how diversity varies in different protein regions; both p24 in the center of Gag and the central region of Nef are particularly highly conserved. In FIGS. 1B, 1D and 1F, the scores for each 9-mer are reordered by coverage (a strategy also used in FIG. 4), to provide a sense of the overall population coverage of a given protein. Coverage of gp120, even with 8 variant 9-mers, is particularly poor (FIGS. 1E and 1F).

FIGS. 2A-2C. Mosaic initialization, scoring, and optimization. FIG. 2A) A set of k populations is generated by random 2-point recombination of natural sequences (1-6 populations of 50-500 sequences each have been tested). One sequence from each population is chosen (initially at random) for the mosaic cocktail, which is subsequently optimized. The cocktail sequences are scored by computing coverage (defined as the mean fraction of natural-sequence 9-mers included in the cocktail, averaged over all natural sequences in the input data set). Any new sequence that covers more epitopes will increase the score of the whole cocktail. FIG. 2B) The fitness score of any individual sequence is the coverage of a cocktail containing that sequence plus the current representatives from other populations. FIG. 2C) Optimization: 1) two "parents" are chosen: the higher-scoring of a randomly chosen pair of recombined sequences, and either (with 50% probability) the higher-scoring sequence of a second random pair, or a randomly chosen natural sequence. 2) Two-point recombination between the two parents is used to generate a "child" sequence. If the child contains unnatural or rare 9-mers, it is immediately rejected, otherwise it is scored (Gaschen et al, Science 296:2354-2360 (2002)). If the score is higher than that of any of four randomly-selected population members, the child is inserted in the population in place of the weakest of the four, thus evolving an improved population; 4) if its score is a new high score, the new child replaces the current cocktail member from its population. Ten cycles of child generation are repeated for each population in turn, and the process iterates until improvement stalls.

FIG. 4A) Non-optimal natural sequences selected from among strains being used in vaccine studies (Kong et al, J. Virol. 77:12764-72 (2003)) including an individual clade A, B, and C viral sequences (Gag: GenBank accession numbers AF004885, K03455, and U52953; Nef core: AF069670, K02083, and U52953). FIG. 4B) Optimum set of natural sequences [isolates US2 (subtype B, USA), 70177 (subtype C, India), and 99TH.R2399 (subtype CRF15_01 B, Thailand); accession numbers AY173953, AF533131, and _AF530576] selected by choosing the single sequence with maximum coverage, followed by the sequence that had the best coverage when combined with the first (i.e. the best complement), and so on, selected for M group coverage FIG. 4C) Consensus sequence cocktail (M group, B- and C-subtypes). FIG. 4D) 3 mosaic sequences, FIG. 4E) 4 mosaic sequences, FIG. 4F) 6 mosaic sequences. FIGS. 4D-4F were all optimized for M group coverage.

FIGS. 7A and 7B. The distribution of 9-mers by frequency of occurrence in natural, consensus, and mosaic sequences. Occurrence counts (y-axis) for different 9-mer frequencies (x-axis) for vaccine cocktails produced by several methods. FIG. 7A: frequencies from 0-60% (for 9-mer frequencies>60%, the distributions are equivalent for all methods). FIG. 7B: Details of low-frequency 9-mers. Natural sequences have large numbers of rare or unique-to-isolate 9-mers (bottom right, FIGS. 7A and 7B); these are unlikely to induce useful vaccine responses. Selecting optimal natural sequences does select for more common 9-mers, but rare and unique 9-mers are still included (top right, FIGS. 7A and 7B). Consensus cocktails, in contrast, under-represent uncommon 9-mers, especially below 20% frequency (bottom left, FIGS. 7A and 7B). For mosaic sequences, the number of lower-frequency 9-mers monotonically increases with the number of sequences (top left, each panel), but unique-to-isolate 9-mers are completely excluded (top left of right panel: * marks the absence of 9-mers with frequencies<0.005).

FIGS. 8A-8D. HLA binding potential of vaccine candidates. FIGS. 8A and 8B) HLA binding motif counts. FIGS. 8C and 8D) number of unfavorable amino acids. In all graphs: natural sequences are marked with black circles (λ); consensus sequences with blue triangles (σ); inferred ancestral sequences with green squares (v); and mosaic sequences with red diamonds (♥). Left panel (FIGS. 8A and 8C) shows HLA-binding-motif counts (FIG. 8A) and counts of unfavorable amino acids (FIG. 8C) calculated for individual sequences; Right panel (FIGS. 8B and 8D) shows HLA binding motifs counts (FIG. 8B) and counts of unfavorable amino acids (FIG. 8D) calculated for sequence cocktails. The top portion of each graph (box-and-whiskers graph) shows the distribution of respective counts (motif counts or counts of unfavorable amino acids) based either on alignment of M group sequences (for individual sequences, FIGS. 8A and 8C) or on 100 randomly composed cocktails of three sequences, one from each A, B and C subtypes (for sequence cocktails, FIGS. 8B and 8D). The alignment was downloaded from the Los Alamos HIV database. The box extends from the 25 percentile to the 75 percentile, with the line at the median. The whiskers extending outside the box show the highest and lowest values. Amino acids that are very rarely found as C-terminal anchor residues are G, S, T, P, N, Q, D, E, and H, and tend to be small, polar, or negatively charged (Yusim et al, J. Virol. 76:8757-8768 (2002)). Results are shown for Gag, but the same qualitative results hold for Nef core and complete Nef. The same procedure was done for supertype motifs with results qualitatively similar to the results for HLA binding motifs (data not shown).

FIG. 9. Mosaic protein sets limited to 4 sequences (k=4), spanning Gag and the central region of Nef optimized for subtype B, subtype C, and the M group.

FIG. 10. Mosaic sets for Env and Pol.

FIG. 11. This plot is alignment independent, based on splintering all M group proteins, (database and CHAVI, one sequence per person) into all possible 9-mers, attending to their frequencies, and then looking for matches and near matches in each vaccine antigen or cocktail with the database.

FIG. 17. Coverage of the HIV database plus CHAVI sequences (N=2020).

FIG. 18. Differences in acute infection patient sequences compared to patient consensus.

FIG. 21. Gag, Nef and Env sequences.

FIG. 22. Mosaic gag and nef genes and M consensus gag and nef genes.

DETAILED DESCRIPTION OF THE INVENTION

Figure 1A:
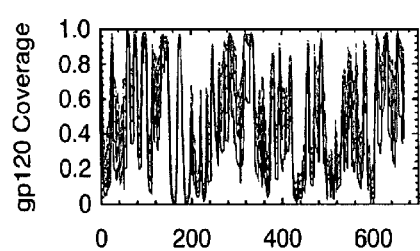
FIGS. 1A-1F. The upper bound of potential epitope coverage of the HIV-1 M group. The upper bound for population coverage of 9-mers for increasing numbers of variants is shown, for k=1-8 variants. A sliding window of length nine was applied across aligned sequences, moving down by one position. Different colors denote results for different numbers of sequences. At each window, the coverage given by the k most common 9-mers is plotted for Gag (FIGS. 1A and 1B), Nef (FIGS. 1C and 1D) and Env gp120 (FIGS. 1E and 1F). Gaps inserted to maintain the alignment are treated as characters. The diminishing returns of adding more variants are evident, since as k increases, increasingly rare forms are added.
Figure 1B:
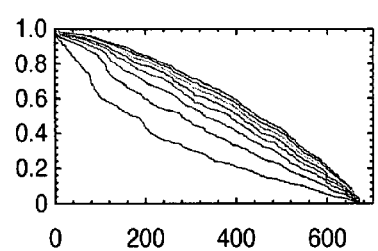
Figure 1C:
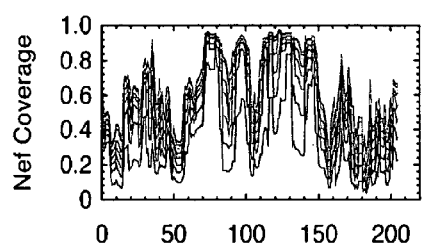
Figure 1D:
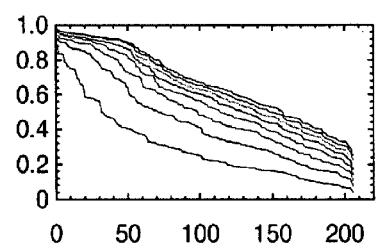
Figure 1E:
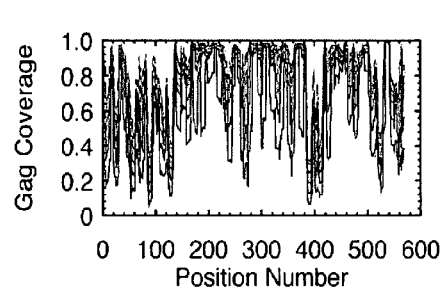
Figure 1F:
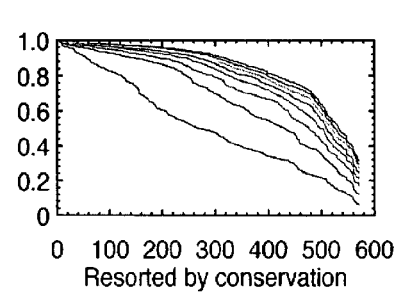

The present invention results from the realization that a polyvalent set of antigens comprising synthetic viral proteins, the sequences of which provide maximum coverage of non-rare short stretches of circulating viral sequences, constitutes a good vaccine candidate. The invention provides a "genetic algorithm" strategy to create such sets of polyvalent antigens as mosaic blends of fragments of an arbitrary set of natural protein sequences provided as inputs. In the context of HIV, the proteins Gag and Nef are ideal candidates for such antigens. To expand coverage, Pol and/or Env can also be used. The invention further provides optimized sets for these proteins.

The genetic algorithm strategy of the invention uses unaligned protein sequences from the general population as an input data set, and thus has the virtue of being "alignment independent". It creates artificial mosaic proteins that resemble proteins found in nature—the success of the consensus antigens in small animals models suggest this works well. 9 Mers are the focus of the studies described herein, however, different length peptides can be selected depending on the intended target. In accordance with the present approach, 9 mers (for example) that do not exist in nature or that are very rare can be excluded—this is an improvement relative to consensus sequences since the latter can contain some 9 mers (for example) that have not been found in nature, and relative to natural strains that almost invariably contain some 9 mers (for example) that are unique to that strain. The definition of fitness used for the genetic algorithm is that the most "fit" polyvalent cocktail is the combination of mosaic strains that gives the best coverage (highest fraction of perfect matches) of all of the 9 mers in the population and is subject to the constraint that no 9 mer is absent or rare in the population.

The mosaics protein sets of the invention can be optimized with respect to different input data sets—this allows use of current data to assess virtues of a subtype or region specific vaccines from a T cell perspective. By way of example, options that have been compared include:

1) Optimal polyvalent mosaic sets based on M group, B clade and C clade. The question presented was how much better is intra-clade coverage than inter-clade or global.
2) Different numbers of antigens: 1, 3, 4, 6
3) Natural strains currently in use for vaccine protocols just to exemplify "typical" strains (Merck, VRC)
4) Natural strains selected to give the best coverage of 9-mers in a population
5) Sets of consensus: A+B+C . . .
6) Optimized cocktails that include one "given" strain in a polyvalent antigen, one ancestral+3 mosaic strains, one consensus+3 mosaic strains.
7) Coverage of 9 mers that were perfectly matched was compared with those that match 8/9, 7/9, and 6/9 or less.

This is a computationally difficult problem, as the best set to cover one 9-mer may not be the best set to cover overlapping 9-mers.

It will be appreciated from a reading of this disclosure that the approach described herein can be used to design peptide reagents to test HIV immune responses, and be applied to other variable pathogens as well. For example, the present approach can be adapted to the highly variable virus Hepatitis C.

The proteins/polypeptides/peptides ("immunogens") of the invention can be formulated into compositions with a pharmaceutically acceptable carrier and/or adjuvant using techniques well known in the art. Suitable routes of administration include systemic (e.g. intramuscular or subcutaneous), oral, intravaginal, intrarectal and intranasal.

The immunogens of the invention can be chemically synthesized and purified using methods which are well known to the ordinarily skilled artisan. The immunogens can also be synthesized by well-known recombinant DNA techniques.

Nucleic acids encoding the immunogens of the invention can be used as components of, for example, a DNA vaccine wherein the encoding sequence is administered as naked DNA or, for example, a minigene encoding the immunogen can be present in a viral vector. The encoding sequences can be expressed, for example, in *mycobacterium*, in a recombinant chimeric adenovirus, or in a recombinant attenuated vesicular stomatitis virus. The encoding sequence can also be present, for example, in a replicating or non-replicating adenoviral vector, an adeno-associated virus vector, an attenuated *mycobacterium tuberculosis* vector, a *Bacillus* Calmette Guerin (BCG) vector, a vaccinia or Modified Vaccinia Ankara (MVA) vector, another pox virus vector, recombinant polio and other enteric virus vector, *Salmonella* species bacterial vector, *Shigella* species bacterial vector, Venezuelean Equine Encephalitis Virus (VEE) vector, a Semliki Forest Virus vector, or a Tobacco Mosaic Virus vector. The encoding sequence, can also be expressed as a DNA plasmid with, for example, an active promoter such as a CMV promoter. Other live vectors can also be used to express the sequences of the invention. Expression of the immunogen of the invention can be induced in a patient's own cells, by introduction into those cells of nucleic acids that encode the immunogen, preferably using codons and promoters that optimize expression in human cells. Examples of methods of making and using DNA vaccines are disclosed in U.S. Pat. Nos. 5,580,859, 5,589,466, and 5,703,055. Examples of methods of codon optimization are described in Haas et al, Current Biology 6:315-324 (1996) and in Andre et al, J. Virol. 72(2):1497-1503 (1998).

It will be appreciated that adjuvants can be included in the compositions of the invention (or otherwise administered to enhance the immunogenic effect). Examples of suitable adjuvants include TRL-9 agonists, TRL-4 agonists, and TRL-7, 8 and 9 agonist combinations (as well as alum). Adjuvants can take the form of oil and water emulsions. Squalene adjuvants can also be used.

The composition of the invention comprises an immunologically effective amount of the immunogen of this invention, or nucleic acid sequence encoding same, in a pharmaceutically acceptable delivery system. The compositions can be used for prevention and/or treatment of virus infection (e.g. HIV infection). As indicated above, the compositions of the invention can be formulated using adjuvants, emulsifiers, pharmaceutically-acceptable carriers or other ingredients routinely provided in vaccine compositions. Optimum formulations can be readily designed by one of ordinary skill in the art and can include formulations for immediate release and/or for sustained release, and for induction of systemic immunity and/or induction of localized mucosal immunity (e.g, the formulation can be designed for intranasal, intravaginal or intrarectal administration). As noted above, the present compositions can be administered by any convenient route including subcutaneous, intranasal, oral, intramuscular, or other parenteral or enteral route. The immunogens can be administered as a single dose or multiple doses. Optimum immunization schedules can be readily determined by the ordinarily skilled artisan and can vary with the patient, the composition and the effect sought.

The invention contemplates the direct use of both the immunogen of the invention and/or nucleic acids encoding same and/or the immunogen expressed as indicated above. For example, a minigene encoding the immunogen can be used as a prime and/or boost.

The invention includes any and all amino acid sequences disclosed herein, as well as nucleic acid sequences encoding same (and nucleic acids complementary to such encoding sequences).

Specifically disclosed herein are vaccine antigen sets optimized for single B or C subtypes, targeting regional epidemics, as well as for all HIV-1 variants in global circulation [the HIV-1 Main (M) group]. In the study described in Example 1 that follows, the focus is on designing polyvalent vaccines specifically for T-cell responses. HIV-1 specific T-cells are likely to be crucial to an HIV-1-specific vaccine response: CTL responses are correlated with slow disease progression in humans (Oxenius et al, J. Infect. Dis. 189:1199-1208 (2004)), and the importance of CTL responses in nonhuman primate vaccination models is well-established. Vaccine elicited cellular immune responses help control pathogenic SIV or SHIV, and reduce the likelihood of disease after challenge with pathogenic virus (Barouch et al, Science 290:486-492 (2000)). Temporary depletion of CD8+ T cells results in increased viremia in SIV-infected rhesus macaques (Schmitz et al, Science 283:857-860 (1999)). Furthermore, the evolution of escape mutations has been associated with disease progression, indicating that CTL responses help constrain viral replication in vivo (Barouch et al, J. Virol. 77:7367-7375 (2003)), and so vaccine-stimulated memory responses that could block potential escape routes may be of value. While the highly variable Envelope (Env) is the primary target for neutralizing antibodies against HIV, and vaccine antigens will also need to be tailored to elicit these antibody responses (Moore & Burton, Nat. Med. 10:769-771 (2004)), T-cell vaccine components can target more conserved proteins to trigger responses that are more likely to cross-react. But even the most conserved HIV-1 proteins are diverse enough that variation will be an issue. Artificial central-sequence vaccine approaches, consensus and ancestral sequences (Gaschen et al, Science 296:2354-2360 (2002), Gao et al, J. Virol. 79:1154-1163 (2005), Doria-Rose et al, J. Virol. 79:11214-11224 (2005)), which essentially "split the differences" between strains, show promise, stimulating responses with enhanced cross-reactivity compared to natural strain vaccines (Gao et al, J. Virol. 79:1154-1163 (2005)) (Liao et al. and Weaver et al., submitted.) Nevertheless, even central strains cover the spectrum of HIV diversity to a very limited extent, and consensus-based peptide reagents fail to detect many autologous CD8+ T-cell responses (Altfeld et al, J. Virol. 77:7330-7340 (2003)).

A single amino acid substitution can mediate T-cell escape, and as one or more amino acids in many T-cell epitopes differ between HIV-1 strains, the potential effectiveness of responses to any one vaccine antigen is limited. Whether a particular mutation will diminish T-cell cross-reactivity is epitope- and T-cell-specific, although some changes can broadly affect between-clade cross-reactivity (Norris et al, AIDS Res. Hum. Retroviruses 20:315-325 (2004)). Including more variants in a polyvalent vaccine could enable responses to a broader range of circulating variants. It could also prime the immune system against common escape variants (Jones et al, J. Exp. Med. 200:1243-1256 (2004)); escape from one T-cell receptor might create a variant that is susceptible to another (Lee et al, J. Exp. Med. 200:1455-1466 (2004)), thus stimulating polyclonal responses to epitope variants may be beneficial (Killian et al, AIDS 19:887-896 (2005)). Immune escape involving avenues that inhibit processing (Milicic et al, J. Immunol. 175:4618-4626 (2005)) or HLA binding (Ammaranond et al, AIDS Res. Hum. Retroviruses 21:395-397 (2005)) prevent epitope presentation, and in such cases the escape variant could not be countered by a T-cell with a different specificity. However, it is possible the presence of T-cells that recognize overlapping epitopes may in some cases block these even escape routes.

Certain aspects of the invention can be described in greater detail in the non-limiting Examples that follow.

Example 1

Experimental Details

HIV-1 Sequence Data.

The reference alignments from the 2005 HIV sequence database (http://hiv.lanl.gov), which contain one sequence per person, were used, supplemented by additional recently available C subtype Gag and Nef sequences from Durban, South Africa (GenBank accession numbers AY856956-AY857186) (Kiepiela et al, Nature 432:769-75 (2004)). This set contained 551 Gag and 1,131 Nef M group sequences from throughout the globe; recombinant sequences were included as well as pure subtype sequences for exploring M group diversity. The subsets of these alignments that contained 18 A, 102 B, 228 C, and 6 G subtype (Gag), and 62 A, 454 B, 284 C, and 13 G subtype sequences (Nef) sequences were used for within- and between-single-clade optimizations and comparisons.

The Genetic Algorithm.

GAs are computational analogues of biological processes (evolution, populations, selection, recombination) used to find solutions to problems that are difficult to solve analytically (Holland, Adaptation in Natural and Artificial Systems: An Introductory Analysis with Applications to Biology, Control, and Artificial Intelligence, (M.I.T. Press, Cambridge, Mass. (1992))). Solutions for a given input are "evolved" though a process of random modification and selection according to a "fitness" (optimality) criterion. GAs come in many flavors; a "steady-state co-evolutionary multi-population" GA was implemented. "Steady-state" refers to generating one new candidate solution at a time, rather than a whole new population at once; and "co-evolutionary" refers to simultaneously evolving several distinct populations that work together to form a complete solution. The input is an unaligned set of natural sequences; a candidate solution is a set of k pseudo-natural "mosaic" sequences, each of which is formed by concatenating sections of natural sequences. The fitness criterion is population coverage, defined as the proportion of all 9-amino-acid sequence fragments (potential epitopes) in the input sequences that are found in the cocktail.

To initialize the GA (FIG. 2), k populations of n initial candidate sequences are generated by 2-point recombination between randomly selected natural sequences. Because the input natural sequences are not aligned, "homologous" crossover is used: crossover points in each sequence are selected by searching for short matching strings in both sequences; strings of c−1=8, were used where a typical epitope length is c=9. This ensures that the recombined sequences resemble natural proteins: the boundaries between sections of sequence derived from different strains are seamless, the local sequences spanning the boundaries are always found in nature, and the mosaics are prevented from acquiring large insertions/deletions or unnatural combinations of amino acids. Mosaic sequence lengths fall within the distribution of natural sequence lengths as a consequence of mosaic construction: recombination is only allowed at identical regions, reinforced by an explicit software prohibition against excessive lengths to prevent reduplication of repeat regions. (Such "in frame" insertion of reduplicated epitopes could provide another way of increasing coverage without generating unnatural 9-mers, but their inclusion would create "unnatural" proteins.) Initially, the cocktail contains one randomly chosen "winner" from each population. The fitness score for any individual sequence in a population is the coverage value for the cocktail consisting of that sequence plus the current winners from the other populations. The individual fitness of any sequence in a population therefore depends dynamically upon the best sequences found in the other populations.

Optimization proceeds one population at a time. For each iteration, two "parent" sequences are chosen. The first parent is chosen using "2-tournament" selection: two sequences are picked at random from the current population, scored, and the better one is chosen. This selects parents with a probability inversely proportional to their fitness rank within the population, without the need to actually compute the fitness of all individuals. The second parent is chosen in the same way (50% of the time), or is selected at random from the set of natural sequences. 2-point homologous crossover between the parents is then used to generate a "child" sequence. Any child containing a 9-mer that was very rare in the natural population (found less than 3 times) is rejected immediately. Otherwise, the new sequence is scored, and its fitness is compared with the fitnesses of four randomly chosen sequences from the same population. If any of the four randomly chosen sequences has a score lower than that of the new sequence, it is replaced in the population by the new sequence. Whenever a sequence is encountered that yields a better score than the current population "winner", that sequence becomes the winner for the current population and so is subsequently used in the cocktail to evaluate sequences in other populations. A few such optimization cycles (typically 10) are applied to each population in turn, and this process continues cycling through the populations until evolution stalls (i.e., no improvement has been made for a defined number of generations). At this point, the entire procedure is restarted using newly generated random starting populations, and the restarts are continued until no further improvement is seen. The GA was run on each data set with n=50 or 500; each run was continued until no further improvement occurred for 12-24 hours on a 2 GHz Pentium processor. Cocktails were generated having k=1, 3, 4, or 6 mosaic sequences.

The GA also enables optional inclusion of one or more fixed sequences of interest (for example, a consensus) in the cocktail and will evolve the other elements of the cocktail in order to optimally complement that fixed strain. As these solutions were suboptimal, they are not included here. An additional program selects from the input file the k best natural strains that in combination provide the best population coverage.

Comparison with Other Polyvalent Vaccine Candidates.

Population coverage scores were computed for other potential mono- or polyvalent vaccines to make direct comparisons with the mosaic-sequence vaccines, tracking identities with population 9-mers, as well as similarities of 8/9 and 7/9 amino acids. Potential vaccine candidates based on natural strains include single strains (for example, a single C strain for a vaccine for southern Africa (Williamson et al, AIDS Res. Hum. Retroviruses 19:133-44 (2003))) or combinations of natural strains (for example, one each of subtype A, B, and C (Kong et al, J. Virol. 77:12764-72 (2003)). To date, natural-strain vaccine candidates have not been systematically selected to maximize potential T-cell epitope coverage; vaccine candidates were picked from the literature to be representative of what could be expected from unselected vaccine candidates. An upper bound for coverage was also determined using only intact natural strains: optimal natural-sequence cocktails were generated by selecting the single sequence with the best coverage of the dataset, and then successively adding the most complementary sequences up to a given k. The comparisons included optimal natural-sequence cocktails of various sizes, as well as consensus sequences, alone or in combination (Gaschen et al, Science 296:2354-60 (2002)), to represent the concept of central, synthetic vaccines. Finally, using the fixed-sequence option in the GA, consensus-plus-mosaic combinations in the comparisons; these scores were essentially equivalent to all-mosaic combinations were included for a given k (data not shown). The code used for performing these analyses are available at: ftp://ftp-t10/pub/btk/mosaics.

Results

Protein Variation.

In conserved HIV-1 proteins, most positions are essentially invariant, and most variable positions have only two to three amino acids that occur at appreciable frequencies, and variable positions are generally well dispersed between conserved positions. Therefore, within the boundaries of a CD8+ T-cell epitope (8-12 amino acids, typically nine), most of the population diversity can be covered with very few variants. FIG. 1 shows an upper bound for population coverage of 9-mers (stretches of nine contiguous amino acids) comparing Gag, Nef, and Env for increasing numbers of variants, sequentially adding variants that provide the best coverage. In conserved regions, a high degree of population coverage is achieved with 2-4 variants. By contrast, in variable regions like Env, limited population coverage is possible even with eight variants. Since each new addition is rarer, the relative benefits of each addition diminish as the number of variants increases.

Vaccine Design Optimization Strategies.

FIG. 1 shows an idealized level of 9-mer coverage. In reality, high-frequency 9-mers often conflict: because of local co-variation, the optimal amino acid for one 9-mer may differ from that for an overlapping 9-mer. To design mosaic protein sets that optimize population coverage, the relative benefits of each amino acid must be evaluated in combination with nearby variants. For example, Alanine (Ala) and Glutamate (Glu) might each frequently occur in adjacent positions, but if the Ala-Glu combination is never observed in nature, it should be excluded from the vaccine. Several optimization strategies were investigated: a greedy algorithm, a semi-automated compatible-9 mer assembly strategy, an alignment-based genetic algorithm (GA), and an alignment-independent GA.

The alignment-independent GA generated mosaics with the best population coverage. This GA generates a user-specified number of mosaic sequences from a set of unaligned protein sequences, explicitly excluding rare or unnatural epitope-length fragments (potentially introduced at recombination breakpoints) that could induce non-protective vaccine-antigen-specific responses. These candidate vaccine sequences resemble natural proteins, but are assembled from frequency-weighted fragments of database sequences recombined at homologous breakpoints (FIG. 2); they approach maximal coverage of 9-mers for the input population.

Selecting HIV Protein Regions for an Initial Mosaic Vaccine.

Figure 3:
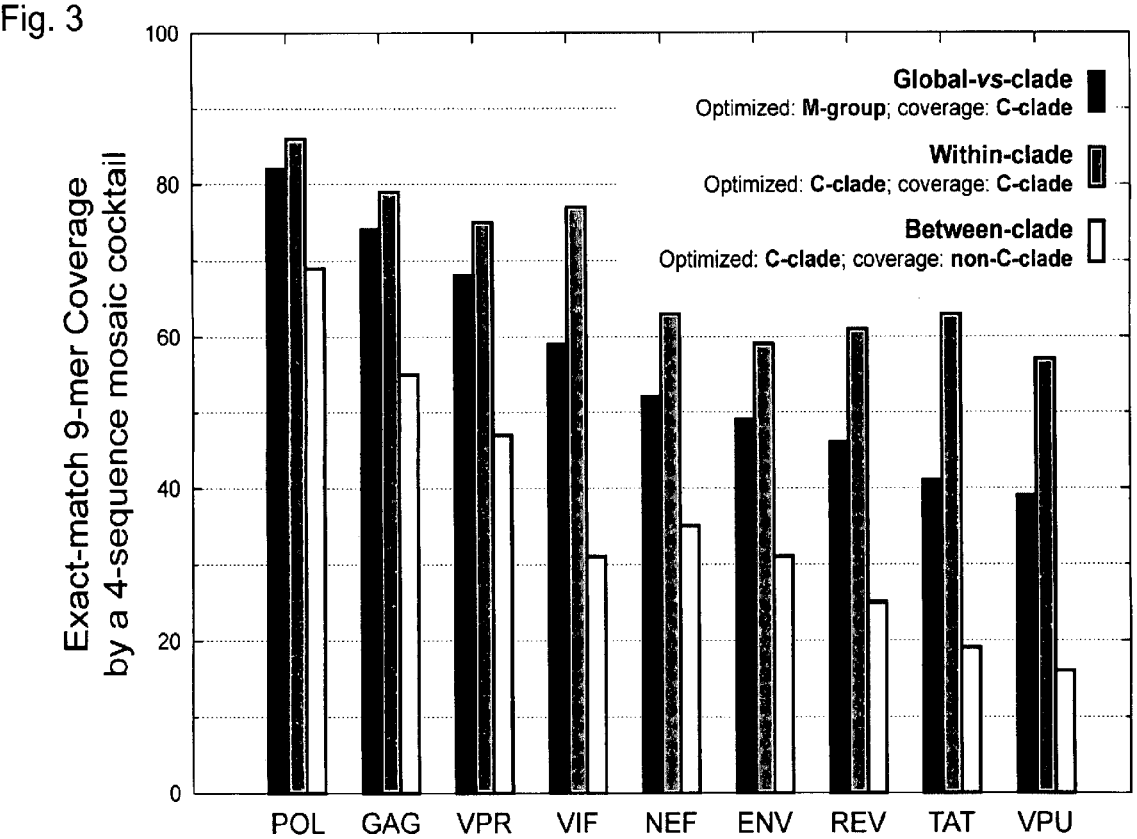
FIG. 3. Mosaic strain coverage for all HIV proteins. The level of 9-mer coverage achieved by sets of four mosaic proteins for each HIV protein is shown, with mosaics optimized using either the M group or the C subtype. The fraction of C subtype sequence 9-mers covered by mosaics optimized on the C subtype (within-clade optimization) is shown in gray. Coverage of 9-mers found in non-C subtype M-group sequences by subtype-C-optimized mosaics (between-clade coverage) is shown in white. Coverage of subtype C sequences by M-group optimized mosaics is shown in black. B clade comparisons gave comparable results (data not shown).
Figure 4A:
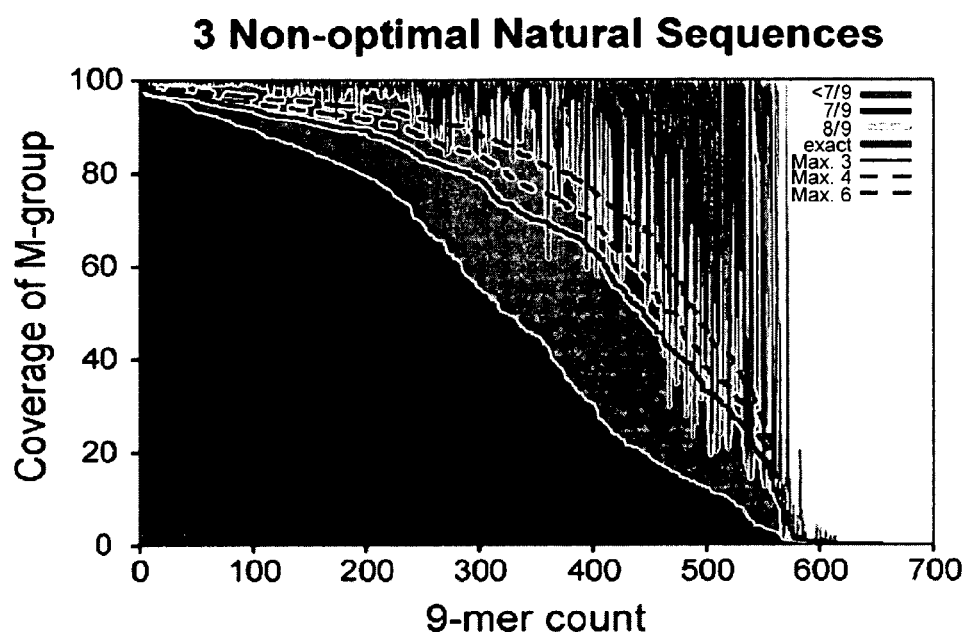
FIGS. 4A-4F. Coverage of M group sequences by different vaccine candidates, nine-mer by nine-mer. Each plot presents site-by-site coverage (i.e., for each nine-mer) of an M-group natural-sequence alignment by a single tri-valent vaccine candidate. Bars along the x-axis represent the proportion of sequences matched by the vaccine candidate for a given alignment position: 9/9 matches (in red), 8/9 (yellow), 7/9 (blue). Aligned 9-mers are sorted along the x-axis by exact-match coverage value. 656 positions include both the complete Gag and the central region of Nef. For each alignment position, the maximum possible matching value (i.e. the proportion of aligned sequences without gaps in that nine-mer) is shown in gray.
Figure 4B:
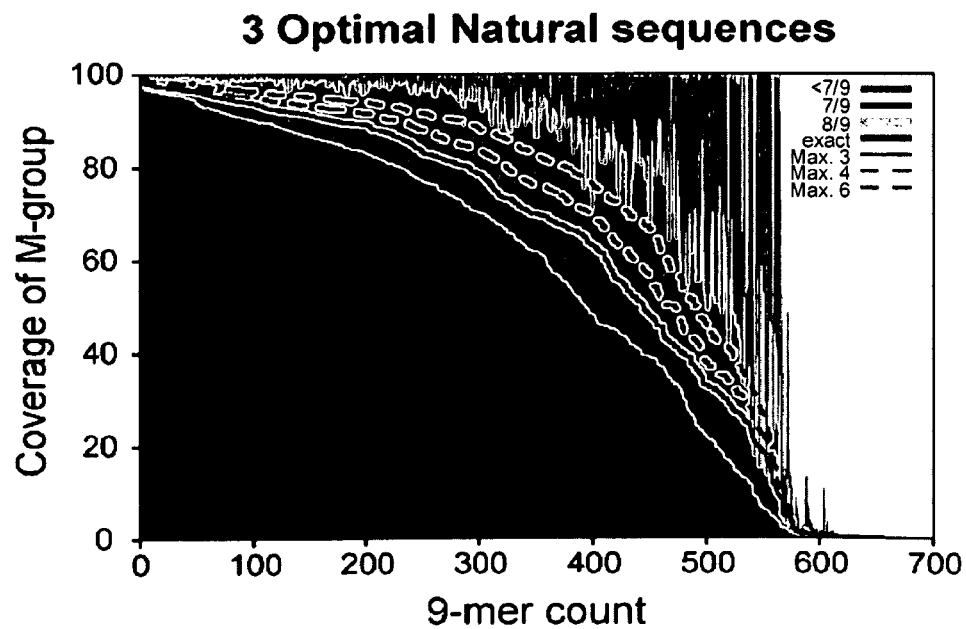
Figure 4C:
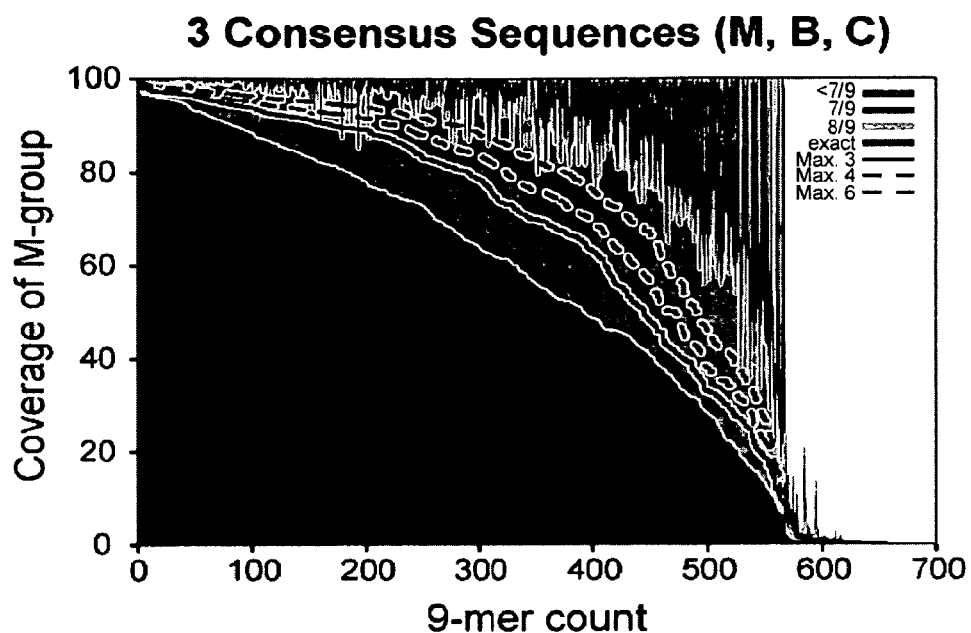
Figure 4D:
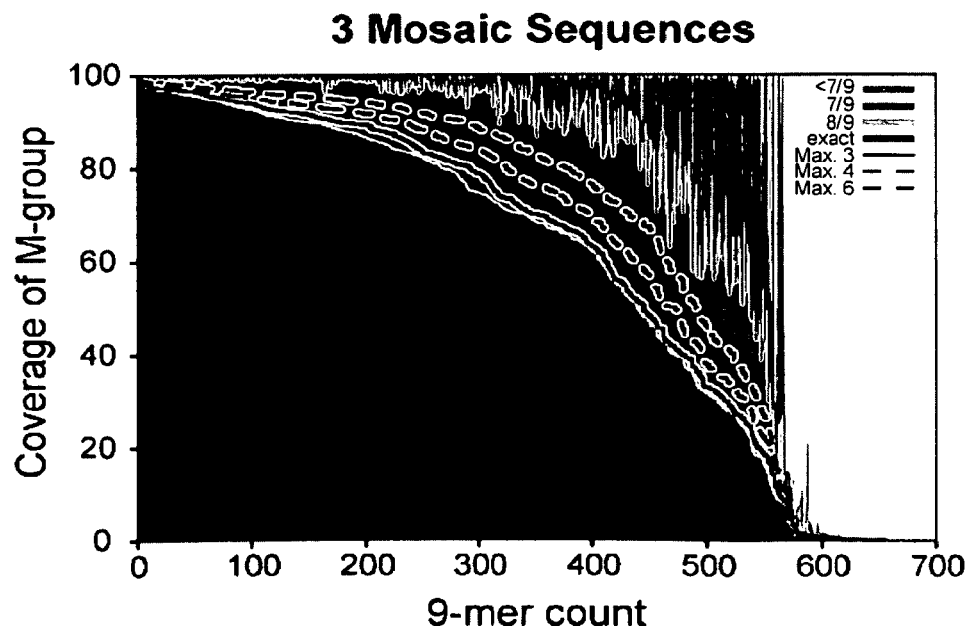
Figure 4E:
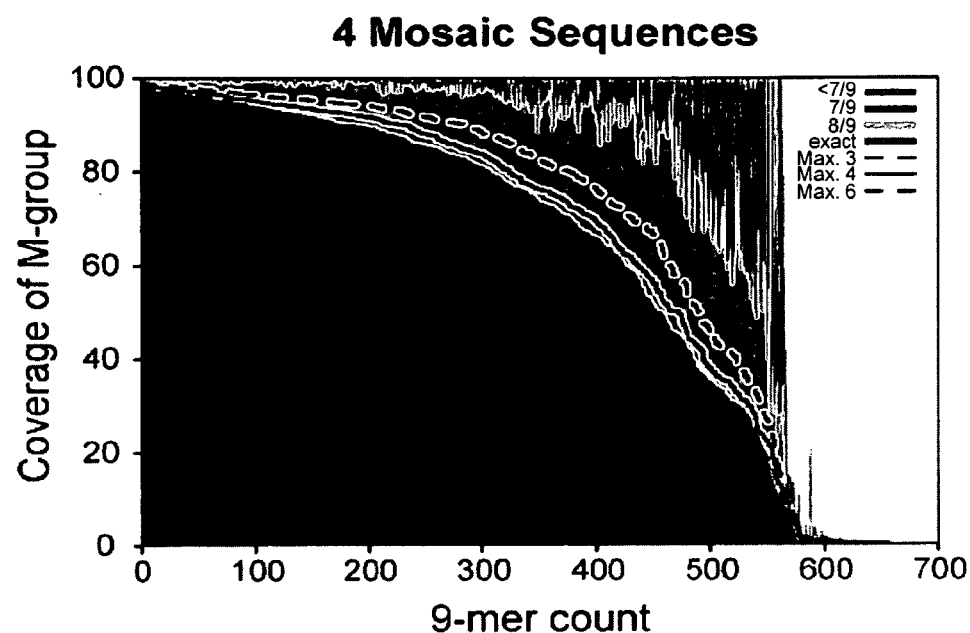
Figure 4F:
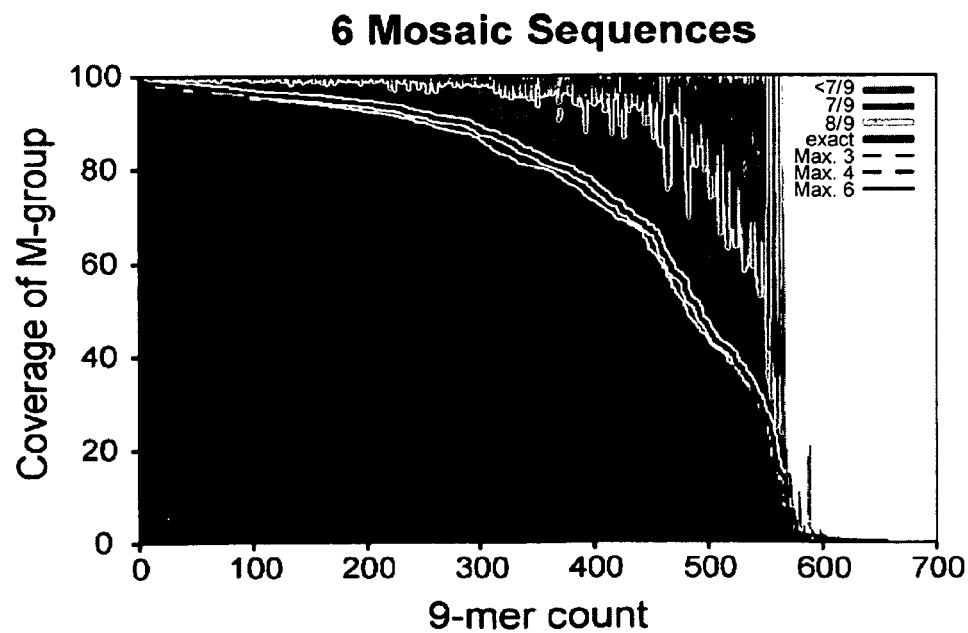

The initial design focused on protein regions meeting specific criteria: i) relatively low variability, ii) high levels of recognition in natural infection, iii) a high density of known epitopes and iv) either early responses upon infection or CD8+ T-cell responses associated with good outcomes in infected patients. First, an assessment was made of the level of 9-mer coverage achieved by mosaics for different HIV proteins (FIG. 3). For each protein, a set of four mosaics was generated using either the M group or the B- and C-subtypes alone; coverage was scored on the C subtype. Several results are notable: i) within-subtype optimization provides the best within-subtype coverage, but substantially poorer between-subtype coverage—nevertheless, B-subtype-optimized mosaics provide better C-subtype coverage than a single natural B subtype protein (Kong et al, J. Virol. 77:12764-72 (2003)); ii) Pol and Gag have the most potential to elicit broadly cross-reactive responses, whereas Rev, Tat, and Vpu have even fewer conserved 9-mers than the highly variable Env protein, iii) within-subtype coverage of M-group-optimized mosaic sets approached coverage of within-subtype optimized sets, particularly for more conserved proteins.

Gag and the central region of Nef meet the four criteria listed above. Nef is the HIV protein most frequently recognized by T-cells (Frahm et al, J. Virol. 78:2187-200 (2004)) and the target for the earliest response in natural infection (Lichterfeld et al, Aids 18:1383-92 (2004)). While overall it is variable (FIG. 3), its central region is as conserved as Gag (FIG. 1). It is not yet clear what optimum proteins for inclusion in a vaccine might be, and mosaics could be designed to maximize the potential coverage of even the most variable proteins (FIG. 3), but the prospects for global coverage are better for conserved proteins. Improved vaccine protection in macaques has been demonstrated by adding Rev, Tat, and Nef to a vaccine containing Gag, Pol, and Env (Hel et al, J. Immunol. 176:85-96 (2006)), but this was in the context of homologous challenge, where variability was not an issue. The extreme variability of regulatory proteins in circulating virus populations may preclude cross-reactive responses; in terms of conservation, Pol, Gag (particularly p24) and the central region of Nef (HXB2 positions 65-149) are promising potential immunogens (FIGS. 1,3). Pol, however, is infrequently recognized during natural infection (Frahm et al, J. Virol. 78:2187-200 (2004)), so it was not included in the initial immunogen design. The conserved portion of Nef that were included contains the most highly recognized peptides in HIV-1 (Frahm et al, J. Virol. 78:2187-200 (2004)), but as a protein fragment, would not allow Nef's immune inhibitory functions (e.g. HLA class I down-regulation (Blagoveshchenskaya, Cell 111:853-66 (2002))). Both Gag and Nef are densely packed with overlapping well-characterized CD8+ and CD4+ T-cell epitopes, presented by many different HLA molecules (http://www.hiv.lanl.gov//content/immunalogy/maps/maps.html), and Gag-specific CD8+ (Masemola et al, J. Virol. 78:3233-43 (2004)) and CD4+ (Oxenius et al, J. Infect. Dis. 189:1199-208 (2004)) T-cell responses have been associated with low viral set points in infected individuals (Masemola et al, J. Virol. 78:3233-43 (2004)).

To examine the potential impact of geographic variation and input sample size, a limited test was done using published subtype C sequences. The subtype C Gag data were divided into three sets of comparable size—two South African sets (Kiepiela et al, Nature 432:769-75 (2004)), and one non-South-African subtype C set. Mosaics were optimized independently on each of the sets, and the resulting mosaics were tested against all three sets. The coverage of 9-mers was slightly better for identical training and test sets (77-79% 9/9 coverage), but essentially equivalent when the training and test sets were the two different South African data sets (73-75%), or either of the South African sets and the non-South African C subtype sequences (74-76%). Thus between- and within-country coverage approximated within-clade coverage, and in this case no advantage to a country-specific C subtype mosaic design was found.

Designing Mosaics for Gag and Nef and Comparing Vaccine Strategies.

To evaluate within- and between-subtype cross-reactivity for various vaccine design strategies, a calculation was made of the coverage they provided for natural M-Group sequences. The fraction of all 9-mers in the natural sequences that were perfectly matched by 9-mers in the vaccine antigens were computed, as well as those having 8/9 or 7/9 matching amino acids, since single (and sometimes double) substitutions within epitopes may retain cross-reactivity. FIG. 4 shows M group coverage per 9-mer in Gag and the central region of Nef for cocktails designed by various strategies: a) three non-optimal natural strains from the A, B, and C subtypes that have been used as vaccine antigens (Kong et al, J. Virol. 77:12764-72 (2003)); b) three natural strains that were computationally selected to give the best M group coverage; c) M group, B subtype, and C subtype consensus sequences; and, d, e, f) three, four and six mosaic proteins. For cocktails of multiple strains, sets of k=3, k=4, and k=6, the mosaics clearly perform the best, and coverage approaches the upper bound for k strains. They are followed by optimally selected natural strains, the consensus protein cocktail, and finally, non-optimal natural strains. Allowing more antigens provides greater coverage, but gains for each addition are reduced as k increases (FIGS. 1 and 4).

Figure 5A:
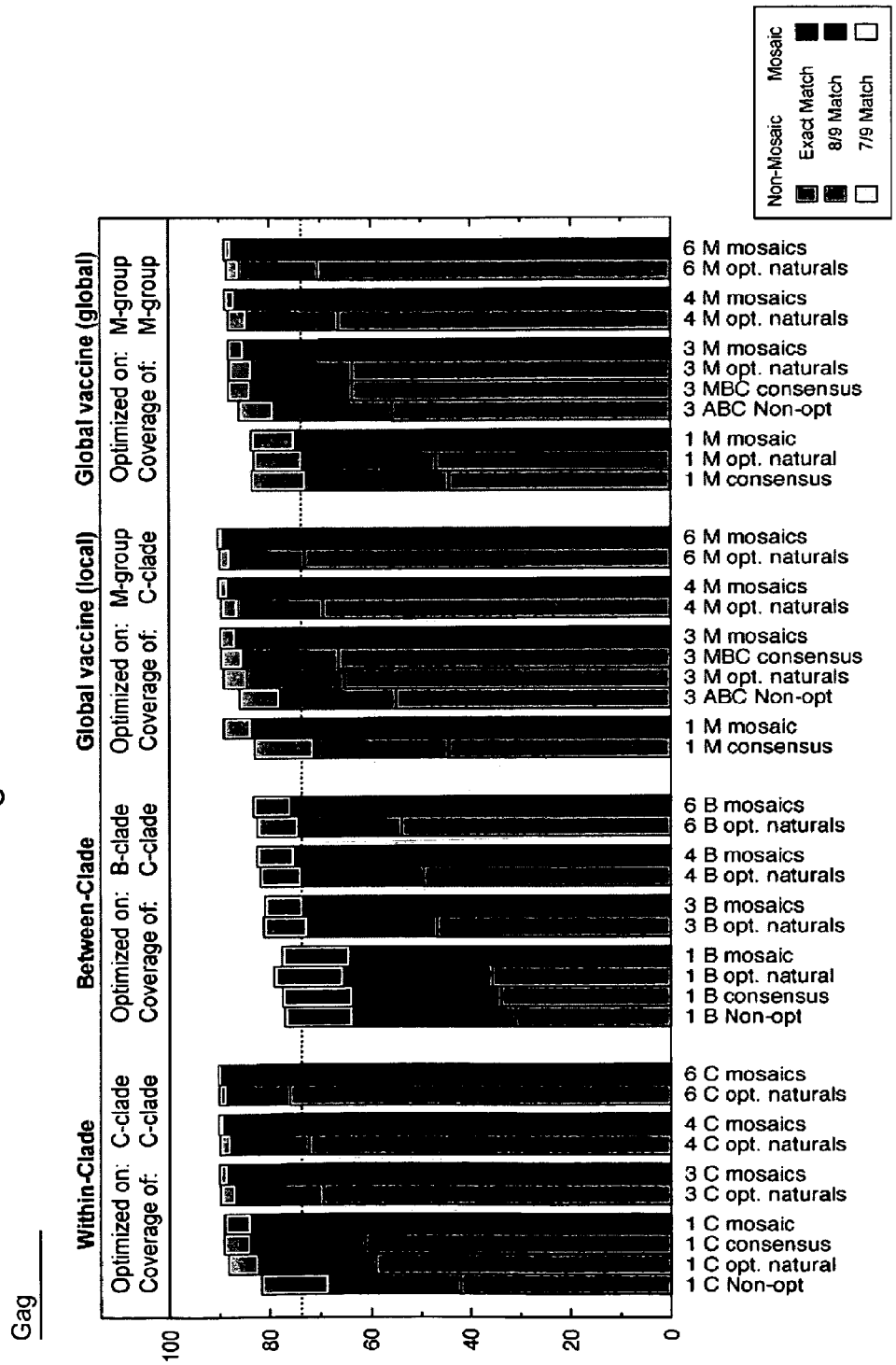
FIGS. 5A and 5B. Overall coverage of vaccine candidates: coverage of 9-mers in C clade sequences using different input data sets for mosaic optimization, allowing different numbers of antigens, and comparing to different candidate vaccines. Exact (blue), 8/9 (one-off; red), and 7/9 (two-off; yellow) coverage was computed for mono- and polyvalent vaccine candidates for Gag (FIG. 5A) and Nef (core) (FIG. 5B) for four test situations: within-clade (C-clade-optimized candidates scored for C-clade coverage), between-clade (B-clade-optimized candidates scored for C-clade coverage), global-against-single-subtype (M-group-optimized candidates scored for C-clade coverage), global-against-global (M-group-optimized candidates scored for global coverage). Within each set of results, vaccine candidates are grouped by number of sequences in the cocktail (1-6); mosaic sequences are plotted with darker colors. "Non-opt" refers to one set of sequences moving into vaccine trials (Kong et al, J. Virol. 77:12764-72 (2003)); "mosaic" denotes sequences generated by the genetic algorithm; "opt. natural" denotes intact natural sequences selected for maximum 9-mer coverage; "MBC consensus" denotes a cocktail of 3 consensus sequences, for M-group, B-subtype, and C-subtype. For ease of comparison, a dashed line marks the coverage of a 4-sequence set of M-group mosaics (73.7-75.6%). Over 150 combinations of mosaic-number, virus subset, protein region, and optimization and test sets were tested. The C clade/B clade/M group comparisons illustrated in this figure are generally representative of within-clade, between-clade, and M group, coverage. In particular, levels of mosaic coverage for B and C clade were very similar, despite there being many more C clade sequences in the Gag collection, and many more B clade sequences in the Nef collection (see FIG. 6 for a full B and C clade comparison). There were relatively few A and G clade sequences in the alignments (24 Gag, 75 Nef), and while 9-mer coverage by M-group optimized mosaics was not as high as for subtypes for B and C clades (4-mosaic coverage for A and G subtypes was 63% for Gag, 74% for Nef), it was much better than a non-optimal cocktail (52% Gag, 52% for Nef).
Figure 5B:
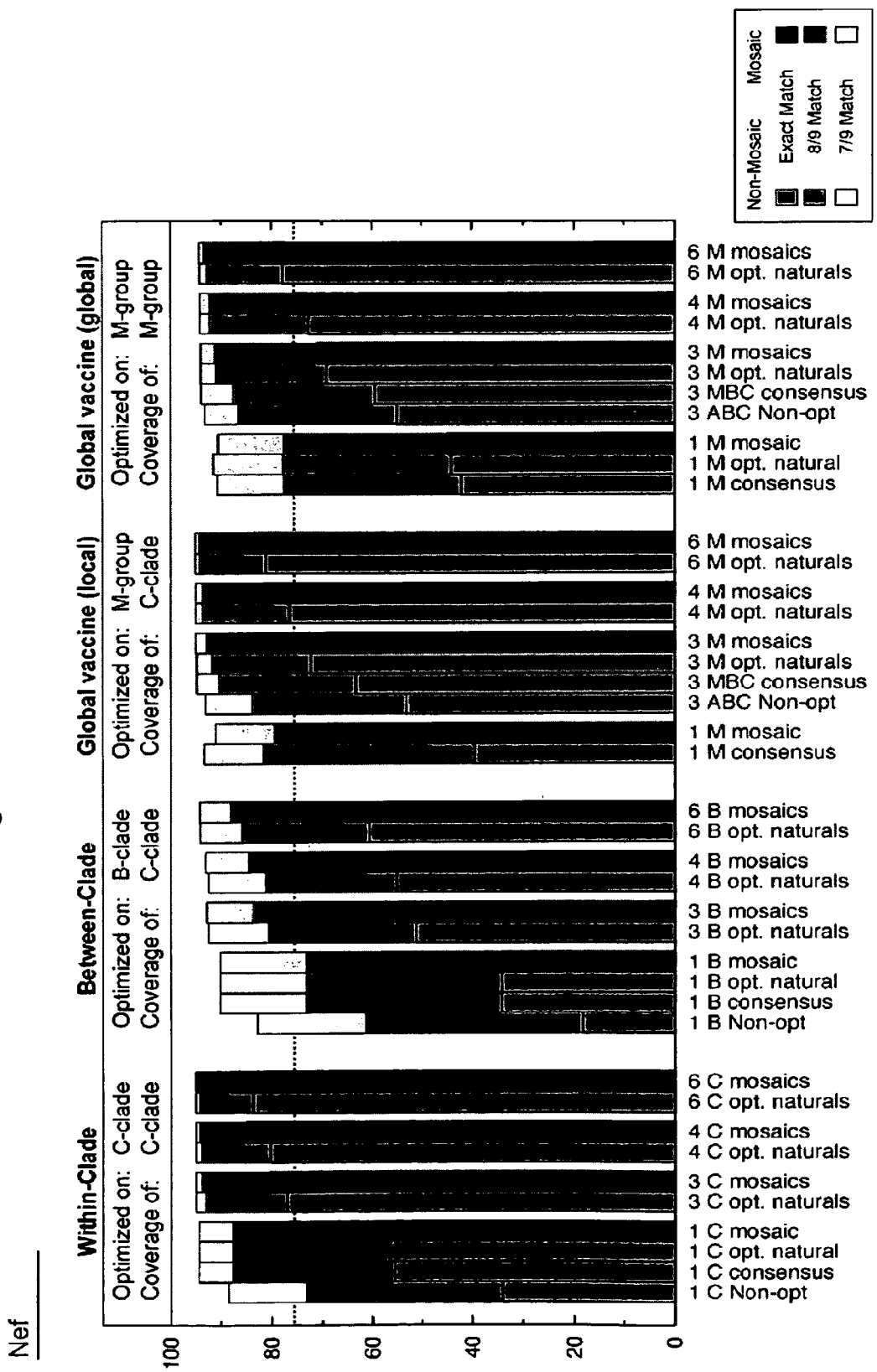
Figure 6A:
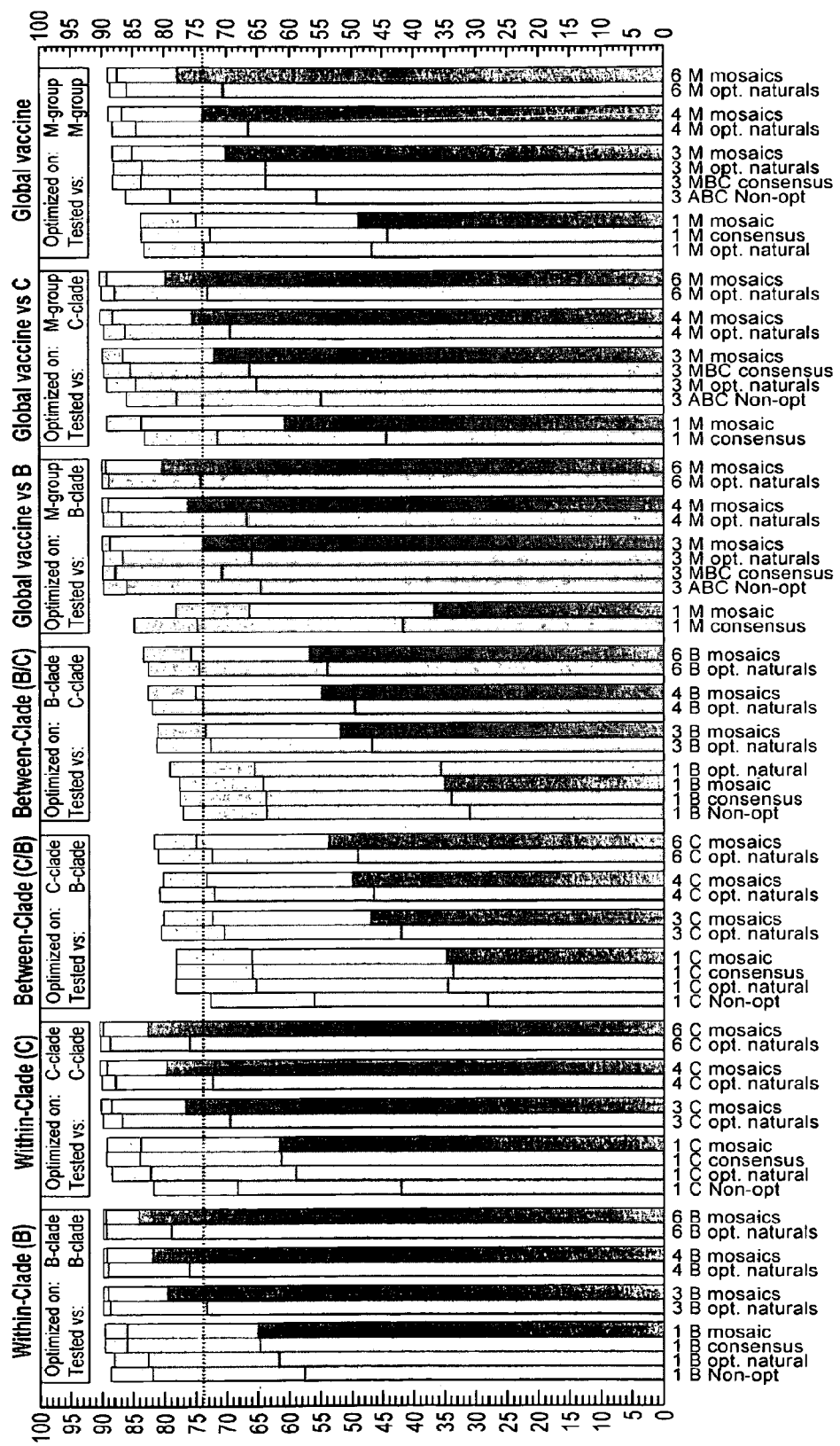
FIGS. 6A and 6B. Overall coverage of vaccine candidates: coverage of 9-mers in B-clade, C-clade, and M-group sequences using different input data sets for mosaic optimization, allowing different numbers of antigens, and comparing to different candidate vaccines. Exact (blue), 8/9 (one-off; red), and 7/9 (two-off; yellow) coverage was computed for mono- and polyvalent vaccine candidates for Gag (FIG. 6A) and Nef (core) (FIG. 6B) for seven test situations: within-clade (B- or C-clade-optimized candidates scored against the same clade), between-clade (B- or C-clade-optimized candidates scored against the other clade), global vaccine against single subtype (M-group-optimized candidates scored against B- or C-clade), global vaccine against global viruses (M-group-optimized candidates scored against all M-group sequences). Within each set of results, vaccine candidates are grouped by number of sequences in the cocktail (1-6); mosaic sequences are plotted with darker colors. "Non-opt" refers to a particular set of natural sequences previously proposed for a vaccine (Kong, W. P. et al. J Virol 77, 12764-72 (2003)); "mosaic" denotes sequences generated by the genetic algorithm; "opt. natural" denotes intact natural sequences selected for maximum 9-mer coverage; "MBC consensus" denotes a cocktail of 3 consensus sequences, for M-group, B-subtype, and C-subtype. A dashed line is shown at the level of exact-match M-group coverage for a 4-valent mosaic set optimized on the M-group.
Figure 6B:
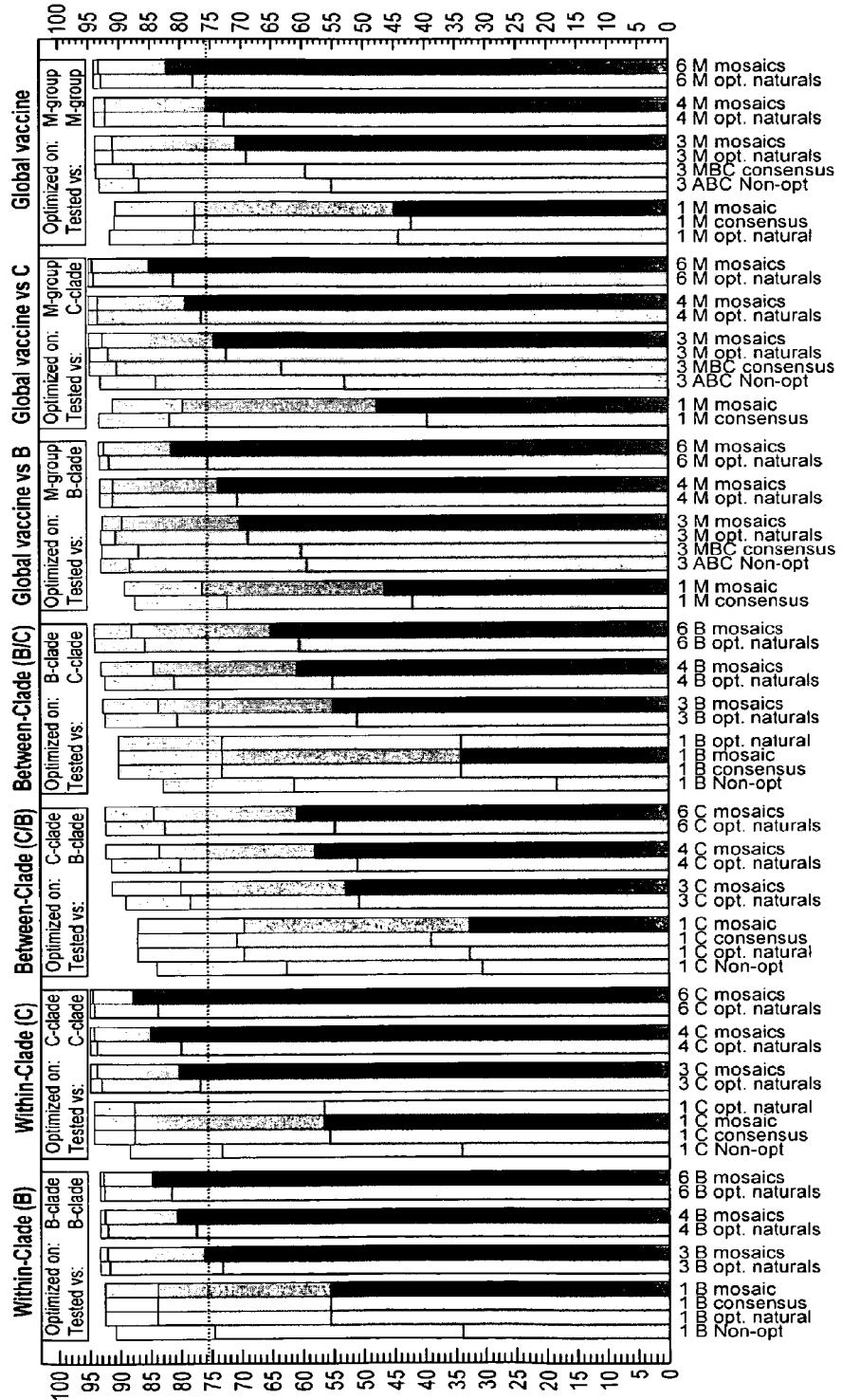
Figure 12:
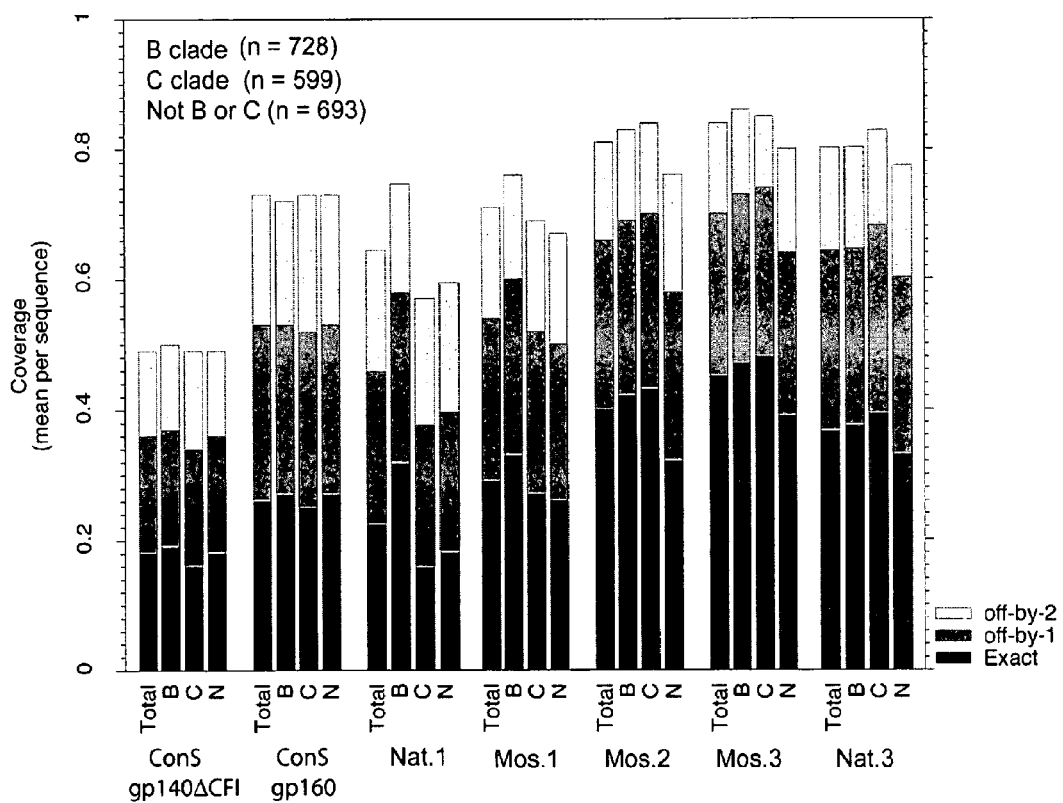
FIG. 12. Additional summaries of coverage.
Figure 13:
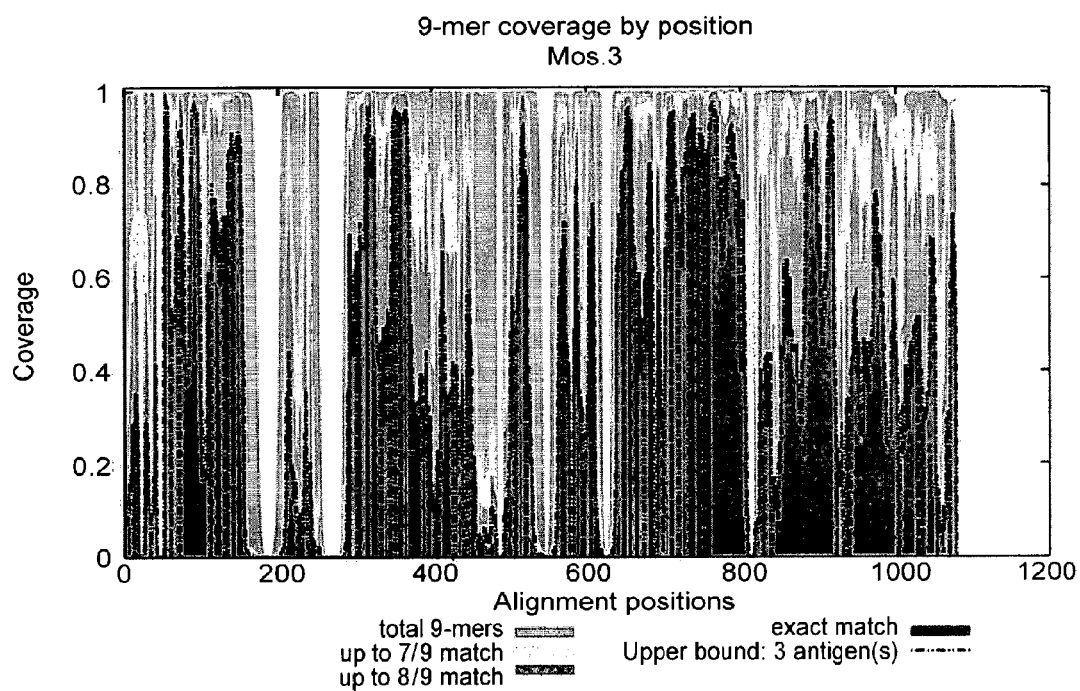
FIG. 13. 9-mer coverage by position (Mos.3 vaccine cocktail).
Figure 14A:
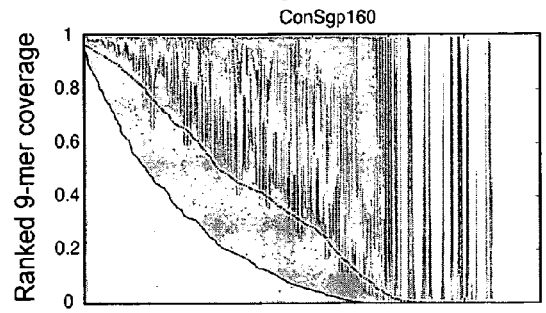
FIGS. 14A-14D. Plots resorted by frequency of 9-mer matches for each vaccine proposed for use.
Figure 14C:
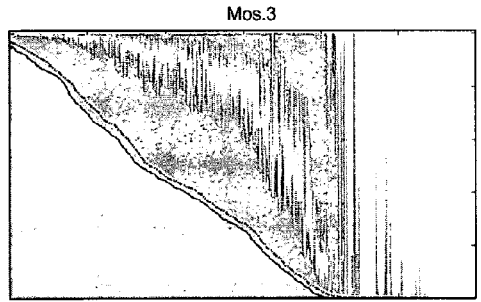
Figure 14B:
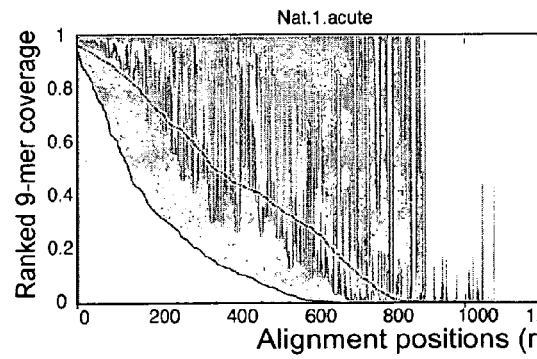
Figure 14D:
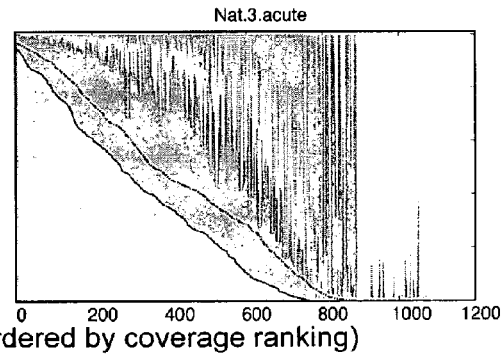
Figure 15A:
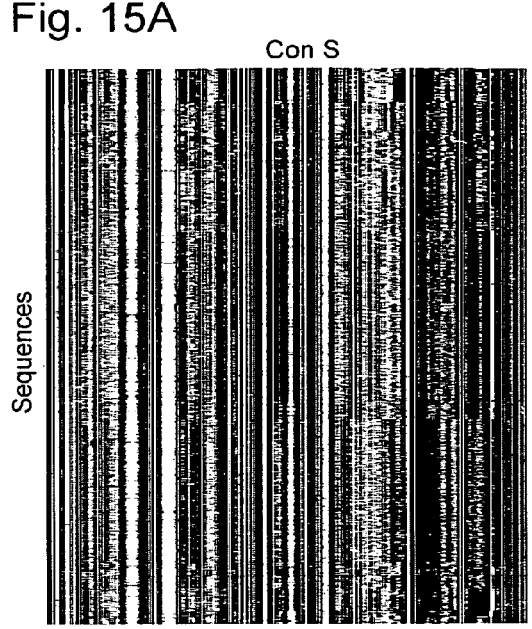
FIGS. 15A-15D. Plots mapping every amino acid in every sequence in the full database alignment.
Figure 15C:
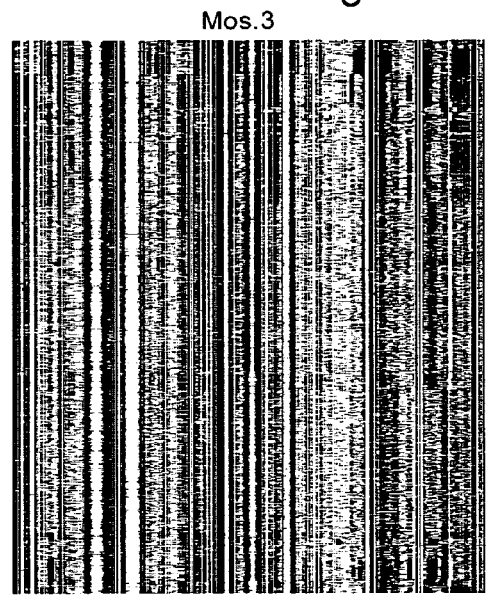
Figure 15B:
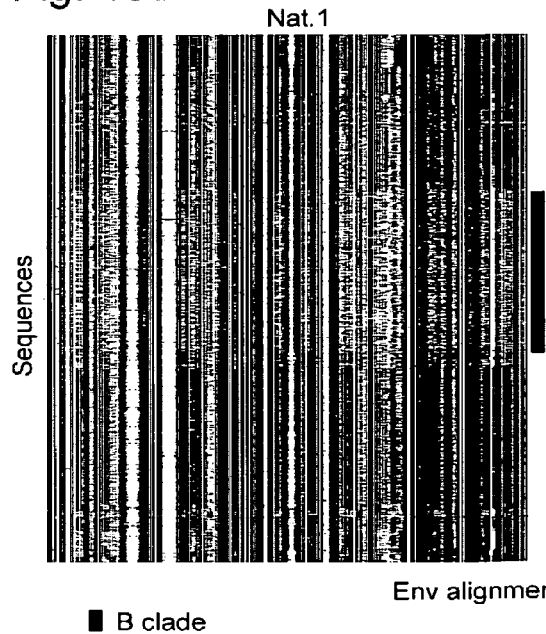
Figure 15D:
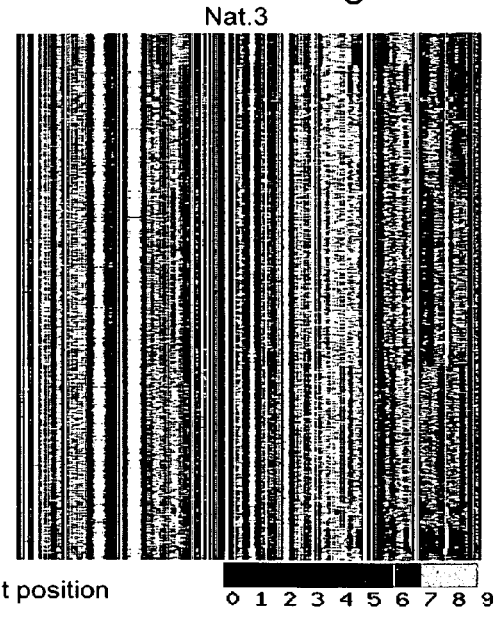
Figure 16:
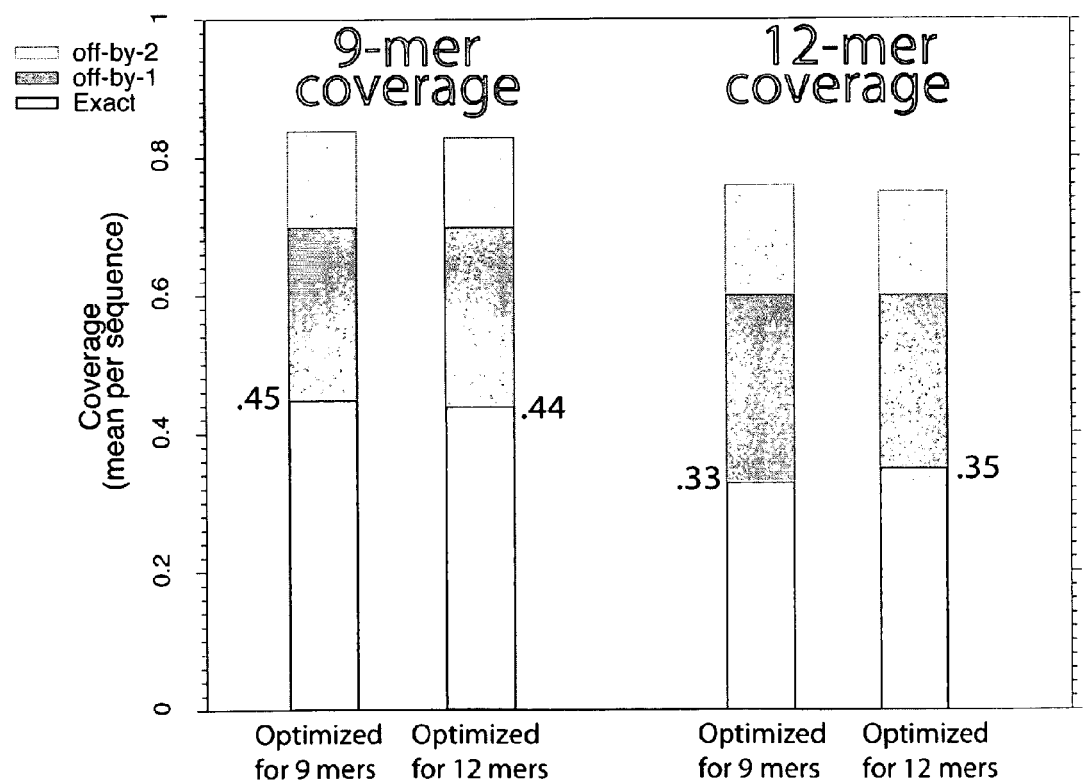
FIG. 16. 3 Mosaic, M group Optimizations.

FIG. 5 summarizes total coverage for the different vaccine design strategies, from single proteins through combinations of mosaic proteins, and compares within-subtype optimization to M group optimization. The performance of a single mosaic is comparable to the best single natural strain or a consensus sequence. Although a single consensus sequence out-performs a single best natural strain, the optimized natural-sequence cocktail does better than the consensus cocktail: the consensus sequences are more similar to each other than are natural strains, and are therefore somewhat redundant. Including even just two mosaic variants, however, markedly increases coverage, and four and six mosaic proteins give progressively better coverage than polyvalent cocktails of natural or consensus strains. Within-subtype optimized mosaics perform best—with four mosaic antigens 80-85% of the 9-mers are perfectly matched—but between-subtype coverage of these sets falls off dramatically, to 50-60%. In contrast, mosaic proteins optimized using the full M group give coverage of approximately 75-80% for individual subtypes, comparable to the coverage of the M group as a whole (FIGS. 5 and 6). If imperfect 8/9 matches are allowed, both M group optimized and within-subtype optimized mosaics approach 90% coverage.

Since coverage is increased by adding progressively rarer 9-mers, and rare epitopes may be problematic (e.g., by inducing vaccine-specific immunodominant responses), an investigation was made of the frequency distribution of 9-mers in the vaccine constructs relative to the natural sequences from which they were generated. Most additional epitopes in a k=6 cocktail compared to a k=4 cocktail are low-frequency (<0.1, FIG. 7). Despite enhancing coverage, these epitopes are relatively rare, and thus responses they induce might draw away from vaccine responses to more common, thus more useful, epitopes. Natural-sequence cocktails actually have fewer occurrences of moderately low-frequency epitopes than mosaics, which accrue some lower frequency 9-mers as coverage is optimized. On the other hand, the mosaics exclude unique or very rare 9-mers, while natural strains generally contain 9-mers present in no other sequence. For example, natural M group Gag sequences had a median of 35 (range 0-148) unique 9-mers per sequence. Retention of HLA-anchor motifs was also explored, and anchor motif frequencies were found to be comparable between four mosaics and three natural strains. Natural antigens did exhibit an increase in number of motifs per antigen, possibly due to inclusion of strain-specific motifs (FIG. 8).

The increase in ever-rarer epitopes with increasing k, coupled with concerns about vaccination-point dilution and reagent development costs, resulted in the initial production of mosaic protein sets limited to 4 sequences (k=4), spanning Gag and the central region of Nef, optimized for subtype B; subtype C, and the M group (these sequences are included in FIG. 9; mosaic sets for Env and Pol are set forth in FIG. 10). Synthesis of various four-sequence Gag-Nef mosaics and initial antigenicity studies are underway. In the initial mosaic vaccine, targeted are just Gag and the center of the Nef protein, which are conserved enough to provide excellent global population coverage, and have the desirable properties described above in terms of natural responses (Bansal et al, Aids 19:241-50 (2005)). Additionally, including B subtype p24 variants in Elispot peptide mixtures to detect natural CTL responses to infection significantly enhanced both the number and the magnitude of responses detected supporting the idea that including variants of even the most conserved proteins will be useful. Finally, cocktails of proteins in a polyvalent HIV-1 vaccine given to rhesus macaques did not interfere with the development of robust responses to each antigen (Seaman et al, J. Virol. 79:2956-63 (2005)), and antigen cocktails did not produce antagonistic responses in murine models (Singh et al, J. Immunol. 169:6779-86 (2002)), indicating that antigenic mixtures are appropriate for T-cell vaccines.

Even with mosaics, variable proteins like Env have limited coverage of 9-mers, although mosaics improve coverage relative to natural strains. For example three M group natural proteins, one each selected from the A, B, and C clades, and currently under study for vaccine design (Seaman et al, J. Virol. 79:2956-63 (2005)) perfectly match only 39% of the 9-mers in M group proteins, and 65% have at least 8/9 matches. In contrast, three M group Env mosaics match 47% of 9-mers perfectly, and 70% have at least an 8/9 match. The code written to design polyvalent mosaic antigens is available, and could readily be applied to any input set of variable proteins, optimized for any desired number of antigens. The code also allows selection of optimal combinations of k natural strains, enabling rational selection of natural antigens for polyvalent vaccines. Included in Table 1 are the best natural strains for Gag and Nef population coverage of current database alignments.

TABLE 1

Natural sequence cocktails having the best available 9-mer coverage for different genes, subtype sets, and numbers of sequences Gag, B-subtype, 1 natural sequence B.US.86.AD87_AF004394
Gag, B-subtype, 3 natural sequences B.US.86.AD87_AF004394
B.US.97.Ac_06_AY247251
B.US.88.WR27_AF286365
Gag, B-subtype, 4 natural sequences B.US.86.AD87_AF004394
B.US.97.Ac_06_AY247251
B.US._.R3_PDC1_AY206652
B.US.88.WR27_AF286365
Gag, B-subtype, 6 natural sequences B.CN._.CNHN24_AY180905
B.US.86.AD87_AF004394
B.US.97.Ac_06_AY247251
B.US._.P2_AY206654
B.US._.R3_PDC1_AY206652
B.US.88.WR27_AF286365
Gag, C-subtype, 1 natural sequence C.IN._.70177_AF533131
Gag, C-subtype, 3 natural sequences C.ZA.97.97ZA012
C.ZA.x.04ZASK161B1
C.IN.-.70177_AF533131
Gag, C-subtype, 4 natural sequences C.ZA.97.97ZA012
C.ZA.x.04ZASK142B1
C.ZA.x.04ZASK161B1
C.IN._.70177_AF533131
Gag, C-subtype, 6 natural sequences C.ZA.97.97ZA012
C.ZA.x.04ZASK142B1
C.ZA.x.04ZASK161B1
C.BW.99.99BWMC168_AF443087
C.IN._.70177_AF533131
C.IN._.MYA1_AF533139
Gag, M-group, 1 natural sequence C.IN._.70177_AF533131
Gag, M-group, 3 natural sequences B.US.90.US2_AY173953
C.IN.-.70177_AF533131
15_01B.TH.99.99TH_R2399_AF530576
Gag, M-group, 4 natural sequences B.US.90.US2_AY173953
C.IN._.70177_AF533131
C.1N.93.93IN999_AF067154
15_01B.TH.99.99TH_R2399_AF530576

TABLE 1-continued

Natural sequence cocktails having the best available 9-mer coverage for different genes, subtype sets, and numbers of sequences Gag, M-group, 6 natural sequences C.ZA.x.04ZASK138B1
B.US.90.US2_AY173953
B.US._.WT1_PDC1_AY206656
C.IN._.70177_AF533131
C.IN.93.93IN999_AF067154
15_01B.TH.99.99TH_R2399_AF530576
Nef (central region), B-subtype, 1 natural sequence B.GB.94.028jh_94_1_NP_AF129346
Nef (central region), B-subtype, 3 natural sequences B.GB.94.028jh_94_1_NP_AF129346
B.KR.96.96KCS4_AY121471
B.FR.83.HXB2_K03455
Nef (central region), B-subtype, 4 natural sequences B.GB.94.028jh_94_1_NP_AF129346
B.KR.96.96KCS4_AY121471
B.US.90.E90NEF_U43108
B.FR.83.HXB2_K03455
Nef (central region), B-subtype, 6 natural sequences B.GB.94.028jh_94_1_NP_AF129346
B.KR.02.02HYJ3_AY7121454
B.KR.96.96KCS4_AY121471
B.CN._.RL42_U71182
B.US.90.E90NEF_U43108
B.FR.83.HXB2_K03455
Nef (central region), C-subtype, 1 natural sequence C.ZA.04.04ZASK139B1
Nef (central region), C-subtype, 3 natural sequences C.ZA.04.04ZASK180B1
C.ZA.04.04ZASK139B1
C.ZA._.ZASW15_AF397568
Nef (central region), C-subtype, 4 natural sequences C.ZA.97.ZA97004_AF529682
C.ZA.04.04ZASK180B1
C.ZA.04.04ZASK139B1
C.ZA._.ZASW15_AF397568
Nef (central region), C-subtype, 6 natural sequences C.ZA.97.ZA97004_AF529682
C.ZA.00.1192M3M
C.ZA.04.04ZASK180B1
C.ZA.04.04ZASK139B1
C.04ZASK184B1
C.ZA._.ZASW15_AF397568
Nef (central region), M-group, 1 natural sequence B.GB.94.028jh_94_1_NP_AF129346
Nef (central region), M-group, 3 natural sequences 02_AG.CM._.98CM1390_AY265107
C.ZA.03.03ZASK020B2
B.GB.94.028jh_94_1_NP_AF129346
Nef (central region), M-group, 4 natural sequences 02_AG.CM._.98CM1390_AY265107
01A1.MM.99.mCSW105_AB097872
C.ZA.03.03ZASK020B2
B.GB.94.028jh_94_1_NP_AF129346
Nef (central region), M-group, 6 natural sequences 02_AG.CM._.98CM1390_AY265107
01A1.MM.99.mCSW105_AB097872
C.ZA.03.03ZASK020B2
C.03ZASK111B1
B.GB.94.028jh_94_1_NP_AF129346
B.KR.01.01CWS2_AF462757

Summarizing, the above-described study focuses on the design of T-cell vaccine components to counter HIV diversity at the moment of infection, and to block viral escape routes and thereby minimize disease progression in infected individuals. The polyvalent mosaic protein strategy developed here for HIV-1 vaccine design could be applied to any variable protein, to other pathogens, and to other immunological problems. For example, incorporating a minimal number of variant peptides into T-cell response assays could markedly increase sensitivity without excessive cost: a set of k mosaic proteins provides the maximum coverage possible for k antigens.

A centralized (consensus or ancestral) gene and protein strategy has been proposed previously to address HIV diversity (Gaschen et al, Science 296:2354-2360 (2002)). Proof-of-concept for the use of artificial genes as immunogens has been demonstrated by the induction of both T and B cell responses to wild-type HIV-1 strains by group M consensus immunogens (Gaschen et al, Science 296:2354-2360 (2002), Gao et al, J. Virol. 79:1154-63 (2005), Doria-Rose et al, J. Virol. 79:11214-24 (2005), Weaver et al, J. Virol., in press)). The mosaic protein design improves on consensus or natural immunogen design by co-optimizing reagents for a polyclonal vaccine, excluding rare CD8+ T-cell epitopes, and incorporating variants that, by virtue of their frequency at the population level, are likely to be involved in escape pathways.

The mosaic antigens maximize the number of epitope-length variants that are present in a small, practical number of vaccine antigens. The decision was made to use multiple antigens that resemble native proteins, rather than linking sets of concatenated epitopes in a poly-epitope pseudo-protein (Hanke et al, Vaccine 16:426-35 (1998)), reasoning that in vivo processing of native-like vaccine antigens will more closely resemble processing in natural infection, and will also allow expanded coverage of overlapping epitopes. T-cell mosaic antigens would be best employed in the context of a strong polyvalent immune response; improvements in other areas of vaccine design and a combination of the best strategies, incorporating mosaic antigens to cover diversity, may ultimately enable an effective cross-reactive vaccine-induced immune response against HIV-1.

Example 2

Group M consensus envelope and trivalent mosaic envelopes (both of which were designed by in silico modeling and are predicted to be superior than wildtype envelopes) will be compared to a monovalent wild-type envelope and trivalent wild-type transmitted envelopes in a 4 arm immunogenicity clinical trial. The mosaic antigens have been designed based on the current Los Alamos database, a set that includes more full length envelopes sampled globally from more than 2000 individuals with a large set of sequences of transmitted viruses primarily from the CHAVI database.

The selection of the natural strains to be used for the comparison is based on the following criteria: For the monovalent natural antigen, use will be made of the single transmitted virus that is the best choice in terms of providing coverage of potential T cell epitopes in the global database. The database is biased towards B clade envelopes, so the single best acute Env is a B clade representative. One A, one B and one C subtype transmitted virus sequence is proposed for inclusion in the trivalent set, to compensate for the biases in sampling inherent in the global sequence collection, and to better reflect the circulating pandemic strains. The A and C natural sequences are those that optimally complement the best B clade sequence to provide potential epitope coverage of the database. Vaccine antigens have been selected from among available SGA sequenced acute samples, each representing a transmitted virus. Therefore, this study, although primarily a T cell study, will also provide important additional data regarding the ability of transmitted envelope vaccines to elicit neutralizing antibodies.

For a mosaic/consensus human trial, the following 4 arm trial is proposed, 20 people per group, with a negative control:
1) Con S (a well studied consensus of the consensus of each clade, based on the 2002 database; Con S has been extensively tested in animal models, and has theoretical coverage roughly comparable to a single mosaic.)
2) A 3 mosaic M group antigen set designed to, in combination, provide optimal global coverage of 9 amino acid long stretches in the database. Such 9-mers represent potential epitope coverage of the database. Unnatural 9-mers are excluded in mosaics, and rare variants minimized.
3) The optimal single best natural protein selected from sequences sampled from acutely infected patients with SGA sequences available; these sequences should correspond to viable, transmitted sequences. As in (2), this sequence will be selected to be the one that provides optimal 9-mer coverage of the database. The B clade currently dominates sampling for the sequence database, so the sequence with the best database coverage will be a B clade sequence.
4) The best natural strains from acute infection SGA sequences that in combination provide the best global coverage. (Note: the B and C dominate the M group sampling hence the code naturally selects one of each as the two best. Thus, the third complementary sequence was forced to be selected from an acute SGA A clade set, to counter this bias and better reflect the global epidemic).
5) Negative control buffer/saline The current M group alignment in the HIV database was combined with all of the newer CHAVI sequences—this includes a total of 2020 sequences:
728 B clade
599 C clade
693 that are all other clades, circulating recombinant forms, and unique recombinants. This was used for the M group vaccine design.

This sampling is obviously skewed toward the B and C clade. As will be shown subsequently, the coverage of "potential epitopes" (9-mers) in other clades is still excellent.

The Sequences

```
M consensus
>ConS
MRVRGIQRNCQHLWRWGTLILGMLMICSAAENLWVTVYYGVPVWK
EANTTLFCASDAKAYDTEVHNVWATHACVPTDPNPQEIVLENVTE
NFNMWKNNMVEQMHEDIISLWDQSLKPCVKLTPLCVTLNCTNVNV
TNTTNNTEEKGEIKNCSFNITTEIRDKKQKVYALFYRLDVVPIDD
NNNNSSNYRLINCNTSAITQACPKVSFEPIPIHYCAPAGFAILKC
NDKKFNGTGPCKNVSTVQCTHGIKPVVSTQLLLNGSLAEEEIIR
SENITNNAKTIIVQLNESVEINCTRPNNNTRKSIRIGPGQAFYAT
GDIIGDIRQAHCNISGTKWNKTLQQVAKKLREHFNNKTIIFKPSS
GGDLEITTHSFNCRGEFFYCNTSGLFNSTWIGNGTKNNNNTNDTI
TLPCRIKQIINMWQGVGQAMYAPPIEGKITCKSNITGLLLTRDGG
NNNTNETEIFRPGGGDMRDNWRSELYKYKVVKIEPLGVAPTKAKR
RVVEREKRAVGIGAVFLGFLGAAGSTMGAASITLTVQARQLLSGI
VQQQSNLLRAIEAQQHLLQLTVWGIKQLQARVLAVERYLKDQQLL
GIWGCSGKLICTTTVPWNSSWSNKSQDEIWDNMTWMEWEREINNY
TDIIYSLIEESQNQQEKNEQELLALDKWASLWNWFDITNWLWYIK
IFIMIVGGLIGLRIVFAVLSIVNRVRQGYSPLSFQTLIPNPRGPD
RPEGIEEEGGEQDRDRSIRLVNGFLALAWDDLRSLCLFSYHRLRD
FILIAARTVELLGRKGLRRGWEALKYLWNLLQYWGQELKNSAISL
LDTTAIAVAEGTDRVIEVVQRACRAILNIPRRIRQGLERALL 3 mosaics
>M_mos_3_1
MRVKGIRKNYQHLWRWGTMLLGMLMICSAAEQLWVTVYYGVPVWR
DAETTLFCASDAKAYEREVHNVWATHACVPTDPNPQEIVLENVTE
EFNMWKNNMVDQMHEDIISLWDESLKPCVKLTPLCVTLNCTDVNV
TKTNSTSWGMMEKGEIKNCSFNMTTELRDKKQKVYALFYKLDIVP
LEENDTISNSTYRLINCNTSAITQACPKVTFEPIPIHYCTPAGFA
ILKCNDKKFNGTGPCKNVSTVQCTHGIRPVVTTQLLLNGSLAEEE
IIIRSENLTNNAKTIIVQLNESVVINCTRPNNNTRKSIRIGPGQT
FYATGDIIGNIRQAHCNISREKWINTTRDVRKKLQEHENKTIIEN
SSSGGDLEITTHSFNCRGEFFYCNTSKLFNSVWGNSSNVTKVNGT
KVKETITLPCKIKQIINMWQEVGRAMYAPPIAGNITCKSNITGLL
LVRDGGNVTNNTEIFRPGGGNMKDNWRSELYKYKVVEIKPLGIAP
TKAKRRVVEREKRAVGLGAVFLGFLGAAGSTMGAASMTLTVQARQ
LLSGIVQQQSNLLRAIEAQQHMLQLTVWGIKQLQARILAVERYLR
DQQLLGIWGCSGKLICTTNVPWNSSWSNKSLDEIWNNMTWMQWEK
EIDNYTSLIYTLIEESQNQQEKNEQDLLALDKWANLWNWFDISNW
LWYIRIFIMIVGGLIGLRIVFAVLSIVNRVRKGYSPLSFQTLTPN
PRGPDRLGRIEEEGGEQDKDRSIRLVNGFLALAWDDLRNLCLFSY
HRLRDLLLIVTRIVELLGRRGWEALKYLWNLLQYWIQELKNSAVS
LLNATAIAVAEGTDRVIEVVQRACRAILHIPRRIRQGLERALL >M_mos_3_2
MRVKETQMNWPNLWKWGTLILGLVIICSASDNLWVTVYYGVPVWK
EATTTLFCASDAKAYDTEVHNVWATYACVPTDPNPQEVVLGNVTE
NFNMWKNNMVEQMHEDIISLWDQSLKPCVRLTPLCVTLNCSNANT
TNTNSTEEIKNCSFNITTSIRDKVQKEYALFYKLDVVPIDNDNTS
YRLISCNTSVITQACPKVSFEPIPIHYCAPAGFAILKCKDKKENG
TGPCTNVSTVQCTHGIRPVVSTQLLLNGSLAEEEVVIRSENFTNN
AKTIIVHLNKSVEINCTRPNNNTRKSIHIGPGRAFYATGEIIGDI
RQAHCNISRAKWNNTLKQIVKKLKEQFNKTIIFNQSSGGDPEITT
HSFNCGGEFFYCNTSGLFNSTWNSTATQESNNTELNGNITLPCRI
```

KQIVNMWQEVGKAMYAPPIRGQIRCSSNITGLILTRDGGNNNSTN

ETFRPGGGDMRDNWRSELYKYKVVKIEPLGVAPTKAKRRVVQREK

RAVGTIGAMFLGFLGAAGSTMGAASLTLTVQARLLLSGIVQQQNN

LLRAIEAQQHLLQLTVWGIKQLQARVLAVERYLKDQQLLGIWGCS

GKLICTTTVPWNTSWSNKSLNEIWDNMTWMEWEREIDNYTGLIYT

LLEESQNQQEKNEQELLELDKWASLWNWFDITKWLWYIKIFIMIV

GGLVGLRIVFTVLSIVNRVRQGYSPLSFQTHLPAPRGPDRPEGIE

EEGGERDRDRSGRLVDGFLAIIWVDLRSLCLFSYHQLRDFILIAA

RTVELLGHSSLKGLRRGWEALKYWWNLLQYWSQELKNSAISLLNT

TAIVVAEGTDRIIEVLQRAGRAILHIPTRIRQGLERLLL

>M_mos_3_3
MRVRGIQRNWPQWWIWGILGFWMLMICNVVGNLWVTVYYGVPVWK

EAKTTLFCASDAKAYEKEVHNVWATHACVPTDPSPQEVVLENVTE

NFNMWKNDMVDQMHEDVISLWDQSLKPCVKLTHLCVTLNCTNATN

TNYNNSTNVTSSMIGEMKNCSFNITTEIRDKSRKEYALFYRLDIV

PLNEQNSSEYRLINCNTSTITQACPKVSFDPIPIHYCAPAGYAIL

KCNNKTFNGTGPCNNVSTVQCTHGIKPVVSTQLLLNGSLAEGEII

IRSENLTDNAKTIIVHLNESVEIVCTRPNNNTRKSVRIGPGQAFY

ATGDIIGDIRQAHCNLSRTQWNNTLKQIVTKLREQFGNKTIVFNQ

SSGGDPEIVMHSFNCGGEFFYCNTTQLFNSTWENSNITQPLTLNR

TKGPNDTITLPCRIKQIINMWQGVGRAMYAPPIEGLIKCSSNITG

LLLTRDGGNNSETKTTTETFRPGGGNMRDNWRNELYKYKVVQIEPL

GVAPTRAKRRVVEREKRAVGIGAVFLGFLGTAGSTMGAASITLTV

QARQVLSGIVQQQSNLLKAIEAQQHLLKLTVWGIKQLQTRVLAIE

RYLKDQQLLGLWGCSGKLICTTAVPWNSSWSNKSQTDIWDNMTWM

QWDREISNYTDTIYRLLEDSQNQQEKNEKDLLALDSWKNLWNWFD

ITNWLWYIKIFIIIVGGLIGLRIIFAVLSIVNRCRQGYSPLSLQT

LIPNPRGPDRLGGIEEEGGEQDRDRSIRLVSGFLALAWDDLRSLC

LFSYHRLRDFILIVARAVELLGRSSLRGLQRGWEALKYLGSLVQY

WGLELKKSAISLLDTIAIAVAEGTDRIIEVIQRICRAIRNIPRRI

RQGFEAALL

Single Optimal Natural Sequence Selected from Available Acute SGA Sequences:

>B.acute.Con.1059
MRVTEIRKNYLWRWGIMLLGMLMICSAAEQLWVTVYYGVPVWKEA
TTTLFCASDAKAYTAEAHNVWATHACVPTDPNPQEVVLENVTENFN
MWKNNMVEQMHEDIISLWDQSLKPCVKLTPLCVTLNCTDLANNTNL
ANNTNSSISSWEKMEKGEIKNCSFNITTVIKDKIQKNYALFNRLDIVPID
DDDTNVTNNASYRLISCNTSVITQACPKISFEPIPIHYCAPAGFAILKCN
DKKFNGTGPCTNVSTVQCTHGIKPVVSTQLLLNGSLAEEEVVIRSENFT
DNVKTIIVQLNESVIINCTRPNNNTRKSITFGPGRAFYTTGDIIGDIRKA -continued YCNISSTQWNNTLRQIARRLREQFKDKTIVFNSSSGGDPEIVMHSFNCGG
EFFYCNTTQLFNSTWNGNDTGEFNNTGKNITYITLPCRIKQIINMWQEV
GKAMYAPPIAGQIRCSSNITGILLTRDGGNSSEDKEIFRPEGGNMRDNW
RSELYKYKVVKIEPLGVAPTKAKRRVVQREKRAVGIGAVFLGFLGAA
GSTMGAASMTLTVQARLLLSGIVQQQNNLLRAIEAQQHLLQLTVWGI
KQLQARVLAVERYLKDQQLLGIWGCSGKLICTTAVPWNASWSNRSLD
NIWNNMTWMEWDREINNYTNLIYNLIEESQNQQEKNEQELLELDKW
ASLWNWFDITKWLWYIKIFIMIVGGLVGLRIVGVILSIVNRVRQGYSPL
SFQTHLPTPRGLDRHEGTEEEGGERDRDRSGRLVDGFLTLIWIDLRSLC
LFSYHRLRDLLLIVTRIVELLGRRGWEILKYWWNLLQYWSQELKNSA
VSLLNATAIAVAEGTDRIIEIVQRIFRAILHIPTRIRQGLERALL 3 Optimal Natural Selected from Available Acute Samples, SGA Sequences:

>B.acute.Con.1059
MRVTEIRKNYLWRWGIMLLGMLMICSAAEQLWVTVYYGVPVWKEA
TTTLFCASDAKAYTAEAHNVWATHACVPTDPNPQEVVLENVTENF
NMWKNNMVEQMHEDIISLWDQSLKPCVKLTPLCVTLNCTDLANNT
NLANNTNSSISSWEKMEKGEIKNCSFNITTVIKDKIQKNYALFNR
LDIVPIDDDDINVTNNASYRLISCNTSVITQACPKISFEPIPIHY
CAPAGFAILKCNDKKENGTGPCTNVSTVQCTHGIKPVVSTQLLLN
GSLAEEEVVIRSENFTDNVKTIIVQLNESVIINCTRPNNNTRKSI
TFGPGRAFYTTGDIIGDIRKAYCNISSTQWNNTLRQIARRLREQF
KDKTIVFNSSSGGDPEIVMHSFNCGGEFFYCNTTQLFNSTWNGND
TGEFNNTGKNITYITLPCRIKQIINMWQEVGKAMYAPPIAGQIRC
SSNITGILLTRDGGNSSEDKEIFRPEGGNMRDNWRSELYKYKVVK
IEPLGVAPTKAKRRVVQREKRAVGIGAVFLGFLGAAGSTMGAASM
TLTVQARLLLSGIVQQQNNLLRAIEAQQHLLQLTVWGIKQLQARV
LAVERYLKDQQLLGIWGCSGKLICTTAVPWNASWSNRSLDNIWNN
MTWMEWDREINNYTNLIYNLIEESQNQQEKNEQELLELDKWASLW
NWFDITKWLWYIKIFIMIVGGLVGLRIVFVILSIVNRVRQGYSPL
SFQTHLPTPRGLDRHEGTEEEGGERDRDRSGRLVDGFLTLIWIDL
RSLCLFSYHRLRDLLLIVTRIVELLGRRGWEILKYWWNLLQYWSQ
ELKNSAVSLLNATAIAVAEGTDRIIEIVQRIFRAILHIPTRIRQG
LERALL >C.acute.Con.0393
MRVRGILRNYQQWWIWGILGFWMLMICSVGGNLWVTVYYGVPVWR
EAKTTLFCASDAKAYEREVHNVWATHACVPTDPNPQELFLENVTE
NFNMWKNDMVDQMHEDIISLWDQSLKPCVKLTPLCVTLNCSNANI
TRNSTDGNTTRNSTATPSDTINGEIKNCSFNITTELKDKKKKEYA
LFYRLDIVPLNEENSNFNEYRLINCNTSAVTQACPKVSFDPIPIH
YCAPAGYAILKCNNKTFNGTGPCNNVSTVQCTHGIKPVVSTQLLL -continued

```
NGSLAEEEIIIRSENLTNNAKTIIVHLKEPVEIVCTRPNNNTRKS

MRIGPGQTFYATDIIGDIRQASCNIDEKTWNNTLNKVGEKLQEHF

PNKTLNFAPSSGGDLEITTHSFNCRGEFFYCNTSKLFYKTEFNST

TNSTITLQCRIKQIINMWQGVGRAMYAPPIEGNITCKSNITGLLL

TRDGGTNDSMTETFRPGGGDMRDNWRSELYKYKVVEIKPLGVAPT

EAKRRVVEREKRALTLGALFLGFLGTAGSTMGAASITLTVQARQL

LSGIVQQQSNLLKAIEAQQHLLQLTVWGIKQLQTRVLAIERYLQD

QQLLGLWGCSGKLICTTAVPWNSSWSNKSQGEIWGNMTWMQWDRE

ISNYTNTIYRLLEDSQIQQEKNEKDLLALDSWKNLWSWFSITNWL

WYIKIFIMIVGGLIGLRIIFAVLSIVNRVRQGYSPLPFQTLIPNP

RGPDRLGRIEEEGGEQDRDRSIRLVNGFLAIAWDDLRSLCLFSYH

RLRDFILIAARAAELLGRSSLRGLQRGWEALKYLGSLVQYWGLEL

KKSAISLLDTVAITVAEGTDRIIEVVQRICRAICNIPRRIRQGFE

AALQ
```

Coverage Comparison of the Four Vaccine Antigens.

Mosaics and naturals are optimized for the first red bar on the left for each vaccine (the total). The "total" represents all sequences, database+CHAVI. The "B" is the subset that are B clade, "C" the subset that are C clade, and "N" the remaining M group sequences that are not B or C (all other clades and recombinants). As B is most common, the single best natural is of course a B, and B thus has the best coverage for Nat.1. Con S, as expected, provides much more even coverage for all clades, and provides better coverage for all the groups except B clade. (Note: in a Con S Macaque study, the natural B was not selected to be optimal, and Con S had better coverage even within B clade than the B vaccine strain that had been used; this was reflected in the number of detected responses to heterogeneous B's. A difference here is that the natural B was selected to be the natural B clade sequence from acute infection that provides optimal coverage). Nat.3 gives good broad coverage, Mos.3 better. (See FIG. 11.)

The mosaics will minimize rare 9-mers but in Env they cannot be excluded or it is not possible to span certain really variable regions to make intact proteins. For all other HIV proteins tested, it was possible to exclude 9-mers that were found at 3 times or less. Still, the 3 best natural Envs contain more than twice the number of rare 9-mer variants relative to the 3 Env mosaics.

FIG. 12 includes additional summaries of coverage; ConS gp160 contains quite a few conserved 9-mers that are missed in gp140DCFI, as one would expect. ConS provides slightly less coverage than a single mosaic, but it is already known that ConS works very well in macaques so serves as a good positive control. 1, 2, and 3 mosaics give increasingly better coverage, and Nat.3 is not as good as Mos.3.

FIG. 13 is alignment dependent, and based on the database alignment (the tow plots above this are alignment independent). Each position represents the 9-mer it initiates as one moves across the protein. The upper bound (black dashed lined) is the sum of the frequencies of the three most common 9-mers starting from each position; it represents the maximal limit that could be achieved for coverage with 3 proteins, and this is not quite achievable in practice because there can be conflicts in a given position for overlapping 9-mers, although the 3 mosaic combination very nearly achieves it. The reason the "total 9-mers" shown in grey varies is because of insertions and deletions in the alignment.

Only the Mos.3 vaccine cocktail is shown in FIG. 13. However, all four vaccines resorted by coverage is shown in FIG. 14, where those positions that start the 9-mers that are best covered by the vaccine are moved to the left. The exact match line is left in all four plots for a reference point. Not only does Mos.3 (red) approach the maximum, but the orange and yellow near-matches that have potential for cross-reactivity are also improved in this vaccine cocktail as compared to the others.

The plots shown in FIG. 15 map every amino acid in every sequence in the full database alignment. A row of pixels is a sequence, a column is an alignment position. White patches are insertions to maintain the alignment. All 9-mers that encompass an amino acid are considered. If every 9-mer that spans the amino acid has a perfect match in the vaccine cocktail, the pixel is yellow, so yellow is good. If one is off, light orange, two off, darker orange . . . through no spanning 9-mer matches represented by black. Note: lots of yellow for 3 mosaics, relative to the other vaccines. There is a big patch of the most yellow for the B clade in Nat.1 as the single best natural is a B clade. Note, all those dark bits: in these regions the sequences in the database are different than any 9-mer in the vaccine, so cross-reactivity would be several limited.

Optimization Using 9-Mers.

9-mers were selected because that is the most common size of an optimal CD8+ T cell epitope. They range from 8-12, and optimal CD4+ T cell epitopes can be even be larger or smaller. As it turns out, coverage of 9-mers is best when optimized for 9-mer coverage, but if optimization on a different size yields very little decrease in coverage for 9-mers. The same goes for all lengths, 8-12, the peak coverage is for the size selected but the coverage is excellent for other lengths, as the solutions are related. 9-versus 12-mers are shown in FIG. 16, 12 being the most extreme value one might reasonably consider. The coverage is nearly identical for 9-mers optimized for 9 or 12, or for 12-mers optimized for 9 or 12; it is 1-2% higher for the length selected for optimization. Naturally, 12-mers have fewer identities than 9-mers in general, because they are longer so it is harder to find a prefect match. A more comprehensive study was made of this for HIV proteins showing that the loss was consistently larger for 12-mers when optimized on 9 rather than vice versa, and that, in other proteins, this difference could be up to 4-5%. Thus, for Env the selection of 9-mers is less of a problem. Given all of the above, 9-mers were selected since this is the most common optimal CTL epitope length, and since optimal coverage of 9-mers provides approaching optimal coverage of other lengths.

Options for the 3 Best Natural Strains: Acute Transmission Cases, SGA Sequences.

Use of all database sequences as a source for natural strains for vaccine cocktails was first explored, and then a comparison was made of that with selecting from a restricted group of just acute SGA sequences, essentially transmitted viruses. Essentially comparable coverage of the full database could be achieved by restricting to acute infection sequences. As these have other obvious advantages, they will be used for the natural sequences.

First, the exploration of coverage using the full database as a source for a natural cocktail. As noted above, the current M group Env one-seq-per-person data set is dominated by B clade infections, closely followed by C clade. Thus, the single best optimal natural selected by the vaccine design program to cover 9-mers in the (database+CHAVI) data set is a B. If one picks from among any sequence in the database, YU-2 comes up as the best single sequence. To get better representation of other clades, the best B was fixed, and then the next best sequence was added to complement YU-2, which is (logically) a C clade sequence, DU467. Those two were then fixed, and the third complement of the antigen was selected. (If the first two are not fixed, and the program is allowed to choose the third, it logically found a B/C recombinant, it has to be forced to select an A. It is believed that forcing the ABC set would improve global coverage, and partly counteract the B & C clade sampling bias among sequences.)

The optimal naturals from the database tend to harken back to older sequences; this is not surprising, as the older sequences tend to be more central in phylogenetic trees, and thus more similar other circulating strains. For this study, however, it is preferred to use more contemporary Envelope proteins sampled during acute infection and sequenced using SGA, as these sequences accurately reflect the transmitted virus. Given that constraint, it is still desired to optimize for 9-mer coverage, so that the cocktail of natural sequences is given the best chance for success in the comparison with mosaics. It turns out when this was done there was an extremely minor loss of coverage when comparing the trivalent cocktail selected from among acute SGA sequences to the trivalent antigen selected from the entire database, (in both cases optimizing for coverage the full database). Thus, by restricting the antigen cocktails to transmitted virus, coverage is not compromised. This alternative has several advantages. Most importantly, it enables a determination of the cross-reactive potential of antibodies generated from acute infection viruses used for the natural cocktail relative to consensus or mosaics as a secondary endpoint of interest, without compromising the primary endpoint focusing on a comparison of T-cell response breadth of coverage. A large set of B (113) and C (40) clade acute samples sequenced from CHAVI study is available, giving a large dataset from which to select an optimum combination. For the selection of the complementary sequence from the A clade, to complete the B and C in the trivalent vaccine. Several acute sequences were available.

Analysis of gp160 was undertaken that included the 8 subtype A gp160s, and also a subregion analysis was done with all 15 in V1-V4, to get an indication of whether or not more sequencing was required. Fortunately, one of the available full length sequences made an excellent complement to the B and C acutes, essentially as good as any of the others. This comparison indicated there was no particular need to do more sequencing at this time. It is believed that this is appropriate since with such a limited A baseline to select from, because the A sequence only needs to complement the choice of B and C clade strains, and many Bs and Cs were available from which to choose. Two of the patients from which the Nat.3 cocktail is derived are below. Nat.1 is just the first one.

B Patient 1059
Patient Sex=M
RiskFactor=PPD
Sample country=USA
Sample city=Long Beach, Calif.
Patient cohort=CA-UCSF
Patient health status=Acute
Viral Load=2,800,000
Infection country=USA
Sample date=Mar. 26, 1998
C Patient 0393
Fiebig Stage=4
Infection country=Malawi
Sample date=17 Jul. 2003
Viral Load=12,048,485
Patient sex=F
CD4count=618 (measured 13 days after sequenced sample)
Patient age=23
STD=GUD,PID FIGS. 17 and 18 illustrate the minimal loss of coverage in selecting from acute SGA sequences, and a highlighter plot of each of the 3 patients env sequences, that shows that the consensus of each patient is equivalent to the most common strains, and thus an excellent estimate of the actual transmitted virus.

Why M Group and not Clade Specific Coverage?

Figure 19:
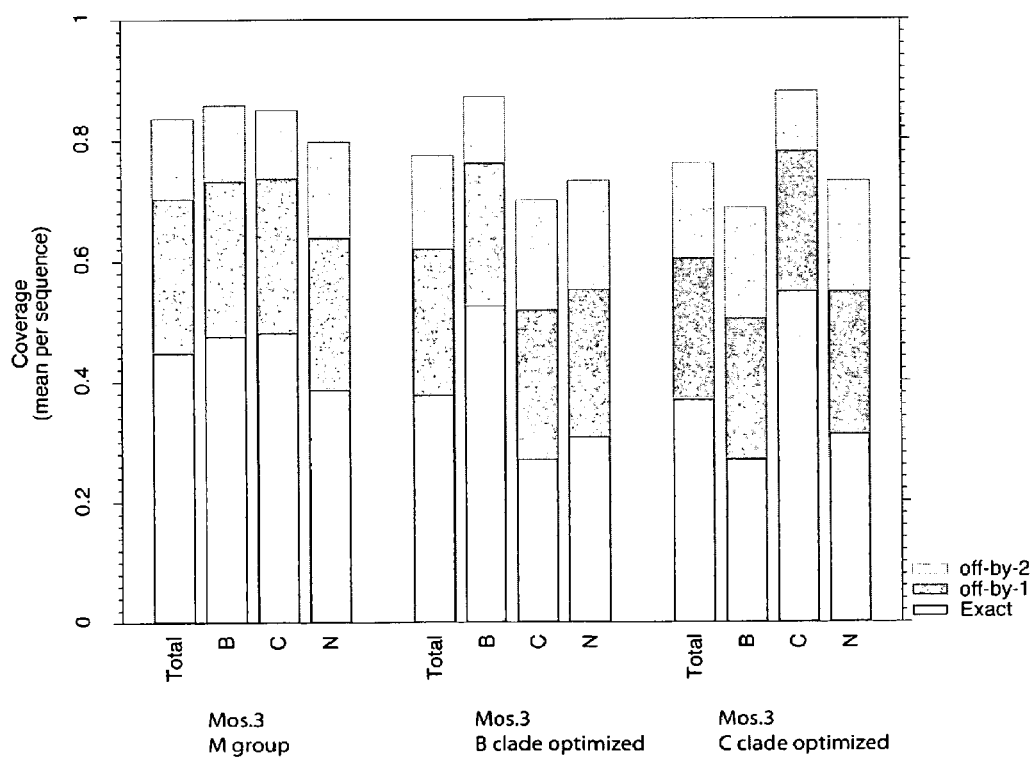
FIG. 19. The compromise and benefit in terms of coverage for Env M group versus subtype-specific design.

It is believed that it is important to strive for a global HIV vaccine, if at all possible, with exploratory methods such as these since many nations have multiclade epidemics, and people travel. While intra-clade coverage can definitely be gained by a within-clade optimized vaccine, the result of such a strategy would be dramatic loss of inter-clade coverage. The hope is that a multivalent mosaic could provide enough breadth to counter viruses of virtually any clades or recombinants. The compromise and benefit in terms of coverage for Env M group versus subtype-specific design is shown in FIG. 19.

Why Env?

Figure 20:
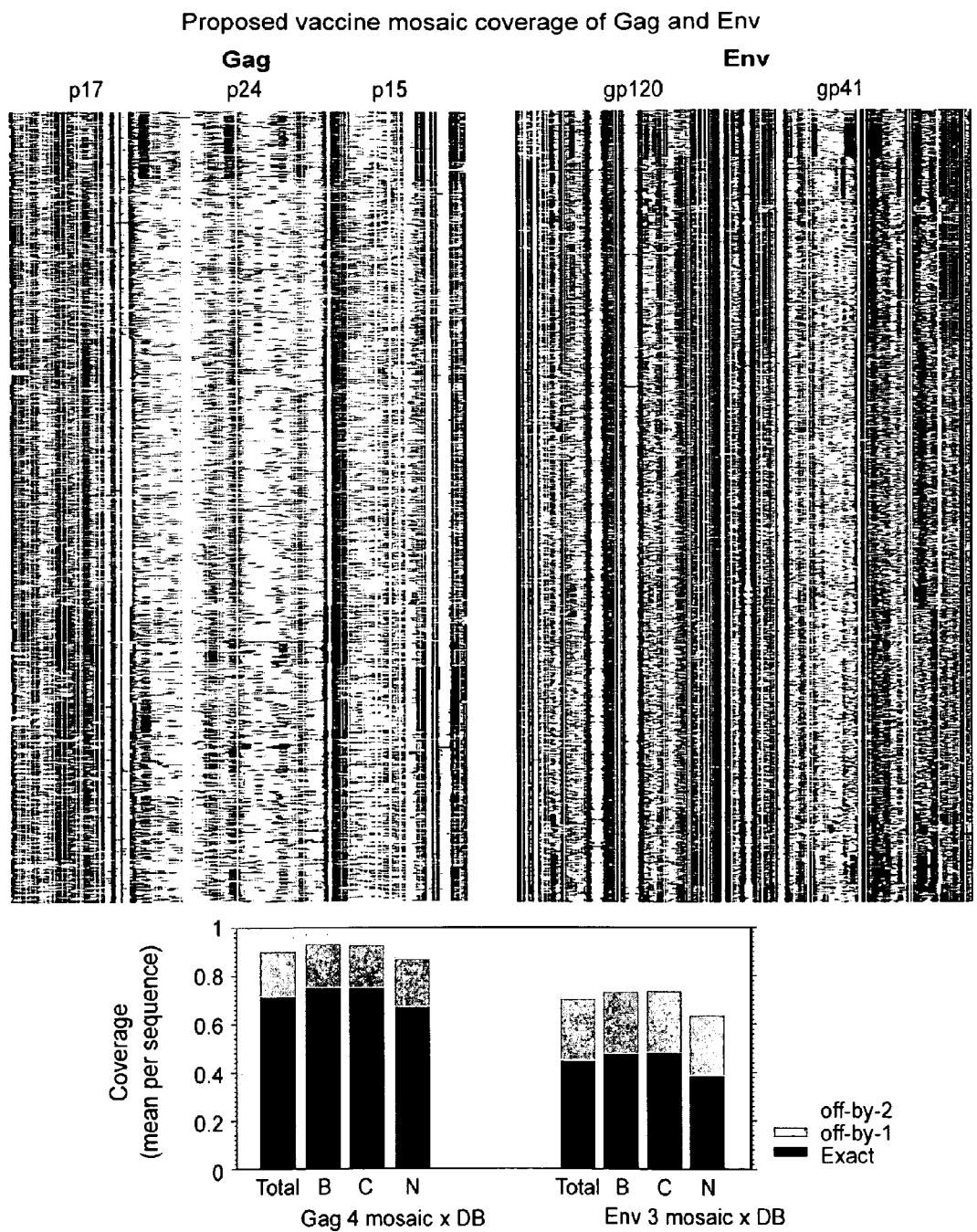
FIG. 20. Proposed vaccine mosaic coverage of Gag and Env.

This proof of concept study is well positioned to see differences in breadth of responses using Env as the test antigen. This is partly because of the theoretical considerations described herein (ENV has twice many conserved 9 mers in the mosaics relative to the best natural strain, and only half as many rare variants) and partly because of the prior animal studies. Env studies with a consensus versus natural in macaques showed a highly significant increase in breadth of responses: 3-4 fold more epitopes per Env protein were recognized (Santra et al, in press, PNAS). Env mosaics have shown an even more profound advantage in a mouse study (up to 10-fold over comparable numbers of natural antigens, manuscript in preparation in collaboration with the VRC). Based on this prior work, it makes sense to start with a small human trial testing the breadth of responses to Env. Ultimately, the hope is to apply the proof of concept gained with Env to a more conserved protein like a Gag where it may be possible to confer broadest protection. Gag gives outstanding coverage of the full M group. Tests of Gag and Nef are ongoing in macaque, using a 4 mosaic vaccine cocktail approach (see Example 3). A coverage comparison of macaque 4 mosaic Gag vaccine and proposed human Env 3 mosaic vaccine against the current database is in FIG. 20. There is more theoretical potential for cross-reactivity with the Gag vaccine, but more progress has been made with Env in the animal models to date, so Env has the best foundation to justify moving forward. The three mosaic Env sequences described above and the sequences used in Example 3 are shown in FIG. 21.

DNA

The DNAs to be used will be in the form of the full gp160 Env. The gp160 would be in the PCMVR plasmid (Gary Nabel) and will be the identical plasmid used in all VRC DNA immunization trials. Dose is anticipated to be 4 mg. The following DNA constructs will be used:

DNA optimal Wildtype Env transmitted/founder env (WT Env)
DNA group M consensus Env (ConS Env)
DNA Trivalent optimal wildtype transmitted/founder Env (WT Tri Env)
DNA Trivalent Mosaic Env

NYVAC

NYVAC (vP866) is a recombinant poxvirus vector which has an 18 gene deletion versus wild-type virus. The NYVAC vector will be licensed from Sanofi-Pasteur and manufactured by a third party contractor and will be propagated on a CEF cell substrate. The Env construct expressed in NYVAC will be gp140C (entire Env with transmembrane and cytoplasmic domain deleted and gp41/gp120 cleavage site mutated) or will be a full gp160. The choice of construct design will depend on the ability to make the NYVAC with gp160 forms vs gp140. The dose of NYVAC is anticipated to be ~1×10^7 TCID50. The following NYVAC constructs will be used:

NYVAC WT Env
NYVAC ConS Env
NYVAC Trivalent Native Env
NYVAC Trivalent Mosaic Env Vaccinations will be given by intramuscular injection.

Design:
Randomized, placebo-controlled, double-blind trial
Duration Per Participant:
Approximately 12 months
Estimated Total Study Duration:
Approximately 18 months Example 3

Construction of the Plasmid DNA Vaccines and Recombinant Vaccinia (rVV)

Mosaic gag and nef genes, group M consensus gag and nef genes were generated by converting amino acid sequences of said Gag and Nef, group M consensus Gag and Nef CON-S to nucleotide sequences using a strategy for optimal gene expression. For use as a DNA vaccine, mosaic gag and nef genes, group M consensus gag and nef genes were subcloned into WLV0001-AM DNA vaccine vector. Endotoxin-free plasmid DNA preparation were produced by Puresyn, Inc. (Malvern, Pa.) for the immunization of rhesus monkeys. For boosting recombinant vaccinia viruses expressing the individual mosaic gag and nef genes, group M consensus gag and nef genes were generated. The methods used were as previously described (Liao et al, Virology 353:268-282 (2006); Earl, BioTechniques 23:1094-1097 (1997)).

Experimental Groups and Vaccination Schedule.

Three groups of rhesus monkeys were immunized with either 10 mg of the empty DNA vector plasmid (group 1, 6 monkeys), or 5 mg each of group M gag and nef plasmid DNA (group 2, 12 monkeys) or 1.25 mg each of 4 mosaic gag and 4 nef plasmid DNA (group 3, 12 monkeys) intramuscularly at Day 0 and Day 30. The monkeys will be boosted with the corresponding rVV expressing the initial immunizing immunogen (10^9 pfu/monkey) 5 month post-immunization with the 2$^{nd}$ DNA immunization.

Myristoylation of Gag and Nef has a potential down regulation effect on immune responses and thus the myris-

TABLE

Protocol Schema

| | | | Injection schedule in weeks | | | |
|---|---|---|---|---|---|---|
| Group | Number | Dose | 0 | 4 | 20 | 24 |
| 1 | 20 | | DNA WT Env | DNA WT Env | NYVAC WT EnvA | NYVAC WT EnvA |
| | 4 | | Placebo | Placebo | Placebo | Placebo |
| 2 | 20 | | DNA ConS Env | DNA ConS Env | NYVAC ConS | NYVAC ConS |
| | 4 | | Placebo | Placebo | Placebo | Placebo |
| 3 | 20 | | DNA Trivalent Native Env | DNA Trivalent Native Env | NYVAC Trivalent Native Env | NYVAC Trivalent Native Env |
| | 4 | | Placebo | Placebo | Placebo | Placebo |
| 4 | 20 | | DNA Trivalent Mosaic Env | DNA Trivalent Mosaic Env | NYVAC Trivalent Mosaic Env | NYVAC Trivalent Mosaic Env |
| | 4 | | Placebo | Placebo | Placebo | Placebo |
| Total | 96 (80/16) | | | | | |

Participants:
Healthy, HIV-1-uninfected volunteers aged 18 to 50 years:
80 vaccines
16 control recipients
96 total participants toylation of Gag and Nef has been mutated in the sequences used in this study.

All documents and other information sources cited above are hereby incorporated in their entirety by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09844590B2). An electronic copy of the "Sequence Listing" will also be available from the USPTO upon request and payment of the fee set forth in 37 CFR 1.19(b)(3).

What is claimed is:

1. A polypeptide or protein comprising any one of the mosaic Gag polypeptide Gag M4.1-4Dmyr selected from the group consisting of SEQ ID Nos: 173-176.

2. A composition comprising at least one polypeptide or protein according to claim 1 and a carrier.

3. A method of inducing an immune response in a mammal comprising administering to said mammal an amount of at least one polypeptide or protein according to claim 1 or claim 2 sufficient to effect said induction.

4. The polypeptide according to claim 1, wherein the polypeptide comprises the amino acid sequence of SEQ ID NO: 173.

5. The polypeptide according to claim 1, wherein the polypeptide comprises the amino acid sequence of SEQ ID NO: 174.

6. The polypeptide according to claim 1, wherein the polypeptide comprises the amino acid sequence of SEQ ID NO: 175.

7. The polypeptide according to claim 1, wherein the polypeptide comprises the amino acid sequence of SEQ ID NO: 176.

8. The composition according to claim 2 comprising the four mosaic Gag M4.1-4Dmyr polypeptides comprising SEQ ID Nos: 173-176.

9. The composition according to claim 2 further comprising an adjuvant.

\* \* \* \* \*